United States Patent
Chen et al.

(10) Patent No.: US 11,807,850 B2
(45) Date of Patent: Nov. 7, 2023

(54) COMPOSITIONS AND METHODS FOR MODULATING GENE EXPRESSION

(71) Applicant: Klogenix LLC, Boston, MA (US)

(72) Inventors: Ci-Di Chen, Boston, MA (US); Ella Zeldich, Boston, MA (US); Carmela Abraham, Boston, MA (US)

(73) Assignee: KLOGENIX LLC, Boston, MA (US)

( * ) Notice: Subject to any disclaimer, the term of this patent is extended or adjusted under 35 U.S.C. 154(b) by 733 days.

(21) Appl. No.: 16/762,711

(22) PCT Filed: Dec. 4, 2018

(86) PCT No.: PCT/US2018/063837
§ 371 (c)(1),
(2) Date: May 8, 2020

(87) PCT Pub. No.: WO2019/113061
PCT Pub. Date: Jun. 13, 2019

(65) Prior Publication Data
US 2021/0171944 A1 Jun. 10, 2021

Related U.S. Application Data

(60) Provisional application No. 62/753,531, filed on Oct. 31, 2018, provisional application No. 62/617,328, (Continued)

(51) Int. Cl.
*C12N 15/113* (2010.01)
*C12N 9/22* (2006.01)
(Continued)

(52) U.S. Cl.
CPC .......... *C12N 15/113* (2013.01); *C12N 5/0686* (2013.01); *C12N 9/22* (2013.01);
(Continued)

(58) Field of Classification Search
CPC .. C12N 15/67; C12N 15/113; C12N 15/1137; C12N 15/09; C12N 2310/20
See application file for complete search history.

(56) References Cited

U.S. PATENT DOCUMENTS
2017/0283831 A1 10/2017 Zhang et al.

FOREIGN PATENT DOCUMENTS
WO WO2017/201527 11/2017

OTHER PUBLICATIONS
Chen et al. (Journal of Molecular Neuroscience, Feb. 2018. vol. 64(2): 175-184).*
(Continued)

*Primary Examiner* — Terra C Gibbs
(74) *Attorney, Agent, or Firm* — K&L Gates LLP

(57) ABSTRACT

The present disclosure relates to compositions and methods for modulating gene expression and in particular to compositions and methods for increasing expression of Klotho. For example, the present disclosure provides methods for increasing expression of a Klotho gene in a human cell comprising introducing into the cell a CRISPR enzyme and a guide RNA comprising a guide sequence that is substantially complementary to a target sequence within or near the Klotho gene, wherein the guide RNA or the CRISPR enzyme associates with a transcriptional activation domain.

11 Claims, 6 Drawing Sheets

Specification includes a Sequence Listing.

Related U.S. Application Data filed on Jan. 15, 2018, provisional application No. 62/595,410, filed on Dec. 6, 2017.

(51) Int. Cl.
*C12N 15/67* (2006.01)
*C12N 5/071* (2010.01)

(52) U.S. Cl.
CPC .......... *C12N 15/67* (2013.01); *C12N 2310/20* (2017.05); *C12N 2501/115* (2013.01)

(56) References Cited

OTHER PUBLICATIONS

Chen (FASEB J. Jun. 2020; 34(6): 7234-7246).*
Höijer et al. (Nature Communications, 2022; 13(627): pp. 1-10).*
King, et al. "Identification of novel small molecules that elevate Klotho expression." Biochem, J., PMC, Jan. 1, 2012, 441(1), pp. 453-461.
Konermann, et al. "Genome-scale transcriptional activation by an engineered CRISPR-Cas9 complex." Nature., PMC, Jan. 29, 2015, 517(7536), pp. 583-588.
Liao, et al. "In Vivo Target Gene Activation via CRISPR/Cas9-Mediated Trans-Epigenetic Modulation." Cell., PMC, Dec. 14, 2017, 171(7), pp. 1495-1507.
Xu, et al. "High-fidelity CRISPR/Cas9-based gene-specific hydroxymethylation rescues gene expression and attenuates renal fibrosis." Nature Communications., Aug. 29, 2018, pp. 1-15.
King, GD et al. Promoter methylation and age-related downregulation of Klotho in rhesus monkey. Age. Sep. 16, 2011. vol. 34, No. 6, pp. 1405-1419.
Li, XX et al. Klotho suppresses growth and invasion of colon cancer cells through inhibition of IGF1R-mediated P13K/AKT pathway. International Journal of Oncology. May 9, 2014, vol. 45, No. 2, pp. 611-618.
International Search Report and Written Opinion of the International Searching Authority for International Application No. PCT/US2018/063837 dated May 8, 2019.
International Preliminary Report on Patentability for International Application No. PCT/US2018/063837 dated Apr. 16, 2020.

* cited by examiner

SEQUENCE LISTING

<160> NUMBER OF SEQ ID NOS: 63

<210> SEQ ID NO 1
<211> LENGTH: 20
<212> TYPE: RNA
<213> ORGANISM: Artificial Sequence
<220> FEATURE:
<223> OTHER INFORMATION: sgRNA1 guide sequence

<400> SEQUENCE: 1
ggcauaaagg ggcgcggcgc                    20

<210> SEQ ID NO 2
<211> LENGTH: 20
<212> TYPE: RNA
<213> ORGANISM: Artificial Sequence
<220> FEATURE:
<223> OTHER INFORMATION: sgRNA2 guide sequence

<400> SEQUENCE: 2
cggcggggcg cgggcauaaa                                              20

<210> SEQ ID NO 3
<211> LENGTH: 20
<212> TYPE: RNA
<213> ORGANISM: Artificial Sequence
<220> FEATURE:
<223> OTHER INFORMATION: sgRNA3 guide sequence

<400> SEQUENCE: 3
gugccuuucu ccgacguccg                                              20

<210> SEQ ID NO 4
<211> LENGTH: 20
<212> TYPE: RNA
<213> ORGANISM: Artificial Sequence
<220> FEATURE:
<223> OTHER INFORMATION: sgRNA4 guide sequence

<400> SEQUENCE: 4
gaaacguccu gcacggcucc                                              20

<210> SEQ ID NO 5
<211> LENGTH: 161
<212> TYPE: RNA
<213> ORGANISM: Artificial Sequence
<220> FEATURE:
<223> OTHER INFORMATION: sgRNA1

<400> SEQUENCE: 5
ggcauaaagg ggcgcggcgc guuuuagagc uaggccaaca ugaggaucac ccaugucugc      60
agggccuagc aaguuaaaau aaggcuaguc cguuaucaac uuggccaaca ugaggaucac     120
ccaugucugc agggccaagu ggcaccgagu cggugcuuuu u                         161

<210> SEQ ID NO 6
<211> LENGTH: 160
<212> TYPE: RNA
<213> ORGANISM: Artificial Sequence
<220> FEATURE:
<223> OTHER INFORMATION: sgRNA2

<400> SEQUENCE: 6
ggcggggcgc gggcauaaag uuuuagagcu aggccaacau gaggaucacc caugucugca      60
gggccuagca aguuaaaaua aggcuagucc guuaucaacu uggccaacau gaggaucacc     120
caugucugca gggccaagug gcaccgaguc ggugcuuuuu                           160

<210> SEQ ID NO 7
<211> LENGTH: 161
<212> TYPE: RNA
<213> ORGANISM: Artificial Sequence
<220> FEATURE:
<223> OTHER INFORMATION: sgRNA3

<400> SEQUENCE: 7

```
gugccuuucu ccgacguccg guuuuagagc uaggccaaca ugaggaucac ccaugucugc      60
agggccuagc aaguuaaaau aaggcuaguc cguuaucaac uuggccaaca ugaggaucac     120
ccaugucugc agggccaagu ggcaccgagu cggugcuuuu u                         161
```

<210> SEQ ID NO 8
<211> LENGTH: 161
<212> TYPE: RNA
<213> ORGANISM: Artificial Sequence
<220> FEATURE:
<223> OTHER INFORMATION: sgRNA4

<400> SEQUENCE: 8

```
gaaacguccu gcacggcucc guuuuagagc uaggccaaca ugaggaucac ccaugucugc      60
agggccuagc aaguuaaaau aaggcuaguc cguuaucaac uuggccaaca ugaggaucac     120
ccaugucugc agggccaagu ggcaccgagu cggugcuuuu u                         161
```

<210> SEQ ID NO 9
<211> LENGTH: 4000
<212> TYPE: DNA
<213> ORGANISM: Homo sapiens

<400> SEQUENCE: 9

```
acaatatatt gtattttga aaatctcaga gtagatttta agtattcttc tttttctttc      60
tttctttctt ttcttttctt tttcttttt tgaaacagac tcttgctctg ttgccaaagc     120
tggagtacag tggtgtgatc tcagctcact gcaacctccg cctcccgggt tcaagtgatt    180
ctcctgcctc agcctcctga gtagctggga ttacaggtgc ctgccaccat gttggtgaat    240
ttttgtattt tagtagaga caggagtttc accatgttgg ccaggctggt ctcgaactcc     300
tgaccttagg tggtccacct gcctcggcct ctcaaagtgc tgggattaca ggtgtgagcc    360
accacgcccg gccagatttt aagtcttctt accacaaaaa aaataagtat gtgaggtaat    420
acatcgtttt attagctcaa tttagccact ctacaaatgt gtatatattt taaaataaca    480
tgctgtacat gaaaatatat ataatttttt gtctgttaaa aattaattaa ttaattaatt    540
ttaaaagag gagggcaggg aatacttgtg tattttgtta actggacaaa tgaaactcta    600
ctttcatttg ctcattaaac aaatacttgt tttgtgctca gcatgattct aggcactggg    660
actactgcat tttggtccat tacttccttg cgcacaaaaa ccctttctt tcaccacgaa     720
tacactatga acatgttttt ttcttcagtg ttggcatctc ttgattcctt ccctccaggt    780
ctttgtgcga gttttactct ttaaaccca gatattgtca tatttttctc tgttaaactt     840
ttccaaacaa ctcaaaatag ggtaattct tcttcttctg aatttctctg acaattattc     900
tatgggtcat ttattaacac agcataatca aacaacttat ttattttcat ctttcttgat   960
cctttcttca gttggatgtt gtctttgagg gcagaggttg tcctctatgt tttgaagtct   1020
ccacacagct catcgttgcc ttgcccgtag ttgtagctca gtgaaataaa aatatgtccg   1080
tagaaggtga tgtctgtgac tggtgagccg agagcttgtg gggttggtgt tgtatttgag   1140
tgcatgtgaa tcagtgcatc tcctgctcca ttggtgttaa aaggctccca tcgtcctggg   1200
aacacaatag gaaagagaac aggtgggaag gcactggatg aaggaatgtg gagaatggag   1260
gaaaagttga tcagattgtt gacaactttc agtgttgaaa ttgtcaccaa atcaaagtc    1320
agtaaataaa tttacaatgt cctttttcttc aatgcatcaa taacttcacc ttcctgttca  1380
aagcacagca agtaattaat ctcttatttg catttgaaac ccaagtttca gatgtttgaa   1440
```

```
ggtggttgta aaaaataaaa accaaaataa agccaaaata aataagcagc agcactaggc    1500
cgggcacagt gtctcacacc tgtaatccca gcattttagg agaccgaggt gggtggatca    1560
caggagatca ggagtttgag accagcctgg tcagcatggt gaaaccctgt ctctactaaa    1620
aatacaaaaa ttagccaggt gtggtggtgt gcccttataa tcccagctac tgggggctg     1680 agacaggaga attgcttgaa cctgggaggc agaggttgca gtgagcagag accatgccac    1740
tgcactccag cctgggcgac agagtgagac tccgtctcac acttgtggaa cccagaactt    1800
agtaaccatg aacagaacct aataaacag  aaagttctgg aaataaagtt taatcatcat    1860
gcaatcttta tcactgggtt aaatgaacaa tcatctggga acatgtcttg gaatgcttaa    1920
agctttgaga tgcatgtgcc tatgtggcag acaaatttca aatgtgaaac gtttagttaa    1980
cttggtcttg cttttaatc  actgctttaa aatttaaaaa atgctgctgg tcaagtaaaa    2040
atagcaatag ataaaatctg ccctgagcaa acagaccata catcaataaa tgaatactta    2100
gcttaagcga ttttccatga gacccatgaa gcatttctaa ttgaaactta acaagctaca    2160
acccaacaga cactccaatc ttcacttcta gaagggaaat gtgatactcc atgtagacgt    2220 agcttttaa  atttagctgg aagacagcgt gacagtgaag ttgtgtgctg taattttta     2280 aaattgctga agtgtcatgg tttgctattt cgtatttatt gaaaaaatgt aaatgctata    2340
tttaacagaa tggcagtaac tctgtttcaa tctgaagact taatcttact aatcatggta    2400
atatatgctg gctggagttg ggaatatttc ataaaatact ggaataaatt tgtgcttata    2460
tttcagggga attaataaaa gcaccttcat ctgcaacatt taaaatgtta ttgcctttaa    2520
atttgtatta aataatgcag ggaggataga tcactggggg agaatggatg cacctctgtg    2580
aggatcttgg tcattcaaca cacgtgtacg ggtgaggaaa ctaaggcacg acttactggg    2640
tagggaggta gggatattag caagatcctt cacttgtctg ggctttctgt ctttgagtca    2700
cctttgcgca gttttcact  ggacttcaca agcctctgag gcggcagggc agacaggaca    2760
tccttatttt atagaggaaa aaacttaggc ttacagaggt ttcctgcccc aaatcacaaa    2820
ggtggagcct agaccttctc agtctccacc aactgtattt cggttagcca caatcctatc    2880
tacccacatc caaatggaca ccgtggctct gcaacttctg tcaaaagggc tctttggcaa    2940
caggaaaaac gtcatggctc cattgtattg tagaggatgg gaatgggtgt tccggctaaa    3000
ttctccctcc cctttccctc cacagctcag atggcaaatg tgcgacccag ggacctcccg    3060
ctccagcaga cctgtgcgca caactttgca cagattacct gctaagtcag agccgaaagg    3120
taacacagat gccaaaggat aataaaggtg aataagagatt  actcaaaatt ggaaacttgg    3180
tgtttggttt ttcaggagaa caatcaacga ctgtgatttg aagttcacca gggtattctg    3240
agagatctaa tcaaagatag agtgctggtt tgaaattatt aaaaggtaac agtaaaaggg    3300
agagcaaaac cccagtccca acgcaaccca taaatctact ttgtcttcct cgaaagaggg    3360
gcgcgggtgg gcgcgtctcc ccgcgagcat ctcacctaag ggggaatccc tttcagcgca    3420
cggcgaagtt cccccctcggc tgtcccacct ggcagtccct ctaggatttc ggccagtccc    3480
taattggctc cagcaatgtc cagccggagc ttctttgggc ctccgagtgg gagaaaagtg    3540
agagcaggtc cttccccagc ggcgcgctcc gctagggccc ggcaggatcc cgcccccaag    3600
tcggggaaag ttggtcggcg ccttttctcc ccgacgaagc cgctccaggg ctgctctcag    3660
aggacgcgcg gcaggcaaag agaatgaacc tgagcgtcca cgaaacgtcc tgcacggctc    3720
ccgggagctg ggaggaacag gtgccttttct ccgacgtccg cgggcgacgc ctgccgcacc    3780
ttgcccgctg ccgcgcccct cccgggcacc cctcgccctc ggcgcccctg cccccacccc    3840
```

```
cagtgccagg gcggaggcag tcccggctcg caggtaatta ttgccagcgg agcccgccgg    3900
ggagcggggg tgggcgcgcc ggcgtgggc gggcgggcgc ggcggggcgc gggcataaag    3960
gggcgcggcg cggggccccg agcctggct cccgcgcagc                           4000

<210> SEQ ID NO 10
<211> LENGTH: 4000
<212> TYPE: DNA
<213> ORGANISM: Homo sapiens

<400> SEQUENCE: 10
gctgcgcggg agccaggctc cggggccccg cgccgcgccc ctttatgccc gcgcccgcc      60 gcgcccgccc gcccaccgcc ggcgcgccca ccccgctcc ccggcgggct ccgctggcaa    120
taattacctg cgagccggga ctgcctccgc cctggcactg ggggtgggg caggggcgcc     180 gagggcgagg ggtgcccggg agggcgcgg cagcgggcaa ggtgcggcag gcgtcgcccg    240
cggacgtcgg agaaaggcac ctgttcctcc cagctcccgg gagccgtgca ggacgtttcg    300
tggacgctca ggttcattct ctttgcctgc cgcgcgtcct ctgagagcag ccctggagcg    360
gcttcgtcgg ggagaaaagg cgccgaccaa ctttccccga cttggggcg ggatcctgcc     420 gggccctagc ggagcgcgcc gctggggaag cacctgctct cacttttctc ccactcggag    480
gcccaaagaa gctccggctg gacattgctg gagccaatta gggactggcc gaaatcctag    540
agggactgcc aggtgggaca gccgaggggg aacttcgccg tgcgctgaaa gggattcccc    600
cttaggtgag atgctcgcgg ggagacgcgc ccaccgcgc ccctctttcg aggaagacaa     660
agtagattta tgggttgcgt tgggactggg gttttgctct cccttttact gttacctttt    720
aataatttca aaccagcact ctatctttga ttagatctct cagaataccc tggtgaactt    780
caaatcacag tcgttgattg ttctcctgaa aaaccaaaca ccaagtttcc aattttgagt    840
aaatctcatt cacctttatt atcctttggc atctgtgtta cctttcggct ctgacttagc    900
aggtaatctg tgcaaagttg tgcgcacagg tctgctggag cggaggtcc ctgggtcgca     960 catttgccat ctgagctgtg gagggaaagg ggagggagaa tttagccgga cacccattc    1020 ccatcctcta caatacaatg gagccatgac gttttttcctg ttgccaaaga gcccttttga    1080
cagaagttgc agagccacgg tgtccatttg gatgtgggta gataggattg tggctaaccg    1140
aaatacagtt ggtggagact gagaaggtct aggctccacc tttgtgattt ggggcaggaa    1200
acctctgtaa gcctaagttt tttcctctat aaaataagga tgtcctgtct gccctgccgc    1260
ctcagaggct tgtgaagtcc agtgaaaaac tgcgcaaagg tgactcaaag acagaaagcc    1320
cagacaagtg aaggatcttg ctaatatccc tacctcccta cccagtaagt cgtgccttag    1380
tttcctcacc cgtacacgtg tgttgaatga ccaagatcct cacagaggtg catccattct    1440
cccccagtga tctatcctcc ctgcattatt taatacaaat ttaaaggcaa taacatttta    1500
aatgttgcag atgaaggtgc ttttattaat tcccctgaaa tataagcaca aatttattcc    1560
agtattttat gaaatattcc caactccagc cagcatatat taccatgatt agtaagatta    1620
agtcttcaga ttgaaacaga gttactgcca ttctgttaaa tatagcattt acatttttc     1680 aataaatacg aaatagcaaa ccatgacact tcagcaattt taaaaaatta cagcacacaa    1740
cttcactgtc acgctgtctt ccagctaaat ttaaaaagct acgtctacat ggagtatcac    1800
atttcccttc tagaagtgaa gattggagtg tctgttgggt tgtagcttgt taagtttcaa    1860
ttagaaatgc ttcatgggtc tcatggaaaa tcgcttaagc taagtattca tttattgatg    1920
```

```
tatggtctgt ttgctcaggg cagattttat ctattgctat ttttacttga ccagcagcat    1980 ttttaaatt ttaaagcagt gattaaaaag caagaccaag ttaactaaac gtttcacatt    2040
tgaaatttgt ctgccacata ggcacatgca tctcaaagct ttaagcattc caagacatgt    2100
tcccagatga ttgttcattt aacccagtga taaagattgc atgatgatta aactttattt    2160
ccagaacttt ctgtttatta aggttctgtt catggttact aagttctggg ttccacaagt    2220
gtgagacgga gtctcactct gtcgcccagg ctggagtgca gtggcatggt ctctgctcac    2280
tgcaacctct gcctcccagg ttcaagcaat tctcctgtct cagcccccca gtagctggga    2340
ttataagggc acaccaccac acctggctaa ttttttgtatt tttagtagag acagggtttc    2400
accatgctga ccaggctggt ctcaaactcc tgatctcctg tgatccaccc acctcggtct    2460
cctaaaatgc tgggattaca ggtgtgagac actgtgcccg gcctagtgct gctgcttatt    2520
tattttggct ttattttggt ttttattttt tacaaccacc ttcaaacatc tgaaacttgg    2580
gtttcaaatg caaataagag attaattact tgctgtgctt tgaacaggaa ggtgaagtta    2640
ttgatgcatt gaagaaaagg acattgtaaa tttatttact gactttgatt ttggtgacaa    2700
tttcaacact gaaagttgtc aacaatctga tcaacttttc ctccattctc cacattcctt    2760
catccagtgc cttcccacct gttctctttc ctattgtgtt cccaggacga tgggagcctt    2820
ttaacaccaa tggagcagga gatgcactga ttcacatgca ctcaaataca acaccaaccc    2880
cacaagctct cggctcacca gtcacagaca tcaccttcta cggacatatt tttatttcac    2940
tgagctacaa ctacgggcaa ggcaacgatg agctgtgtgg agacttcaaa acatagagga    3000
caacctctgc cctcaaagac aacatccaac tgaagaaagg atcaagaaag atgaaaataa    3060
ataagttgtt tgattatgct gtgttaataa atgacccata gaataattgt cagagaaatt    3120
cagaagaaga agaaattacc ctattttgag ttgtttggaa aagtttaaca gagaaaaata    3180
tgacaatatc tggggtttaa agagtaaaac tcgcacaaag acctggaggg aaggaatcaa    3240
gagatgccaa cactgaagaa aaaaacatgt tcatagtgta ttcgtggtga aaagaaaggg    3300
tttttgtgcg caaggaagta atggaccaaa atgcagtagt cccagtgcct agaatcatgc    3360
tgagcacaaa acaagtattt gtttaatgag caaatgaaag tagagtttca tttgtccagt    3420
taacaaaata cacaagtatt ccctgccctc ctctttttaa aattaattaa ttaattaatt    3480
tttaacagac aaaaaattat atatattttc atgtacagca tgttatttta aaatatatac    3540
acatttgtag agtggctaaa ttgagctaat aaacgtatgt attacctcac atacttattt    3600
tttttgtggt aagaagactt aaaatctggc cgggcgtggt ggctcacacc tgtaatccca    3660
gcactttgag aggccgaggc aggtggacca cctaaggtca ggagttcgag accagcctgg    3720
ccaacatggt gaaactcctg tctctactaa aaatacaaaa attcaccaac atggtggcag    3780
gcacctgtaa tcccagctac tcaggaggct gaggcaggag aatcacttga acccgggagg    3840
cggaggttgc agtgagctga gatcacacca ctgtactcca gctttggcaa cagagcaaga    3900
gtctgtttca aaaagaaaa aagaaaagaa aagaagaaaa gaaagaaaaa gaagaatact    3960
taaaatctac tctgagattt tcaaaaatac aatatattgt                          4000
```

<210> SEQ ID NO 11
<211> LENGTH: 3800
<212> TYPE: DNA
<213> ORGANISM: Homo sapiens

<400> SEQUENCE: 11

```
acaatatatt gtattttttga aaatctcaga gtagatttta agtattcttc tttttctttc    60
```

```
ttttcttctt ttcttttctt ttttcttttt tgaaacagac tcttgctctg ttgccaaagc    120
tggagtacag tggtgtgatc tcagctcact gcaacctccg cctcccgggt tcaagtgatt    180
ctcctgcctc agcctcctga gtagctggga ttacaggtgc ctgccaccat gttggtgaat    240
ttttgtattt ttagtagaga caggagtttc accatgttgg ccaggctggt ctcgaactcc    300
tgaccttagg tggtccacct gcctcggcct ctcaaagtgc tgggattaca ggtgtgagcc    360
accacgcccg gccagatttt aagtcttctt accacaaaaa aaataagtat gtgaggtaat    420
acatacgttt attagctcaa tttagccact ctacaaatgt gtatatattt taaaataaca    480
tgctgtacat gaaaatatat ataattttt gtctgttaaa aattaattaa ttaattaatt    540 ttaaaagag gagggcaggg aatacttgtg tattttgtta actggacaaa tgaaactcta    600
ctttcatttg ctcattaaac aaatacttgt tttgtgctca gcatgattct aggcactggg    660
actactgcat tttggtccat tacttccttg cgcacaaaaa cccttctctt tcaccacgaa    720
tacactatga acatgttttt ttcttcagtg ttggcatctc ttgattcctt ccctccaggt    780
ctttgtgcga gttttactct ttaaacccca gatattgtca tatttttctc tgttaaactt    840
ttccaaacaa ctcaaaatag ggtaatttct tcttcttctg aatttctctg acaattattc    900
tatgggtcat ttattaacac agcataatca aacaacttat ttattttcat ctttcttgat    960
cctttcttca gttggatgtt gtctttgagg gcagaggttg tcctctatgt tttgaagtct   1020
ccacacagct catcgttgcc ttgcccgtag ttgtagctca gtgaaataaa aatatgtccg   1080
tagaaggtga tgtctgtgac tggtgagccg agagcttgtg gggttggtgt tgtatttgag   1140
tgcatgtgaa tcagtgcatc tcctgctcca ttggtgttaa aaggctccca tcgtcctggg   1200
aacacaatag gaaagagaac aggtgggaag gcactggatg aaggaatgtg gagaatggag   1260
gaaaagttga tcagattgtt gacaactttc agtgttgaaa ttgtcaccaa aatcaaagtc   1320
agtaaataaa tttacaatgt ccttttcttc aatgcatcaa taacttcacc ttcctgttca   1380
aagcacagca agtaattaat ctcttatttg catttgaaac ccaagtttca gatgtttgaa   1440
ggtggttgta aaaataaaa accaaaataa agccaaaata aataagcagc agcactaggc   1500
cgggcacagt gtctcacacc tgtaatccca gcatttagg agaccgaggt gggtggatca   1560
caggagatca ggagtttgag accagcctgg tcagcatggt gaaaccctgt ctctactaaa   1620
aatacaaaaa ttagccaggt gtggtggtgt gcccttataa tcccagctac tggggggctg   1680
agacaggaga attgcttgaa cctgggaggc agaggttgca gtgagcagag accatgccac   1740
tgcactccag cctgggcgac agagtgagac tccgtctcac acttgtggaa cccagaactt   1800
agtaaccatg aacagaacct taataaacag aaagttctgg aaataaagtt taatcatcat   1860
gcaatcttta tcactgggtt aaatgaacaa tcatctggga acatgtcttg gaatgcttaa   1920
agctttgaga tgcatgtgcc tatgtggcag acaaatttca aatgtgaaac gtttagttaa   1980
cttggtcttg cttttaatc actgctttaa aatttaaaaa atgctgctgg tcaagtaaaa   2040
atagcaatag ataaaatctg ccctgagcaa acagaccata catcaataaa tgaatactta   2100
gcttaagcga ttttccatga gacccatgaa gcatttctaa ttgaaactta acaagctaca   2160
acccaacaga cactccaatc ttcacttcta gaagggaaat gtgatactcc atgtagacgt   2220 agcttttaa atttagctgg aagacagcgt gacagtgaag ttgtgtgctg taattttta   2280 aaattgctga agtgtcatgg tttgctattt cgtatttatt gaaaaaatgt aaatgctata   2340
tttaacagaa tggcagtaac tctgtttcaa tctgaagact taatcttact aatcatggta   2400
```

```
atatatgctg gctggagttg ggaatatttc ataaaatact ggaataaatt tgtgcttata    2460
tttcagggga attaataaaa gcaccttcat ctgcaacatt taaaatgtta ttgccttttaa   2520 atttgtatta aataatgcag ggaggataga tcactggggg agaatggatg cacctctgtg    2580
aggatcttgg tcattcaaca cacgtgtacg ggtgaggaaa ctaaggcacg acttactggg    2640
tagggaggta gggatattag caagatcctt cacttgtctg ggctttctgt ctttgagtca    2700
cctttgcgca gtttttcact ggacttcaca agcctctgag gcggcagggc agacaggaca    2760
tccttatttt atagaggaaa aaacttaggc ttacagaggt ttcctgcccc aaatcacaaa    2820
ggtggagcct agaccttctc agtctccacc aactgtattt cggttagcca caatcctatc    2880
tacccacatc caaatggaca ccgtggctct gcaacttctg tcaaagggc tctttggcaa     2940 caggaaaaac gtcatggctc cattgtattg tagaggatgg gaatgggtgt tccggctaaa    3000
ttctccctcc cctttccctc cacagctcag atggcaaatg tgcgacccag ggacctcccg    3060
ctccagcaga cctgtgcgca caactttgca cagattacct gctaagtcag agccgaaagg    3120
taacacagat gccaaaggat aataaaggtg aatgagattt actcaaaatt ggaaacttgg    3180
tgtttggttt ttcaggagaa caatcaacga ctgtgatttg aagttcacca gggtattctg    3240
agagatctaa tcaaagatag agtgctggtt tgaaattatt aaaaggtaac agtaaaaggg    3300
agagcaaaac cccagtccca acgcaaccca taaatctact ttgtcttcct cgaaagaggg    3360
gcgcgggtgg gcgcgtctcc ccgcgagcat ctcacctaag ggggaatccc tttcagcgca    3420
cggcgaagtt cccctcggc tgtcccacct ggcagtccct ctaggatttc ggccagtccc     3480
taattggctc cagcaatgtc cagccggagc ttctttgggc ctccgagtgg gagaaaagtg    3540
agagcaggtg cttccccagc ggcgcgctcc gctagggccc ggcaggatcc cgcccccaag    3600
tcggggaaag ttggtcggcg ccttttctcc ccgacgaagc cgctccaggg ctgctctcag    3660
aggacgcgcg gcaggcaaag agaatgaacc tgagcgtcca cgaaacgtcc tgcacggctc    3720
ccgggagctg ggaggaacag gtgccttttct ccgacgtccg cgggcgacgc ctgccgcacc   3780
ttgcccgctg ccgcgcccct                                                3800

<210> SEQ ID NO 12
<211> LENGTH: 3800
<212> TYPE: DNA
<213> ORGANISM: Homo sapiens

<400> SEQUENCE: 12
aggggcgcgg cagcgggcaa ggtgcggcag gcgtcgcccg cggacgtcgg agaaaggcac      60
ctgttcctcc cagctcccgg gagccgtgca ggacgtttcg tggacgctca ggttcattct    120
ctttgcctgc cgcgcgtcct ctgagagcag ccctggagcg gcttcgtcgg ggagaaaagg    180
cgccgaccaa ctttccccga cttggggcg ggatcctgcc gggccctagc ggagcgcgcc     240
gctggggaag cacctgctct cacttttctc ccactcggag gcccaaagaa gctccggctg    300
gacattgctg gagccaatta gggactggcc gaaatcctag agggactgcc aggtgggaca    360
gccgaggggg aacttcgccg tgcgctgaaa gggattcccc cttaggtgag atgctcgcgg    420
ggagacgcgc ccaccgcgc ccctctttcg aggaagacaa agtagattta tgggttgcgt     480
tgggactggg gttttgctct cccttttact gttacctttt aataatttca aaccagcact    540
ctatctttga ttagatctct cagaatacct tggtgaactt caaatcacag tcgttgattg    600
ttctcctgaa aaaccaaaca ccaagttcc aattttgagt aaatctcatt caccttttatt    660 atcctttggc atctgtgtta cctttcggct ctgacttagc aggtaatctg tgcaaagttg    720
```

```
tgcgcacagg tctgctggag cgggaggtcc ctgggtcgca catttgccat ctgagctgtg    780
gagggaaagg ggagggagaa tttagccgga acacccattc ccatcctcta caatacaatg    840
gagccatgac gttttcctg ttgccaaaga gcccttttga cagaagttgc agagccacgg     900
tgtccatttg gatgtgggta gataggattg tggctaaccg aaatacagtt ggtggagact    960
gagaaggtct aggctccacc tttgtgattt ggggcaggaa acctctgtaa gcctaagttt   1020
tttcctctat aaaataagga tgtcctgtct gccctgccgc ctcagaggct tgtgaagtcc   1080
agtgaaaaac tgcgcaaagg tgactcaaag acagaaagcc cagacaagtg aaggatcttg   1140
ctaatatccc tacctcccta cccagtaagt cgtgccttag tttcctcacc cgtacacgtg   1200
tgttgaatga ccaagatcct cacagaggtg catccattct ccccagtga tctatcctcc    1260 ctgcattatt aatacaaat ttaaaggcaa taacatttta aatgttgcag atgaaggtgc    1320
ttttattaat tcccctgaaa tataagcaca aatttattcc agtatttat gaaatattcc    1380 caactccagc cagcatatat taccatgatt agtaagatta agtcttcaga ttgaaacaga   1440
gttactgcca ttctgttaaa tatagcattt acattttttc aataaatacg aaatagcaaa   1500
ccatgacact tcagcaattt taaaaaatta cagcacacaa cttcactgtc acgctgtctt   1560
ccagctaaat ttaaaaagct acgtctacat ggagtatcac atttcccttc tagaagtgaa   1620
gattggagtg tctgttgggt tgtagcttgt taagtttcaa ttagaaatgc ttcatgggtc   1680
tcatggaaaa tcgcttaagc taagtattca tttattgatg tatggtctgt ttgctcaggg   1740
cagattttat ctattgctat ttttacttga ccagcagcat ttttaaatt ttaaagcagt    1800 gattaaaaag caagaccaag ttaactaaac gttcacatt tgaaatttgt ctgccacata    1860
ggcacatgca tctcaaagct ttaagcattc caagacatgt tcccagatga ttgttcattt   1920
aacccagtga taaagattgc atgatgatta aactttattt ccagaactt ctgtttatta    1980 aggttctgtt catggttact aagttctggg ttccacaagt gtgagacgga gtctcactct   2040
gtcgcccagg ctggagtgca gtggcatggt ctctgctcac tgcaacctct gcctcccagg   2100
ttcaagcaat tctcctgtct cagcccccca gtagctggga ttataagggc acaccaccac   2160
acctggctaa ttttttgtatt tttagtagag acagggtttc accatgctga ccaggctggt   2220
ctcaaactcc tgatctcctg tgatccaccc acctcggtct cctaaaatgc tgggattaca   2280
ggtgtgagac actgtgcccg gcctagtgct gctgcttatt tatttttggct ttatttttggt  2340 ttttatttt tacaaccacc ttcaaacatc tgaaacttgg gtttcaaatg caaataagag   2400
attaattact tgctgtgctt tgaacaggaa ggtgaagtta ttgatgcatt gaagaaaagg   2460
acattgtaaa tttatttact gactttgatt ttggtgacaa tttcaacact gaaagttgtc   2520
aacaatctga tcaactttttc ctccattctc cacattcctt catccagtgc cttcccacct  2580
gttctctttc ctattgtgtt cccaggacga tgggagcctt ttaacaccaa tggagcagga   2640
gatgcactga ttcacatgca ctcaaataca acaccaaccc cacaagctct cggctcacca   2700
gtcacagaca tcaccttcta cggacatatt tttatttcac tgagctacaa ctacgggcaa   2760
ggcaacgatg agctgtgtgg agacttcaaa acatagagga caacctctgc cctcaaagac   2820
aacatccaac tgaagaaagg atcaagaaag atgaaaataa ataagttgtt tgattatgct   2880
gtgttaataa atgacccata gaataattgt cagagaaatt cagaagaaga agaaattacc   2940
ctattttgag ttgttggaa aagtttaaca gagaaaaata tgacaatatc tggggttaa    3000 agagtaaaac tcgcacaaag acctggaggg aaggaatcaa gagatgccaa cactgaagaa   3060
```

-continued

| | |
|---|---|
| aaaaacatgt tcatagtgta ttcgtggtga aaagaaaggg ttttgtgcg caaggaagta | 3120 |
| atggaccaaa atgcagtagt cccagtgcct agaatcatgc tgagcacaaa acaagtattt | 3180 |
| gtttaatgag caaatgaaag tagagtttca tttgtccagt taacaaaata cacaagtatt | 3240 |
| ccctgccctc ctcttttaa aattaattaa ttaattaatt tttaacagac aaaaaattat | 3300 |
| atatattttc atgtacagca tgttatttta aaatatatac acatttgtag agtggctaaa | 3360 |
| ttgagctaat aaacgtatgt attacctcac atacttattt tttttgtggt aagaagactt | 3420 |
| aaaatctggc cgggcgtggt ggctcacacc tgtaatccca gcactttgag aggccgaggc | 3480 |
| aggtggacca cctaaggtca ggagttcgag accagcctgg ccaacatggt gaaactcctg | 3540 |
| tctctactaa aaatacaaaa attcaccaac atggtggcag gcacctgtaa tcccagctac | 3600 |
| tcaggaggct gaggcaggag aatcacttga acccgggagg cggaggttgc agtgagctga | 3660 |
| gatcacacca ctgtactcca gctttggcaa cagagcaaga gtctgtttca aaaagaaaa | 3720 |
| aagaaaagaa aagaagaaaa gaaagaaaaa gaagaatact aaaatctac tctgagattt | 3780 |
| tcaaaaatac aatatattgt | 3800 |

<210> SEQ ID NO 13
<211> LENGTH: 100
<212> TYPE: DNA
<213> ORGANISM: Homo sapiens

<400> SEQUENCE: 13

| | |
|---|---|
| cgaaacgtcc tgcacggctc ccgggagctg ggaggaacag gtgcctttct ccgacgtccg | 60 |
| cgggcgacgc ctgccgcacc ttgcccgctg ccgcgcccct | 100 |

<210> SEQ ID NO 14
<211> LENGTH: 100
<212> TYPE: DNA
<213> ORGANISM: Homo sapiens

<400> SEQUENCE: 14

| | |
|---|---|
| aggggcgcgg cagcgggcaa ggtgcggcag gcgtcgcccg cggacgtcgg agaaaggcac | 60 |
| ctgttcctcc cagctcccgg gagccgtgca ggacgtttcg | 100 |

<210> SEQ ID NO 15
<211> LENGTH: 3039
<212> TYPE: DNA
<213> ORGANISM: Homo sapiens

<400> SEQUENCE: 15

| | |
|---|---|
| atgcccgcca gcgccccgcc gcgccgcccg cggccgccgc cgccgtcgct gtcgctgctg | 60 |
| ctggtgctgc tgggcctggg cggccgccgc ctgcgtgcgg agccgggcga cggcgcgcag | 120 |
| acctgggccc gtttctcgcg gcctcctgcc cccgaggccg cgggcctctt ccagggcacc | 180 |
| ttccccgacg gcttcctctg ggcgtgggc agcgccgcct accagaccga ggcggctgg | 240 |
| cagcagcacg gcaagggtgc gtccatctgg gatacgttca cccaccaccc cctggcaccc | 300 |
| ccgggagact cccggaacgc cagtctgccg ttgggcgccc cgtcgccgct gcagcccgcc | 360 |
| accggggacg tagccagcga cagctacaac aacgtcttcc gcgacacgga ggcgctgcgc | 420 |
| gagctcgggg tcactcacta ccgcttctcc atctcgtggg cgcgagtgct ccccaatggc | 480 |
| agcgcgggcg tccccaaccg cgaggggctg cgctactacc ggcgcctgct ggagcggctg | 540 |
| cgggagctgg gcgtgcagcc cgtggtcacc ctgtaccact gggaccgtgcc ccagcgcctg | 600 |
| caggacgcct acggcggctg ggccaaccgc gccctggccg accacttcag ggattacgcg | 660 |

```
gagctctgct tccgccactt cggcggtcag gtcaagtact ggatcaccat cgacaacccc    720
tacgtggtgg cctggcacgg ctacgccacc gggcgcctgg cccccggcat ccggggcagc    780
ccgcggctcg ggtacctggt ggcgcacaac ctcctcctgg ctcatgccaa agtctggcat    840
ctctacaata cttcttccg tcccactcag ggaggtcagg tgtccattgc cctaagctct    900
cactggatca atcctcgaag aatgaccgac cacagcatca agaatgtca aaaatctctg    960 gactttgtac taggttggtt tgccaaaccc gtatttattg atggtgacta tcccgagagc   1020
atgaagaata accttcatc tattctgcct gattttactg aatctgagaa aaagttcatc   1080
aaaggaactg ctgacttttt tgctcttgc tttggaccca ccttgagttt caacttttg   1140 gaccctcaca tgaagttccg ccaattggaa tctcccaacc tgaggcaact gctttcctgg   1200
attgaccttg aatttaacca tcctcaaata tttattgtgg aaaatggctg gtttgtctca   1260
gggaccacca agagagatga tgccaaatat atgtattacc tcaaaaagtt catcatggaa   1320
accttaaaag ccatcaagct ggatggggtg gatgtcatcg ggtaccgc atggtccctc   1380 atggatggtt tcgagtggca cagaggttac agcatcaggc gtggactctt ctatgttgac   1440
tttctaagcc aggacaagat gttgttgcca aagtcttcag ccttgttcta ccaaaagctg   1500
atagagaaaa atggcttccc tcctttacct gaaaatcagc ccctagaagg acatttccc   1560 tgtgactttg cttggggagt tgttgacaac tacattcaag tagataccac tctgtctcag   1620
tttaccgacc tgaatgttta cctgtgggat gtccaccaca gtaaaaggct tattaaagtg   1680
gatggggttg tgaccaagaa gaggaaatcc tactgtgttg actttgctgc catccagccc   1740
cagatcgctt tactccagga aatgcacgtt acacattttc gcttctccct ggactgggcc   1800
ctgattctcc ctctgggtaa ccagtcccag gtgaaccaca ccatcctgca gtactatcgc   1860
tgcatggcca gcgagcttgt ccgtgtcaac atcaccccag tggtgccct gtggcagcct   1920 atggccccga accaaggact gccgcgcctc ctggccaggc agggcgcctg ggagaacccc   1980
tacactgccc tggcctttgc agagtatgcc cgactgtgct ttcaagagct cggccatcac   2040
gtcaagcttt ggataacgat gaatgagccg tatacaagga atatgacata cagtgctggc   2100
cacaaccttc tgaaggccca tgccctggct tggcatgtgt acaatgaaaa gtttaggcat   2160
gctcagaatg ggaaaatatc catagccttg caggctgatt ggatagaacc tgcctgccct   2220
ttctcccaaa aggacaaaga ggtggccgag agagttttgg aatttgacat tggctggctg   2280
gctgagccca ttttcggctc tggagattat ccatgggtga tgagggactg gctgaaccaa   2340
agaaacaatt ttcttcttcc ttatttcact gaagatgaaa aaaagctaat ccagggtacc   2400
tttgactttt tggctttaag ccattatacc accatccttg tagactcaga aaagaagat   2460 ccaataaaat acaatgatta cctagaagtg caagaaatga ccgacatcac gtggctcaac   2520
tcccccagtc aggtggcggt agtgccctgg gggttgcgca agtgctgaa ctggctgaag   2580 ttcaagtacg agacctccc catgtacata atatccaacg gaatcgatga cgggctgcat   2640
gctgaggacg accagctgag ggtgtattat atgcagaatt acataaacga agctctcaaa   2700
gcccacatac tggatggtat caatctttgc ggatactttg cttattcgtt taacgaccgc   2760
acagctccga ggtttggcct ctatcgttat gctgcagata gtttgagcc caaggcatcc   2820 atgaaacatt acaggaaaat tattgacagc aatggttcc cgggcccaga aactctggaa   2880
agattttgtc cagaagaatt caccgtgtgt actgagtgca gttttttca cacccgaaag   2940 tctttactgg ctttcatagc ttttctattt tttgcttcta ttatttctct ctcccttata   3000
```
ttttactact cgaagaaagg cagaagaagt tacaaatag                 3039

<210> SEQ ID NO 16
<211> LENGTH: 5003
<212> TYPE: RNA
<213> ORGANISM: Homo sapiens

<400> SEQUENCE: 16

| | | | | | |
|---|---|---|---|---|---|
| cgcgcagcau | gcccgccagc | gccccgccgc | gccgcccgcg | gccgccgccg | ccgucgcugu | 60 |
| cgcugcugcu | ggugcugcug | ggccugggcg | gccgccgccu | gcgugcggag | ccgggcgacg | 120 |
| gcgcgcagac | cugggcccgu | uucucgcggc | cuccugcccc | cgaggccgcg | ggccucuucc | 180 |
| agggcacccuu | ccccgacggc | uuccucuggg | ccguggcag | cgccgccuac | agaccgagg | 240 |
| gcggcuggca | gcagcacggc | aagggugcgu | ccaucuggga | uacguucacc | caccacccc | 300 |
| uggcaccccc | gggagacucc | cggaacgcca | gucugccguu | gggcgccccg | ucgccgcugc | 360 |
| agcccgccac | cggggacgua | gccagcgaca | gcuacaacaa | cgucuuccgc | gacacggagg | 420 |
| cgcugcgcga | gcucggggguc | acucacuacc | gcuucuccau | cucgugggcg | cgagugcucc | 480 |
| ccaauggcag | cgcgggcguc | cccaaccgcg | aggggcugcg | cuacuaccgg | cgccugcugg | 540 |
| agcggcugcg | ggagcugggc | gugcagcccg | uggucacccu | guaccacugg | gaccugcccc | 600 |
| agcgccugca | ggacgccuac | ggcggcuggg | ccaaccgcgc | ccuggccgac | cacuucaggg | 660 |
| auuacgcgga | gcucugcuuc | cgccacuucg | gcggucaggu | caaguacugg | aucaccaucg | 720 |
| acaaccccua | cguggugggcc | uggcacggcu | acgccaccgg | gcgccuggcc | ccggcaucc | 780 |
| ggggcagccc | cgcggcucggg | uaccgguggg | cgcacaaccu | ccuccuggcu | caugccaaag | 840 |
| ucuggcaucu | cuacaauacu | ucuuuccguc | ccacucaggg | aggucaggug | uccauugccc | 900 |
| uaagcucuca | cuggaucaau | ccucgaagaa | ugaccgacca | cagcaucaaa | gaaugucaaa | 960 |
| aaucucugga | cuuuguacua | gguugguug | ccaaacccgu | auuuauugau | ggugacuauc | 1020 |
| ccgagagcau | gaagaauaac | cuuucaucua | uucugccuga | uuuacugaa | ucugagaaaa | 1080 |
| aguucaucaa | aggaacugcu | gacuuuuug | cucuugcuu | uggacccacc | uugaguuuuc | 1140 |
| aacuuuugga | cccucacaug | aaguccgcc | aauuggaauc | ucccaaccug | aggcaacugc | 1200 |
| uuuccuggau | ugaccuugaa | uuuaaccauc | ucaaauauu | uauuguggaa | aauggcuggu | 1260 |
| uugucucagg | gaccaccaag | agagaugaug | ccaaauauau | guauuaccuc | aaaaaguuca | 1320 |
| ucauggaaac | cuuaaaagcc | aucaagcugg | auggggugga | ugucaucggg | uauaccgcau | 1380 |
| ggucccucau | ggaugguuuc | gaguggcaca | gagguuacag | caucaggcgu | ggacucuucu | 1440 |
| auguugacuu | ucuaagccag | gacaagaugu | uguugccaaa | gucuucagcc | uuguucuacc | 1500 |
| aaaagcugau | agagaaaaau | ggcuucccuc | cuuuaccuga | aaaucagccc | cuagaaggga | 1560 |
| cauuucccug | ugacuuugcu | uggggagaug | uugacaacua | cauucaagua | gauaccacuc | 1620 |
| ugucucaguu | uaccgaccug | aauguuuacc | ucugggaugu | ccaccacagu | aaaaggcuua | 1680 |
| uuaaagugga | uggggcuugug | accaagaaga | ggaaauccua | cugguuugac | uuugcugcca | 1740 |
| uccagcccca | gaucgcuuua | cuccaggaaa | ugcacguuac | acauuucgc | uucucccugg | 1800 |
| acugggcccu | gauucucccu | cuggguaacc | agucccaggu | gaaccacacc | auccugcagu | 1860 |
| acuaucgcug | cauggccagc | gagcuugucc | gugucaacau | caccccagug | guggccugu | 1920 |
| ggcagccuau | ggccccgaac | caaggacugc | cgcgccuccu | ggcaggcag | ggcgccuggg | 1980 |
| agaaccccua | cacugcccug | gccuuugcag | aguaugcccg | acugcucuuu | caagagcucg | 2040 |
| gccaucacgu | caagcuuugg | auaacgauga | augagccgua | uacaaggaau | augacauaca | 2100 |

-continued

```
gugcuggcca caaccuucug aaggcccaug cccuggcuug gcauguguac aaugaaaagu    2160
uuaggcaugc ucagaaugggg aaaauauccca uagccuugca ggcugauugg auagaaccug   2220
ccugcccuuu ucccccaaaag gacaaagagg uggccgagag aguuuuggaa uuugacauug    2280
gcuggcuggc ugagcccauu uucggcucug gagauuaucc auggguugaug agggacuggc   2340 ugaaccaaag aaacaauuuu cuucuucccuu auuucacuga gaugaaaaa aagcuaaucc    2400 agggguaccuu ugacuuuuug gcuuuaagcc auuauaccac cauccuugua gacucagaaa   2460
aagaagaucc aauaaaauac aaugauuacc uagaagugca agaaaugacc gacaucacgu    2520
ggcucaacuc ccccagucag guggcgguag ugcccugggg guugcgcaaa gugcugaacu    2580
ggcugaaguu caaguacgga gacuccccca uguacauaau auccaacgga aucgaugacg    2640
ggcugcaugc ugaggacgac cagcugaggg uguauuauau gcagaauuac auaaacgaag    2700
cucucaaagc ccacauacug gaugguauca aucuuugcgg auacuuugcu uauucguuua    2760
acgaccgcac agcuccgagg uuuggccucu aucguuaugc ugcagaucag uuugagccca    2820
aggcauccau gaaacauuac aggaaaauua uugacagcaa ugguuucccg ggcccagaaa    2880
cucuggaaag auuuugucca gaagaauuca ccgugugugac ugagugcagu uuuuucaca    2940 cccgaaaguc uuuacuggcu uucauagcuu uucuauuuuu ugcuucuauu auuucucucu    3000
cccuuauauu uuacuacucg aagaaaggca gaagaaguua caaauaguuc ugaacauuuu    3060
ucuauucauu cauuuugaaa uaauuaugca gacacaucag cuguuaacca uuugcaccuc    3120
uaaguguugu gaaacuguaa auuucauaca uuugacuucu agaaaacauu uuguggcuu    3180 augacagagg uuuugaaaug ggcauaggug aucguaaaau auugaauaau gcgaauagug    3240
ccugaauuug uucucuuuuu gggugauuaa aaaacugaca ggcacuauaa uuucuguaac    3300
acacuaacaa aagcaugaaa aauaggaacc acaccaaugc aacauuugug cagaaauuug    3360
aaugacaaga uuaggaauau uuucuucugc acccacuucu aaauuuaaug uuuuucgga    3420 aguaguaauu gcaagaguuc gaauagaaag uuauguacca aguaaccauu ucucagcugc    3480
cauaauaaug ccuagugggcu uccccucugu caaaucuagu uuccauggga aaagaagaug    3540
gcagauacag gagagacgac agagggguccu aggcuggaau guuccuuucg aaagcaaugc    3600
uucuaucaaa uacuaguauu aauuuuauga ucugguuaau gacauacuug gagagcaaau    3660
uauggaaaug uguauuuuau augauuuuug aggccugguc uaaacccugu gcccugagg    3720 gaucugucuc acuggcaucu uguugagggc cuugcacaua ggaaacuuuu gauaaguauc    3780
ugcggaaaaa caaacaugaa uccgugauua uggggcucuu caggaagcau aaagcaauug    3840
ugaaauacag uauaccgcag uggcucuagg uggaggaaag gaggaaaaag ugcuuauuau    3900
gugcaacauu augauuaauc ugauuauaca ccauuuuuga gcagaucuug gaaugaauga    3960
caugaccuuu cccuagagaa uaaggaugaa auaaucacuc auucuaugaa cagugacacu    4020
acuuucuauu cuuuagcugu acuguaauuu cuuuuagauug uaguuuuac aaauucuuaa    4080 uagguucaaa agcaaucugg ucugaauaac acuggauuug uuucugugau cucugagguc    4140 uauuuuuaugu uuuugcugcu acuucugugg aaguagcuuu gaacuaguuu acuuugaac    4200 uuucacgcug aaacaugcua gugauaucua gaaagggcua uuaggucuc auccuuuaau    4260 gccccuuaaa uaagucuugc ugauuuucag acagggaagu cucucuauua cacuggagcu    4320
guuuuauaga uaagucaauau uuguaucagg caagauaaac caaugucauau acaggcauug   4380 ccaaccucac ugacacaggg ucauagugua uaauaauaua cuguacuaua uaauauauca    4440
```

| | |
|---|---:|
| ucuuuagagg uaugauuuuu ucaugaaaga uaagcuuuug guaauauuca uuuuaaagug | 4500 |
| gacuuauuaa aauuggaugc uagagaauca aguuuauuuu auguauauau uuuucugauu | 4560 |
| auaagaguaa uauauguuca uuguaaaaau uuuuaaaaca cagaaacuau augcaaagaa | 4620 |
| aaaauaaaaa uuaucuauaa ucucagaacc cagaaauagc cacuauuaac auuccuacg | 4680 |
| uauuuuauuu uacauagauc auauuguaua uaguuaguau cuuuauuaau uuuuauuaug | 4740 |
| aaacuuuccu uugucauuau uagcuuucaa aagcaugauu uuuaauaguu guugaguauu | 4800 |
| ccaccacagg aauguaucac aacuuaaccg uucccguuug uuagacuagu uucuuauuaa | 4860 |
| uguugaugaa uguuguuuaa aaauaauuuu guugcuacau uuacuuuaau uuccuugacu | 4920 |
| guaaagagaa guauuuugc uccuugauaa aguauuauau uaauaauaaa ucugccugca | 4980 |
| acuuuugcc uucuuucaua auc | 5003 |

<210> SEQ ID NO 17
<211> LENGTH: 47745
<212> TYPE: DNA
<213> ORGANISM: Homo sapiens

<400> SEQUENCE: 17

| | |
|---|---:|
| atgcccgcca gcgccccgcc gcgccgcccg cggccgccgc cgccgtcgct gtcgctgctg | 60 |
| ctggtgctgc tgggcctggg cggccgccgc ctgcgtgcgg agccgggcga cggcgcgcag | 120 |
| acctgggccc gtttctcgcg gcctcctgcc cccgaggccg cgggcctctt ccagggcacc | 180 |
| ttccccgacg gcttcctctg ggccgtgggc agcgccgcct accagaccga gggcggctgg | 240 |
| cagcagcacg gcaagggtgc gtccatctgg gatacgttca cccaccaccc cctggcaccc | 300 |
| ccgggagact cccggaacgc cagtctgccg ttgggcgccc cgtcgccgct gcagcccgcc | 360 |
| accggggacg tagccagcga cagctacaac aacgtcttcc gcgacacgga ggcgctgcgc | 420 |
| gagctcgggg tcactcacta ccgcttctcc atctcgtggg cgcgagtgct ccccaatggc | 480 |
| agcgcgggc tccccaaccg cgaggggctg cgctactacc ggcgcctgct ggagcggctg | 540 |
| cgggagctgg gcgtgcagcc cgtggtcacc ctgtaccact gggacctgcc ccagcgcctg | 600 |
| caggacgcct acggcggctg gccaaccgc gccctggccg accacttcag ggattacgcg | 660 |
| gagctctgct ccgccactt cggcggtcag gtcaagtact ggatcaccat cgacaacccc | 720 |
| tacgtggtgg cctggcacgg ctacgccacc gggcgcctgg ccccggcat ccggggcagc | 780 |
| ccgcggctcg ggtacctggt ggcgcacaac ctcctcctgg tgagtgcgag gggccaggcg | 840 |
| gagggccacg caggggagac agagggcctc cacaggggcc aggggaagt gtgggaactg | 900 |
| agtctccccc agacgaggct tcacttggac acgtgtatgt ggtcaccggg ggaaactgag | 960 |
| cagttctgac ttcccttgga aggcgtgaa ttaggagaga aatcccttag tgggcacacg | 1020 |
| agtgagtgcc ccttggagtc catctgtgga aaggaagcgg tgataggttt ccgcagtgag | 1080 |
| gaaagaaact cctttctctg ggtgtagagg aattcctaga ggtgagggcg gggaggattt | 1140 |
| gctaggagta actgcaggaa gagaatgagc agggtggatg aaagaaacac gtttgttctt | 1200 |
| aagccgcaca gatagcatta ctctctggag ctgtcacgag ttcagtgtta atccaataag | 1260 |
| atctgtcttg cttgtggcac aagttcacac tgttgtgaaa gtgtcaaaac acaactcccg | 1320 |
| gagagtcaga tttaaactgt gtttggaggt cccttctgcg gcagggcagg gaactgcatc | 1380 |
| caccaatctt attcaccggg gtgtgaagac cgctttatac aatctcaaac aaagctagtc | 1440 |
| atagaaacac agaaacaact gcagggtgat atagattgtt ctaccacatc tatatttcca | 1500 |
| cagtgctctc tacagttgaa agggttcctc acttatgaca ttgttagcct gataaaatta | 1560 |

```
attgtaacac ccttgtgcaa aatattttat taattttgac agcaggaaat attgctatgc    1620
catggtaaag ttgtctcaag tatttcttcc tcctttttc tccttagtgt tcaaatttag     1680
gcaccattgt tttggggatt catttataat catgtcagtt gttagtacac tttgtacaga    1740
gttttgtatc acaataaaat attttatgta catgtataaa catttaata  aaagtgttta    1800 aatgtacaac ttttggtacc caattctgat cacttgtggg cctactggaa gacttatttt    1860
taaatttaga attcagccac atattctgaa caaagtcagt actaaaacca tttctaaaca    1920
cttttaatta aagccataga taatatgggc agagcagtac tgggttattg aggtgactta    1980
gtgctctgag ctgctggtaa tgttgtaata atggctaaat tagattttat gtcagttcca    2040
caaaacctgt tgctgctac  tggccataaa agaatgttgg atttgtttgg aaacacattg    2100
tgatttttgt gatttcatac ttatgtatgt cttttcataa ggatgtttta gagcggtgat    2160
tcttatactt tttcaatcct tttatggatc tgaaaaactc taaagaccac cagtgtatgg    2220
ctggtgatag aaaaactatg gaagaatgg  tctcactttt tgaagaaaac ataagcaagt    2280
tatcagttca tactggaagc aaataaatgg atcagctgga ggatctaata gatcatgccc    2340
ataaaatctt tactttagat ttaaatccta caagttctat ttttagagtc cctaggataa    2400
acttgcatat acaaagtagt caattgttat tatagtgact tataggatca ttttattata    2460
agataaagac ttgcgtgctc tctggtgctc tggtgtttta aataatcaac atgttttaga    2520 tcttttgcc  cactcatggc cctctgatta acttctcagt tatattttc  aatgcttaca    2580 caaaaatttt gccaaacact aaccatcctt cctagaaatg cagtggactt tgtatttagg    2640
gaaattagta acaggtgaat gctccatttg ctgatgttgc aaacaaactg ttagttggtg    2700
taaagtatta attttgcttt cacatttctt ttggtttggt gtttagtcat tcttgtatct    2760
tatttagaag cgagttccca ttgtcaaaga aagtatcttg aattaatttt gttgtatgag    2820
atactttcat tctgttttca atgacccttc tcggtgtgta tatagggt  gggggaagcg    2880 agaatagaaa aatttgagct tacctgaaaa agataaaaca ttctgcagat tttgataaaa    2940
gggcatttta gctggggctt agatattgct gctgtacaga tatagggcc  agttgtgttc    3000 cgggatctga tgttggtgaa ggataaagac tggctagcac ccttccctca ctccctctgt    3060
gtttccacta acttacaaat gggctaagga gatcccctgg gatgatggga agcttgaccc    3120
ctcctagaga gtcaagaatc attgatggcc tggaggacag gaggcagaac aaacaaacag    3180
caggacaaat aatggaggcc ctgctcagaa tggaggtctt ggtgttcttt gtgggttcct    3240
catactggag tgagccttgg caaaaatggt gtgtgtgtgt gtgtgtgtgt gtgagagaga    3300
gagagagaga gagagaggag acagaagaga aggagaagag gggagagggg aggagggaca    3360
gagagagaga ggtctcctac aaagagcttg gagctcaggc tgctttgctc atttgagtgt    3420
aatccaggag gatgcaccct ttctctcgga cttgaagacc aactgctcag ccttcacagc    3480
tcttgaaaca aagttcttaa tgtcccctga aatcagcact agggactgta gttggggagt    3540
tcagccccag cagtgcctct gagtctttgt tctgtatatg ggttctaaga ggattagaat    3600
caagttggaa atacacgtgt tcccatttcc caccttcaac tccctcacc  gcctgagatt    3660 cttgcaaaca tttgtgcaag gaacctgtga aaaagacttc tttcacgtaa ggaagtaggg    3720
ctaggagata ttaatctggg cattgttgag cattagcatc agtgtgcagg tctcagccca    3780
tctgtctgca atgtttgttg aagccatcac ttccttgtcc cttgaatcct cctcaacttg    3840
gatttcaggc cctggctctc ccttgcttct cctctcagct ccctggcgat tccctcttag    3900
```

```
tctcctttgc ttgttcctcc tcaccttgcc tgtaaatagt ggagggctca gggctctgtc    3960
tagattcact ccaggccatt gctttgaata ctgctgcatc ccgatgactg gagattttga    4020
gtctccaccc aggtttcccc gagcatcaga ctggcataga caaccgcctt ctccacgtgg    4080
atgtctaatg ggcatgtcac atcgaacaca tcccaaacca aaccctgct tccccttctc    4140
tattatgatg acttttact cttccagttg ttggaccccg aatcttaact actcccttt     4200
ttcatgtctt gtttctaatc catcaacaaa tcctgcagct ctacctacct ccaggatgtg    4260
tccagaatca aaccacttct ccccttatct atgactacga tggaggtgca agacaccatc    4320
caaccttgcc tgggtaatgg gaacagcctc actgctgggg ttcttatttc tgccttgccc    4380
cctgcagtgt gccatgatgg atgctctaca gggtgacatt atgtgtggac aagacagagt    4440
ccttgctttt tcaaatccca cctgttcttc tggagccagc taacacgctc ccttgggccc    4500
catgcctgaa tgccatctct tccttctatg gcatcctgca caggacttcg ctttgctcag    4560
atgcctcctc ccgcgctctt cccttttattt aaccatttgt ctccattta ccccttcgct    4620
atctgggta atcctgttcc cttcatctgt atctctgaaa atggcatctt gccctcccctt    4680
ggtgctcaga aggtggcttc tggtttaccg aatagcctga tttcacctt ataaactcat     4740
gctactagaa ttttctctcc ttgtcagtct ttctagccac tttccaatgg aacagagact    4800
accaaatcct aatctgataa ggaaaaatag gtaaacataa cgtggcagac tctgacatct    4860
gcagtgaaaa tttaaggttc atcatcaaat gtatgattcc attgtgaaaa tgtccagtta    4920
aaagctatct gtagtcacca tgcagcatta tgaagaagtt ttcagaataa gggcaggtgg    4980
taaagtctcc tggccagctt taggagtata tattggaagg ggctttgtta gctgattgaa    5040
tttttattcc ccaagtaatt agtatgagcg atttgtctac tgtatatatg ctcaaattac    5100
atatactatg cacttttgag aaatacttta caagttttc tttcattaaa atgtatttgg    5160
ggccgggcgc agtggctcac acctgtaatc ccagcacttt gggaggctga ggcgggtgga    5220
tcacctgaga tcaggagttt gagaacagcc tggccaacat ggtgaaaccc cgtctctact    5280
aaaaatatgg aaaattcacc agacgtggtg gcaggtgcct gtaatcccag ctacttggga    5340
ggctgaggca ggagaatcgt ttgaacatgg gaggcagagg ttgtagtgag ctgagatcgc    5400
accattgcac tccatcctga gcaacaagag cgaaactcca tctcaaaaaa atgtatttg    5460
tacataacta gaataatcaa ctggattgaa agttaatata aatttttagaa tactactgaa    5520
ttcaatagtg catttagtca gaaatagtta aaatatctcc caaacagctt gaatcactcc    5580
tttttgaaca cattgttttt tgaaggttac agtcaagtcc aagaaaaaat tttaaaatag    5640
gaaagaatt aatcaaatca tttcaaaatc atagcagtgt tttaacaatg ccaattattt    5700
tgagttgaag aaaagaagga aaatgtaaac tatgcattca agtaatgtca atgcaccttc    5760
tcaggtgcaa aatgaatgaa caattaactg tgccagctga atatgtagca atcacggctt    5820
ttgcacatag aagccttctg aattatctta tattctcaaa aatatcattg ctctaaacta    5880
gaattttatt ataattaatt tgtgcaaaag ttgtctttct ttcaatgaat gttgtctttt    5940
tgaggcataa aggaaattt aggtggagga ggagaataga atacatgctt actgggagga    6000
caagtaataa taggtgagta aaaacacaca gcttattgaa ttgtctcaga tccacatttt    6060
ctccagaaat gcaaagttat acttgaaatc tatatttaaa cagataagca gaatgtgact    6120
tttatatgct ctattttgat gtattctgag tatgaagata acctgaagga tgcctttttc    6180
cctcttttat cttggggtaa actcttactt acccttcaga gacttgactc aaatatttc     6240
attctgcaat aaccacaggt agaatggatc atttactcag ttgtggctct cttaagagca    6300
```

```
cagactacct atcatattta tttcaaaatt tgtagtgctt atctcagtgc ttggcacaga   6360
ggaaagaaat acaatttta ataaaggcat aagtggagag gtaaaataca tatttctggt   6420
ttcaacgtgt ccatattctt tcttgtaaat ggaatattgc gcttgcagtc tgctctcaca   6480
caatatctgg gaaggagttt taaagagtga ggaagaacag taaagatttt cctaggcaga   6540
tacgttatgt gacctttgtt gatttccaga gcacataata tcccaatttc atccagtgga   6600
caggaaaaga gaggaagagg gaaaaggtgg cctctcaagt gcctgacctg gaagctgcac   6660
ctatcactgt cccttgggca gaactcagtc acatggtcaa aaggagtctg caaataattg   6720 tccctgagg agccgggtgc tcagtgaatg attctattaa gttgaaatca gatgggaaca   6780
gatcatttag gataaccagc aggctctacc acattgccta actcccaggc atattgtgag   6840
aattaaaagc accttatata tgtcaacgtg ttttgaaaaa atacaaaaag ctctacaaaa   6900
gtgagctata aatttatcat taataataat agtaataata gcaaaatact gagaaatgg   6960 tcctcttgag ctgtttagaa ggaatcatac aaatgcatta gacatggtag cctcacttaa   7020
ctacttaatt tgcctcttct ttgaaattat ttcaatagca tttgaccaaa aactatcaaa   7080
tcatttttga aataacgtat ttttacataa aacacattat caaatatctt tctggatcca   7140
gcttggtggt aaaaagatac atactaaagt ttatgactga tataacttta tatattgact   7200
aaaccaaaga taaatattga ttgaacttt gtggccccag tttcaataga tttttttatt   7260
aacatttttt gtttgaagta cagatgtcac gtcatccatg aaccggtatc attatagctt   7320
gataaaatac tcaaactgaa agcagtgatg tacattaatt ttaaatataa tggttaagca   7380
aatgttattt ccatatctat aagtgcattt tatttgataa ttagaatgtt agaatcagaa   7440
ggaatttgga aaatcccagg ttacacttct ctccaggacg aactccttac agtggctctc   7500
ctggggtcag ctagcttttg cttgacccct tgaagcagga ggaactcagt tccactcaag   7560 ttgcccccttt gattttctct ttcatattga acctgctgct gcacaggact cctccgtgac   7620
tgtctctttg ccttcctaaa tctcaaagaa taaagcaagt cacttttga caagacatct   7680 ttcacatatt tgaaaagaca tctttcacat atttgaaaag accagtacgt tttgttcttc   7740
ctagaatttt ctccttcatg ctaatgtctg ctccaagaag acatggaggt gactggacat   7800
ttagtcagga acatttcttg agagcttacc ctgtggcagg caggtgcaat gttgaattct   7860 gagaaatga atgtaacctt tgaacaggtg gctctgtctt ctgacgttc aggataaggt   7920 ggaggagagg agagggaaa gtcgacctat ctccccagcg gggagggttt agggttgtct   7980
gtgggacctg cctctgtctc atcatccatc accattgtcc tgctgatggg tgcagaggac   8040
tgaggacgag tggttggagt tctccctgtg ccggaccctg tagagagtcc agagccctgg   8100
ctcccaaagg aggcatattt gtaggctctc tttcgtgagg gtccagagga cggctgcaaa   8160
gctgcagggg aggatggggg catgggaggc aagcccgttg ccctgtcaga gcctcttggg   8220
gatgctgctc ttccccgcct gtcctctctt ctctttgatt tctcatcatg tggtcctctt   8280
tcctctgcct tttcctctct tcggtgtccc aagttcttcc atagagacct gtgtcccctt   8340
gttcccatca ggcctttatg ccagccctgc acaggtgcgg ggacagtggt aggggcgtct   8400
cactcccgac tcaactacat tctcccagaa attgtctgca gtcaaacaca actcagcgtg   8460
gacattgctc accaaaggta tactgcttgg gctgcacgag agattcagtt ttctcctatc   8520
tatctggcat gggctgtgag ggggctccta acctaggggg cctttttact ccttcctggc   8580
cagagctgcc atttccaagt ttctgcactg tcagaaaaga gggataaggt aagattcctg   8640
```

-continued

```
ccctcatgtc acagattagt aggggagagg taattgtcaa ataattacag taaaatgtat    8700
aaatgcctta agagaaataa gtacttgctt aggaacctat ttcaagaaag gagagatagg    8760
ttagcgtttt ggggaggtag tacgggagca gtcagggaaa gcaatacttg taagatcaga    8820
ggctggcaat cttttctgt agagggctaa gttttggact ttgcagatcc tacagtgtct     8880
gttgcaacta ttacacagtt ctgtggttgc agcatgaatg cagccatggg caatgtgtta    8940
atgaatgggc acagctgtgt tcaataaaa ctttatttac aaaaataggt agtgggccct     9000
gctgctgggc ttggcttgct gggcacacaa agtgagaagg gcattgtgcc tttctaggaa    9060
acatcccttg caaagtcagt acaggtgaga cagtgtggcc attcccacca cagcatgagg    9120
tcttttgaat ggctgaagcg tcaggtggga aggatgagg agctgaagaa gaaagcctgg     9180
gaatttccaa ggcctctctt aacatttgct gtgcagaacc aagcagtgcc ccaggtgttc    9240
agagtaggct tcagcgatta catttcttgt tagacactga attttgttca tgccgcccaa    9300
gattgcatta acaattttgg ctgtcacctt accgcggact caaattagtt tgcagtcagc    9360
taaaacctct caggtttttt cccccagct tgtgaattgc tgtgaagcca aacatccctg     9420
tcatctcttt ggtagtttat tttcaaactt tcaatcttat taaatttcat ctccaatgtg    9480
caaagataag aggaagttta ccgctgatgg tggtttattc tttaaaactg gacatcagct    9540
aaatgtgtta aggtaatccg ttagaggaat gttggtacgc ttatacagtg gaatactaat    9600
tggttattaa aatgttgatg tatgattatt aaaaggcagc ccatgttatg tctcttctgt    9660
atgaataagt atgtaaaaag tatgtaaaga ttactgtata gttcatgggt gggactgggc    9720
tctctctagc ctctgtcctt cattctccct gccagtgcct tttcccttgc agtgtccctt    9780
ccctggctgc atactcaaga ctggatttgc ccagccaaac cccattaact cacagaagca    9840
agaggaaaaa aataaattct tattagttca attctccaaa ttggggggcgg tctatttcac    9900 agcaataggt aactgacgta aaaggaaagg aaacaatgaa gtaattccag aaaatttcct    9960
atagctggag gacatgcatt ttcatattga atggaagaa tggggtgggg gggtcatacc    10020
tctgtgttat tgcagggtcc tggctcctag ggacctaggc acctcttcag tcagtgaatt    10080
atagcttgga aaattggcta agtcggggaa ctgtacaagg ggtcatcact ttttatgtag    10140
ccatgctcta tgaaccatct ttataactcc ctggcttctg gcagttaagc accactcact    10200
atctggcctc tgtaatttca acttctgacc atccccgtgg gtggcaacaa gcccagctct    10260
gtgacacctc tgctaccagc agccctggcc tggagagcgg tgcccccact gaatgtctca    10320
gtgagattgg caccccccatg agcatattcc tgagggtgca gtgaatgctc tttctcccta    10380
cttgggactt ctgggaaaca ctgtcctctg gtgggttgtt tgacctcaca taatatactg    10440
gttcttgcat gccagcttct ctctgcttct tgattctttt atcagctgtt agggcaacaa    10500
tgtcaggcat ttccgcctgc tcagcattgg gcatcccttt ttacaggctt ctcagagcca    10560
ccctagcagc aactttaccg cgtctcctgg ggtccttgct ggatcgtgaa acatacttc     10620 cggagaaagt gttccctaga taatgaatta tttcttgtcc tgtgttaagt tccagttcct    10680
tggtcaagga ccccagcgct actcctcagg atttgcagtg catgctcaat cttgaagcaa    10740
tgttgggata tagtatcttt tcttctctat caggcccagc tgtctccagg tgggttatac    10800
taggatttaa tcctcgttag tgccgggtca gctcctgagg ggtgcacctg ttgctttttta   10860 gggacgaggc ctcttcagca taaagaagtg ctatctctta ctaggaagaa atgggccacc    10920
tctgtaagct ccaaatattc ccaggtttcc ccaaccgggg ccttgacctt ggcataactg    10980
atctgccttg gctgagcatt taaacatccc taaatctctg caagtctatc aggtcctagg    11040
```

```
cctgctgcta agtttctcta ctcttccact gtaggagaga aggctgtggc tcttatattg   11100
agcctttaac tgtttgttat tggccctcag tttctcatta gctctctgta gagtctcaat   11160
acaatatatc agaaagcatt caattccatc tccttgtagg cagggaatgc ctaaatcatt   11220
gcacctacaa tgacattctc caccaggata tttcccaggt tactgctgtt gaaatattta   11280
gcaattgaag caccatttgt gcaaggggac tatctgcccc tacacaacac tcagaatggc   11340
attctctttg cttccagaa agtgaatgag ctggttcccc aacccctctt gtgttagttt   11400
gagtcctgaa agaagtaaat gtcaagatag gattagatgt acaagaaatt tattggggaa   11460
agaattgtga aggataaagg ggaaggagct aggggaggca ttgaaccttt ggatcatgat   11520
gtgtgtccaa caactatgaa ggagagtggg cagggagaag gatgggctgg gaagagtttc   11580
agttggcact gtgggtctca gaacaaccca ggcataggct gatggggacg ccttgagcca   11640
atgttgccca ttggcggagt ccacatcttg ctgaaatggg cctgcattag ttcccctgcc   11700
atgtttagtc atctgggagt agccgatgag aatcatgatc ttaggatcaa ctgcaatggc   11760
agattcaaag gggtagcaac tgatggcctc agtcaactgt gctccttata gcaggaacac   11820
tgagcagtgc atttcttggc catcacaaag actagtgagg agtgcccttc agagaaggga   11880
atgaaaatta tttccagcct agaatttgat acttatctaa actgtcaatc attcatgaga   11940
gtcaaagtcc caaaaaataa atcttccata aacccttct caggaagtta ttggagggta   12000
accgccacat aacatgagga agacaaggag gaagacatgg gatctatgaa agggcaggtc   12060
taacccagga aaaggatgat gaactgtaga cccatgatgt cagatgtgca gcagactaag   12120
atcagccagt gcagaatggg ggagattcca gaagtgtgtc cccccaaaat attggaggct   12180
catgtgactt ccctggggaa gtttctgctg agaggctatt ggaaattgag ggaagaatta   12240
gccacagtcc caagaaaaac agagccaatc aaaaagcaat gcaattatga acttcaaaga   12300
aaacaaaaat aagaaggaaa acagtcttac ttactacatt acaaggtcca gctgtgaatg   12360
atattcatgt tggcagaata atgtcaatac caaatgtcgg ttaaacccaa aactattgta   12420
taactaaatt gcctgtgtaa gagagctaaa cccttatcta gcataatagg aagtcagtgg   12480
atacttcctg aagtgtggat gtgtggagat gtaaattcca aaagaaaacg tcttaagagt   12540
caaaagtggt tgcctctaga gagaactggg ggaattgtag ggcaatgtag gacagggaac   12600
tgtgattttt cttgtaagtt gttctgacat tttaaaccat gaacatatat tacttgtatt   12660 tttaattta aaaagacata aatatttttt ctatcacttt aaatattaat tttgctagtt   12720
atagcacata tttatagcat tacactctgt agagctcttt tggattcaag ttttggaaa   12780 ttttcaaagt tttagattaa tgcctttgtg agttttcatc cctttgatga taacaagtta   12840
caaagaaata gggttatgaa taaaccttgt gggatattgt tagtcacctt ctctcaagtc   12900
gatctgtccc atgaatcaat gtttcaaaca ttgaccagca tttgatactt aataagcaac   12960
gagtaagttt tgttgaacc aatgaatact cttaaaatat attttttcaa gtggcaacag   13020
tactatctta tttgcactct acttttcttt ttgaccctaa gaatgtcaca aaaatgttta   13080
gcaactgtca agattattac atacagagat gactattgtg ttctcagata tgctgtatgt   13140
cttagttcat tttgtacagc tataagagta gctgagacta ggttatttat ttatttattt   13200
atttattttt tgagacggag tcttgctgtg ttgcccaggc tggagtgcag tggcacaatc   13260
tcggctcact ccaagctccg cctcccaggt tcacgccatt ctcctgcctc agcctcccga   13320
gtagctggga ctacaggcac ctgccgccat gcctggctaa tttttttgtat ttttagtaga   13380
```

```
gacgggttt caccgtgtta gtcgggatgg tctcgatctc ctgaccttgt gatccactca    13440
cctcggcctc ccaaagtgct gggattacag gcgtgagcca ccgcgcctgg ccctattttt    13500 tttttttta aggaattta ttttcctcaca gttctgttgg ctgggaagtc caagggcaag    13560
tctctggcat ctggtgagag acttcttgct gctttctccc atggtggaag gtgagagggc    13620
aagagagaga caaaaggagg ctgaactcat ccttttacaa ggaacccatg cctgagatat    13680
tgaacccact tctatgataa cagcattaat tcattgatga ggacagagac ctcattgcct    13740
aattggccta aagtgagacc tcttaaaggt ctcgcttaat actattacaa tggcaattaa    13800
atttcaacat gagttttgga ggggcaagca ttcaaatcat agcaccatat aatacaataa    13860
aaattttctg agctaagttt ggtaaattta ttctaggaat ccatgttgtc tcctagttat    13920
cttcccttcc atagtactga tgcattttg ttaaccatta cctaattttg cttgagtcta    13980
ttatttctga aattcacatt atcttcccctt ttaaagttga gaaaattttc attcttcaag    14040
cgccttattt tctataatct ctcaaagtaa ctgatggctg ttgcatgatc ataagtgcaa    14100
attattttgc tagaccacac ttggagatga tgaatttgga atggcatgca gactcccgac    14160
atcaggagtc ttgtctcctg caataatcag gaacccaggc ttaaaaggga gcaggtacaa    14220
cagaagggca aggggtgaca atgctggtga agacatttg aggaaagcta tcaacatgaa    14280
acagaataaa ataaacagaa aagcaaacca gggaaaataa attatgcagg aattaaacac    14340
atacacaaac tgaaacagga accatcagaa catataaaaa attcttgaac atcagtaaca    14400
caatagttga acaaaatat ttagtaaaat atttgaaaag taaggtcaaa gcaatgctgt    14460
aaaagtagta caagatgata aagaaataga acacattttt gaaagggaaa aagatttaaa    14520
ggatattcat aaagatccaa catcagacta atagaagttc tggaaagaga gaataaggaa    14580
atacaggtca ggaaatttgt aaagaaataa tataataaaa tgccccagaa ctgaagaaca    14640
tgagctttta actttaaaga gccgactgag ttcctagctc aatgaatgta tagacatgta    14700
agggtattga aagttcacct tcagtgtcat gttttcctaag aagctaatgg aagatatgca    14760
ccagcaaaat tgtagtaaat acataggaag aaatagtata tagaaaaagt atggtttcaa    14820
tccataagaa ataaaggaaa ctcccaggac gagagcagct cttgacagca tctagtccaa    14880
actggacttg gaggctggaa acttctagca gggaaggaag agctctgggt gaaaaagtag    14940
actcaacaga atagatacga tcatagaaaa catgatagag aatcactaac acattgaaaa    15000
aatcacatat agaatattct gcacgcttaa taatgaggtc attatttatt caagggaaaa    15060
ttaaaagctg tttagaaaag ggaaatgtta tagtgcccta tttggctcta aaatgaacat    15120 ttatataagga atcttcatgt aaatactaac aatgatttaa ataagaacag acattcgga    15180 aaataaggga agaaaatggg gcatgtaaaa gagctaactc ctcattatcc taatgaatta    15240
ttaaatttca caatagcata gtatttagaa atatgatagt tattacgaga agaaagagct    15300
aaaaggttgc cagtggggag caggagtgag ggttagagac gggattgggg gagatgctta    15360
ctgttttcat gataagcctt tggtactatt tgattttaaa ctatataaat gcatttatta    15420
atttaaagta atttaaaaaa cccataccac tggataatgc ttgataattt ctagagtcct    15480 tttttttgt attttgggc aggtaaattc attgagagac ccagagagtt tagctgactt    15540
tcctgtgggt accaagggtc agagctgggg tcaaaactca ggttttctga accccctattc    15600 ccagtgtaca ttccatgact ccaggctgcc tcccgcattg cacaggttac atctagggt    15660 gtgctagcaa atgcctagac catcctcgtc cacatcagca tctgaaatgg acaagaatgt    15720
tagtcatgac ttgccactaa cgtctttaac cttaattgac atctgagagt gtcatcatta    15780
```

```
catcattaca aaaacactaa cccagataca tctgttccca ttactatttc tgcgtaattc    15840
ccccagactt aattgcttta aataaccatt ttatttggtt tacaaactta tgggtcagga    15900
ttaggggagg gctcacccac gcagttttc tctggtccgc agtcatctga agcttgaacg     15960
gggtggggca tgcaagacgg ctcacacatg tgatccgcgg ttgagcctgg ctgtggacca    16020
gagcatctct gttggcctcg cttacacaag tggtctcaga ttagtagcct ctgtacatgg    16080
aaactagctt ccctcccggc aagcatccca agagaactag gaggaagtgg tatggacttc    16140
tttcttctt cttcttcttc ttttcactta ttcttgatat catgtagctt catttctatc     16200
agagcagtca catgcccaca gattcaaggg ggagggtcca cagatccgcc aatgggagga    16260
acagccaggt tatatcgtaa aagatcatgg ggcatgggag atacccatct attttctgta    16320
aaaaatacat tttgccacag catcactggc tttccagctc acagtgatct gcctggaatg    16380
cctttttccg tctctccagg atctacatct ttcaatataa ggtttagaaa ctacctccta    16440
caggaagact tccttgattt ccctcagcaa gaaagaatct ttccttcctc tgaatcgcca    16500
ttgcattaaa aaaaaaatcc atcttctggc gttttcactt tcagacttat actgtaatta    16560
ttctatgtac ctatgtttga cccctcacga tgcccagcat aataatttgt ctattgagta    16620
aatatttgct taatgaaata atcattacat gataactcaa atagcagtcc tgaaaaagtg    16680
catttcaattt cagatctctc ttttttcttc cttcacaatt ctcatttccg aaaaatgaaa    16740
gaagccagag gatcctttat gaggagttac agtataactt atgcgtggct gtttcctgtg    16800
tttactgcta ctcagtgaga aatacgggag atgggagagt gaaaaaccat gtcatttaca    16860
atttgattaa aaagcttttt atcttttcct ttcacgttta agccttgccg ttttaaaaat    16920
ttccctttcg tcacagggga tcaagcagca gttaacgctg cagttccctg ttctggaaac    16980
actctcaaag gtgtttcaac acattttgtc tcaactctga ctcctgcccc gctgcccac     17040
gccatccagc cacactgaag gtcttgcatt tgtgccttgg ggcattattt tttttttactc   17100
ttctccctgc ctggaaggtt cttcccaacc tgccctaccg ccatagccac agaaccaacc    17160
cttcactttc cttaagtcta tggtcacaag ctccttctca aaggaggcac acctctaacc    17220
acccccattt ggtgacttcc tgtctcctgg aggccccgg aactagtctt ctctacttcc     17280
agcaacccac tttacgagca gcggagaaga ctgactactt ctgggggcct cgaggagaca    17340
ggaagtcacc aaatttacag gtgctgtgga tgaaactgtg tgataatgaa tttattgggc    17400
ttgttttttt agcttctgaa tagaagaacc aataagatca ttttttttaaa aaagataaaa    17460
acagacaaac acaaaccctc tagtataaaa gcattttttt ttaaaaaaga tgaacacaca    17520
ccctcagatt gccttctttt gaaaaggcaa tctgagattc cttatgaaat ccccagacag    17580
aagctgtttc tttgaatta atatgctgta cactgtagag ccaagaggct tatagagtgt     17640
taattaacac cccttgtcaa acatttgtaa atgaatctgg ctaaagctca aggaaaccag    17700
gttttctgt gtgataaaat ataatctttg gagattattt atgatcacaa agggagactg     17760
tacagaaaat tttcctagac ttggaaatga ggcaggatta ttggtgtcca tctggactga    17820
ggcctcaggc aggcctgcct agttaatccc attctcctat cctcattctc tgggggtgaa    17880
gaaggcagtg caccttttgtt caatttgctg cttaccatgg attagggcat tttaaattct   17940
gtaagggtag ttttaacttt gtagaaaact gatagcgatg ggaaggattc ttgcctaata    18000
gggacacaaa cggattttgt tctgtagaga tgtaaatgaa aagatgaaaa tcacaacaca    18060
tttaatgaaa ggaaaataaa gactcttgtg agtgccacca aaaaaaaaaa taaataaaat    18120
```

```
gtatctcctc tccgtggcac cccaggcctt ccttacctca ctctatttct tcatagcact    18180
tattgcctta gaacattctt tataatttac atttattatg tttgttgttg gttgtcgctc    18240
ctcctgctaa aatggaatct ccgtgagggc acgggttttt ctttgatttg ttccctgttg    18300
tgccccaaag tgctagaatc atgccaggca cacaatagat gctcaataaa tacttctgga    18360
atgaaaatcc ccctccactt agaccagtga gttccaaact tttttgatct tgacccatag    18420
taagaaaggc attttccatg ttgaatatac accattgaaa caaaattttc acagaaaaaa    18480
cttaccatta ttacaggcag tgcactgtga tatttcctaa tctcttctat tttgattttc    18540
aaaattgctg aggctactca taggttgatt tcacaagtgg agtttgtgtt atgaaaaact    18600
ttgacttaac accatgtcga aactgctacc acaaaaaggc aaatgcgaaa gaaggggaa     18660 agagcaggcc gatgactttc cgctatccac cactccataa agcatatttc attttcctgt    18720
aattgtatcc tgttcaatga tgtagaaatc ctcacacact cacatgccac ttttctttg    18780 ggtgaaaagc gttctctact gcaagatgaa ttgagttatt tcaaaagcaa agagctataa    18840
atgagcctgt taaagaaagt ctcaaggaga gtctgttggc atctgctgtt gataacttaa    18900
agcaggagaa ttagataagg aggcagaagt agaatgttta gaaataaaa gtgaccatta    18960 tagaggaaaa actgcttgtc tcagttttgt tgatattgga gagtagctct ttcatgaggg    19020
tattgtggaa ttattggcaa ttatactaat agatgtttac tgaaaaaatc ctatttgact    19080
gatgaaccat ggaatacttt tgctgacctt gtggaaaaca tcacttatct gagttcctta    19140
tcttcttgtc tcttttttct catctagcct atgcctccct acctgttccc tcatggttct    19200
cattttgttg ctattagaaa aacagagata caaaaaccag gaattggaac ccctctgtgt    19260
ctccagtaat aattctgtga ttaatgggtt agatggattc tggtcacaag ctggatattt    19320
tgttaacaac ctagcgtcaa tgacttggaa tgattttcac cgcagcatga tttagtattg    19380
aatagaatga tttaactaat gttaattagt tctgtacaga taaattaatg aagcaagaag    19440
ctcaatctct gatttattga tgtatttacc cagtgtaagt tatgaaatct tttttatttc    19500
atttgaagga agtttttatt taaatacaaa taaataagcc ctttattgtc acctactttg    19560
gaaaagtcca gataaaacaa tcttaagtaa caaaactcca aaattacaac atgatttca    19620 aaaactaccc tgacctttgt cttgcctggt tgttacagtg tacttttaac taaacggatt    19680
cttatagaat ctcaagtttg gttatatttg tattaaggaa ctctatattt gcatttgacc    19740
agccctaact aaaacaagct taaggaagaa aagggacttt acgacaagga caaaggattg    19800
aagaagaact ccagggactt tagatgttaa caactgtatt tgtcactaaa gtaaccatta    19860
ctgtcaaggt gggttctcct tctccctcac taaacacatg cacacacacc acacacacat    19920
acacatacca catacatacc acacatgc acacacacca cacacacc acaccacaca        19980 cacagaaata cacacagaca tacacacatg cacttatgct tgggtcagtt tggctttat    20040 catcccagag agtctcttcc catgtcagca actccagatt cacttcctct cctaatatag    20100
gacagtcaca tgtctctatt ccagcaaaac aatctcaggg aaggtatctc attggcctgg    20160
cttgggtcat tcaacttgaa gtacaagaag agaaaacagt attctttat ttttatagat     20220 ttcctgtaaa atcagtggat aatggtaaaa atttcatgac agcaggtgtt ttaccttatt    20280
tatgtttact atctctagaa cccagtatga tagttcataa taaatgctta ctaaaacaat    20340
tatcaaactg tacacttaaa aattaaaga gtaaatttta agttgtgtat gtttaccac       20400 agtaaaacaa aataaaataa acctattatt gatcttattg tctatttctc aaaagtagca    20460
tacgtcataa tttcatgtga tttctaaagg agatctaatc tcaaacttag ttcttagagt    20520
```

```
aaaataaaag gttttggcaa tcatatacag cagtagactt taccttgaag atttaacaaa   20580
ggtttgaaag caaaatgcta tgatactgaa tatactaatg tttgagggct tgtgaaaagg   20640
tcttaatata ggaatcatat atcttctttt agattgtgtc ttggggaaca ttgggggtca   20700
gtttttctat cagtgttagt atgtagtaag taatggcata catctaagct tgagattttg   20760
ctcatttctg tattcttagc acttatatat ccaacatata ataggtgttg gataatattt   20820
gttgaataaa tgactaaata aatgtcttgg catgagaatt atgccatcta caaaaccgtc   20880
acttttaaaa aaacaacaa agattttga acctgtagat ccagccagaa agcaagaaat    20940
atcttcacct ttccagactg acttattttt tggtctagct gtgtactatg catgagctgt   21000
caactttaat actttatttt ttaatgccta ggtctagtga gttacaatgt gatgtagact   21060
gattgaatta aaggcccaa tgttgtcctc tcttcattgt atccatgcct tttgtcatgt    21120
aactttgcag tgtcctctac tctaggtgtc cattcagctt atcctttgac tctggccttc   21180
ttctcctttg actctggctt tatccatgtg acttacttta gccaacaatc ataatgctgg   21240
caaacactga gaaaatgctt attagtgtct gcttagtctc ttgcttctct gcaattgcca   21300
tgagaaaatg cccaagctag tacactggag gatgagacat gtggggcaga agcaacctgt   21360
cccatttgtc ccagccaaca ccatcctaga ttaaccagat gagaccagag cagaagacat   21420
gttcagtgga gcccaaccca gctcacgaat aatatttctt catgagcatg tgagcaatgt   21480
gtaactaatg caccatgctc ttttattct gcacttccaa acatctctca gattgccctg   21540
ttgttttgct tttcagtagt catcaccttt gtccagaacc ttaattgtat ctgcattttg   21600
gcagtatcct gccaattttc cacatccagc tgttcacatt ctaatgcatt ctgcaatgga   21660
tgattttgag catatgactg atcatcactg tctcagaaat ttatgctaat ctattgtgac   21720
ctattctgtc aaatccaaat aactttacat tcaaaactt tcatattctg gccccatact    21780
gtctattgta atcttatttt ctaaaagcca caaactatta atcctgtagc ctaattaggt   21840
tgatatcatc attttcacaa cacgttgggt aaattcttat atctgttcct ttaatcatag   21900
tttccatgct tagacactcc attgccctcc ctaagcacca gccagagtcc actatggggg   21960 gatatttaa aggctctttt ccctaaccc atctgcccca gaggtggcac aggctagaaa     22020
agatagtcca attatttggc ttaattattt ggatcttaca gttttttgg gagagttcca    22080 gatgatttga tgaaatgcaa catggtcaaa acattttggg tggagaataa tttaatcaac   22140
tagaccattt ggtgaaaaat aaatcccagt tactagactt cccagtatta ataattttgg   22200
tatgccagga attttaaaa catttctaac aaatttttc agaaatcaga atgactgaaa    22260
ggtataacaa taggaaatta ggaaatcaat aagtaatcat tgaaaagtga gtgattgaat   22320
tagttggaac aatctatgcc atccatcctg tgggggaaaa aatgaaaaca gctaaacaag   22380
cagagcagac atcatcaact tagaaaaaca atatagtaaa taatttgaac tagaaaattt   22440
tccaaaattg aaaattccag ttttaaaaaa tttgtgtttt cttattcaaa aagcaataca   22500
tatttcgtta cataaaagtc agaaaatcag agaagcagaa gaacataata aatgcccact   22560
gtcctactca atagagacta taactgctat ctctgtacaa atcctttaaa atcctgtctt   22620
atgtgtattt attttacatc tgtacatatg attccaaaat taggtaatac tgtacgtggt   22680
ctatctatag ctaactatag tttgtaattt aataagctat atttgtccat ggtgatcatt   22740
tattgctcat aaaattaata aattataatt tatttatcaa cactgatcat tgttgctaa    22800 taatttattt catttaatgt cttattcctg ggttatttta actaatccct attgttagcc   22860
```

```
ctttaggttg tttcaactaa tttaagaatt ataaatggcc catagtagtt acttaataaa    22920
tatttgagtg aaaggataaa tgaatgaata attccacatt attggatgtt caagttgttt    22980
ccattcaact ttattgttgt gggggagtat aatacaatct tggtgaagag ccaccaactt    23040
aggaagaact atgaagaagc atgttattta ctcctgcttg tgggtggggt gcattgggaa    23100
aggaatgcct aaatgcacgt ggggagccaa acaagacttc acaggggaga tgggaattga    23160
gccaaatttg gaagaagtga gaattttcag ttgataattg gggaagatag tactaagagt    23220
aagtggggtt cattaggaac tacttcttag aagaggcaag tccagaacag aaggcagaaa    23280
gggatatgga tatgaaggaa aagtagaatg caacttcagg gctagtaggt tggcatccaa    23340
cgtaggtaca gccctggatg aggagtaatg agaaactgac ctggctgtag caaaacagct    23400
aggctgggaa gtgatgctgt ttacatttat atgcgattct actggtcttc ctgttacttt    23460
gtagaagact gtaaggcttg gtgctcagag ctagaaatgc aacttatttg atttgctaag    23520
aagtccaaag caggtagggg tgccaagctg ctgcctgttc acacatattc gtctaactgg    23580
gtgtcaggga aagcagatat gagcccctt gcattggtta aatcctgagc aacttttaag    23640
gaactgcaca cagagactac tggctatttt ttgtggataa agttgtagat agttattttt    23700
gggaaattat ttatgtgttc tattaggtgg ttgttttgtg ggaggctgtt tgaaattctg    23760
tcttaaggaa ctgcagctta taaaccatag tgctgataga aataagagaa ataatttggt    23820
ctgcgagcac aaacatcagg ctagttggca tgcttatgta aacaccacac agtagcagtg    23880
acttttaagg aagtcctcag acaatgtaat cccaatactc ttcttgaagt tgaggtaata    23940
gggtgccaga aagaaaaaga aaataaatct ctagtgcctt ctaaaatttt ttcaatcctt    24000 tgacctttt gaaaacggtc acctttaatt cagaactaaa gtaacatctg gagggccctt    24060
ttcttagata gggagaagac ataaatgagc tatttgaatt attttctgct tatgggctgc    24120
atttcatttc ttccaccatt ggtctcagtc catttaatta agattatttg taggattaaa    24180
ttaatccttt aagaattatt ccatttcaat ttttaaaaaa tctaatgaat gatagataac    24240
aaaaagcggt ccattcagta ttaccccctga acatatttg ggtgattggt gataccatcc    24300
atgtctctcc aacttcagct tcatatactc agctgagtac caggcatctt cattgaaagc    24360
tagacttgtg acctaaatag aacttgatcc cttcccttcc ccaactcctt attttttgtt    24420
ttctttgagt tccttgattc ctcttcccct cctcacatgc aacatgtaac atccaattca    24480
tcagcaggtt ctacagattc tgccttcaat aatagcctaa atctagccac ttgttactat    24540
cttttttggt ccaaaccatc atgatctttt gcctggacca ttgcaatagt tgtctaactg    24600
gtatccttgc tcccattttg tcctcctaga tcctattttc cacgtagtag ccactgattt    24660
ttggaaactt atcaatcatt acccagacac aatgagtaca tttacatagt tgtttgattc    24720
catttacata aagtcccaca atcactctat gtactgggaa tcacaacagt ggtctcctat    24780
gttgagaatt gattaagagt cacaaggaaa caaggagtaa tattccattg tattaacaga    24840
ccacactgtt catacattct cctgtaaatg gacatttatg ttgttttcag ttttttttgct    24900 attgtgatta aagctattag gttggtgcca aagtaattgc agtttttgcc attacttttt    24960
aaatggcaaa aactgcaatt actttggcac caacctaata ctgtaagtat ctttgaactt    25020
accaatcaaa cattactaca acacttgaat aagaaacact tccatagcat ttacaattct    25080
aagtgctttc catgtattga cttagttaat cctcacaagg atataaccat gaggtgctat    25140
tactatccct actttacaga tgaggaaata gaggcacaga cttcagataa tttgcccaag    25200
gtcccacagc taataagggg gcagaattag gaaagcctgg ctgagtctat gctctcatca    25260
```

```
cttgctcaac tctgcctgga atgcccttcc cgtaccctct accgcctctg cccaatcctc   25320
cgggttctct gctccttcca cacaccccca tctcaggtcc cagtcttttt tagcattctt   25380 cacttttttct gttacagatc ctcagacaat gcttccttga agaagacttg cctgtctaaa   25440
ctgccttccc atcccaatcc ctgttacctt ctatcctttc tctgctttgt tttcatttgt   25500
tatctctctt cttcccaaga atgtaagctc cataagaaca ggatcatatt ttgaatcccc   25560
tagaaaagtg cctagtgtaa tatttgttga atgaatatga tccctgcaat taaaagctaa   25620
atatatatat ttttttaact aacagattac tgtagtagtt tcaaagatga atttatgttt   25680
cggagaaaat cagtattctc ttgccacata aattgtaggt aattatattt ctatacctga   25740
atagctttgc caatgactaa gatattaatc tattatatat ttattaatct atagatcttt   25800
aaaattgatg cacatgtttt ataagcaatt tgatgaattt tgatgactac atacacctgt   25860
atgtgtatgg atatctgtaa caaatatcca agtaaagata tagaatattc tcattacccc   25920
agaaagtttc tttgtgactt ctaatcaatt ctcacctccg taggaaaccg ctgttgtgat   25980
tcccatcacc acagactgat tttgggactt tatgtaaatg gaatcaaaca actctgtgaa   26040
tgtactctgt gtctgagttc tttcaatcta cacaatcttt ttgacattaa tccatattac   26100
tgcctagaag agtagttcac tctttgcatt aatgaatagt attccattgt ataaacaaac   26160
cacactgttt atacattctc ctgtgaatgg acatttgtgt tgttttcagt tttctgctat   26220
tgcgatttaa gctactataa gcattttttt ttaattgtga tggggtttcg ctcttgttcc   26280
ccaggctgga gtgcagtggc agcgatctca gctcactgca gcttctgcca cgtgggtcca   26340
agcgattctc ctgcctcagc ctcccgagta cctgggatta caggcatgtg ccaccacacc   26400
tggctaagtt tcgtattttc agtagagacg gggtttcacc atgttggtca ggctggtctc   26460
gaagtcctga cctcaggtga tccacccacc tcggcctccc aaagtgctgg gattacagtc   26520
ttgagccact gtgcccggcc agcatctttg aacatatcaa tttgtaagtt ttatcttaat   26580
attgtacaag tcttttgggg ggcttatgtt gtcatttctc ttggtaaata cctaggtatg   26640
aacttgctag attatagaga aaatctatct ttaattttat aagaaactgt caaatagttt   26700
tccaaagtgg tggtactatt tatactccca ccatcaatgt atgaaatttc cgttgtttta   26760
cgtccttgcc agaatttgtt ggtagtcttt ttttttttt gaggcagcat ctcactgtgt   26820
tgcccaggca tacaatggtg tgatctcggc tcactgcaac ctctgcctcc caggttcaag   26880
ggattttcat gcctcagcat cccaagcagc tgggactaca gaggcgtgcc accacaccca   26940
gctaattttt gtattttag tagagatggg gtttcaccat gttgcccaag ttggtctcga   27000
actcctggct tcaagtgatt cgcccgcctc agcctcccaa attgctggga ttataggcgt   27060
gagtcactgt acccagcctg ttgccagtat ttttagttgt aggcatctta gtgggtgtga   27120
gtgctcgttg gggttttaat ttgcattttc ctgatagtgt tgatgttgag acatttcta   27180 tgtgtttact gagcattggt gaagattctc ttgtgaaata tctattcaaa tattttgctc   27240
atggtgggaa gggagttat ttttctttta ctactgatag gtaggcttac gtatttattt   27300
cggatataat tattttgtca attatatact aatcataaac aaaaactgat aaattggacg   27360
acgtcaaaat taaaacctgc tcatcaaatg ttagcgaaat gtaaaggcaa atcacatact   27420
gaggggagat attttaatat atgtatattt atatagtgct ttctgtgttc taagaagtat   27480
tttcctactc caagataaag agactattct cttacatttt gttctataag ttttatagtt   27540 ttagcttta gctttggatc tatgatctgt ctcaaatttt tatgcaagat tggggtttaa   27600
```

```
tttttttcata cacttttcca gttgtcaagg atcatttgtt gaaacgtctt tcctgttgcc    27660
acataattgc tttgatgcat tcgttagaaa tcagttggct gtgggtttat tttggaatttt   27720 tctgttctgc tcctttgatg tatttgtcta tccttatgcc aatatcaccc tatattaaat    27780
aattatagct ttataataag tcttgaaatc aggtaatgtg aatgtttcaa ctgtgttttt    27840
ccttttctta gttattttag ctgttttatg ttcttattgt atatatttta gaatcaactt   27900
attcatttct acaaaaagtt tattgggatt ctggatgaga tggtgttgat tcagtaggtc    27960
aatctgggga aatctgataa caatattgac tcttccaatc catgaaaatg gtatctcatt    28020
ctttatttac atattcttta atttctgtta gcaatgtgtt ataattgtag caaacttgca    28080
catcttttgt taaattatttt tctaagtatt ttacgatttt ggtaccactg taagtggcat   28140
tgtatttaaa atttatttttc tgtttgtttt ctgttcatat ataaatgcaa ttgattttct    28200
tttttttttt tttttttttt tttttttgag acagaggctt actttgtcac ccaggctgga    28260
gtgcagtggc gtgatcagca ctcactgcag acttgaactc ctgggctgaa gggagcctct    28320
cacctcagcc tcccaagtag ctgggactat gggtgtgagc cagtgttcct ggccaaatgc    28380
agctgatttt tgtattgaca ttgtattctg ccaacttgct aaattaactt attcgttta    28440 atagttttc tgtttttta aaaatcttag gatttctaca cagacaatca tgttttaat     28500 gaacaacaaa gtttgttttt ttgtttgttt gttttccct tttcaatcaa catgcctttt    28560
atgtttttat ttgccttact gcactggcta ggacctccag tacaatttta atagcaatgg    28620
tgagagtgtt taaatgtact cctgtgtata ttttattctt ttggaactta ttataaatgg    28680
aattgtttcc ttaattttct ttttggactg ttcattgcta ttgtacagaa atacaactga    28740
ctattgtgtg ttgatcttgt accttgcaat tttgctgaaa tcgtttattt tttgcaatag    28800 attttgtga attcttagg atttccata tgtagaatca tgttatctgt gaatagggat      28860
agttttactt cttttctaac ttggatagtt ttttccttcc taattgctct ggcaagaact    28920
tctagtacaa tgttagagag caatagtgaa agcaggcatc ttccttcaa tcctgatgtt    28980 agggggtgaag ctctcagcct ttcactgtaa tgttggctgt ggattttcat aatttttttgt  29040 ttgtttgttt ttttgtttga dacggagttt tccttgttgc ctgggctgga gtgcagtggc    29100
gtgatctcgg ctcatcacaa cctctgcctc ctgggttcaa gcgattctcc tgcctcagcc    29160
tccagagtag ctgggattac aggtgcctgc caccacaccg actaattttg tatttttagt    29220
agagacgggg tttctcgatg ttggtcaggc tgctctcgaa ctcctgacct cagatgatcc    29280
gcccgcctcg gcctcccaaa gtgctgggat tacaggcatg agccaccacg cccggcccat    29340
aaatgctttt cttaatcata ttaaggaagt tccttttctag tcgtagttttt ctgagtgttt   29400 ttattatgaa agactttcag attttttgtaa aatgcttttc ctgcgttaat tgagataatc   29460
atatgggttt tctccccctt tactctattg atgtaatgca ttacaacgat tttttttaat   29520
gtttacccat ctttgcattc ctggaataaa tactagttga ttgtgctgta taattcttaa   29580
aatatgctgc tggatttgtt ttgttagtat ttggttgcat tcttttgcat ctatattcat    29640
aagggatatt gatctgtaac tattattttc ttgtggtggc tttatctggc tttggtatca    29700
agataatgct ggccacattg gctaagttag aaagtgttct ttcttctatt ttttgaagag    29760
cttgaaaaga gtcgtgttaa ttcttctta aatatttggt acaattcact attaaagcca    29820
ctagtcctgg gcttttcctta gtttgaaagt ttttgattac taattcaatc tcttttacac    29880
ctagattaga ttttgtattt tttccttagc cactttggg aatgtgtgtg cttccgggaa    29940
tttggccagg tcatctctgt tatctaattt gctggcatcc aaatgttcat aatgttctct    30000
```

```
tgtaatcctt tttattatag aaatgatata cagaaaaggt cagttaccac tttcttttat    30060
gattgcatta atttgcttct tttctctttt tttctctagt cagtcttgct aaaggttggt    30120
ctgttttgtt gatttttttc aaagaaccaa cttttgattt tgttgattct ataattttc     30180 tgctctgtat tttgtgtata tccattctaa tttttattag ttcctttatt ctgttagctg    30240
tgagtttagt tggctcttct tttttatttt cttaaggtgg aagactaagt tattgagata    30300
tatcttgttt tttttttga tgtaggtatt taaagctata aaatttcctc tgagcattgc     30360
ttttgctgca atttataagt attggtatgt tacatattca gttagttttt tatatacaca    30420
tttaagcttt tgctaatcta ccttgtgatt tcttcattga cttattgctt gtttgagtgt    30480
gtcaacaatt tccacgtatt tgtgaatatt ctagttttcc ttttgttatt gatttctagt    30540
ttcatttcat tgtggtaaga aacaatactt tttatgatct caacagttta aaatttatta    30600
agacttattt tctggtctaa catatgatct atcctggaaa atgtatcatg tgcacttgag    30660
aaaaatgtat attctgattt ttttaggtgg gtggcatgtt ctattaatat atatgtctgt    30720
tagctctagg tgaattatag tgatgttcaa agcctccatt ttgttattaa tataaccatg    30780
ccagattttt aatgctgtcc atttgcataa tatgtctctt tccattcttt ttcttttaca    30840
tgatcacttt atatttatag tatatttctt gcacacagaa tgtaattgaa acttacttt     30900 ctaaaatcta cttttctttt tttttttttg agatggagtc ttgctctgtt gcccaggctg    30960
gagtgcagtg gcacaatctt ggctcactgc aatctctgct tcccgggttc aagcaattct    31020
cctgtctcag cctcccgagt agctgggatt acaggcacct gtattttag tagagacggg     31080 gtttcaccat gttggtcagg ctggtcttga actcctgacc tcgtgatcca cctgccttgg    31140
cctcccaaag tgctgggatt acaggcgtga gccactgcac ccagcccta aaatctgctt     31200 tcatagcatc tgtcttgtac ttggaacatt tagtccatgt gtatttgaat atttattgat    31260
atgtttgggt ttatgtttac aatcctgcta tttgttttct ttttgttcca tgtgtttttt    31320 gtttttatt tctgcatctt ttggaaaaat cagatttttt ggtaattcat ttttcttatt     31380
ttattggctt tttagagaaa cctttaata tctttgtgag ttttagggat tacattattt      31440
attcttatta ttattccatt tagaattaat attgttaatc ccattcaaaa atttgtttat    31500
ttcgcttttc agttctagaa ttttcatgtt ttcttcagtt gttgtttctc tgttgttatt    31560
ctccatttgt tcattatatc tatcttttct ttgaaatcct taaaaatatt tataatagct    31620
attttaaagt cctctgctaa tcccaatgtc tgggacatct tggcttctgt tgatattgaa    31680
tacttctttt tttcccctta attaagggtt tcatttttcct gcttttttcac atatctagta   31740 gattttatt atgctctgtg tgctatgaat gagatattat aggaagcctg gtcaatattg     31800
tctcttttta aagggtgttg tatttagttc tgccaagaag ttaaattacc agatttactt    31860
gatgtggctt tagtctttgt tagagctggt ctattcctgc tttgttctta cttctcaggt    31920
aatgaccttc ctgagtttca gctggatgcc tgaagtgctc agctgcattt ttctactctg    31980
gctattctga aatgcaatat tttccagacc tacccaacct ttggtattca tctcccagac    32040
ctgtggctgc ttctctttgc tgagcctcac aaaatcttgt cctgtgcatg gacagccaag    32100
gatccttggg aaatctcatg cagacttcta ggtccttcct ttgtgtagat ttcttctctc    32160
cagtacgttg acctgcttca gagtcctcat cattgctttc ttccttttca gctcagcaat    32220
actgctgtgt attgtgtggg cttcatttgc ctcagccata cctagaacac aacccaaggc    32280
agaaagctgg agtggacctg aggctcatca cctgtttcct tccacccacc atttaaaagc    32340
```

```
agcttatttg tgtgaaactt tttgttgggt tctgtggggg atacgtatag gcaaatgaca   32400
gggagcttat aatttagcca aagagaaaat gtctatatgt tctgtggaat tcagagtatt   32460
ttcctcgact tccaaaatta ttttcctcga cttccaaaat ttggggctac tagctagttg   32520
gtaggaagga attccagatc cattttctt ctagattttt ttcagactcc atgtttcaaa   32580
atctagatgg aaggtaagaa ggaagcaagg agggcatcac atacgagaga gacttatacc   32640
ccaaagtgga tcattagcac attatgagat aatatggtat tattctcaga ggcctgccat   32700
ataaaattcc ttctaattta tttttaatg gtatgtgcct gaaagttttc tgtctttcat   32760
gatcttgaaa gcaaataag aaccagagta gcttatgaga gagttttcct gcttcagccc   32820
agaaaaatgt tgcttctgtc ctagacccctt tgatctggtt cttagtgcca gccttcattc   32880
ctctagatct gttttattgaa tactggctct gttgcagaga ctttgctaga atctgagaga   32940
taaaagactc aatgccttca aaacacctac aatccagaca cttaaataaa tgcaataata   33000
tatggttaag gtcttggata gaggaccatc atagaaacac atagaacaga catttagtcc   33060
atgctaggga gagggaagat gtcaaggaat gcttcctgga ggtggcgaca tctaagctga   33120
gttttaaagt gggtgtaaga gtgaaggaac tgggaatagg caaaacatac cttagagagc   33180
tgcacctcca aagcatggaa ggctagataa tcttagaact tcaagtgggg ttcaatgtgc   33240
ctgggacttg gatttcaggc agagaccata gggcaagttg gagaacaggt gggcagggtg   33300
agatgaagca gagactttta ataaccatca aacaggcctg ccatccaact gctatcagcc   33360
attttccctt tttgaatttt attttttaa tctctagagc aatacatgtt tatggtagga   33420
aatgaaaaaa atatatagat gggtaaaatg aagtgaatta taccacccac aatcctgctg   33480
taaaacaggt tttaacaagt tataaatccc tccagatcaa agtgctacta aactctactt   33540 gctatttat aaccttttc tgttcagagt attttagaaa cgttttaca tgttaattga   33600 tattcttttg cattatcctg aataatggta tttctttagt tatactatca tgtattaaaa   33660
cattcataca tggtaaacat atttgaatat tagacatttc aattgttttc aatgtttggc   33720
tattaaaaat agtatttaga tgaatgttct tggccataca gttaataact tcactgagtc   33780
cttgtcaata actttattaa atcccaatct taagacaaca agcctataag attaacatac   33840
caggaataat tagaaagcat tgcaagacta tatgtaacca tctccctgtt aatcatcctt   33900
atttgttgca acatcctaaa tagcgacctt cccacactct gcctcataat atttaatctg   33960
tcaaatgtac catccgcaaa gggagtgaac tggctcgtga agaggtggtg aagctggttc   34020
aactcagttt aacagacaat gagggcctcc gtgtgccagg gagggagtga gggaactcca   34080
cagggagctc attctgggga gggatgcccc tcattatctg cagtaaatga tattagagaa   34140
gtatgtgtga gactcttggt gtccagagga ggggcatgca gcacagtatg ggggtccatg   34200
gggttgcagc gatttcttag agacggtgcc atgcctggga tgaccaccaa gttaggatgc   34260
tgtaaagagt aatcaaataa gtttcaacag ggttttggca tgaggtgagc agttaatcca   34320
aatgatatct gaaatgcttt ctaatgctgc aagtgtattc ctctgtaaaa taatcaacta   34380
cttaaaagac actctcactt gcattatgtc atttaatcct cacagtgtcc ctacgggaca   34440
atagatgtca ttcccacttg tacagagcag taagtgaggc tcacaccggt catagttaga   34500
ggagtaggga atctaaacct aagtctcttc tactccaaac cccaagtttt atcagtatgt   34560
cacatcgcta ctgtgggctg aattccttag caggggttgt ttcctccacc tgcaatattc   34620
ttccttttgg tttgttcatc ctctagagag agaagggata cgcattcatg gagatcctac   34680
tgttgcaaac tctgcattag gagttttaca tgaattgtct catttagtcc tcacaacagt   34740
```

```
cctgtgaggc acaggaaagt tagatttacc tgcccaaatt aaggaatgtg gccaactcaa    34800
gagtgacgaa ggccaggtgc ggtggctcat gcctgtaatc tcagcacttt gggaggctga    34860
ggtgggaggc tgaggatcgc ttgagcccag gagtttaaga ccagccaggg caacacagca    34920
agatttaatc tctactagaa ataaaaaaga aattagccag gtgcctgtag tcccagttac    34980
ttgggaggtt gaagtgggac gattgcttga gcctgggagg tagaggctgc agtgagccat    35040
gatcccatca cttcactcca gtcagggtga cagagtgaga cccagtctta aaacaaaaca    35100
aaacaaaaaa gagtgatgga gcaggaactt tatctgccat cagagaccat atatgtcttt    35160
ccttatggcc caggtcattt atcatgtcct tgctaaacct cctcctctga gccttgttaa    35220
agtcctcaag gttagaagag tggtctataa ttataaaaaa ttccattgta tgacttcagc    35280
tacctgcaaa actgaccgag attaatgcat tctttgtttg ctttcactct ttcattccct    35340
gttcagcgct tattctacag aaaggtgcct ggtagattta ggacatgact gttcataggc    35400
ctcaaatgcg gtcaaattag gaaagtcccc tggttttttgg tctcaagagg ttaattgctg    35460
agtactagcc tggactgctc aatggatttt atgtttaact gttgtgttta tttgtttgtt    35520 tgttttttgtt ttgtgagaca tatctttctc tgtcacctgg gctggaggtc agtggtgtga    35580
acatggctca ccgaagcctc catctcctgg gctcaagtga tcctcctgcc tcagccttcc    35640
tagtagctgg gactacaggc acacagcacc atgactggtt aagttttgga ttttttggta    35700
gaaatggggt ctcactcttt gcgcaggcta gttgtgaact cctggtatca agggattctc    35760
ccaatgtgct gggatttcgg cctcccaaag tgctgggact gcaggcatga gccatcatgc    35820
ccagcctctg tttaactgtt aacatcatga ggtttccttt caatgaggaa gggaggcctg    35880
gggaggtgtg atgggaaga tggagaaggg taggagacat cataaaactg acagaagtgt    35940
ggcacgatta agaccctggt ttcttagacc acataagcaa gtgccactat tcttttgatc    36000
aacatttgat tctctatttc cttcttagca tatagatagc tgcttcaggt cgtgaaaaaa    36060
tacatttagt gaaatgaaac atagtagata tgttcaccaa gaaactaaaa agaaaagtta    36120
gccacaaact atcttatttc attgaaatgt ttggctgaac ccataagaat gttgatgagg    36180
ccattcttgg atgcctgtac tgaaatgaac cacgagagga atatttagga tatgttgaag    36240
aggctgtttg gcttaatgaa caaaggagtt tctgcaggcc cagggagtgg aatgaaaatt    36300
ggcatgatca ttttggagaa tatatggagt caaacagaga atttgaatgg agttttcaaa    36360
gaggatatgt tagggaata aaggctgata acaacacttt gtatttgtag gaaaatagggg    36420 agagtaaatc aaggaattca aagagaaaga gaaactcact tcaagtaggg gagaaaaaac    36480
ccctataatt ttcactcttc cttgtaaata aaaggaaac aaatgaaaat aagatattag    36540
aagtcagtaa gaatttatgg gagtataaag ttggttttat ggatgcaaag cccttttcac    36600
tgctgtacga aactcctggc tgcatgctaa caatggacaa ctgatttcct tgcagctgta    36660
ttttgctgtt ttttgctctt ggcttggacc tagcaccctg ggtctgtggg aaaccagaac    36720
tgtcccagag ttctggaggg taggccaagg ttagatgctg gagtgggttc tttaatttat    36780
tgtactgatt cttcttggga agaaagaaga ttgcttgtta gaatttttagc tacgagagat    36840 gactatgaaa cagtaaatta actccaacga cctgagtcat tttgaaaact cccagtctca    36900
ggataaaaaa tataatccta tttagaaatt cctggtgtga tcacagatgt agcattggtt    36960 ctttttcatga aacccgtaaa ttaaaaagta cataatccaa agtcaattaa atagtaagct    37020
attataacaa attcttttat ttcattagct tttcaaaatg tggataacta cacactcaac    37080
```

```
ccaaggaatc tacattttc cactgactgc taaagaccaa tggaaataac tctagtcccc   37140
gtagcacctc actgtggggt gacctacctt tgaaataatg tattggttct agctgatttt   37200
tatattgtta gtcattaagt taggcttgat gagaaacaga tataatctga tttggggatt   37260
caagtattat attgcatttc tcctcacaac tagagataaa tttgccatgg tttttctctt   37320
cataggctca tgccaaagtc tggcatctct acaatacttc tttccgtccc actcagggag   37380
gtcaggtgtc cattgcccta agctctcact ggatcaatcc tcgaagaatg accgaccaca   37440
gcatcaaaga atgtcaaaaa tctctggact ttgtactagg ttggtttgcc aaacccgtat   37500
ttattgatgg tgactatccc gagagcatga agaataacct ttcatctatt ctgcctgatt   37560
ttactgaatc tgagaaaaag ttcatcaaag gaactgctga cttttttgct ctttgctttg   37620
gacccacctt gagttttcaa cttttggacc ctcacatgaa gttccgccaa ttggaatctc   37680
ccaacctgag gcaactgctt tcctggattg accttgaatt taaccatcct caaatattta   37740
ttgtggaaaa tggctggttt gtctcaggga ccaccaagag agatgatgcc aaatatatgt   37800
attacctcaa aaagttcatc atggaaacct taaaaggtat gattgtgggt aaagttctca   37860
tttcctgcca aaatcttctg gaaaaaaatc tctaagatta tctaacataa atgatgtgaa   37920
tttatatttt taaatcctaa tggagacatt cattttggca atagtagaat gcattcattt   37980
aacacctttc tcatttggag tcttgaggaa cttgaattaa ttttttaaaaa cccatttgta   38040
aatgagaaac tgggttataa tatttgtaat tacttaactt tcagttatta atctagattt   38100
ttagattaaa ttgaacataa aacaaatccc aggatatcta gctctctgca catgtttttc   38160
agttcttgtt attttggttg aataaaacac tttaaagaaa aaggaatgtc catgttttct   38220
agagaaaata gtataaatag atcatgcttt taaagccttc atttatttat ttattgcatc   38280
agacacaaag ctgggtgtct aggatggaaa gtggtacaag acatctttcc agccctgtag   38340
aatatctatt ataaataagg aactattttt tcaaggtgct cagaaatcca aaaaacatat   38400
tagataggcc aattttgagg gcatttattt gtagagttat ataggtttga ttagagtctt   38460
tcgtcaagaa gaaaaatcat tggcttacca aacgagaagc attacacttt atttatttaa   38520
gtaggaaacg ctcagctgct cttgaaccat gatgcaagtg cccagcgaag ggtcatgttg   38580
ctcttgtccc ctcttcctt tgcagccatc aagctggatg gggtggatgt catcgggtat   38640
accgcatggt ccctcatgga tggtttcgag tggcacagag gttacagcat caggcgtgga   38700
ctcttctatg ttgactttct aagccaggac aagatgttgt tgccaaagtc ttcagccttg   38760
ttctaccaaa agctgataga gaaaaatggc ttccctcctt tacctgaaaa tcagccccta   38820
gaagggacat ttccctgtga ctttgcttgg ggagttgttg acaactacat tcaagtaagt   38880
cagctgacaa aaccaatcag cagtctcacc aagccctatc actagtaagt agtgcttcct   38940
tcctaggctg attgtcatgg cacattgtcc gttctttgag ccaaaaacaa ttccttatga   39000
gtacactaag ggcacaattt ggaatgctgc accccttctct ccaaaactct tccaatcttc   39060
atcttgttta agttagatcc aaagataaat aaatttaaag catatcaata tttaagatcc   39120
gattaagaca gtaaaaagat aaaacactct cttttcatac tgtggttttt gatcctttt   39180
aaggcagttg agttttttca tgaacaggat ctaacacaga actccaaagc ctctgagttt   39240
cagtggtgct gctgagactg aggcaggaac attaggcaga gtcctccaga ggcacaactg   39300
tgggctccac aaatgtgcag aaatacccta agaaagtaaa ccctagatcc aatgattcac   39360
tggtcagaat gtcttttta gcaatagtca ttgaaatgat acgaaatttc ttcagaatga   39420
tcaaccaata tttattgagc atcttctcag tagtaagccc ttaacattct ttcagacttc   39480
```

```
ctaaattttg aagggcttg ttttccagca tttgactgga tactctagta agcacttatt   39540
ggatgtctag tgtgtccgaa gccttgtgtt agttgctcgg gtcgcttggt taaggggagt   39600
gcaggtagag ggtatactga gatgagtaag ggtaaccttt gctttcaaag gagcaaagga   39660
gtctactgag cgaaaacaat gtatgcacaa atgatgcaat ggagtgaagc gggcatggtg   39720
gtaagtaaca agggcgggc tgggggattg ctgctgatag agtcccaagt gtgaaaatag   39780
ccctcaagac agagacagag ttcagtgtcc atagacaagc agttggcttt gacatgttgg   39840
gttatggtag ccaattaatt ggttctgcaa atcacagctt gaaggaaac acttggaaga   39900
atgtgaaatg ggttgctgtt ttcttgtaaa tatccaattg aaatctttta tttataagga   39960
aataaattaa caccatcctt agtacatttt ttgctggttg ggattattct tcttttttcag   40020
accacccagt tcattttaca ggcagtctca gacttaaacc ctcgccttcc atttaaaaga   40080
tgactggctc acgcctgtaa tcccagcact ttgggaggcc gaggcgggcg gatcatgagg   40140
tcaggagatc aagaccatcc tgaataacac ggtgaaaccc cgtctctact aaaaatacaa   40200
aaaaaaaaa aaaattatc cgggtgtggt ggcgggcacc tgtagtccca gctactctgg   40260
aggctgggc aggagaatgg catgaaccca ggaggcggag cttgcagtga gccgagattg   40320
cgccactgca ctccagcctg ggtgacagag caagagtccg tctcttaaaa aaaaaatga   40380
ctggatgtgt catcttttat gccaggatat gtgagcccag gagaaaggct tctgagctcc   40440
ctcctgctcg gtgtgcaatt ttctgccctg ccccgactct ctccttctct cccagcctcc   40500
tgctatttga aatctcctta tcctaatttc cctcctcaga gtggattcca ctgtggggtt   40560
cagagaggat ctgaggtggg agaagtgagg ctggtgagga agaaggggag gagaaaggga   40620
agaagacctc cgtagccttc cttcctcctc ctctttactg gggttgggga tagatcggat   40680
ggtccctggt ccttgttcta tctcttgacc ttctgcctgc tccctgctga gcacggatct   40740
ctgatagcag cctgagtctg gcaggttcag tcctttgtat gcggcacaat ctcccagcca   40800
gcattgctgt gcagatcatg ggaacgaatg cagaacaaga gtggggtgt cggagggagc   40860
cctacttctc ctgttctatt cctcatcagg gggctgtgcg ctggctttgg gaattggtaa   40920
atagtgagaa agtcttaagg gtacatccta tttccttgag ggagaagaga aaacgctggt   40980
cagaagcaat aagtatagca gtgaatagca agggagatgg gagataattc cttttcctac   41040
tacactctag aagctattgt tttagaatct gacctaaggt cagccactaa ttggccccag   41100
aggtctctct ctcagatcac acggtccttt tttcctcatc agcttgggga ccccacccct   41160
cctcctggca gtctcctcct gtgcagaacc caacaaacac aaaattaagt cactctcaaa   41220
cccacagcag atgagagctt ctctggaagc tccctggtgg ggaaaggctg caattgctat   41280
tttcttcttc tggttttcac ctcaggcttt gtgttatatt gacagtaccc ttctcaagct   41340
aactccctaa ctgacctgac gtagtcaaaa taagttcttt gtatgtcagt tctgaggtgt   41400
gtgtgttttc acttacaaac agtactctac agctttaaga cattatatta aagtcctgag   41460
aagtgatttt taaaccactg aacttcatct tttccctcct ggctagtatt tcagactttc   41520
agtgtttgag gcatgcattt cacctgaaca acttgaaaaa taatatccta agaagcacac   41580
aacctgactt taggctcatt cacatggatt gtcactttac ttggacccac tttctcggct   41640
gagaggtttg ttttcccata accacggatg ctcatagtta atataaatat tgaactcact   41700
atgtagtgag gacatagagc ctctttaaca ttggtccctg ttaggagaaa gtttctccca   41760
taacatacta aatacatgtt ttaatagccg ttccttctga aaggtccaac ttcactattt   41820
```

```
tatttttta gtaaaatctt agttaacaaa ttaatggagg ttaggtggaa ttttgcccca    41880
aaagtcctgt attttctttt tttttttttc tttttttttg acagagtctt gctctgtcgc    41940
ccaggctgga gtgcagtggc gtgatctcgg ctcactgcaa gctccgcctc ctaaggtcac    42000
gccattctcc tgcctcagcc tcctgagtag ctggggctac aggtgcccgc caccgcaccc    42060
ggctaatttt ttgtattttt agtagagacc gggtttcact gtgttagcca ggatggtctc    42120
aatctcctga cctcgggatc cacccacctc ggcctcccaa agtgctggga ttacaggcgt    42180
gagccaccat gcccggcctg tcctgtattt tcaagaaact tttttttttcc tccagaaatg    42240 atacccctagt ctttcatatt tgttttcaga tggactgaat aaaagctgtt gttttggaac    42300
aatcacggtt aaaaaaaaaa gttatgaatt tagtcaactc agagctctat aaaaataatc    42360
caaaaaattc cttcaaactc tgaacgcttc aaaagagcgt gcaaatattc tgtccttcaa    42420
agctaaggaa acatgatttg tggggtgcat cacagtggaa aaatactctg acagcattcc    42480
cacagcatta ggggaagtgc atgtgtgggt gttctgcaag ggacaattct ccagaaaagg    42540
caatttccct ttgacatgct gttttttaatg acttttctttt ataaacacac ttatctctcc    42600
agagaaatag cagtgcattt gcaacaggcc cgtaaaatgc aacaaaacct ctgctatggt    42660
ttctgacccc tgctttttata cagagcatca gaccaaggaa cctgttctaa caggattatt    42720 tcagaggga acacaggctt agggtgcaga tcttccagct ggattttca ctttgcattc    42780 cctccacagc agacacatga aggaatgatt ttgtgatttt gatttataa tttgcacact    42840 tttcctaaat actttttta aattttat tgggaggatt ttatagcata tgattgagaa    42900
ctataatcat catcattgtt acagaagaat aatttagaaa aatttttaa ctacgttaaa    42960 aattccacta tgggtggatg acaatattgt tctttccttc cacattctcc ctccttagac    43020
tttcttttct ttttttctat tttttttttg agatgaagtc tcgctctgtc actcaggctg    43080
gagtgcagtg ccatgatcct ggctcactgc aacctctgcc tcccgggttc aagtgattct    43140
cccgcctcag cttcctgagt agctgggatt acaggtgtgc accaccacac ctggctactt    43200
tttgtatttt tagtagagat ggggtttcac catgttggtc aggctggtct caaactcctg    43260
atctcatgat ctgcccgcct tggccccgca aagtgccggg attacaggcg tgagccactg    43320
cgcctggcct ctctctcgga cttcctacca tcagtcagat tgaatttgtt aaattctgtc    43380
actgacccta aacccaacaa aaggcaagag ttatgtttat ttagcacttc ctctacctat    43440
agcaaacctc aatttagagc gtaattttaa gcacaattta attataaata tcttttcatt    43500
ttcttactta actcactcag tttttaaat ctttctttt gagacaagat cttgctctgt    43560
cactgaggcc gatgtacagt gatgtgatca tgacttactg cagccttgac ctcccaggct    43620
taggtgatcc tcatacctca gcctcccgag caactaggac tacaggcccg tgccaccatg    43680
ccgggccaag acggggtttg gacgtgttgc cccagctggt ctccaactcc tggcctcaag    43740
tgaccctccc gcctcggcct ctcaaagtgc tgggattata ggcatgagcc accgcacctg    43800
gccaactcac tcacatttta gtttttctct ttttttcatc tagttttttt tctttttaaa    43860
tttgaaagcc tcatgacatt aatgatttct tacattaaaa gaaaacacc caaaaatact    43920 ctgcttacat aacaccgaca agtagtgtgc aagactcatt agcatttgtc atctgaagtg    43980
accaaatcca gacttttggg ggtcacatta agaaacagt tgaagagtta gaactatggg    44040
taaagcgagt gtgcatatca gaaagtggaa tattgtcttc ctcaggagct gacaatttat    44100
gaaaaatagt tcaattctc agctagaaag gcttctattt ttgctcatat tcctggctag    44160
ttttgctgaa ataattgctt tgaattactt cctcaggact gcccaggtga cgctaatgtt    44220
```

```
tactctgccc ttcacaggta gataccactc tgtctcagtt taccgacctg aatgtttacc    44280
tgtgggatgt ccaccacagt aaaaggctta ttaaagtgga tggggttgtg accaagaaga    44340
ggaaatccta ctgtgttgac tttgctgcca tccagcccca gatcgcttta ctccaggaaa    44400
tgcacgttac acattttcgc ttctccctgg actgggccct gattctccct ctgggtaacc    44460
agtcccaggt gaaccacacc atcctgcagt actatcgctg catggccagc gagcttgtcc    44520
gtgtcaacat caccccagtg gtggcccgtg ggcagcctat ggccccgaac caaggactgc    44580
cgcgcctcct ggccaggcag ggcgcctggg agaaccccta cactgccctg cctttgcag    44640 agtatgcccg actgtgcttt caagagctcg gccatcacgt caagctttgg ataacgatga    44700
atgagccgta taaggaat atgacataca gtgctggcca caaccttctg aaggcccatg    44760
ccctggcttg gcatgtgtac aatgaaaagt ttaggcatgc tcagaatggg aaaatatcca    44820
tagccttgca ggctgattgg atagaacctg cctgcccttt ctcccaaaag acaaagagg    44880 tggctgagag agtttggaa tttgacattg gctggctggc tgagcccatt ttcggctctg    44940
gagattatcc atgggtgatg agggactggc tgaaccaaag aaacaatttt cttcttcctt    45000
atttcactga agatgaaaaa aagctaatcc agggtacctt tgacttttg ctttaagcc    45060 attataccac catccttgta gactcagaaa agaagatcc aataaaatac aatgattacc    45120
tagaagtgca agaaatgacc gacatcacgt ggctcaactc ccccagtcag gtggcggtag    45180
tgccctgggg gttgcgcaaa gtgctgaact ggctgaagtt caagtacgga gacctcccca    45240
tgtacataat atccaatgga atcgatacg ggctgcatgc tgaggacgac cagctgaggg    45300
tgtattatat gcagaattac ataaacgaag ctctcaaagg taaggagccc tagctgcggc    45360
tatctcctga aggttatgtc accagagggc atgacacttg attaaatctc caacatcaac    45420
acacactgcc acccttggaa tggagggcta tccattttgt gcctcactga acagtccaa    45480 gagatatcta gcattcccc aaggataaag gagtgtagct aaaagtagaa gaccagaaat    45540
ccctagcccc tactctggat ctatgcaagc ctagattctt gtcttccatc ttggatggct    45600
ccacagcagt cttaactgtt tcatgtacat aaagcagtac ataagattt aaccttgctg    45660 ggcatggtgg ctcacacctg taatcccagc attttgaag gccaaggcag gaggattgct    45720
tgagcctaga gtttgagac cagcctggc aacatagtga gaccttgtct ctactaaaaa    45780
tcacaaaaat tagctgggca cggtggcata tacgcctgca gattcagtta cttgggagga    45840
gaggcgggag gattgcttga gcttgggagg tccagctgca gtgaatcatg atcacagcac    45900
tgcaatctgg cctgggtgac agagcaagac actatttcaa aaaaaaaaag accaagcatg    45960
gtggctcatg cctgtaatcc cagcactttg ggaggctgag gcaggtggat catctgaggt    46020
cagaagttca agaccagcct gaccaacatg gtgaaacccc gtctctactg aaaatacgaa    46080
aattatccag gtgtagtgat gcacacctgt aatctcagct actcgggagg ctgaggcaga    46140
agaatcactt gaactgggga cgtggaggct gcagtgagcc aagattgcac cattgcactc    46200
cagcctgggt gacagagcaa gactccatct caaaaaaaaa aaaaaaaaaa aaaggattta    46260
acccaagtat atcatagtag attgaattat gtaaaacacc catttaacaa ccaggtccag    46320
gtttgttctc tctgtgtagt aaatcaatca ctgtgacaca ggttttgcaa aagagaaaag    46380
atttatttgt aagggaccca agcgaggggg tgggagaata acttccaatc ctgcctctct    46440
gaagacaagg cttaggaata tgtatgggtt agggaatggg tggtctaagg catggtgaag    46500
agtgattggc aggggggaa aatgaagtaa caggttagac acatgcacag aaaatggtgg    46560
```

```
tgttagcatg atctgagggc agagttttgg gccctctgac gtcaaaagac cacctctcag    46620
gcacttgtgc aggcccagtg aagggtcag tggtcttaac tagtttgaac tggacaggag     46680
ctgccccaag ttcttggaaa acaactgaa gtgaccattg ccatggtaac ctatgaatgt     46740
catcagtaaa gtagccagtg aaggttaagt ttcagcatac aatgggacaa ccttcagctt    46800
catggaaaaa ggaaaaaaaa aaaacacata cacacacgaa aagcaagtga ccaaaagcaa    46860
gcaggacagg cagacctgat ccaattaacc cctgggtttc aaccctgcta aatgcagctc    46920
aatatttgtc ttgataattt gcctatttgg ctttacataa aataaagcct tttctgatga    46980
aatctaattg agtctgaagt tgtattaaat ggtatcggaa acttcccagc aggaaggcta    47040
cgtaaaagtg gccgggcgtg gtgactcacg cctgtaatcc cagcactttg ggaggctgag    47100
gcaggcagat cacaaggtca agaaatcgag accatcctgg ccaacatggc gaaatcccat    47160
ctctactaaa aaaaaaaata caaaaatttg ccaggtgtgg tggtgctcac ctgtagtccc    47220
agctactcag gaggctgagg caggagaatc tgttgaacct gggaggcgga ggttgcagtg    47280
agtcaagatg gtgccattgc actccagcct gtgtgacaga gcaagactcc gtctcaaaaa    47340
aaaaaaaaag tgatgtgttg tgtgcaaaat acgtaataac tactctccta tccttttgtt    47400
tttccagccc acatactgga tggtatcaat cttttgcggat actttgctta ttcgtttaac    47460
gaccgcacag ctccgaggtt tggcctctat cgttatgctg cagatcagtt tgagcccaag    47520
gcatccatga aacattacag gaaaattatt gacagcaatg gtttcccggg cccagaaact    47580
ctggaaagat tttgtccaga agaattcacc gtgtgtactg agtgcagttt ttttcacacc    47640
cgaaagtctt tactggcttt catagctttt ctatttttgg cttctattat ttctctctcc    47700
cttatatttt actactcgaa gaaaggcaga agaagttaca aatag                   47745
```

<210> SEQ ID NO 18
<211> LENGTH: 47745
<212> TYPE: DNA
<213> ORGANISM: Homo sapiens

<400> SEQUENCE: 18

```
ctatttgtaa cttcttctgc ctttcttcga gtagtaaaat ataagggaga gagaaataat       60
agaagcaaaa aatagaaaag ctatgaaagc cagtaaagac tttcgggtgt gaaaaaaact      120
gcactcagta cacacggtga attcttctgg acaaaatctt tccagagttt ctgggcccgg     180
gaaaccattg ctgtcaataa ttttcctgta atgtttcatg gatgccttgg gctcaaactg      240
atctgcagca taacgataga ggccaaacct cggagctgtg cggtcgttaa acgaataagc      300
aaagtatccg caaagattga taccatccag tatgtgggct ggaaaaacaa aaggatagga     360
gagtagttat tacgtatttt gcacacaaca catcactttt ttttttttt gagacggagt      420 cttgctctgt cacacaggct ggagtgcaat ggcaccatct tgactcactg caacctccgc     480
ctcccaggtt caacagattc tcctgcctca gcctcctgag tagctgggac tacaggtgag     540
caccaccaca cctggcaaat ttttgtattt tttttttag tagagatggg atttcgccat      600
gttggccagg atggtctcga tttcttgacc ttgtgatctg cctgcctcag cctcccaaag     660
tgctgggatt acaggcgtga gtcaccacgc ccggccactt ttacgtagcc ttcctgctgg    720
gaagtttccg ataccattta atacaacttc agactcaatt agatttcatc agaaaaggct     780 ttatttatg taaagccaaa taggcaaatt atcaagacaa atattgagct gcatttagca     840
gggttgaaac ccaggggtta attggatcag gtctgcctgt cctgcttgct tttggtcact    900
tgcttttcgt gtgtgtatgt gttttttttt tttccttttt ccatgaagct gaaggttgtc    960
```

```
ccattgtatg ctgaaactta accttcactg gctactttac tgatgacatt cataggttac    1020
catggcaatg gtcacttcag ttgttttttcc aagaacttgg ggcagctcct gtccagttca    1080
aactagttaa gaccactgac ccttccactg ggcctgcaca agtgcctgag aggtggtctt    1140
ttgacgtcag agggcccaaa actctgccct cagatcatgc taacaccacc attttctgtg    1200
catgtgtcta acctgttact tcattttccc ccctgccaa tcactcttca ccatgcctta    1260
gaccacccat tccctaaccc atacatattc ctaagccttg tcttcagaga ggcaggattg    1320
gaagttattc tcccaccccc tcgcttggtc cccttacaaa taaatctttt ctcttttgca    1380
aaacctgtgt cacagtgatt gatttactac acagagagaa caaacctgga cctggttgtt    1440
aaatgggtgt tttacataat tcaatctact atgatatact tgggttaaat cctttttttt    1500
tttttttttt ttttgagatg gagtcttgct ctgtcaccca ggctggagtg caatggtgca    1560
atcttggctc actgcagcct ccacgtcccc agttcaagtg attcttctgc ctcagcctcc    1620
cgagtagctg agattacagg tgtgcatcac tacacctgga taattttcgt attttcagta    1680
gagacggggt ttcaccatgt tggtcaggct ggtcttgaac ttctgacctc agatgatcca    1740
cctgcctcag cctcccaaag tgctgggatt acaggcatga gccaccatgc ttggtctttt    1800
tttttttgaa atagtgtctt gctctgtcac ccaggccaga ttgcagtgct gtgatcatga    1860
ttcactgcag ctggacctcc caagctcaag caatcctccc gcctctcctc ccaagtaact    1920
gaatctgcag gcgtatatgc caccgtgccc agctaatttt tgtgattttt agtagagaca    1980
aggtctcact atgttgccca ggctggtctc aaacttctag gctcaagcaa tcctcctgcc    2040
ttggccttcc aaaatgctgg gattacaggt gtgagccacc atgcccagca aggttaaatc    2100
tttatgtact gctttatgta catgaaacag ttaagactgc tgtggagcca tccaagatgg    2160
aagacaagaa tctaggcttg catagatcca gagtaggggc tagggatttc tggtcttcta    2220
cttttagcta cactccttta tccttgggga aatgctagat atctcttgga ctgtttcagt    2280
gaggcacaaa atggatagcc ctccattcca agggtggcag tgtgtgttga tgttggagat    2340
ttaatcaagt gtcatgccct ctggtgacat aaccttcagg agatagccgc agctagggct    2400
ccttaccttt gagagcttcg tttatgtaat tctgcatata atacaccctc agctggtcgt    2460
cctcagcatg cagcccgtca tcgattccat tggatattat gtacatgggg aggtctccgt    2520
acttgaactt cagccagttc agcactttgc gcaaccccca gggcactacc gccacctgac    2580
tgggggagtt gagccacgtg atgtcggtca tttcttgcac ttctaggtaa tcattgtatt    2640
ttattggatc ttctttttct gagtctacaa ggatggtggt ataatggctt aaagccaaaa    2700
agtcaaaggt accctggatt agctttttt catcttcagt gaaataagga agaagaaaat    2760
tgtttctttg gttcagccag tccctcatca cccatggata atctccagag ccgaaaatgg    2820
gctcagccag ccagccaatg tcaaattcca aaactctctc agccacctct ttgtcctttt    2880
gggagaaagg gcaggcaggt tctatccaat cagcctgcaa ggctatggat attttcccat    2940
tctgagcatg cctaaacttt tcattgtaca catgccaagc cagggcatgg gccttcagaa    3000
ggttgtggcc agcactgtat gtcatattcc ttgtatacgg ctcattcatc gttatccaaa    3060
gcttgacgta atggccgagc tcttgaaagc acagtcgggc atactctgca aaggccaggg    3120
cagtgtaggg gttctcccag gcgcccctgcc tggccaggag gcgcggcagt ccttggttcg    3180
gggccatagg ctgccacagg gccaccactg gggtgatgtt gacacggaca agctcgctgg    3240
ccatgcagcg atagtactgc aggatggtgt ggttcacctg ggactggtta cccagaggga    3300
```

```
gaatcagggc ccagtccagg gagaagcgaa aatgtgtaac gtgcatttcc tggagtaaag    3360
cgatctgggg ctggatggca gcaaagtcaa cacagtagga tttcctcttc ttggtcacaa    3420
ccccatccac tttaataagc cttttactgt ggtggacatc ccacaggtaa acattcaggt    3480
cggtaaactg agacagagtg gtatctacct gtgaagggca gagtaaacat tagcgtcacc    3540
tgggcagtcc tgaggaagta attcaaagca attatttcag caaaactagc caggaatatg    3600
agcaaaaata gaagcctttc tagctgagaa tgtgaactat ttttcataaa ttgtcagctc    3660
ctgaggaaga caatattcca ctttctgata tgcacactcg ctttacccat agttctaact    3720
cttcaactgt ttctttaatg tgaccccaa aagtctggat ttggtcactt cagatgacaa     3780
atgctaatga gtcttgcaca ctacttgtcg gtgttatgta agcagagtat ttttgggtgt    3840
ttttctttta atgtaagaaa tcattaatgt catgaggctt tcaaatttaa aaagaaaaaa    3900
aactagatga aaaaagaaa aaacttaaaa tgtgagtgag ttggccaggt gcggtggctc     3960
atgcctataa tcccagcact ttgagaggcc gaggcgggag ggtcacttga ggccaggagt    4020
tggagaccag ctggggcaac acgtccaaac ccgtcttgg cccggcatgg tggcacgggc     4080
ctgtagtcct agttgctcgg gaggctgagg tatgaggatc acctaagcct gggaggtcaa    4140
ggctgcagta agtcatgatc acatcactgt acatcggcct cagtgacaga gcaagatctt    4200
gtctcaaaaa agaagattta aaaaactgag tgagttaagt aagaaaatga aaagatattt    4260
ataattaaat tgtgcttaaa attacgctct aaattgaggt ttgctatagg tagaggaagt    4320
gctaaataaa cataactctt gccttttgtt gggtttaggg tcagtgacag aatttaacaa    4380
attcaatctg actgatggta gaaagtccga gagagaggcc aggcgcagtg gctcacgcct    4440
gtaatcccgg cactttgcgg ggccaaggcg ggcagatcat gagatcagga gtttgagacc    4500
agcctgacca catggtgaaa accccatctc tactaaaaat acaaaaagta gccaggtgtg    4560
gtggtgcaca cctgtaatcc cagctactca ggaagctgag gcgggagaat cacttgaacc    4620
cgggaggcag aggttgcagt gagccaggat catggcactg cactccagcc tgagtgacag    4680
agcgagactt catctcaaaa aaaaataga aaaaagaaa agaaagtcta aggagggaga     4740
atgtggaagg aaagaacaat attgtcatcc acccatagtg gaatttttaa cgtagttaaa    4800
aaatttttct aaattattct tctgtaacaa tgatgatgat tatagttctc aatcatatgc    4860
tataaaatcc tcccaaataa aaatttaaaa aaagtattta ggaaaagtgt gcaaattata    4920
aaatcaaaat cacaaaatca ttccttcatg tgtctgctgt ggagggaatg caaagtgaaa    4980
aatccagctg gaagatctgc accctaagcc tgtgttcccc tctgaaataa tcctgttaga    5040
acaggttcct tggtctgatg ctctgtataa agcaggggt cagaaaccat agcagaggtt     5100
ttgttgcatt ttacgggcct gttgcaaatg cactgctatt tctctggaga gataagtgtg    5160
tttataaaga aaagtcatta aaaacagcat gtcaaaggga aattgccttt tctggagaat    5220
tgtcccttgc agaacaccca cacatgcact tcccctaatg ctgtgggaat gctgtcagag    5280
tattttccca ctgtgatgca ccccacaaat catgtttcct tagctttgaa ggacagaata    5340
tttgcacgct cttttgaagc gttcagagtt tgaaggaatt ttttggatta ttttttataga   5400 gctctgagtt gactaaattc ataactttt ttttaaccg tgattgttcc aaaacaacag      5460
cttttattca gtccatctga aaacaaatat gaaagactag ggtatcattt ctggaggaaa    5520 aaaaagttt cttgaaaata caggacaggc cgggcatggt ggctcacgcc tgtaatccca    5580
gcactttggg aggccgaggt gggtggatcc cgaggtcagg agattgagac catcctggct    5640
aacacagtga aacccggtct ctactaaaaa tacaaaaaat tagccgggtg cggtggcggg    5700
```

-continued

```
cacctgtagc cccagctact caggaggctg aggcaggaga atggcgtgac cttaggaggc      5760
ggagcttgca gtgagccgag atcacgccac tgcactccag cctgggcgac agagcaagac      5820
tctgtcaaaa aaaagaaaa aaaaaaaag aaaatacagg acttttgggg caaaattcca        5880
cctaacctcc attaatttgt taactaagat tttactaaaa aaataaaata gtgaagttgg      5940
acctttcaga aggaacggct attaaaacat gtatttagta tgttatggga gaaactttct     6000
cctaacaggg accaatgtta aagaggctct atgtcctcac tacatagtga gttcaatatt     6060
tatattaact atgagcatcc gtggttatgg gaaaacaaac ctctcagccg agaaagtggg     6120
tccaagtaaa gtgacaatcc atgtgaatga gcctaaagtc aggttgtgtg cttcttagga     6180
tattattttt caagttgttc aggtgaaatg catgcctcaa acactgaaag tctgaaatac     6240
tagccaggag ggaaaagatg aagttcagtg gtttaaaaat cacttctcag gactttaata     6300
taatgtctta aagctgtaga gtactgtttg taagtgaaaa cacacacacc tcagaactga     6360
catacaaaga acttattttg actacgtcag gtcagttagg gagttagctt gagaagggta     6420
ctgtcaatat aacacaaagc ctgaggtgaa aaccagaaga agaaaatagc aattgcagcc     6480
tttccccacc agggagcttc cagagaagct ctcatctgct gtgggtttga gagtgactta     6540
attttgtgtt tgttgggttc tgcacaggag gagactgcca ggaggagggg tggggtcccc     6600
aagctgatga ggaaaaaagg accgtgtgat ctgagagaga gacctctggg gccaattagt     6660
ggctgacctt aggtcagatt ctaaaacaat agcttctaga gtgtagtagg aaaaggaatt     6720
atctcccatc tcccttgcta ttcactgcta tacttattgc ttctgaccag cgttttctct     6780
tctccctcaa ggaaatagga tgtaccctta agactttctc actatttacc aattcccaaa     6840
gccagcgcac agcccctga tgaggaatag aacaggagaa gtagggctcc ctccgacacc      6900
cccactcttg ttctgcattc gttcccatga tctgcacagc aatgctggct gggagattgt     6960
gccgcataca aaggactgaa cctgccagac tcaggctgct atcagagatc cgtgctcagc     7020
agggagcagg cagaaggtca agagatagaa caaggaccag ggaccatccg atctatcccc     7080
aaccccagta aagaggagga ggaaggaagg ctacggaggt cttcttccct ttctcctccc     7140
cttcttcctc accagcctca cttctcccac ctcagatcct tctctgaaccc cacagtggaa     7200 tccactctga ggagggaaat taggataagg agatttcaaa tagcaggagg ctgggagaga     7260
aggagagagt cggggcaggg cagaaaattg cacaccgagc aggagggagc tcagaagcct     7320
ttctcctggg ctcacatatc ctggcataaa agatgacaca tccagtcatt ttttttttta     7380
agagacggac tcttgctctg tcacccaggc tggagtgcag tggcgcaatc tcggctcact     7440
gcaagctccg cctcctgggt tcatgccatt ctcctgcccc agcctccaga gtagctggga     7500
ctacaggtgc ccgccaccac acccggataa ttttttttt tttttttgta ttttagtag      7560 agacggggtt tcaccgtgtt attcaggatg gtcttgatct cctgacctca tgatccgccc     7620
gcctcggcct cccaaagtgc tgggattaca ggcgtgagcc agtcatcttt taaatgaag      7680 gcgagggttt aagtctgaga ctgcctgtaa aatgaactgg gtggtctgaa aaagaagaat    7740
aatcccaacc agcaaaaat gtactaagga tggtgttaat ttatttcctt ataaataaaa     7800
gatttcaatt ggatatttac aagaaaacag caacccattt cacattcttc caagtgtttc     7860
ctttcaagct gtgatttgca gaaccaatta attggctacc ataacccaac atgtcaaagc     7920
caactgcttg tctatggaca ctgaactctg tctctgtctt gagggctatt ttcacacttg     7980
ggactctatc agcagcaatc ccccagcccc gcccttgtta cttaccacca tgcccgcttc     8040
```

```
actccattgc atcatttgtg catacattgt tttcgctcag tagactcctt tgctcctttg    8100
aaagcaaagg ttacccttac tcatctcagt ataccctcta cctgcactcc ccttaaccaa    8160
gcgacccgag caactaacac aaggcttcgg acacactaga catccaataa gtgcttacta    8220
gagtatccag tcaaatgctg gaaaacaagc cccttcaaaa tttaggaagt ctgaaagaat    8280
gttaagggct tactactgag aagatgctca ataaatattg gttgatcatt ctgaagaaat    8340
ttcgtatcat ttcaatgact attgctaaaa aagacattct gaccagtgaa tcattggatc    8400
tagggtttac tttcttaggg tatttctgca catttgtgga gcccacagtt gtgcctctgg    8460
aggactctgc ctaatgttcc tgcctcagtc tcagcagcac cactgaaact cagaggcttt    8520
ggagttctgt gttagatcct gttcatgaaa aaactcaact gccttaaaaa ggatcaaaaa    8580
ccacagtatg aaaagagagt gttttatctt tttactgtct taatcggatc ttaaatattg    8640
atatgcttta aatttattta tctttggatc taacttaaac aagatgaaga ttggaagagt    8700
tttggagaga agggtgcagc attccaaatt gtgcccttag tgtactcata aggaattgtt    8760
tttggctcaa agaacggaca atgtgccatg acaatcagcc taggaaggaa gcactactta    8820
ctagtgatag gcttggtgac gactgctgat tggttttgtc agctgactta cttgaatgta    8880
gttgtcaaca actccccaag caaagtcaca gggaaatgtc ccttctaggg ctgattttc    8940
aggtaaagga gggaagccat ttttctctat cagcttttgg tagaacaagg ctgaagactt    9000
tggcaacaac atcttgtcct ggcttagaaa gtcaacatag aagagtccac gcctgatgct    9060
gtaacctctg tgccactcga aaccatccat gagggaccat gcggtatacc cgatgacatc    9120
caccccatcc agcttgatgg ctgcaaaggg aagaggggac aagagcaaca tgacccttcg    9180
ctgggcactt gcatcatggt tcaagagcag ctgagcgttt cctacttaaa taaataaagt    9240
gtaatgcttc tcgtttggta agccaatgat ttttcttctt gacgaaagac tctaatcaaa    9300
cctatataac tctacaaata aatgccctca aaattggcct atctaatatg ttttttggat    9360
ttctgagcac cttgaaaaaa tagttcctta tttataatag atattctaca gggctggaaa    9420
gatgtcttgt accactttcc atcctagaca cccagctttg tgtctgatgc aataaataaa    9480
taaatgaagg ctttaaaagc atgatctatt tatactattt tctctagaaa acatggacat    9540
tcctttttct ttaaagtgtt ttattcaacc aaaataacaa gaactgaaaa acatgtgcag    9600
agagctagat atcctgggat ttgttttatg ttcaatttaa tctaaaaatc tagattaata    9660
actgaaagtt aagtaattac aaatattata acccagtttc tcatttacaa atgggttttt    9720
aaaaattaat tcaagttcct caagactcca aatgagaaag gtgttaaatg aatgcattct    9780
actattgcca aaatgaatgt ctccattagg atttaaaaat ataaattcac atcatttatg    9840
ttagataatc ttagagattt ttttccagaa gattttggca ggaaatgaga actttaccca    9900
caatcatacc ttttaaggtt tccatgatga actttttgag gtaatacata tatttggcat    9960
catctctctt ggtggtccct gagacaaacc agccatttc cacaataaat atttgaggat   10020
ggttaaattc aaggtcaatc caggaaagca gttgcctcag gttgggagat tccaattggc   10080
ggaacttcat gtgagggtcc aaaagttgaa aactcaaggt gggtccaaag caaagagcaa   10140
aaaagtcagc agttccttg atgaactttt tctcagattc agtaaaatca ggcagaatag   10200
atgaaaggtt attcttcatg ctctcgggat agtcaccatc aataaatacg ggtttggcaa   10260
accaacctag tacaaagtcc agagattttt gacattcttt gatgctgtgg tcggtcattc   10320
ttcgaggatt gatccagtga gagcttaggg caatggacac ctgacctccc tgagtgggac   10380
ggaaagaagt attgtagaga tgccagactt tggcatgagc ctatgaagag aaaaaccatg   10440
```

```
gcaaatttat ctctagttgt gaggagaaat gcaatataat acttgaatcc ccaaatcaga    10500
ttatatctgt ttctcatcaa gcctaactta atgactaaca atataaaaat cagctagaac    10560
caatacatta tttcaaaggt aggtcacccc acagtgaggt gctacgggga ctagagttat    10620
ttccattggt ctttagcagt cagtggaaaa atgtagattc cttgggttga gtgtgtagtt    10680
atccacattt tgaaaagcta atgaaataaa agaatttgtt ataatagctt actatttaat    10740
tgactttgga ttatgtactt tttaatttac gggtttcatg aaaagaacca atgctacatc    10800
tgtgatcaca ccaggaattt ctaaatagga ttatattttt tatcctgaga ctgggagttt    10860
tcaaaatgac tcaggtcgtt ggagttaatt tactgtttca tagtcatctc tcgtagctaa    10920
aattctaaca agcaatcttc tttcttccca agaagaatca gtacaataaa ttaaagaacc    10980
cactccagca tctaaccttg cctaccctc cagaactctg gacagttct ggtttcccac    11040 agacccaggg tgctaggtcc aagccaagag caaaaacag caaaatacag ctgcaaggaa    11100
atcagttgtc cattgttagc atgcagccag gagtttcgta cagcagtgaa aagggctttg    11160
catccataaa accaactta tactcccata aattcttact gacttctaat atcttatttt    11220
catttgtttc ctttttattt acaaggaaga gtgaaaatta tagggttttt ttctccccta    11280
cttgaagtga gtttctcttt ctctttgaat tccttgattt actctcccta ttttcctaca    11340
aatacaagtg ttgtttatca gcctttattc ccctaacata tcctctttga aaactccatt    11400
caaattctct gtttgactcc atatattctc caaaatgatc atgccaattt tcattccact    11460
ccctgggcct gcagaaactc ctttgttcat taagccaaac agcctcttca acatatccta    11520
aatattcctc tcgtggttca tttcagtaca ggcatccaag aatggcctca tcaacattct    11580
tatgggttca gccaaacatt tcaatgaaat aagatagttt gtggctaact tttctttta    11640 gtttcttggt gaacatatct actatgtttc atttcactaa atgtattttt tcacgacctg    11700
aagcagctat ctatatgcta agaaggaaat agagaatcaa atgttgatca aaagaatagt    11760
ggcacttgct tatgtggtct aagaaaccag ggtcttaatc gtgccacact tctgtcagtt    11820
ttatgatgtc tcctacccttt ctccatcttc cccatcacac ctccccaggc ctcccttcct    11880
cattgaaagg aaacctcatg atgttaacag ttaaacagag gctgggcatg atggctcatg    11940
cctgcagtcc cagcactttg ggaggccgaa atcccagcac attgggagaa tcccttgata    12000
ccaggagttc acaactagcc tgcgcaaaga gtgagacccc atttctacca aaaaatccaa    12060
aacttaacca gtcatggtgc tgtgtgcctg tagtcccagc tactaggaag gctgaggcag    12120
gaggatcact tgagcccagg agatggaggc ttcggtgagc catgttcaca ccactgacct    12180
ccagcccagg tgacagagaa agatatgtct cacaaaacaa aaacaaacaa acaaataaac    12240
acaacagtta aacataaaat ccattgagca gtccaggcta gtactcagca attaacctct    12300
tgagaccaaa accagggga cttttcctaat ttgaccgcat ttgaggccta tgaacagtca    12360
tgtcctaaat ctaccaggca ccttctgta gaataagcgc tgaacaggga atgaaagagt    12420
gaaagcaaac aaagaatgca ttaatctcgg tcagttttgc aggtagctga agtcatacaa    12480 tggaatttt tataattata gaccactctt ctaaccttga ggactttaac aaggctcaga    12540
ggaggaggtt tagcaaggac atgataaatg acctgggcca taaggaaaga catatatggt    12600
ctctgatggc agataaagtt cctgctccat cactctttt tgttttgttt tgttttaaga    12660
ctgggtctca ctctgtcacc ctgactggag tgaagtgatg ggatcatggc tcactgcagc    12720
ctctacctcc caggctcaag caatcgtccc acttcaacct cccaagtaac tgggactaca    12780
```

```
ggcacctggc taatttctttt tttatttcta gtagagatta aatcttgctg tgttgccctg   12840
gctggtctta aactcctggg ctcaagcgat cctcagcctc ccacctcagc ctcccaaagt   12900
gctgagatta caggcatgag ccaccgcacc tggccttcgt cactcttgag ttggccacat   12960
tccttaattt gggcaggtaa atctaacttt cctgtgcctc acaggactgt tgtgaggact   13020
aaatgagaca attcatgtaa aactcctaat gcagagtttg caacagtagg atctccatga   13080
atgcgtatcc cttctctctc tagaggatga acaaaccaaa aggaagaata ttgcaggtgg   13140
aggaaacaac ccctgctaag gaattcagcc cacagtagcg atgtgacata ctgataaaac   13200
ttggggtttg gagtagaaga gacttaggtt tagattccct actcctctaa ctatgaccgg   13260
tgtgagcctc acttactgct ctgtacaagt gggaatgaca tctattgtcc cgtagggaca   13320
ctgtgaggat taaatgacat aatgcaagtg agagtgtctt ttaagtagtt gattatttta   13380
cagaggaata cacttgcagc attagaaagc atttcagata tcatttggat taactgctca   13440
cctcatgcca aaaccctgtt gaaacttatt tgattactct ttacagcatc ctaacttggt   13500
ggtcatccca ggcatggcac cgtctctaag aaatcgctgc aaccccatgg accccatac    13560 tgtgctgcat gccctcctc tggacaccaa gagtctcaca catacttctc taatatcatt    13620
tactgcagat aatgaggggc atccctcccc agaatgagct ccctgtggag ttccctcact   13680
ccctccctgg cacacggagg ccctcattgt ctgttaaact gagttgaacc agcttcacca   13740
cctcttcacg agccagttca ctcccttgc ggatggtaca tttgacagat taaatattat     13800
gaggcagagt gtgggaaggt cgctatttag gatgttgcaa caaataagga tgattaacag   13860
ggagatggtt acatatagtc ttgcaatgct ttctaattat tcctggtatg ttaatcttat    13920
aggcttgttg tcttaagatt gggatttaat aaagttattg acaaggactc agtgaagtta   13980
ttaactgtat ggccaagaac attcatctaa atactatttt taatagccaa acattgaaaa   14040
caattgaaat gtctaatatt caaatatgtt taccatgtat gaatgtttta atacatgata   14100
gtataactaa agaaatacca ttattcagga taatgcaaaa gaatatcaat taacatgtaa   14160
aaacgtttct aaaatactct gaacagaaaa aggttataaa atagcaagta gagtttagta   14220
gcactttgat ctggagggat ttataacttg ttaaaacctg ttttacagca ggattgtggg   14280
tggtataatt cacttcattt tacccatcta tatatttttt tcatttccta ccataaacat    14340
gtattgctct agagattaaa aaaataaaat tcaaaagggg aaaatggctg atagcagttg   14400
gatggcaggc ctgtttgatg gttattaaaa gtctctgctt catctcaccc tgcccacctg   14460
ttctccaact tgcccatgg tctctgcctg aaatccaagt cccaggcaca ttgaaccca     14520 cttgaagttc taagattatc tagccttcca tgctttggag gtgcagctct ctaaggtatg   14580
ttttgcctat tcccagttcc ttcactctta cacccacttt aaaactcagc ttagatgtcg   14640
ccacctccag gaagcattcc ttgacatctt ccctctccct agcatggact aaatgtctgt   14700
tctatgtgtt tctatgatgg tcctctatcc aagaccttaa ccatatatta ttgcatttat    14760
ttaagtgtct ggattgtagg tgttttgaag gcattgagtc ttttatctct cagattctag   14820
caaagtctct gcaacagagc cagtattcaa taaacagatc tagaggaatg aaggctggca   14880
ctaagaacca gatcaaaggg tctaggacag aagcaacatt tttctgggct gaagcaggaa   14940
aactctctca taagctactc tggttcttat tttgctttca agatcatgaa agacagaaaa   15000
ctttcaggca cataccatta aaaaataaat tagaaggaat tttatatggc aggcctctga   15060
gaataatacc atattatctc ataatgtgct aatgatccac tttggggtat aagtctctct   15120
cgtatgtgat gccctccttg cttccttctt accttccatc tagattttga aacatggagt   15180
```

```
ctgaaaaaaa tctagaagaa aaatggatct ggaattcctt cctaccaact agctagtagc   15240
cccaaatttt ggaagtcgag gaaaataatt ttggaagtcg aggaaaatac tctgaattcc   15300
acagaacata tagacatttt ctctttggct aaattataag ctccctgtca tttgcctata   15360
cgtatccccc acagaaccca acaaaaagtt tcacacaaat aagctgcttt taaatggtgg   15420
gtggaaggaa acaggtgatg agcctcaggt ccactccagc tttctgcctt gggttgtgtt   15480
ctaggtatgg ctgaggcaaa tgaagcccac acaatacaca gcagtattgc tgagctgaaa   15540
aggaagaaag caatgatgag gactctgaag caggtcaacg tactggagag aagaaatcta   15600
cacaaaggaa ggacctagaa gtctgcatga gatttcccaa ggatccttgg ctgtccatgc   15660
acaggacaag attttgtgag gctcagcaaa gagaagcagc cacaggtctg ggagatgaat   15720
accaaaggtt gggtaggtct ggaaaatatt gcatttcaga atagccagag tagaaaaatg   15780
cagctgagca cttcaggcat ccagctgaaa ctcaggaagg tcattacctg agaagtaaga   15840
acaaagcagg aatagaccag ctctaacaaa gactaaagcc acatcaagta aatctggtaa   15900
tttaacttct tggcagaact aaatacaaca cccctttaaaa agagacaata ttgaccaggc   15960
ttcctataat atctcattca tagcacacag agcataataa aaatctacta gatatgtgaa   16020
aaagcaggaa aatgaaaccc ttaattaagg ggaaaaaaag aagtattcaa tatcaacaga   16080
agccaagatg tcccagacat tgggattagc agaggacttt aaaatagcta ttataaatat   16140
ttttaaggat ttcaaagaaa agatagatat aatgaacaaa tggagaataa caacagagaa   16200
acaacaactg aagaaaacat gaaaattcta gaactgaaaa gcgaaataaa caaattttg    16260 aatgggatta acaatattaa ttctaaatgg aataataata agaataaata atgtaatccc   16320
taaaactcac aaagatatta aaaggtttct ctaaaaagcc aataaaataa gaaaatgaa    16380 ttaccaaaaa atctgattt tccaaaagat gcagaaataa aaaacaaaaa acacatggaa    16440
caaaaagaaa acaaatagca ggattgtaaa cataaaccca aacatatcaa taaatattca   16500
aatacacatg gactaaatgt tccaagtaca agacagatgc tatgaaagca gattttaggg   16560
gctgggtgca gtggctcacg cctgtaatcc cagcactttg ggaggccaag gcaggtggat   16620
cacgaggtca ggagttcaag accagcctga ccaacatggt gaaacccgt ctctactaaa    16680 aatacaggtg cctgtaatcc cagctactcg ggaggctgag acaggagaat tgcttgaacc   16740
cgggaagcag agattgcagt gagccaagat tgtgccactg cactccagcc tgggcaacag   16800
agcaagactc catctcaaaa aaaaaaaaaa gaaagtagat tttagaaaag taagtttcaa   16860
ttacattctg tgtgcaagaa atatactata aatataagt gatcatgtaa aagaaaaaga    16920
atggaaagag acatattatg caaatggaca gcattaaaaa tctggcatgg ttatattaat   16980
aacaaaatgg aggctttgaa catcactata attcacctag agctaacaga catatatatt   17040
aatagaacat gccacccacc taaaaaaatc agaatataca tttttctcaa gtgcacatga   17100
tacattttcc aggatagatc atatgttaga ccagaaaata agtcttaata aattttaaac   17160
tgttgagatc ataaaaagta ttgtttctta ccacaatgaa atgaaactag aaatcaataa   17220
caaaaggaaa actagaatat tcacaaatac gtggaaattg ttgacacact caaacaagca   17280
ataagtcaat gaagaaatca caaggtagat tagcaaaagc ttaaatgtgt atataaaaaa   17340
ctaactgaat atgtaacata ccaatactta taaattgcag caaaagcaat gctcagagga   17400
aattttatag ctttaaatac ctacatcaaa aaaaaaaaca agatatatct caataactta   17460
gtcttccacc ttaagaaaat aaaaaagaag agccaactaa actcacagct aacagaataa   17520
```

```
aggaactaat aaaaattaga atggatatac acaaaataca gagcagaaaa attatagaat    17580
caacaaaatc aaaagttggt tctttgaaaa aaatcaacaa aacagaccaa cctttagcaa    17640
gactgactag agaaaaaaag agaaagaag caaattaatg caatcataaa agaaagtggt    17700
aactgacctt ttctgtatat catttctata ataaaaagga ttacaagaga acattatgaa    17760
catttggatg ccagcaaatt agataacaga gatgacctgg ccaaattccc ggaagcacac    17820
acattaccaa aagtggctaa ggaaaaaata caaaatctaa tctaggtgta aaagagattg    17880
aattagtaat caaaaacttt caaactaaga aaagcccagg actagtggct ttaatagtga    17940
attgtaccaa atatttaaag aagaattaac acgactcttt tcaagctctt caaaaaatag    18000 aagaagaac actttctaac ttagccaatg tggccagcat tatcttgata ccaaagccag    18060
ataaagccac cacaagaaaa taatagttac agatcaatat cccttatgaa atagatgca    18120 aaagaatgca accaaatact aacaaaacaa atccagcagc atattttaag aattatacag    18180
cacaatcaac tagtatttat tccaggaatg caaagatggg taaacattaa aaaaaatcgt    18240
tgtaatgcat tacatcaata gagtaaaggg ggagaaaacc catatgatta tctcaattaa    18300
cgcaggaaaa gcattttaca aaaatctgaa agtctttcat aataaaaaca ctcagaaaac    18360
tacgactaga aaggaacttc cttaatatga ttaagaaaag catttatggg ccgggcgtgg    18420
tggctcatgc ctgtaatccc agcactttgg gaggccgagg cgggcggatc atctgaggtc    18480
aggagttcga gagcagcctg accaacatcg agaaaccccg tctctactaa aaatacaaaa    18540
ttagtcggtg tggtggcagg cacctgtaat cccagctact ctggaggctg aggcaggaga    18600
atcgcttgaa cccaggaggc agaggttgtg atgagccgag atcacgccac tgcactccag    18660
cccaggcaac aagagaaact ccgtctcaaa caaaaaaaca aacaaacaaa aaattatgaa    18720
aatccacagc caacattaca gtgaaaggct gagagcttca cccctaacat caggattgaa    18780
aggaagatgc ctgctttcac tattgctctc taacattgta ctagaagttc ttgccagagc    18840
aattaggaag gaaaaaacta tccaagttag aaaagaagta aaactatccc tattcacaga    18900
taacatgatt ctacatatgg aaaatcctaa agaattcaca aaaatctatt gcaaaaaata    18960
aacgatttca gcaaaattgc aaggtacaag atcaacacac aatagtcagt tgtatttctg    19020
tacaatagca atgaacagtc caaaagaaa attaagaaaa caattccatt tataataagt    19080
tccaaaagaa taaatatac acaggagtac atttaaacac tctcaccatt gctattaaaa    19140
ttgtactgga ggtcctagcc agtgcagtaa ggcaaataaa aacataaaag gcatgttgat    19200
tgaaaaggga aaaacaaaca aacaaaaaaa caaactttgt tgttcattaa aaacatgatt    19260
gtctgtgtag aaatcctaag atttttaaaa aaacagaaaa actattaaaa cgaataagtt    19320
aatttagcaa gttggcagaa tacaatgtca atacaaaaat cagctgcatt tggccaggaa    19380
cactggctca cacccatagt cccagctact tgggaggctg aggtgagagg ctcccttcag    19440
cccaggagtt caagtctgca gtgagtgctg atcacgccac tgcactccag cctgggtgac    19500
aaagtaagcc tctgtctcaa aaaaaaaaaa aaaaaaaaa aaaaagaaaa atcaattgca    19560
tttatatatg aacagaaaac aaacagaaaa taaattttaa atacaatgcc acttacagtg    19620
gtaccaaaat cgtaaaatac ttagaaaata atttaacaaa agatgtgcaa gtttgctaca    19680
attataacac attgctaaca gaaattaaag aatatgtaaa taagaatga gataccattt    19740 tcatggattg aagagtcaa tattgttatc agatttcccc agattgacct actgaatcaa    19800
caccatctca tccagaatcc caataaactt tttgtagaaa tgaataagtt gattctaaaa    19860
tatatacaat aagaacataa aacagctaaa ataactagaa aaaggaaaaa cacagttgaa    19920
```

```
acattcacat tacctgattt caagacttat tataaagcta taattattta atataggg tg   19980
atattggcat aaggatagac aaatacatca aaggagcaga acagaaaatt ccaaaataaa   20040
cccacagcca actgatttct aacgaatgca tcaaagcaat tatgtggcaa caggaaagac   20100
gtttcaacaa atgatccttg acaactggaa aagtgtatga aaaaattaaa ccccaatctt   20160
gcataaaaat ttgagacaga tcatagatcc aaagctaaaa gctaaaacta taaaacttat   20220
agaacaaaat gtaagagaat agtctcttta tcttggagta ggaaaatact tcttagaaca   20280
cagaaagcac tatataaata tacatatatt aaaatatctc ccctcagtat gtgatttgcc   20340
tttacatttc gctaacattt gatgagcagg ttttaatttt gacgtcgtcc aatttatcag   20400
tttttgttta tgattagtat ataattgaca aaataattat atccgaaata aatacgtaag   20460
cctacctatc agtagtaaaa gaaaataac tcccctccc accatgagca aaatatttga    20520
atagatattt cacaagagaa tcttcaccaa tgctcagtaa acacatagaa atgtcctcaa   20580
catcaacact atcaggaaaa tgcaaattaa accccaacg agcactcaca cccactaaga    20640
tgcctacaac taaaaatact ggcaacaggc tgggtacagt gactcacgcc tataatccca   20700
gcaatttggg aggctgaggc gggcgaatca cttgaagcca ggagttcgag accaacttgg   20760
gcaacatggt gaaaccccat ctctactaaa aatacaaaaa ttagctgggt gtggtggcac   20820
gcctctgtag tcccagctgc ttgggatgct gaggcatgaa aatcccttga acctgggagg   20880
cagaggttgc agtgagccga gatcacacca ttgtatgcct gggcaacaca gtgagatgct   20940
gcctcaaaaa aaaaaaaga ctaccaacaa attctggcaa ggacgtaaaa caacggaaat    21000
ttcatacatt gatggtggga gtataaatag taccaccact ttggaaaact atttgacagt   21060
ttcttataaa attaaagata gattttctct ataatctagc aagttcatac ctaggtattt   21120
accaagagaa atgacaacat aagcccccca aaagacttgt acaatattaa gataaaactt   21180
acaaattgat atgttcaaag atgctggccg ggcacagtgg ctcaagactg taatcccagc   21240
actttgggag gccgaggtgg gtggatcacc tgaggtcagg acttcgagac cagcctgacc   21300
aacatggtga aaccccgtct ctactgaaaa tacgaaactt agccaggtgt ggtggcacat   21360
gcctgtaatc ccaggtactc gggaggctga ggcaggagaa tcgcttggac ccacgtggca   21420
gaagctgcag tgagctgaga tcgctgccac tgcactccag cctggggaac aagagcgaaa   21480
ccccatcaca attaaaaaaa aatgcttata gtagcttaaa tcgcaatagc agaaaactga   21540
aaacaacaca aatgtccatt cacaggagaa tgtataaaca gtgtggtttg tttatacaat   21600
ggaatactat tcattaatgc aaagagtgaa ctactcttct aggcagtaat atggattaat   21660
gtcaaaaaga ttgtgtagat tgaaagaact cagacacaga gtacattcac agagttgttt   21720
gattccattt acataaagtc ccaaaatcag tctgtggtga tgggaatcac aacagcggtt   21780
tcctacggag gtgagaattg attagaagtc acaagaaac tttctggggt aatgagaata    21840
ttctatatct ttacttggat attttgttaca gatatccata cacatacagg tgtatgtagt   21900
catcaaaatt catcaaattg cttataaaac atgtgcatca attttaaaga tctatagatt   21960
aataaatata taatagatta atatcttagt cattggcaaa gctattcagg tatagaaata   22020
taattaccta caatttatgt ggcaagagaa tactgatttt ctccgaaaca taaattcatc   22080
tttgaaacta ctacagtaat ctgttagtta aaaaaatata tatatttagc ttttaattgc   22140
agggatcata ttcattcaac aaatattaca ctaggcactt ttctagggga ttcaaaatat   22200
gatcctgttc ttatggagct tacattcttg ggaagaagag agataacaaa tgaaaacaaa   22260
```

```
gcagagaaag gatagaaggt aacagggatt gggatgggaa ggcagtttag acaggcaagt   22320
cttcttcaag gaagcattgt ctgaggatct gtaacagaaa aagtgaagaa tgctaaaaaa   22380
gactgggacc tgagatgggg gtgtgtggaa ggagcagaga acccggagga ttgggcagag   22440
gcggtagagg gtacgggaag ggcattccag gcagagttga gcaagtgatg agagcataga   22500
ctcagccagg ctttcctaat tctgcccccct tattagctgt gggaccttgg gcaaattatc   22560
tgaagtctgt gcctctattt cctcatctgt aaagtaggga tagtaatagc acctcatggt   22620
tatatccttg tgaggattaa ctaagtcaat acatggaaag cacttagaat tgtaaatgct   22680
atggaagtgt ttcttattca agtgttgtag taatgtttga ttggtaagtt caaagatact   22740
tacagtatta ggttggtgcc aaagtaattg cagttttgc catttaaaaa gtaatggcaa   22800
aaactgcaat tactttggca ccaacctaat agctttaatc acaatagcaa aaaaactgaa   22860
aacaacataa atgtccattt acaggagaat gtatgaacag tgtggtctgt taatacaatg   22920
gaatattact ccttgtttcc ttgtgactct taatcaattc tcaacatagg agaccactgt   22980
tgtgattccc agtacataga gtgattgtgg gactttatgt aaatggaatc aaacaactat   23040
gtaaatgtac tcattgtgtc tgggtaatga ttgataagtt tccaaaaatc agtggctact   23100
acgtggaaaa taggatctag gaggacaaaa tgggagcaag gataccagtt agacaactat   23160
tgcaatggtc caggcaaaag atcatgatgg tttggaccaa aaaagatagt aacaagtggc   23220
tagatttagg ctattattga aggcagaatc tgtagaacct gctgatgaat tggatgttac   23280
atgttgcatg tgaggagggg aagaggaatc aaggaactca aagaaaacaa aaaataagga   23340
gttggggaag ggaagggatc aagttctatt taggtcacaa gtctagcttt caatgaagat   23400
gcctggtact cagctgagta tatgaagctg aagttggaga gacatggatg gtatcaccaa   23460
tcacccaaat atgtttcagg ggtaaactg aatggaccgc ttttgttat ctatcattca   23520 ttagatttt taaaaattga atggaataa ttcttaaagg attaatttaa tcctacaaat   23580
aatcttaatt aaatggactg agaccaatgg tggaagaaat gaaatgcagc ccataagcag   23640
aaaataattc aaatagctca tttatgtctt ctccctatct aagaaaaggg ccctccagat   23700
gttactttag ttctgaatta aaggtgaccg ttttcaaaaa ggtcaaagga ttgaaaaaat   23760
tttagaaggc actagagatt tattttcttt ttctttctgg caccctatta cctcaacttc   23820
aagaagagta ttgggattac attgtctgag gacttcctta aaagtcactg ctactgtgtg   23880
gtgtttacat aagcatgcca actagcctga tgtttgtgct cgcagaccaa attatttctc   23940
ttatttctat cagcactatg gtttataagc tgcagttcct taagacagaa tttcaaacag   24000
cctcccacaa aacaaccacc taatagaaca cataaataat ttcccaaaaa taactatcta   24060
caactttatc cacaaaaaat agccagtagt ctctgtgtgc agttccttaa aagttgctca   24120
ggatttaacc aatgcaaggg ggctcatatc tgctttccct gacacccagt tagacgaata   24180
tgtgtgaaca ggcagcagct tggcacccct acctgctttg gacttcttag caaatcaaat   24240
aagttgcatt tctagctctg agcaccaagc cttacagtct tctacaaagt aacaggaaga   24300
ccagtagaat cgcatataaa tgtaaacagc atcacttccc agcctagctg ttttgctaca   24360
gccaggtcag tttctcatta ctcctcatcc agggctgtac ctacgttgga tgccaaccta   24420
ctagccctga agttgcattc tacttttcct tcatatccat atcctttct gccttctgtt   24480 ctggacttgc ctcttctaag aagtagttcc taatgaaccc cacttactct tagtactatc   24540
ttccccaatt atcaactgaa aattctcact tcttccaaat ttggctcaat tcccatctcc   24600
cctgtgaagt cttgtttggc tccccacgtg catttaggca ttcctttccc aatgcacccc   24660
```

```
acccacaagc aggagtaaat aacatgcttc ttcatagttc ttcctaagtt ggtggctctt   24720
caccaagatt gtattatact cccccacaac aataaagttg aatggaaaca acttgaacat   24780
ccaataatgt ggaattattc attcatttat cctttcactc aaatatttat taagtaacta   24840
ctatgggcca tttataattc ttaaattagt tgaaacaacc taaagggcta acaataggga   24900
ttagttaaaa taacccagga ataagacatt aaatgaaata aattattagc aacaaatgat   24960
cagtgttgat aaataaatta taatttatta attttatgag caataaatga tcaccatgga   25020
caaatatagc ttattaaatt acaaactata gttagctata gatagaccac gtacagtatt   25080
acctaatttt ggaatcatat gtacagatgt aaaataaata cacataagac aggattttaa   25140
aggatttgta cagagatagc agttatagtc tctattgagt aggacagtgg gcatttatta   25200
tgttcttctg cttctctgat tttctgactt ttatgtaacg aaatatgtat tgcttttga    25260 ataagaaaac acaaattttt taaaactgga attttcaatt ttggaaaatt ttctagttca   25320
aattatttac tatattgttt ttctaagttg atgatgtctg ctctgcttgt ttagctgttt   25380 tcatttttc ccccacagga tggatggcat agattgttcc aactaattca atcactcact    25440
tttcaatgat tacttattga tttcctaatt tcctattgtt ataccttca gtcattctga    25500 tttctgaaaa aatttgttag aaatgtttta aaaattcctg gcataccaaa attattaata   25560
ctgggaagtc tagtaactgg gatttatttt tcaccaaatg gtctagttga ttaaattatt   25620
ctccaccaaa atgtttttga ccatgttgca tttcatcaaa tcatctggaa ctctcccaaa   25680
aaaactgtaa gatccaaata attaagccaa ataattggac tatcttttct agcctgtgcc   25740
acctctgggg cagatgggtt aggggaaaag agcctttaaa atatccccc atagtggact    25800 ctggctggtg cttagggagg gcaatggagt gtctaagcat ggaaactatg attaaaggaa   25860
cagatataag aatttaccca acgtgttgtg aaaatgatga tatcaaccta attaggctac   25920
aggattaata gtttgtggct tttagaaaat aagattacaa tagacagtat ggggccagaa   25980
tatgaaaagt tttgaatgta aagttatttg gatttgacag aataggtcac aatagattag   26040
cataaatttc tgagacagtg atgatcagtc atatgctcaa aatcatccat tgcagaatgc   26100
attagaatgt gaacagctgg atgtggaaaa ttggcaggat actgccaaaa tgcagataca   26160
attaaggttc tggacaaagg tgatgactac tgaaaagcaa aacaacaggg caatctgaga   26220
gatgtttgga agtgcagaat aaaaagagca tggtgcatta gttacacatt gctcacatgc   26280
tcatgaagaa atattattcg tgagctgggt tgggctccac tgaacatgtc ttctgctctg   26340
gtctcatctg gttaatctag gatggtgttg gctgggacaa atgggacagg ttgcttctgc   26400
cccacatgtc tcatcctcca gtgtactagc ttgggcattt tctcatggca attgcagaga   26460
agcaagagac taagcagaca ctaataagca ttttctcagt gtttgccagc attatgattg   26520
ttggctaaag taagtcacat ggataaagcc agagtcaaag gagaagaagg ccagagtcaa   26580
aggataagct gaatggacac ctagagtaga ggacactgca aagttacatg acaaaaggca   26640
tggatacaat gaagagagga caacattggg gcctttaatt caatcagtct acatcacatt   26700
gtaactcact agacctaggc attaaaaaat aaagtattaa agttgacagc tcatgcatag   26760
tacacagcta gaccaaaaaa taagtcagtc tggaaaggtg aagatatttc ttgctttctg   26820
gctggatcta caggttcaaa aatctttgtt gtttttttta aaagtgacgg ttttgtagat   26880
ggcataattc tcatgccaag acatttattt agtcatttat tcaacaaata ttatccaaca   26940
cctattatat gttggatata taagtgctaa gaatacagaa atgagcaaaa tctcaagctt   27000
```

```
agatgtatgc cattacttac tacatactaa cactgataga aaaactgacc cccaatgttc    27060
cccaagacac aatctaaaag aagatatatg attcctatat taagacccttt tcacaagccc    27120 tcaaacatta gtatattcag tatcatagca ttttgctttc aaaccttttgt taaatcttca    27180 aggtaaagtc tactgctgta tatgattgcc aaaaccttttt attttactct aagaactaag    27240
tttgagatta gatctccttt agaaatcaca tgaaattatg acgtatgcta cttttgagaa    27300
atagacaata agatcaataa taggtttatt ttatttttgtt ttactgtggt aaaacataca    27360
caacttaaaa tttactcttt taattttttaa gtgtacagtt tgataattgt tttagtaagc    27420
atttattatg aactatcata ctgggttcta gagatagtaa acataaaataa ggtaaaacac    27480 ctgctgtcat gaaattttta ccattatcca ctgatttttac aggaaatcta taaaaataaa    27540
agaatactgt tttctcttct tgtacttcaa gttgaatgac ccaagccagg ccaatgagat    27600
accttccctg agattgtttt gctggaatag agacatgtga ctgtcctata ttaggagagg    27660
aagtgaatct ggagttgctg acatgggaag agactctctg ggatgataaa agccaaactg    27720
acccaagcat aagtgcatgt gtgtatgtct gtgtgtattt ctgtgtgtgt ggtgtggtgt    27780
gtgtgtggtg tgtgtgcatg tgtgtggtat gtatgtggta tgtgtatgtg tgtgtggtgt    27840
gtgtgcatgt gtttagtgag ggagaaggag aacccacctt gacagtaatg gttactttag    27900
tgacaaatac agttgttaac atctaaagtc cctggagttc ttcttcaatc ctttgtcctt    27960
gtcgtaaagt ccctttttctt ccttaagctt gttttagtta gggctggtca aatgcaaata    28020
tagagttcct taatacaaat ataaccaaac ttgagattct ataagaatcc gtttagttaa    28080
aagtacactg taacaaccag gcaagacaaa ggtcagggta gttttttgaaa atcatgttgt    28140 aattttggag ttttgttact taagattgtt ttatctggac ttttccaaag taggtgacaa    28200
taaagggctt atttatttgt atttaaataa aaacttcctt caaatgaaat aaaaaagatt    28260
tcataactta cactgggtaa atacatcaat aaatcagaga ttgagcttct tgcttcatta    28320
atttatctgt acagaactaa ttaacattag ttaaatcatt ctattcaata ctaaatcatg    28380
ctgcggtgaa aatcattcca agtcattgac gctaggttgt taacaaaata tccagcttgt    28440
gaccagaatc catctaaccc attaatcaca gaattattac tggagacaca gaggggttcc    28500
aattcctggt ttttgtatct ctgttttttct aatagcaaca aaatgagaac catgagggaa    28560
caggtaggga ggcataggct agatgagaaa aaagagacaa gaagataagg aactcagata    28620
agtgatgttt tccacaaggt cagcaaaagt attccatggt tcatcagtca aataggattt    28680
tttcagtaaa catctattag tataattgcc aataattcca caatacccctc atgaaagagc    28740 tactctccaa tatcaacaaa actgagacaa gcagttttttc ctctataatg gtcactttta    28800
ttttctaaac attctacttc tgcctcctta tctaattctc ctgctttaag ttatcaacag    28860
cagatgccaa cagactctcc ttgagacttt ctttaacagg ctcatttata gctctttgct    28920
tttgaaataa ctcaattcat cttgcagtag agaacgcttt tcacccaaag aaaaagtggc    28980
atgtgagtgt gtgaggattt ctacatcatt gaacaggata caattacagg aaaatgaaat    29040
atgctttatg gagtggtgga tagcggaaag tcatcggcct gctcttttccc ccttcttttcg    29100 catttgcctt tttgtggtag cagtttcgac atggtgttaa gtcaaagttt tcataacac    29160 aaactccact tgtgaaatca acctatgagt agcctcagca attttgaaaa tcaaaataga    29220
agagattagg aaatatcaca gtgcactgcc tgtaataatg gtaagttttt tctgtgaaaa    29280
ttttgtttca atggtgtata ttcaacatgg aaaatgcctt tcttactatg ggtcaagatc    29340
aaaaaagttt ggaactcact ggtctaagtg gagggggatt ttcattccag aagtatttat    29400
```

```
tgagcatcta ttgtgtgcct ggcatgattc tagcactttg gggcacaaca gggaacaaat    29460
caaagaaaaa cccgtgccct cacggagatt ccatttagc aggaggagcg acaaccaaca     29520
acaaacataa taaatgtaaa ttataaagaa tgttctaagg caataagtgc tatgaagaaa    29580
tagagtgagg taaggaaggc ctggggtgcc acggagagga gatacatttt atttattttt    29640
ttttttggtg gcactcacaa gagtctttat tttcctttca ttaaatgtgt tgtgattttc    29700
atcttttcat ttacatctct acagaacaaa atccgtttgt gtccctatta ggcaagaatc    29760
cttcccatcg ctatcagttt tctacaagtt aaaaactacc cttacagaat ttaaaatgcc    29820
ctaatccatg gtaagcagca aattgaacaa aggtgcactg ccttcttcac ccccagagaa    29880
tgaggatagg agaatgggat taactaggca ggcctgcctg aggcctcagt ccagatggac    29940
accaataatc ctgcctcatt tccaagtcta ggaaaatttt ctgtacagtc tcccttgtg    30000 atcataaata atctccaaag attatatttt atcacacaga aaaacctggt ttccttgagc    30060
tttagccaga ttcatttaca aatgtttgac aagggggtgtt aattaacact ctataagcct    30120
cttggctcta cagtgtacag catattaaat tcaaagaaac agcttctgtc tggggatttc    30180
ataaggaatc tcagattgcc ttttcaaaag aaggcaatct gagggtgtgt gttcatctt    30240 tttaaaaaaa aatgctttta tactagaggg tttgtgtttg tctgttttta tcttttttaa    30300
aaaaatgatc ttattggttc ttctattcag aagctaaaaa aacaagccca ataaattcat    30360
tatcacacag tttcatccac agcacctgta aatttggtga cttcctgtct cctcgaggcc    30420 cccagagta gtcagtcttc tccgctgctc gtaaagtggg ttgctggaag tagagaagac    30480
tagttccggg ggcctccagg agacaggaag tcaccaaatg ggggtggtta gaggtgtgcc    30540
tcctttgaga aggagcttgt gaccatagac ttaaggaaag tgaagggttg gttctgtggc    30600
tatggcggta gggcaggttg ggaagaacct tccaggcagg gagaagagta aaaaaaaata    30660
atgccccaag gcacaaatgc aagaccttca gtgtggctgg atggcgtggg gcagcggggc    30720
aggagtcaga gttgagacaa aatgtgttga aacacctttg agagtgtttc cagaacaggg    30780
aactgcagcg ttaactgctg cttgatcccc tgtgacgaaa gggaaatttt taaaacggca    30840
aggcttaaac gtgaaaggaa aagataaaaa gcttttaat caaattgtaa atgacatggt     30900
ttttcactct cccatctccc gtatttctca ctgagtagca gtaaacacag gaaacagcca    30960
cgcataagtt atactgtaac tcctcataaa ggatcctctg gcttctttca tttttcggaa    31020
atgagaattg tgaaggaaga aaaagagag atctgaattg aaatgcactt tttcaggact    31080
gctatttgag ttatcatgta atgattattt cattaagcaa atatttactc aatagacaaa    31140
ttattatgct gggcatcgtg aggggtcaaa cataggtaca tagaataatt acagtataag    31200
tctgaaagtg aaaacgccag aagatggatt ttttttttaa tgcaatggcg attcagagga    31260
aggaaagatt ctttcttgct gagggaaatc aaggaagtct tcctgtagga ggtagtttct    31320
aaaccttata ttgaaagatg tagatcctgg agagacggaa aaaggcattc caggcagatc    31380
actgtgagct ggaaagccag tgatgctgtg gcaaaatgta ttttttacag aaaatagatg    31440
ggtatctccc atgccccatg atcttttacg atataacctg gctgttcctc ccattggcgg    31500
atctgtggac cctccccctt gaatctgtgg gcatgtgact gctctgatag aaatgaagct    31560
acatgatatc aagaataagt gaaaagaaga agaagaagaa gaaagaagt ccataccact     31620 tcctcctagt tctcttggga tgcttgccgg gagggaagct agtttccatg tacagaggct    31680
actaatctga gaccacttgt gtaagcgagg ccaacagaga tgctctggtc cacagccagg    31740
```

```
ctcaaccgcg gatcacatgt gtgagccgtc ttgcatgccc caccccgttc aagcttcaga    31800
tgactgcgga ccagagaaaa actgcgtggg tgagccctcc cctaatcctg acccataagt    31860
ttgtaaacca aataaaatgg ttatttaaag caattaagtc tggggaatt acgcagaaat     31920 agtaatggga acagatgtat ctgggttagt gtttttgtaa tgatgtaatg atgcactct    31980 cagatgtcaa ttaaggttaa agacgttagt ggcaagtcat gactaacatt cttgtccatt   32040
tcagatgctg atgtggacga ggatggtcta ggcatttgct agcacacccc tagatgtaac   32100
ctgtgcaatg cgggaggcag cctggagtca tggaatgtac actgggaata ggggttcaga   32160
aaacctgagt tttgacccca gctctgaccc ttggtaccca caggaaagtc agctaaactc   32220
tctgggtctc tcaatgaatt tacctgcccc aaaatacaaa aaaaaggac tctagaaatt    32280 atcaagcatt atccagtggt atgggttttt taaattactt taaattaata aatgcattta   32340
tatagtttaa aatcaaatag taccaaaggc ttatcatgaa aacagtaagc atctccccca   32400
atcccgtctc taaccctcac tcctgctccc cactggcaac cttttagctc tttcttctcg   32460
taataactat catatttcta aatactatgc tattgtgaaa tttaataatt cattaggata   32520
atgaggagtt agctctttta catgccccat tttcttccct tattttccga aatgtctgtt   32580
cttatttaaa tcattgttag tatttacatg aagattccta tataaatgtt cattttagag   32640
ccaaataggg cactataaca tttccctttt ctaaacagct tttaattttc ccttgaataa   32700
ataatgacct cattattaag cgtgcagaat attctatatg tgatttttc aatgtgttag    32760 tgattctcta tcatgttttc tatgatcgta tctattctgt tgagtctact ttttcaccca   32820
gagctcttcc ttccctgcta gaagtttcca gcctccaagt ccagtttgga ctagatgctg   32880
tcaagagctg ctctcgtcct gggagtttcc tttatttctt atggattgaa accatacttt   32940
ttctatatac tatttcttcc tatgtattta ctacaatttt gctggtgcat atcttccatt   33000
agcttcttag gaaacatgac actgaaggtg aactttcaat acccttacat gtctatacat   33060
tcattgagct aggaactcag tcggctcttt aaagttaaaa gctcatgttc ttcagttctg   33120
gggcatttta ttatattatt tctttacaaa tttcctgacc tgtatttcct tattctctct   33180
ttccagaact tctattagtc tgatgttgga tcttttatgaa tatcctttaa atcttttcc   33240 cttttcaaaaa tgtgttctat ttctttatca tcttgtacta cttttacagc attgctttga   33300
ccttactttt caaatatttt actaaatatt ttgtttcaac tattgtgtta ctgatgttca   33360
agaatttttt atatgttctg atggttcctg tttcagtttg tgtatgtgtt taattcctgc   33420
ataatttatt ttccctggtt tgcttttctg tttattttat tctgtttcat gttgatagct   33480
ttcctcaaat gtctttcacc agcattgtca cccttgccc ttctgttgta cctgctccct    33540
tttaagcctg ggttcctgat tattgcagga gacaagactc ctgatgtcgg gagtctgcat   33600
gccattccaa attcatcatc tccaagtgtg gtctagcaaa ataatttgca cttatgatca   33660
tgcaacagcc atcagttact ttgagagatt atagaaaata aggcgcttga agaatgaaaa   33720
ttttctcaac tttaaaaggg aagataatgt gaatttcaga aataatagac tcaagcaaaa   33780
ttaggtaatg gttaacaaaa atgcatcagt actatggaag ggaagataac taggagacaa   33840
catggattcc tagaataaat ttaccaaact tagctcagaa aatttttatt gtattatatg   33900
gtgctatgat ttgaatgctt gcccctccaa aactcatgtt gaaatttaat tgccattgta   33960
atagtattaa gcgagacctt taagaggtct cactttaggc caattaggca atgaggtctc   34020
tgtcctcatc aatgaattaa tgctgttatc atagaagtgg gttcaatatc tcaggcatgg   34080
gttccttgta aaaggatgag ttcagcctcc ttttgtctct ctcttgccct ctcaccttcc   34140
```

```
accatgggag aaagcagcaa gaagtctctc accagatgcc agagacttgc ccttggactt    34200
cccagccaac agaactgtga ggaaataaat tcctttaaaa aaaaaaaaaa tagggccagg    34260
cgcggtggct cacgcctgta atcccagcac tttgggaggc cgaggtgagt ggatcacaag    34320
gtcaggagat cgagaccatc ccgactaaca cggtgaaacc ccgtctctac taaaaataca    34380
aaaaattagc caggcatggc ggcaggtgcc tgtagtccca gctactcggg aggctgaggc    34440
aggagaatgg cgtgaacctg ggaggcggag cttggagtga gccgagattg tgccactgca    34500
ctccagcctg ggcaacacag caagactccg tctcaaaaaa taaataaata aataaataaa    34560
taacctagtc tcagctactc ttatagctgt acaaaatgaa ctaagacata cagcatatct    34620
gagaacacaa tagtcatctc tgtatgtaat aatcttgaca gttgctaaac attttgtga     34680 cattcttagg gtcaaaaaga aaagtagagt gcaaataaga tagtactgtt gccacttgaa    34740
aaaatatatt ttaagagtat tcattggttc aacaaaaact tactcgttgc ttattaagta    34800
tcaaatgctg gtcaatgttt gaaacattga ttcatgggac agatcgactt gagagaaggt    34860
gactaacaat atcccacaag gtttattcat aaccctattt ctttgtaact tgttatcatc    34920
aaagggatga aaactcacaa aggcattaat ctaaaacttt gaaaattctc caaaacttga    34980
atccaaaaga gctctacaga gtgtaatgct ataaatatgt gctataacta gcaaaattaa    35040
tatttaaagt gatagaaaaa atatttatgt cttttaaaa ttaaaaatac aagtaatata     35100
tgttcatggt ttaaaatgtc agaacaactt acaagaaaaa tcacagttcc ctgtcctaca    35160
ttgccctaca attcccccag ttctctctag aggcaaccac ttttgactct taagacgttt    35220
tcttttggaa tttacatctc cacacatcca cacttcagga agtatccact gacttcctat    35280
tatgctagat aaggggtttag ctctcttaca caggcaattt agttatacaa tagttttggg    35340
tttaaccgac atttggtatt gacattattc tgccaacatg aatatcattc acagctggac    35400
cttgtaatgt agtaagtaag actgttttcc ttcttatttt tgttttcttt gaagttcata    35460
attgcattgc ttttttgattg gctctgtttt ctttgggact gtggctaatt cttccctcaa    35520
tttccaatag cctctcagca gaaacttccc cagggaagtc acatgagcct ccaatatttt    35580 gggggggacac acttctggaa tctcccccat tctgcactgg ctgatcttag tctgctgcac    35640
atctgacatc atgggtctac agttcatcat ccttttcctg ggttagacct gcccttcat    35700 agatcccatg tcttcctcct tgtcttcctc atgttatgtg gcggttaccc tccaataact    35760
tcctgagaaa gggtttatgg aagatttatt ttttgggact ttgactctca tgaatgattg    35820
acagtttaga taagtatcaa attctaggct ggaaataatt ttcattccct tctctgaagg    35880
gcactcctca ctagtctttg tgatggccaa gaaatgcact gctcagtgtt cctgctataa    35940
ggagcacagt tgactgaggc catcagttgc taccccttg aatctgccat tgcagttgat     36000
cctaagatca tgattctcat cggctactcc cagatgacta acatggcag gggaactaat     36060 gcaggcccat ttcagcaaga tgtggactcc gccaatgggc aacattggct caaggcgtcc    36120
ccatcagcct atgcctgggt tgttctgaga cccacagtgc caactgaaac tcttcccagc    36180
ccatccttct ccctgcccac tctccttcat agttgttgga cacacatcat gatccaaagg    36240
ttcaatgcct cccctagctc cttcccctttt atccttcaca attctttccc caataaattt    36300
cttgtacatc taatcctatc ttgacattta cttctttcag gactcaaact aacacaagag    36360
gggttgggga accagctcat tcactttctg gaaagcaaag agaatgccat tctgagtgtt    36420 gtgtagggc agatagtccc cttgcacaaa tggtgcttca attgctaaat atttcaacag     36480
```

```
cagtaacctg ggaaatatcc tggtggagaa tgtcattgta ggtgcaatga tttaggcatt    36540
ccctgcctac aaggagatgg aattgaatgc tttctgatat attgtattga gactctacag    36600
agagctaatg agaaactgag ggccaataac aaacagttaa aggctcaata taagagccac    36660
agccttctct cctacagtgg aagagtagag aaacttagca gcaggcctag gacctgatag    36720
acttgcagag atttagggat gtttaaatgc tcagccaagg cagatcagtt atgccaaggt    36780
caaggccccg gttggggaaa cctgggaata tttggagctt acagaggtgg cccattcttc    36840
cctagtaaga gatagcactt ctttatgctg aagaggcctc gtccctaaaa agcaacaggt    36900
gcacccctca ggagctgacc cggcactaac gaggattaaa tcctagtata acccacctgg    36960
agacagctgg gcctgataga aagaaaaga tactatatcc caacattgct tcaagattga    37020
gcatgcactg caaatcctga ggagtagcgc tggggtcctt gaccaaggaa ctggaactta    37080
acacaggaca agaaataatt cattatctag ggaacacttt ctccggaagt atgttttcac    37140
gatccagcaa ggaccccagg agacgcggta aagttgctgc tagggtggct ctgagaagcc    37200
tgtaaaaagg gatgccaat gctgagcagg cggaaatgcc tgacattgtt gccctaacag    37260
ctgataaaag aatcaagaag cagagagaag ctggcatgca agaaccagta tattatgtga    37320
ggtcaaacaa cccaccagag gacagtgttt cccagaagtc ccagtaggg agaaagagca    37380 ttcactgcac cctcaggaat atgctcatgg gggtgccaat ctcactgaga cattcagtgg    37440
gggcaccgct ctccaggcca gggctgctgg tagcagaggt gtcacagagc tgggcttgtt    37500
gccacccacg gggatggtca gaagttgaaa ttacagaggc cagatagtga gtggtgctta    37560
actgccagaa gccagggagt tataaagatg gttcatagag catggctaca taaaaagtga    37620 tgacccctg tacagttccc cgacttagcc aattttccaa gctataattc actgactgaa    37680
gaggtgccta ggtccctagg agccaggacc ctgcaataac acagaggtat gacccccca    37740 ccccattctt cccattcaat atgaaaatgc atgtcctcca gctataggaa attttctgga    37800
attacttcat tgtttccttt cctttttacgt cagttaccta ttgctgtgaa atagaccgcc    37860
cccaatttgg agaattgaac taataagaat ttatttttt cctcttgctt ctgtgagtta    37920
atggggtttg gctgggcaaa tccagtcttg agtatgcagc cagggaaggg acactgcaag    37980
ggaaaaggca ctgcaggga gaatgaagga cagaggctag agagagccca gtcccaccca    38040
tgaactatac agtaatcttt acatacttt tacatactta ttcatacaga agagacataa    38100
catgggctgc ctttttaataa tcatacatca acattttaat aaccaattag tattccactg    38160
tataagcgta ccaacattcc tctaacggat taccttaaca catttagctg atgtccagtt    38220
ttaaagaata aaccaccatc agcggtaaac ttcctcttat cttttgcacat tggagatgaa    38280 atttaataag attgaaagtt tgaaaataaa ctaccaaaga gatgacaggg atgtttggct    38340
tcacagcaat tcacaagctg ggggaaaaa acctgagagg ttttagctga ctgcaaacta    38400
atttgagtcc gcggtaaggt gacagccaaa attgttaatg caatcttggg cggcatgaac    38460
aaaattcagt gtctaacaag aaatgtaatc gctgaagcct actctgaaca cctggggcac    38520
tgcttggttc tgcacagcaa atgttaagag aggccttgga aattcccagg ctttcttctt    38580
cagctcctca tccttttccca cctgacgctt cagccattca aaagacctca tgctgtggtg    38640
ggaatggcca cactgtctca cctgtactga cttttgcaagg gatgtttcct agaaaggcac    38700
aatgcccttc tcactttgtg tgcccagcaa gccaagccca gcagcagggc ccactaccta    38760
tttttgtaaa taaagtttta ttgaaacaca gctgtgccca ttcattaaca cattgcccat    38820
ggctgcattc atgctgcaac cacagaactg tgtaatagtt gcaacagaca ctgtaggatc    38880
```

```
tgcaaagtcc aaaacttagc cctctacaga aaaagattgc cagcctctga tcttacaagt    38940
attgctttcc ctgactgctc ccgtactacc tccccaaaac gctaacctat ctctcctttc    39000
ttgaaatagg ttcctaagca agtacttatt tctcttaagg catttataca ttttactgta    39060
attatttgac aattacctct cccctactaa tctgtgacat gagggcagga atcttacctt    39120
atccctcttt tctgacagtg cagaaacttg gaaatggcag ctctggccag gaaggagtaa    39180
aaaggccccc taggttagga gcccctcac agcccatgcc agatagatag gagaaaactg    39240
aatctctcgt gcagcccaag cagtatacct ttggtgagca atgtccacgc tgagttgtgt    39300
ttgactgcag acaatttctg ggagaatgta gttgagtcgg gagtgagacg cccctaccac    39360
tgtccccgca cctgtgcagg gctggcataa aggcctgatg ggaacaaggg gacacaggtc    39420
tctatggaag aacttgggac accgaagaga ggaaaaggca gaggaaagag gaccacatga    39480
tgagaaatca aagagaagag aggacaggcg gggaagagca gcatcccaa gaggctctga    39540 cagggcaacg ggcttgcctc ccatgccccc atcctcccct gcagctttgc agccgtcctc    39600
tggaccctca cgaaaagagc cctacaaata tgcctccttt gggagccagg gctctggact    39660
ctctacaggg tccggcacag ggagaactcc aaccactcgt cctcagtcct ctgcacccat    39720
cagcaggaca atggtgatgg atgatgagac agaggcaggt cccacagaca accctaaacc    39780
ctccccgctg gggagatagg tcgactttcc cctctcctct cctccacctt atcctgaaac    39840
gtcagaagac agagccacct gttcaaaggt tacattcata ttctcagaat tcaacattgc    39900
acctgcctgc cacagggtaa gctctcaaga aatgttcctg actaaatgtc cagtcacctc    39960
catgtcttct tggagcagac attagcatga aggagaaaat tctaggaaga acaaaacgta    40020
ctggtctttt caaatatgtg aaagatgtct tttcaaatat gtgaaagatg tcttgtcaaa    40080
aagtgacttg ctttattctt tgagatttag gaaggcaaag agacagtcac ggaggagtcc    40140
tgtgcagcag caggttcaat atgaaagaga aaatcaaggg ggcaacttga gtggaactga    40200
gttcctcctg cttcaaaggg tcaagcaaaa gctagctgac cccaggagag ccactgtaag    40260
gagttcgtcc tggagagaag tgtaacctgg gattttccaa attccttctg attctaacat    40320
tctaattatc aaataaaatg cacttataga tatggaaata acatttgctt aaccattata    40380
tttaaaatta atgtacatca ctgctttcag tttgagtatt ttatcaagct ataatgatac    40440
cggttcatgg atgacgtgac atctgtactt caaacaaaaa atgttaataa aaaaatctat    40500
tgaaactggg gccacaaaag ttcaatcaat atttatcttt ggtttagtca atatataaag    40560
ttatatcagt cataaacttt agtatgtatc tttttaccac caagctggat ccagaaagat    40620
atttgataat gtgttttatg taaaaatacg ttatttcaaa aatgatttga tagttttttgg   40680 tcaaatgcta ttgaaataat ttcaaagaag aggcaaatta agtagttaag tgaggctacc    40740
atgtctaatg catttgtatg attccttcta aacagctcaa gaggaccatt tctcaagtat    40800
tttgctatta ttactattat tattaatgat aaatttatag ctcacttttg tagagctttt    40860 tgtattttt caaaacacgt tgacatatat aaggtgcttt taattctcac aatatgcctg    40920
ggagttaggc aatgtggtag agcctgctgg ttatcctaaa tgatctgttc ccatctgatt    40980
tcaacttaat agaatcattc actgagcacc cggctcctca ggggacaatt atttgcagac    41040
tccttttgac catgtgactg agttctgccc aagggacagt gataggtgca gcttccaggt    41100
caggcacttg agaggccacc ttttccctct tcctctcttt tcctgtccac tggatgaaat    41160
tgggatatta tgtgctctgg aaatcaacaa aggtcacata acgtatctgc ctaggaaaat    41220
```

```
ctttactgtt cttcctcact ctttaaaact ccttcccaga tattgtgtga gagcagactg   41280
caagcgcaat attccattta caagaaagaa tatggacacg ttgaaaccag aaatatgtat   41340
tttacctctc cacttatgcc tttattaaaa attgtatttc tttcctctgt gccaagcact   41400
gagataagca ctacaaattt tgaaataaat atgataggta gtctgtgctc ttaagagagc   41460
cacaactgag taaatgatcc attctacctg tggttattgc agaatgaaaa tatttgagtc   41520
aagtctctga agggtaagta agagtttacc ccaagataaa gaggggaaaa aggcatcctt   41580
caggttatct tcatactcag aatacatcaa aatagagcat ataaaagtca cattctgctt   41640
atctgtttaa atatagattt caagtataac tttgcatttc tggagaaaat gtggatctga   41700
gacaattcaa taagctgtgt gttttttactc acctattatt acttgtcctc ccagtaagca   41760
tgtattctat tctcctcctc cacctaaaat ttcctttatg cctcaaaaag acaacattca   41820
ttgaaagaaa gacaactttt gcacaaatta attataataa aattctagtt tagagcaatg   41880 atattttga gaataaaga taattcagaa ggcttctatg tgcaaaagcc gtgattgcta   41940
catattcagc tggcacagtt aattgttcat tcattttgca cctgagaagg tgcattgaca   42000
ttacttgaat gcatagttta catttttcctt cttttcttca actcaaaata attggcattg   42060
ttaaaacact gctatgattt tgaaatgatt tgattaattc ttttcctatt ttaaaatttt   42120
ttcttggact tgactgtaac cttcaaaaaa caatgtgttc aaaaaggagt gattcaagct   42180
gtttgggaga tattttaact atttctgact aaatgcacta ttgaattcag tagtattcta   42240
aaatttatat taactttcaa tccagttgat tattctagtt atgtacaaaa tacattttt   42300 tgagatggag tttcgctctt gttgctcagg atggagtgca atggtgcgat ctcagctcac   42360
tacaacctct gcctcccatg ttcaaacgat tctcctgcct cagcctccca gtagctggg   42420 attacaggca cctgccacca cgtctggtga attttccata ttttagtag agacggggtt   42480 tcaccatgtt ggccaggctg ttctcaaact cctgatctca ggtgatccac ccgcctcagc   42540
ctcccaaagt gctgggatta caggtgtgag ccactgcgcc cggccccaaa tacattttaa   42600
tgaaagaaaa acttgtaaag tatttctcaa aagtgcatag tatatgtaat ttgagcatat   42660
atacagtaga caaatcgctc atactaatta cttggggaat aaaaattcaa tcagctaaca   42720
aagccccttc caatatatac tcctaaagct ggccaggaga ctttaccacc tgcccttatt   42780
ctgaaaactt cttcataatg ctgcatggtg actacagata gcttttaact ggacattttc   42840
acaatggaat catacatttg atgatgaacc ttaaattttc actgcagatg tcagagtctg   42900
ccacgttatg tttacctatt tttccttatc agattaggat ttggtagtct ctgttccatt   42960
ggaaagtggc tagaaagact gacaaggaga gaaaattcta gtagcatgag tttataaagg   43020
tgaaatcagg ctattcggta aaccagaagc caccttctga gcaccaaggg agggcaagat   43080
gccattttca gagatacaga tgaagggaac aggattaccc cagatagcga aggggtaaaa   43140
tggagacaaa tggttaaata aagggaagag cgcgggagga ggcatctgag caaagcgaag   43200
tcctgtgcag gatgccatag aaggaagaga tggcattcag gcatgggcc caaggagcg   43260 tgttagctgg ctccagaaga acaggtggga tttgaaaaag caaggactct gtcttgtcca   43320
cacataatgt caccctgtag agcatccatc atggcacact gcaggggca aggcagaaat   43380 aagaacccca gcagtgaggc tgttcccatt acccaggcaa ggttggatgg tgtcttgcac   43440
ctccatcgta gtcatagata aggggagaag tggtttgatt ctggacacat cctggaggta   43500
ggtagagctg caggatttgt tgatggatta gaaacaagac atgaaaaagg ggagtagtta   43560
agattcgggg tccaacaact ggaagagtaa aaagtcatca taatagagaa ggggaagcag   43620
```

```
gggtttggtt tgggatgtgt tcgatgtgac atgcccatta gacatccacg tggagaaggc   43680
ggttgtctat gccagtctga tgctcgggga acctgggtg gagactcaaa atctccagtc    43740
atcgggatgc agcagtattc aaagcaatgg cctggagtga atctagacag agccctgagc   43800
cctccactat ttacaggcaa ggtgaggagg aacaagcaaa ggagactaag agggaatcgc   43860
cagggagctg agaggagaag caagggagag ccagggcctg aaatccaagt tgaggaagga   43920
ttcaagggac aagaagtgat ggcttcaaca acattgcag acagatgggc tgagacctgc    43980
acactgatgc taatgctcaa caatgcccag attaatatct cctagcccta cttccttacg   44040
tgaaagaagt cttttcaca ggttccttgc acaaatgttt gcaagaatct caggcggtga    44100
ggggagttga aggtgggaaa tgggaacacg tgtatttcca acttgattct aatcctctta   44160
gaacccatat acagaacaaa gactcagagg cactgctggg gctgaactcc ccaactacag   44220
tccctagtgc tgatttcagg ggacattaag aactttgttt caagagctgt gaaggctgag   44280
cagttggtct tcaagtccga gagaaaaggt gcatcctcct ggattacact caaatgagca   44340
aagcagcctg agctccaagc tctttgtagg agacctctct ctctctgtcc ctcctcccct   44400
ctcccctctt ctccttctct tctgtctcct ctctctctct ctctctctct ctcacacaca   44460
cacacacaca cacacaccat ttttgccaag gctcactcca gtatgaggaa cccacaaaga   44520
acaccaagac ctccattctg agcagggcct ccattatttg tcctgctgtt tgtttgttct   44580
gcctcctgtc ctccaggcca tcaatgattc ttgactctct aggaggggtc aagcttccca   44640
tcatcccagg ggatctcctt agcccatttg taagttagtg gaaacacaga gggagtgagg   44700
gaagggtgct agccagtctt tatccttcac caacatcaga tcccggaaca caactggccc   44760
ctatatctgt acagcagcaa tatctaagcc ccagctaaaa tgccttttta tcaaaatctg   44820
cagaatgttt tatcttttc aggtaagctc aaatttttct attctcgctt cccccaaccc    44880
ctatatacac accgagaaag gtcattgaaa acagaatgaa agtatctcat acaacaaaat   44940
taattcaaga tactttcttt gacaatggga actcgcttct aaataagata caagaatgac   45000
taaacaccaa accaaaagaa atgtgaaagc aaaattaata ctttacacca actaacagtt   45060
tgtttgcaac atcagcaaat ggagcattca cctgttacta atttccctaa atacaaagtc   45120
cactgcattt ctaggaagga tggttagtgt ttggcaaatt ttttgtgtaa gcattgaaaa   45180
atataactga gaagttaatc agagggccat gagtgggcaa aaagatctaa acatgttga    45240 ttatttaaaa caccagagca ccagagagca cgcaagtctt tatcttataa taaaatgatc   45300
ctataagtca ctataataac aattgactac tttgtatatg caagtttatc ctagggactc   45360
taaaaataga acttgtagga tttaaatcta aagtaaagat tttatgggca tgatctatta   45420
gatcctccag ctgatccatt tatttgcttc cagtatgaac tgataacttg cttatgtttt   45480
cttcaaaaag tgagaccatt cttcccatag ttttttctatc accagccata cactggtggt   45540
ctttagagtt tttcagatcc ataaaaggat tgaaaaagta taagaatcac cgctctaaaa   45600
catccttatg aaaagacata cataagtatg aaatcacaaa aatcacaatg tgtttccaaa   45660
caaatccaac attctttat ggccagtagc agcaaacagg ttttgtggaa ctgacataaa    45720
atctaattta gccattatta caacattacc agcagctcag agcactaagt cacctcaata   45780
acccagtact gctctgccca tattatctat ggctttaatt aaaagtgttt agaaatggtt   45840
ttagtactga ctttgttcag aatatgtggc tgaattctaa atttaaaaat aagtcttcca   45900
gtaggcccac aagtgatcag aattgggtac caaaagttgt acatttaaac acttttatta   45960
```

```
aaatgtttat acatgtacat aaaatatttt attgtgatac aaaactctgt acaaagtgta    46020
ctaacaactg acatgattat aaatgaatcc ccaaaacaat ggtgcctaaa tttgaacact    46080
aaggagaaaa aaggaggaag aaatacttga dacaacttta ccatggcata gcaatatttc    46140
ctgctgtcaa aattaataaa atattttgca caagggtgtt acaattaatt ttatcaggct    46200
aacaatgtca taagtgagga acccttcaa ctgtagagag cactgtggaa atatagatgt     46260
ggtagaacaa tctatatcac cctgcagttg tttctgtgtt tctatgacta gctttgtttg    46320
agattgtata aagcggtctt cacaccccgg tgaataagat tggtggatgc agttccctgc    46380
cctgccgcag aagggacctc caaacacagt ttaaatctga ctctccggga gttgtgtttt    46440
gacactttca caacagtgtg aacttgtgcc acaagcaaga cagatcttat tggattaaca    46500
ctgaactcgt gacagctcca gagagtaatg ctatctgtgc ggcttaagaa caaacgtgtt    46560
tctttcatcc accctgctca ttctcttcct gcagttactc ctagcaaatc ctccccgccc    46620
tcacctctag gaattcctct acacccagag aaaggagttt cttcctcac tgcggaaacc     46680 tatcaccgct tcctttccac agatggactc caaggggcac tcactcgtgt gcccactaag    46740
ggatttctct cctaattcca cgccttccaa gggaagtcag aactgctcag tttccccgg    46800 tgaccacata cacgtgtcca agtgaagcct cgtctggggg agactcagtt cccacacttc    46860
cccctggccc ctgtggaggc cctctgtctc ccctgcgtgg ccctccgcct ggcccctcgc    46920
actcaccagg aggaggttgt gcgccaccag gtacccgagc cgcgggctgc cccggatgcc    46980
gggggccagg cgcccggtgg cgtagccgtg ccaggccacc acgtaggggt tgtcgatggt    47040
gatccagtac ttgacctgac cgccgaagtg gcggaagcag agctccgcgt aatccctgaa    47100
gtggtcggcc agggcgcggt tggcccagcc gccgtaggcg tcctgcaggc gctggggcag    47160
gtcccagtgt acagggtga ccacgggctg cacgcccagc tcccgcagcc gctccagcag     47220
gcgccggtag tagcgcagcc cctcgcggtt ggggacgccc gcgctgccat tggggagcac    47280
tcgcgcccac gagatggaga agcggtagtg agtgaccccg agctcgcgca gcgcctccgt    47340
gtcgcggaag acgttgttgt agctgtcgct ggctacgtcc ccggtggcgg gctgcagcgg    47400
cgacggggcg cccaacggca gactggcgtt ccggagtct cccggggtg ccaggggtg      47460 gtgggtgaac gtatcccaga tggacgcacc cttgccgtgc tgctgccagc cgccctcgt    47520 ctggtaggcg gcgctgccca cggcccagag gaagccgtcg gggaaggtgc cctgaagag    47580 gcccgcggcc tcggggcag gaggccgcga gaaacgggcc caggtctgcg cgccgtcgcc    47640
cggctccgca cgcaggcggc ggccgcccag gcccagcagc accagcagca gcgacagcga    47700
cggcggcggc ggccgcgggc ggcgcggcgg ggcgctggcg ggcat                    47745
```

<210> SEQ ID NO 19
<211> LENGTH: 51745
<212> TYPE: DNA
<213> ORGANISM: Homo sapiens

<400> SEQUENCE: 19

```
acaatatatt gtattttga aaatctcaga gtagatttta agtattcttc ttttctttc       60 ttttcttctt ttcttttctt ttttcttttt tgaaacagac tcttgctctg ttgccaaagc    120
tggagtacag tggtgtgatc tcagctcact gcaacctccg cctcccgggt tcaagtgatt    180
ctcctgcctc agcctcctga gtagctggga ttacaggtgc ctgccaccat gttggtgaat    240
ttttgtattt ttagtagaga caggagtttc accatgttgg ccaggctggt ctcgaactcc    300
tgaccttagg tggtccacct gcctcggcct ctcaaagtgc tgggattaca ggtgtgagcc    360
```

```
accacgcccg gccagatttt aagtcttctt accacaaaaa aaataagtat gtgaggtaat    420
acatacgttt attagctcaa tttagccact ctacaaatgt gtatatattt taaaataaca    480
tgctgtacat gaaaatatat ataatttttt gtctgttaaa aattaattaa ttaattaatt    540
ttaaaaagag gagggcaggg aatacttgtg tattttgtta actggacaaa tgaaactcta    600
ctttcatttg ctcattaaac aaatacttgt tttgtgctca gcatgattct aggcactggg    660
actactgcat tttggtccat tacttccttg cgcacaaaaa ccctttcttt tcaccacgaa    720
tacactatga acatgttttt ttcttcagtg ttggcatctc ttgattcctt ccctccaggt    780
ctttgtgcga gttttactct ttaaacccca gatattgtca tattttctc tgttaaactt    840 ttccaaacaa ctcaaaatag ggtaatttct tcttcttctg aatttctctg acaattattc    900
tatgggtcat ttattaacac agcataatca aacaacttat ttattttcat ctttcttgat    960
cctttcttca gttggatgtt gtctttgagg gcagaggttg tcctctatgt tttgaagtct   1020
ccacacagct catcgttgcc ttgcccgtag ttgtagctca gtgaaataaa aatatgtccg   1080
tagaaggtga tgtctgtgac tggtgagccg agagcttgtg gggttggtgt tgtatttgag   1140
tgcatgtgaa tcagtgcatc tcctgctcca ttggtgttaa aaggctccca tcgtcctggg   1200
aacacaatag gaaagagaac aggtgggaag gcactggatg aaggaatgtg gagaatggag   1260
gaaaagttga tcagattgtt gacaactttc agtgttgaaa ttgtcaccaa aatcaaagtc   1320
agtaaataaa tttacaatgt cctttctctt aatgcatcaa taacttcacc ttcctgttca   1380
aagcacagca gtaattaat ctcttatttg catttgaaac ccaagtttca gatgtttgaa   1440
ggtggttgta aaaaataaaa accaaaataa agccaaaata aataagcagc agcactaggc   1500
cgggcacagt gtctcacacc tgtaatccca gcattttagg agaccgaggt gggtggatca   1560
caggagatca ggagtttgag accagcctgg tcagcatggt gaaaccctgt ctctactaaa   1620
aatacaaaaa ttagccaggt gtggtggtgt gcccttataa tcccagctac tggggggctg   1680
agacaggaga attgcttgaa cctgggaggc agaggttgca gtgagcagag accatgccac   1740
tgcactccag cctgggcgac agagtgagac tccgtctcac acttgtggaa cccagaactt   1800
agtaaccatg aacagaacct taataaacag aaagttctgg aaataaagtt taatcatcat   1860
gcaatcttta tcactgggtt aaatgaacaa tcatctggga acatgtcttg gaatgcttaa   1920
agctttgaga tgcatgtgcc tatgtggcag acaaatttca aatgtgaaac gtttagttaa   1980
cttggtcttg cttttaatc actgctttaa aatttaaaaa atgctgctgg tcaagtaaaa   2040
atagcaatag ataaaatctg ccctgagcaa acagaccata catcaataaa tgaatactta   2100
gcttaagcga ttttccatga gacccatgaa gcatttctaa ttgaaactta acaagctaca   2160
acccaacaga cactccaatc ttcacttcta gaagggaaat gtgatactcc atgtagacgt   2220 agcttttttaa atttagctgg aagacagcgt gacagtgaag ttgtgtgctg taattttta   2280 aaattgctga agtgtcatgg tttgctattt cgtatttatt gaaaaaatgt aaatgctata   2340
tttaacagaa tggcagtaac tctgtttcaa tctgaagact taatcttact aatcatggta   2400
atatatgctg gctggagttg ggaatatttc ataaaatact ggaataaatt tgtgcttata   2460
tttcagggga attaataaaa gcaccttcat ctgcaacatt taaaatgtta ttgcctttaa   2520
atttgtatta aataatgcag ggaggataga tcactggggg agaatggatg cacctctgtg   2580
aggatcttgg tcattcaaca cacgtgtacg ggtgaggaaa ctaaggcacg acttactggg   2640
tagggaggta gggatattag caagatcctt cacttgtctg ggctttctgt ctttgagtca   2700
```

```
cctttgcgca gtttttcact ggacttcaca agcctctgag gcggcagggc agacaggaca    2760
tccttatttt atagaggaaa aaacttaggc ttacagaggt ttcctgcccc aaatcacaaa    2820
ggtggagcct agaccttctc agtctccacc aactgtattt cggttagcca caatcctatc    2880
tacccacatc caaatggaca ccgtggctct gcaacttctg tcaaaagggc tctttggcaa    2940
caggaaaaac gtcatggctc cattgtattg tagaggatgg gaatgggtgt tccggctaaa    3000
ttctccctcc cctttccctc cacagctcag atggcaaatg tgcgacccag ggacctcccg    3060
ctccagcaga cctgtgcgca caactttgca cagattacct gctaagtcag agccgaaagg    3120
taacacagat gccaaaggat aataaaggtg aatgagattt actcaaaatt ggaaacttgg    3180
tgtttggttt ttcaggagaa caatcaacga ctgtgatttg aagttcacca gggtattctg    3240
agagatctaa tcaaagatag agtgctggtt tgaaattatt aaaaggtaac agtaaaaggg    3300
agagcaaaac cccagtccca acgcaaccca taaatctact ttgtcttcct cgaaagaggg    3360
gcgcgggtgg gcgcgtctcc ccgcgagcat ctcacctaag ggggaatccc tttcagcgca    3420
cggcgaagtt cccccctcggc tgtcccacct ggcagtccct ctaggatttc ggccagtccc    3480
taattggctc cagcaatgtc cagccggagc ttctttgggc ctccgagtgg gagaaaagtg    3540
agagcaggtg cttccccagc ggcgcgctcc gctagggccc ggcaggatcc cgcccccaag    3600
tcggggaaag ttggtcggcg ccttttctcc ccgacgaagc cgctccaggg ctgctctcag    3660
aggacgcgcg gcaggcaaag agaatgaacc tgagcgtcca cgaaacgtcc tgcacggctc    3720
ccgggagctg ggaggaacag gtgcctttct ccgacgtccg cgggcgacgc ctgccgcacc    3780
ttgcccgctg ccgcgcccct cccgggcacc cctcgccctc ggcgcccctg cccccacccc    3840
cagtgccagg gcggaggcag tcccggctcg caggtaatta ttgccagcgg agcccgccgg    3900
ggagcggggg tgggcgcgcc ggcggtgggc gggcgggcgc ggcggggcgc gggcataaag    3960
gggcgcggcg cggggcccccg gagcctggct cccgcgcagc atgcccgcca gcgccccgcc    4020
gcgccgcccg cggccgccgc cgccgtcgct gtcgctgctg ctggtgctgc tgggcctggg    4080
cggccgccgc ctgcgtgcgg agccgggcga cggcgcgcag acctgggccc gtttctcgcg    4140
gcctcctgcc cccgaggccg cgggcctctt ccagggcacc ttccccgacg gcttcctctg    4200
ggccgtgggc agcgccgcct accagaccga gggcggctgg cagcagcacg gcaagggtgc    4260
gtccatctgg gatacgttca cccaccaccc cctggcaccc ccgggagact cccggaacgc    4320
cagtctgccg ttgggcgccc cgtcgccgct gcagcccgcc accggggacg tagccagcga    4380
cagctacaac aacgtcttcc gcgacacgga ggcgctgcgc gagctcgggg tcactcacta    4440
ccgcttctcc atctcgtggg cgcgagtgct ccccaatggc agcgcgggcg tccccaaccg    4500
cgaggggctg cgctactacc ggcgcctgct ggagcggctg cgggagctgg gcgtgcagcc    4560
cgtggtcacc ctgtaccact gggacctgcc ccagcgcctg caggacgcct acggcggctg    4620
ggccaaccgc gccctggccg accacttcag ggattacgcg gagctctgct tccgccactt    4680
cggcggtcag gtcaagtact ggatcaccat cgacaacccc tacgtggtgg cctggcacgg    4740
ctacgccacc gggcgcctgg cccccggcat ccggggcagc ccgcggctcg ggtacctggt    4800
ggcgcacaac ctcctcctgg tgagtgcgag gggccaggcg gagggccacg caggggagac    4860
agagggcctc cacaggggcc aggggaagt gtgggaactg agtctccccc agacgaggct    4920
tcacttggac acgtgtatgt ggtcaccggg ggaaactgag cagttctgac ttcccttgga    4980
aggcgtggaa ttaggagaga aatcccttag tgggcacacg agtgagtgcc ccttggagtc    5040
catctgtgga aaggaagcgg tgataggttt ccgcagtgag gaaagaaact cctttctctg    5100
```

```
ggtgtagagg aattcctaga ggtgagggcg gggaggattt gctaggagta actgcaggaa    5160
gagaatgagc agggtggatg aaagaaacac gtttgttctt aagccgcaca gatagcatta    5220
ctctctggag ctgtcacgag ttcagtgtta atccaataag atctgtcttg cttgtggcac    5280
aagttcacac tgttgtgaaa gtgtcaaaac acaactcccg gagagtcaga tttaaactgt    5340
gtttggaggt cccttctgcg gcagggcagg gaactgcatc caccaatctt attcaccggg    5400
gtgtgaagac cgctttatac aatctcaaac aaagctagtc atagaaacac agaaacaact    5460
gcagggtgat atagattgtt ctaccacatc tatatttcca cagtgctctc tacagttgaa    5520
agggttcctc acttatgaca ttgttagcct gataaaatta attgtaacac ccttgtgcaa    5580
aatattttat taattttgac agcaggaaat attgctatgc catggtaaag ttgtctcaag    5640
tatttcttcc tccttttttc tccttagtgt tcaaatttag gcaccattgt tttgggggatt   5700 catttataat catgtcagtt gttagtacac tttgtacaga gttttgtatc acaataaaat    5760
attttatgta catgtataaa cattttaata aaagtgttta aatgtacaac ttttggtacc    5820
caattctgat cacttgtggg cctactggaa gacttatttt taaatttaga attcagccac    5880
atattctgaa caaagtcagt actaaaacca tttctaaaca cttttaatta aagccataga    5940
taatatgggc agagcagtac tgggttattg aggtgactta gtgctctgag ctgctggtaa    6000
tgttgtaata atggctaaat tagattttat gtcagttcca caaacctgt ttgctgctac     6060 tggccataaa agaatgttgg atttgtttgg aaacacattg tgattttgt gatttcatac     6120 ttatgtatgt cttttcataa ggatgtttta gagcggtgat tcttatactt tttcaatcct    6180
tttatggatc tgaaaaactc taaagaccac cagtgtatgg ctggtgatag aaaaactatg    6240
ggaagaatgg tctcactttt tgaagaaaac ataagcaagt tatcagttca tactggaagc    6300
aaataaatgg atcagctgga ggatctaata gatcatgccc ataaaatctt tactttagat    6360
ttaaatccta caagttctat ttttagagtc cctaggataa acttgcatat acaaagtagt    6420
caattgttat tatagtgact tataggatca ttttattata agataaagac ttgcgtgctc    6480
tctggtgctc tggtgttta aataatcaac atgttttaga tcttttttgcc cactcatggc    6540 cctctgatta acttctcagt tatattttc aatgcttaca caaaaatttt gccaaacact     6600
aaccatcctt cctagaaatg cagtggactt tgtatttagg gaaattagta acaggtgaat    6660
gctccatttg ctgatgttgc aaacaaactg ttagttggtg taaagtatta attttgcttt    6720
cacatttctt ttggtttggt gtttagtcat tcttgtatct tatttagaag cgagttccca    6780
ttgtcaaaga aagtatcttg aattaatttt gttgtatgag atactttcat tctgttttca    6840
atgacctttc tcggtgtgta tatagggggtt gggggaagcg agaatagaaa atttgagct    6900 tacctgaaaa agataaaaca ttctgcagat tttgataaaa gggcattta gctgggctt      6960 agatattgct gctgtacaga tatagggggcc agttgtgttc cgggatctga tgttggtgaa    7020
ggataaagac tggctagcac ccttccctca ctccctctgt gtttccacta acttacaaat    7080
gggctaagga gatcccctgg gatgatggga agcttgaccc ctcctagaga gtcaagaatc    7140
attgatggcc tggaggacag gaggcagaac aaacaaacag caggacaaat aatgaggcc     7200 ctgctcagaa tggaggtctt ggtgttcttt gtgggttcct catactggag tgagccttgg    7260
caaaaatggt gtgtgtgtgt gtgtgtgtgt gtgagagaga gagagagaga gagagaggag    7320
acagaagaga aggagaagag gggagagggg aggagggaca gagagagaga ggtctcctac    7380
aaagagcttg gagctcaggc tgctttgctc atttgagtgt aatccaggag gatgcacctt    7440
```

-continued

```
ttctctcgga cttgaagacc aactgctcag ccttcacagc tcttgaaaca aagttcttaa      7500
tgtcccctga aatcagcact agggactgta gttggggagt tcagccccag cagtgcctct      7560
gagtctttgt tctgtatatg ggttctaaga ggattagaat caagttggaa atacacgtgt      7620
tcccatttcc caccttcaac tcccctcacc gcctgagatt cttgcaaaca tttgtgcaag      7680
gaacctgtga aaaagacttc tttcacgtaa ggaagtaggg ctaggagata ttaatctggg      7740
cattgttgag cattagcatc agtgtgcagg tctcagccca tctgtctgca atgtttgttg      7800
aagccatcac ttcttgtccc ttgaatcctt cctcaacttg gatttcaggc cctggctctc      7860
ccttgcttct cctctcagct ccctggcgat tccctcttag tctcctttgc ttgttcctcc      7920
tcaccttgcc tgtaaatagt ggagggctca gggctctgtc tagattcact ccaggccatt      7980
gctttgaata ctgctgcatc ccgatgactg gagattttga gtctccaccc aggtttcccc      8040
gagcatcaga ctggcataga caaccgcctt ctccacgtgg atgtctaatg ggcatgtcac      8100
atcgaacaca tcccaaacca aacccctgct tcccttctc tattatgatg actttttact      8160
cttccagttg ttggacccg aatcttaact actccccttt tcatgtctt gtttctaatc      8220 catcaacaaa tcctgcagct ctacctacct ccaggatgtg tccagaatca aaccacttct      8280 cccttatct atgactacga tggaggtgca agacaccatc caaccttgcc tgggtaatgg      8340
gaacagcctc actgctgggg ttcttatttc tgccttgccc cctgcagtgt gccatgatgg      8400
atgctctaca gggtgacatt atgtgtggac aagacagagt ccttgctttt tcaaatccca      8460
cctgttcttc tggagccagc taacacgctc ccttgggccc catgcctgaa tgccatctct      8520
tccttctatg gcatcctgca caggacttcg ctttgctcag atgcctcctc ccgcgctctc      8580 cccttattt aaccatttgt ctccatttta ccccttcgct atctggggta atcctgttcc      8640
cttcatctgt atctctgaaa atggcatctt gccctccctt ggtgctcaga aggtggcttc      8700
tggtttaccg aatagcctga tttcaccttt ataaactcat gctactagaa ttttctctcc      8760
ttgtcagtct ttctagccac tttccaatgg aacagagact accaaatcct aatctgataa      8820
ggaaaaatag gtaaacataa cgtggcagac tctgacatct gcagtgaaaa tttaaggttc      8880
atcatcaaat gtatgattcc attgtgaaaa tgtccagtta aaagctatct gtagtcacca      8940
tgcagcatta tgaagaagtt ttcagaataa gggcaggtgg taaagtctcc tggccagctt      9000
taggagtata tattgaagg ggctttgtta gctgattgaa ttttattcc ccaagtaatt      9060 agtatgagcg atttgtctac tgtatatatg ctcaaattac atatactatg cacttttgag      9120
aaatacttta caagttttt tttcattaaa atgtatttgg ggccgggcgc agtggctcac      9180
acctgtaatc ccagcacttt gggaggctga ggcgggtgga tcacctgaga tcaggagttt      9240
gagaacagcc tggccaacat ggtgaaaccc cgtctctact aaaaatatgg aaaattcacc      9300
agacgtggtg gcaggtgcct gtaatcccag ctacttggga ggctgaggca ggagaatcgt      9360
ttgaacatgg gaggcagagg ttgtagtgag ctgagatcgc accattgcac tccatcctga      9420
gcaacaagag cgaaactcca tctcaaaaaa atgtattttg tacataacta gaataatcaa      9480
ctggattgaa agttaatata aattttagaa tactactgaa ttcaatagtg catttagtca      9540
gaaatagtta aaatatctcc caaacagctt gaatcactcc ttttgaaca cattgttttt      9600 tgaaggttac agtcaagtcc aagaaaaaat tttaaaatag gaaaagaatt aatcaaatca      9660
tttcaaaatc atagcagtgt tttaacaatg ccaattattt tgagttgaag aaaagaagga      9720
aaatgtaaac tatgcattca agtaatgtca atgcaccttc tcaggtgcaa aatgaatgaa      9780
caattaactg tgccagctga atatgtagca atcacggctt ttgcacatag aagccttctg      9840
```

-continued

```
aattatctta tattctcaaa aatatcattg ctctaaacta gaattttatt ataattaatt    9900
tgtgcaaaag ttgtctttct ttcaatgaat gttgtctttt tgaggcataa aggaaatttt    9960
aggtggagga ggagaataga atacatgctt actgggagga caagtaataa taggtgagta   10020
aaaacacaca gcttattgaa ttgtctcaga tccacatttt ctccagaaat gcaaagttat   10080
acttgaaatc tatatttaaa cagataagca gaatgtgact tttatatgct ctattttgat   10140
gtattctgag tatgaagata acctgaagga tgccttttc ccctctttat cttggggtaa    10200
actcttactt accttcaga gacttgactc aaatattttc attctgcaat aaccacaggt    10260
agaatggatc atttactcag ttgtggctct cttaagagca cagactacct atcatattta   10320
tttcaaaatt tgtagtgctt atctcagtgc ttggcacaga ggaagaaat acaatttta     10380 ataaaggcat aagtggagag gtaaaataca tatttctggt ttcaacgtgt ccatattctt   10440
tcttgtaaat ggaatattgc gcttgcagtc tgctctcaca caatatctgg gaaggagttt   10500
taaagagtga ggaagaacag taaagatttt cctaggcaga tacgttatgt gacctttgtt   10560
gatttccaga gcacataata tcccaatttc atccagtgga caggaaaaga gaggaagagg   10620
gaaaaggtgg cctctcaagt gcctgacctg gaagctgcac ctatcactgt cccttgggca   10680
gaactcagtc acatggtcaa aaggagtctg caaataattg tcccctgagg agccgggtgc   10740
tcagtgaatg attctattaa gttgaaatca gatgggaaca gatcatttag gataaccagc   10800
aggctctacc acattgccta actcccaggc atattgtgag aattaaaagc accttatata   10860
tgtcaacgtg ttttgaaaaa atacaaaaag ctctacaaaa gtgagctata aatttatcat   10920
taataataat agtaataata gcaaaatact tgagaaatgg tcctcttgag ctgtttagaa   10980
ggaatcatac aaatgcatta gacatggtag cctcacttaa ctacttaatt tgcctcttct   11040
ttgaaattat ttcaatagca tttgaccaaa aactatcaaa tcattttga aataacgtat     11100 ttttacataa aacacattat caaatatctt tctggatcca gcttggtggt aaaaagatac   11160
atactaaagt ttatgactga tataacttta tatattgact aaaccaaaga taaatattga   11220
ttgaactttt gtggccccag tttcaataga tttttttatt aacattttt gtttgaagta    11280 cagatgtcac gtcatccatg aaccggtatc attatagctt gataaaatac tcaaactgaa   11340
agcagtgatg tacattaatt ttaaatataa tggttaagca aatgttattt ccatatctat   11400
aagtgcattt tatttgataa ttagaatgtt agaatcagaa ggaatttgga aaatcccagg   11460
ttacacttct ctccaggacg aactccttac agtggctctc ctggggtcag ctagcttttg   11520
cttgacccct tgaagcagga ggaactcagt tccactcaag ttgcccccctt gattttctct   11580 ttcatattga acctgctgct gcacaggact cctccgtgac tgtctctttg ccttcctaaa   11640
tctcaaagaa taaagcaagt cactttttga caagacatct ttcacatatt tgaaaagaca   11700 tcttcacat atttgaaaag accagtacgt tttgttcttc ctagaatttt ctccttcatg    11760
ctaatgtctg ctccaagaag acatggaggt gactggacat ttagtcagga acatttcttg   11820
agagcttacc ctgtggcagg caggtgcaat gttgaattct gagaatatga atgtaacctt   11880
tgaacaggtg gctctgtctt ctgacgtttc aggataaggt ggaggagagg agagggaaa    11940 gtcgacctat ctccccagcg gggagggttt agggttgtct gtgggacctg cctctgtctc   12000
atcatccatc accattgtcc tgctgatggg tgcagaggac tgaggacgag tggttggagt   12060
tctccctgtg ccggaccctg tagagagtcc agagccctgg ctcccaaagg aggcatattt   12120
gtagggctct tttcgtgagg gtccagagga cggctgcaaa gctgcagggg aggatggggg   12180
```

```
catgggaggc aagcccgttg ccctgtcaga gcctcttggg gatgctgctc ttccccgcct  12240
gtcctctctt ctctttgatt tctcatcatg tggtcctctt tcctctgcct tttcctctct  12300
tcggtgtccc aagttcttcc atagagacct gtgtccccett gttcccatca ggcctttatg  12360
ccagccctgc acaggtgcgg ggacagtggt aggggcgtct cactcccgac tcaactacat  12420
tctcccagaa attgtctgca gtcaaacaca actcagcgtg gacattgctc accaaaggta  12480
tactgcttgg gctgcacgag agattcagtt ttctcctatc tatctggcat gggctgtgag  12540
ggggctccta acctaggggg ccttttact ccttcctggc cagagctgcc atttccaagt  12600
ttctgcactg tcagaaaaga gggataaggt aagattcctg ccctcatgtc acagattagt  12660
aggggagagg taattgtcaa ataattacag taaaatgtat aaatgcctta agagaaataa  12720
gtacttgctt aggaacctat ttcaagaaag gagagatagg ttagcgtttt ggggaggtag  12780
tacgggagca gtcagggaaa gcaatacttg taagatcaga ggctggcaat cttttctgt  12840 agagggctaa gttttggact ttgcagatcc tacagtgtct gttgcaacta ttacacagtt  12900
ctgtggttgc agcatgaatg cagccatggg caatgtgtta atgaatgggc acagctgtgt  12960
ttcaataaaa ctttatttac aaaaataggt agtgggccct gctgctgggc ttggcttgct  13020
gggcacacaa agtgagaagg gcattgtgcc tttctaggaa acatcccttg caaagtcagt  13080
acaggtgaga cagtgtggcc attcccacca cagcatgagg tcttttgaat ggctgaagcg  13140
tcaggtggga aaggatgagg agctgaagaa gaaagcctgg gaatttccaa ggcctctctt  13200
aacatttgct gtgcagaacc aagcagtgcc ccaggtgttc agagtaggct tcagcgatta  13260
catttcttgt tagacactga attttgttca tgccgcccaa gattgcatta acaatttgg  13320 ctgtcacctt accgcggact caaattagtt tgcagtcagc taaaacctct caggtttttt  13380
ccccccagct tgtgaattgc tgtgaagcca aacatccctg tcatctcttt ggtagtttat  13440
tttcaaactt tcaatcttat taaatttcat ctccaatgtg caaagataag aggaagttta  13500
ccgctgatgg tggtttattc tttaaaactg gacatcagct aaatgtgtta aggtaatccg  13560
ttagaggaat gttggtacgc ttatacagtg gaatactaat tggttattaa aatgttgatg  13620
tatgattatt aaaaggcagc ccatgttatg tctcttctgt atgaataagt atgtaaaag  13680 tatgtaaaga ttactgtata gttcatgggt gggactgggc tctctctagc ctctgtcctt  13740
cattctccct gccagtgcct tttcccttgc agtgtccctt ccctggctgc atactcaaga  13800
ctggatttgc ccagccaaac cccattaact cacagaagca agaggaaaaa aataaattct  13860
tattagttca attctccaaa ttgggggcgg tctatttcac agcaataggt aactgacgta  13920
aaaggaaagg aaacaatgaa gtaattccag aaaatttcct atagctggag gacatgcatt  13980
ttcatattga atgggaagaa tggggtgggg gggtcatacc tctgtgttat tgcagggtcc  14040
tggctcctag ggacctaggc acctcttcag tcagtgaatt atagcttgga aaattggcta  14100
agtcggggaa ctgtacaagg ggtcatcact ttttatgtag ccatgctcta tgaaccatct  14160
ttataactcc ctggcttctg gcagttaagc accactcact atctggcctc tgtaatttca  14220
acttctgacc atccccgtgg gtggcaacaa gcccagctct gtgacacctc tgctaccagc  14280
agccctggcc tggagagcgg tgccccccact gaatgtctca gtgagattgg caccccatg  14340 agcatattcc tgagggtgca gtgaatgctc tttctcccta cttgggactt ctgggaaaca  14400
ctgtcctctg gtggggttgtt tgacctcaca taatatactg gttcttgcat gccagcttct  14460
ctctgcttct tgattctttt atcagctgtt agggcaacaa tgtcaggcat ttccgcctgc  14520
tcagcattgg gcatcccttt ttacaggctt ctcagagcca ccctagcagc aactttaccg  14580
```

```
cgtctcctgg ggtccttgct ggatcgtgaa aacatacttc cggagaaagt gttccctaga   14640
taatgaatta tttcttgtcc tgtgttaagt tccagttcct tggtcaagga ccccagcgct   14700
actcctcagg atttgcagtg catgctcaat cttgaagcaa tgttgggata tagtatcttt   14760
tcttctctat caggcccagc tgtctccagg tgggttatac taggatttaa tcctcgttag   14820
tgccgggtca gctcctgagg ggtgcacctg ttgcttttta gggacgaggc ctcttcagca   14880
taaagaagtg ctatctctta ctagggaaga atgggccacc tctgtaagct ccaaatattc   14940
ccaggtttcc ccaaccgggg ccttgacctt ggcataactg atctgccttg gctgagcatt   15000
taaacatccc taaatctctg caagtctatc aggtcctagg cctgctgcta agtttctcta   15060
ctcttccact gtaggagaga aggctgtggc tcttatattg agcctttaac tgtttgttat   15120
tggccctcag tttctcatta gctctctgta gagtctcaat acaatatatc agaaagcatt   15180
caattccatc tccttgtagg cagggaatgc ctaaatcatt gcacctacaa tgacattctc   15240
caccaggata tttcccaggt tactgctgtt gaaatattta gcaattgaag caccatttgt   15300
gcaaggggac tatctgcccc tacacaacac tcagaatggc attctctttg ctttccagaa   15360
agtgaatgag ctggttcccc aacccctctt gtgttagttt gagtcctgaa agaagtaaat   15420
gtcaagatag gattagatgt acaagaaatt tattgggaa agaattgtga aggataaagg   15480
ggaaggagct aggggaggca ttgaaccttt ggatcatgat gtgtgtccaa caactatgaa   15540
ggagagtggg cagggagaag gatgggctgg gaagagtttc agttggcact gtgggtctca   15600
gaacaaccca ggcataggct gatggggacg ccttgagcca atgttgccca ttggcggagt   15660
ccacatcttg ctgaaatggg cctgcattag ttcccctgcc atgtttagtc atctgggagt   15720
agccgatgag aatcatgatc ttaggatcaa ctgcaatggc agattcaaag gggtagcaac   15780
tgatggcctc agtcaactgt gctccttata gcaggaacac tgagcagtgc atttcttggc   15840
catcacaaag actagtgagg agtgcccttc agagaaggga atgaaaatta tttccagcct   15900
agaatttgat acttatctaa actgtcaatc attcatgaga gtcaaagtcc caaaaaataa   15960
atcttccata aacccttct caggaagtta ttggagggta accgccacat aacatgagga   16020
agacaaggag gaagacatgg gatctatgaa agggcaggtc taacccagga aaaggatgat   16080
gaactgtaga cccatgatgt cagatgtgca gcagactaag atcagccagt gcagaatggg   16140
ggagattcca gaagtgtgtc cccccaaaat attggaggct catgtgactt ccctggggaa   16200
gtttctgctg agaggctatt ggaaattgag ggaagaatta gccacagtcc caagaaaaac   16260
agagccaatc aaaaagcaat gcaattatga acttcaaaga aaacaaaaat aagaaggaaa   16320
acagtcttac ttactacatt acaaggtcca gctgtgaatg atattcatgt tggcagaata   16380
atgtcaatac caaatgtcgg ttaaacccaa aactattgta taactaaatt gcctgtgtaa   16440
gagagctaaa cccttatcta gcataatagg aagtcagtgg atacttcctg aagtgtggat   16500
gtgtggagat gtaaattcca aaagaaaacg tcttaagagt caaagtggt tgcctctaga   16560 gagaactggg ggaattgtag ggcaatgtag gacagggaac tgtgattttt cttgtaagtt   16620
gttctgacat tttaaaccat gaacatatat tacttgtatt tttaatttta aaagacata   16680 aatattttt ctatcacttt aaatattaat tttgctagtt atagcacata tttatagcat   16740
tacactctgt agagctcttt tggattcaag ttttggagaa ttttcaaagt tttagattaa   16800
tgcctttgtg agttttcatc cctttgatga taacaagtta caaagaaata gggttatgaa   16860
taaaccttgt gggatattgt tagtcacctt ctctcaagtc gatctgtccc atgaatcaat   16920
```

```
gtttcaaaca ttgaccagca tttgatactt aataagcaac gagtaagttt ttgttgaacc    16980
aatgaatact cttaaaatat attttttcaa gtggcaacag tactatctta tttgcactct    17040
acttttcttt ttgaccctaa gaatgtcaca aaaatgttta gcaactgtca agattattac    17100
atacagagat gactattgtg ttctcagata tgctgtatgt cttagttcat tttgtacagc    17160
tataagagta gctgagacta ggttatttat ttatttattt atttattttt tgagacggag    17220
tcttgctgtg ttgcccaggc tggagtgcag tggcacaatc tcggctcact ccaagctccg    17280
cctcccaggt tcacgccatt ctcctgcctc agcctcccga gtagctggga ctacaggcac    17340
ctgccgccat gcctggctaa ttttttgtat ttttagtaga cggggtttt caccgtgtta     17400 gtcgggatgg tctcgatctc ctgaccttgt gatccactca cctcggcctc ccaaagtgct    17460
gggattacag gcgtgagcca ccgcgcctgg ccctatttt tttttttta aaggaattta      17520 tttcctcaca gttctgttgg ctgggaagtc caagggcaag tctctggcat ctggtgagag    17580
acttcttgct gctttctccc atggtggaag gtgagagggc aagagagaga caaaaggagg    17640
ctgaactcat cctttacaa ggaacccatg cctgagatat tgaacccact tctatgataa     17700
cagcattaat tcattgatga ggacagagac ctcattgcct aattggccta agtgagacc     17760 tcttaaaggt ctcgcttaat actattacaa tggcaattaa atttcaacat gagttttgga    17820
ggggcaagca ttcaaatcat agcaccatat aatacaataa aaattttctg agctaagttt    17880
ggtaaattta ttctaggaat ccatgttgtc tcctagttat cttcccttcc atagtactga    17940 tgcattttg ttaaccatta cctaattttg cttgagtcta ttatttctga aattcacatt     18000
atcttccctt ttaaagttga gaaaattttc attcttcaag cgccttattt tctataatct    18060
ctcaaagtaa ctgatggctg ttgcatgatc ataagtgcaa attatttgc tagaccacac     18120 ttggagatga tgaatttgga atggcatgca gactcccgac atcaggagtc ttgtctcctg    18180
caataatcag gaacccaggc ttaaaaggga gcaggtacaa cagaagggca aggggtgaca    18240
atgctggtga aagacatttg aggaaagcta tcaacatgaa acagaataaa ataaacagaa    18300
aagcaaacca gggaaaataa attatgcagg aattaaacac atacacaaac tgaaacagga    18360
accatcagaa catataaaaa attcttgaac atcagtaaca caatagttga aacaaaatat    18420
ttagtaaaat atttgaaaag taaggtcaaa gcaatgctgt aaaagtagta caagatgata    18480
aagaaataga acacattttt gaaagggaaa aagatttaaa ggatattcat aaagatccaa    18540
catcagacta atagaagttc tggaaagaga gaataaggaa atacaggtca ggaaatttgt    18600
aaagaaataa tataataaaa tgccccagaa ctgaagaaca tgagctttta actttaaaga    18660
gccgactgag ttcctagctc aatgaatgta tagacatgta agggtattga agttcacct     18720 tcagtgtcat gtttcctaag aagctaatgg aagatatgca ccagcaaaat tgtagtaaat    18780
acataggaag aaatagtata tagaaaaagt atggtttcaa tccataagaa ataaaggaaa    18840
ctcccaggac gagagcagct cttgacagca tctagtccaa actggacttg gaggctggaa    18900
acttctagca gggaaggaag agctctgggt gaaaaagtag actcaacaga atagatacga    18960
tcatagaaaa catgatagag aatcactaac acattgaaaa aatcacatat agaatattct    19020
gcacgcttaa taatgaggtc attatttatt caagggaaaa ttaaaagctg tttagaaaag    19080
ggaaatgtta tagtgcccta tttggctcta aaatgaacat ttatatagga atcttcatgt    19140
aaatactaac aatgatttaa ataagaacag acatttcgga aaataaggga agaaaatggg    19200
gcatgtaaaa gagctaactc ctcattatcc taatgaatta ttaaatttca caatagcata    19260
gtatttagaa atatgatagt tattacgaga agaaagagct aaaaggttgc cagtggggag    19320
```

```
caggagtgag ggttagagac gggattgggg gagatgctta ctgttttcat gataagcctt    19380
tggtactatt tgattttaaa ctatataaat gcatttatta atttaaagta atttaaaaaa    19440
cccataccac tggataatgc ttgataattt ctagagtcct tttttttgt attttggggc     19500
aggtaaattc attgagagac ccagagagtt tagctgactt tcctgtgggt accaagggtc    19560
agagctgggg tcaaaactca ggttttctga acccctattc ccagtgtaca ttccatgact    19620
ccaggctgcc tcccgcattg cacaggttac atctaggggt gtgctagcaa atgcctagac    19680
catcctcgtc cacatcagca tctgaaatgg acaagaatgt tagtcatgac ttgccactaa    19740
cgtctttaac cttaattgac atctgagagt gtcatcatta catcattaca aaacactaa    19800
cccagataca tctgttccca ttactatttc tgcgtaattc ccccagactt aattgcttta    19860
aataaccatt ttatttggtt tacaaactta tgggtcagga ttaggggagg gctcacccac    19920
gcagttttc tctggtccgc agtcatctga agcttgaacg gggtggggca tgcaagacgg     19980
ctcacacatg tgatccgcgg ttgagcctgg ctgtggacca gagcatctct gttggcctcg    20040
cttacacaag tggtctcaga ttagtagcct ctgtacatgg aaactagctt ccctcccggc    20100
aagcatccca agagaactag gaggaagtgg tatggacttc ttttcttctt cttcttcttc    20160
ttttcactta ttcttgatat catgtagctt catttctatc agagcagtca catgcccaca    20220
gattcaaggg ggagggtcca cagatccgcc aatgggagga acagccaggt tatatcgtaa    20280
aagatcatgg ggcatgggag atacccatct atttctgta aaaatacat tttgccacag      20340
catcactggc tttccagctc acagtgatct gcctggaatg ccttttttccg tctctccagg   20400
atctacatct ttcaatataa ggtttagaaa ctacctccta caggaagact tccttgattt    20460
ccctcagcaa gaaagaatct ttccttcctc tgaatcgcca ttgcattaaa aaaaaaatcc    20520
atcttctggc gttttcactt tcagacttat actgtaatta ttctatgtac ctatgtttga   20580
cccctcacga tgcccagcat aataatttgt ctattgagta aatatttgct taatgaaata   20640
atcattacat gataactcaa atagcagtcc tgaaaaagtg catttcaatt cagatctctc    20700
ttttttcttc cttcacaatt ctcatttccg aaaaatgaaa gaagccagag gatcctttat    20760
gaggagttac agtataactt atgcgtggct gtttcctgtg tttactgcta ctcagtgaga   20820
aatacgggag atgggagagt gaaaaaccat gtcatttaca atttgattaa aaagcttttt   20880
atctttcct ttcacgttta agccttgccg ttttaaaaat ttcccttcg tcacagggga     20940
tcaagcagca gttaacgctg cagttccctg ttctggaaac actctcaaag gtgtttcaac    21000
acatttgtc tcaactctga ctcctgcccc gctgccccac gccatccagc cacactgaag    21060
gtcttgcatt tgtgccttgg ggcattattt ttttttactc ttctccctgc ctggaaggtt   21120
cttcccaacc tgccctaccg ccatagccac agaaccaacc cttcactttc cttaagtcta   21180
tggtcacaag ctccttctca aaggaggcac acctctaacc accccatttt ggtgacttcc   21240
tgtctcctgg aggcccccgg aactagtctt ctctacttcc agcaacccac tttacgagca   21300
gcggagaaga ctgactactt ctgggggcct cgaggagaca ggaagtcacc aaatttacag    21360
gtgctgtgga tgaaactgtg tgataatgaa tttattgggc ttgttttttt agcttctgaa    21420
tagaagaacc aataagatca ttttttaaa aagataaaa acagacaaac acaaccctc       21480
tagtataaaa gcattttttt ttaaaaaga tgaacacaca ccctcagatt gccttctttt     21540
gaaaaggcaa tctgagattc cttatgaaat ccccagacag aagctgtttc tttgaattta   21600
atatgctgta cactgtagag ccaagaggct tatagagtgt taattaacac cccttgtcaa    21660
```

```
acatttgtaa atgaatctgg ctaaagctca aggaaaccag gttttctgt gtgataaaat    21720
ataatctttg gagattattt atgatcacaa agggagactg tacagaaaat tttcctagac    21780
ttggaaatga ggcaggatta ttggtgtcca tctggactga ggcctcaggc aggcctgcct    21840
agttaatccc attctcctat cctcattctc tggggtgaa gaaggcagtg cacctttgtt    21900
caatttgctg cttaccatgg attagggcat tttaaattct gtaagggtag ttttttaactt   21960
gtagaaaact gatagcgatg ggaaggattc ttgcctaata gggacacaaa cggattttgt    22020
tctgtagaga tgtaaatgaa aagatgaaaa tcacaacaca tttaatgaaa ggaaaataaa    22080
gactcttgtg agtgccacca aaaaaaaaaa taaataaaat gtatctcctc tccgtggcac    22140
cccaggcctt ccttacctca ctctatttct tcatagcact tattgcctta gaacattctt    22200
tataatttac atttattatg tttgttgttg gttgtcgctc ctcctgctaa aatgaatct    22260
ccgtgagggc acgggttttt ctttgatttg ttccctgttg tgccccaaag tgctagaatc    22320
atgccaggca cacaatagat gctcaataaa tacttctgga atgaaaatcc ccctccactt    22380
agaccagtga gttccaaact tttttgatct tgacccatag taagaaaggc attttccatg    22440
ttgaatatac accattgaaa caaaattttc acagaaaaaa cttaccatta ttacaggcag    22500
tgcactgtga tatttcctaa tctcttctat tttgattttc aaaattgctg aggctactca    22560
taggttgatt tcacaagtgg agtttgtgtt atgaaaaact ttgacttaac accatgtcga    22620
aactgctacc acaaaaaggc aaatgcgaaa gaaggggggaa agagcaggcc gatgactttc    22680
cgctatccac cactccataa agcatatttc attttcctgt aattgtatcc tgttcaatga    22740
tgtagaaatc ctcacacact cacatgccac ttttttcttttg ggtgaaaagc gttctctact   22800
gcaagatgaa ttgagttatt tcaaaagcaa agagctataa atgagcctgt taagaaagt    22860
ctcaaggaga gtctgttggc atctgctgtt gataacttaa agcaggagaa ttagataagg    22920
aggcagaagt agaatgttta gaaataaaaa gtgaccatta tagaggaaaa actgcttgtc    22980
tcagttttgt tgatattgga gagtagctct ttcatgaggg tattgtggaa ttattggcaa    23040
ttatactaat agatgtttac tgaaaaaatc ctatttgact gatgaaccat ggaatacttt    23100
tgctgacctt gtggaaaaca tcacttatct gagttcctta tcttcttgtc tcttttttct    23160
catctagcct atgcctccct acctgttccc tcatggttct cattttgttg ctattagaaa    23220
aacagagata caaaaccag gaattggaac ccctctgtgt ctccagtaat aattctgtga    23280
ttaatgggtt agatggattc tggtcacaag ctggatattt tgttaacaac ctagcgtcaa    23340
tgacttggaa tgattttcac cgcagcatga tttagtattg aatagaatga tttaactaat    23400
gttaattagt tctgtacaga taaattaatg aagcaagaag ctcaatctct gatttattga    23460
tgtatttacc cagtgtaagt tatgaaatct ttttatttc atttgaagga agttttatt    23520
taaatacaaa taaataagcc ctttattgtc acctactttg gaaaagtcca gataaaacaa    23580
tcttaagtaa caaactcca aaattacaac atgattttca aaaactaccc tgacctttgt    23640
cttgcctggt tgttacagtg tacttttaac taaacggatt cttatagaat ctcaagtttg    23700
gttatatttg tattaaggaa ctctatattt gcatttgacc agccctaact aaaacaagct    23760
taaggaagaa aagggacttt acgacaagga caaggattg aagaagaact ccagggactt    23820
tagatgttaa caactgtatt tgtcactaaa gtaaccatta ctgtcaaggt gggttctcct    23880
tctccctcac taaacacatg cacacacacc acacacacat acacatacca catacatacc    23940
acacacatgc acacacacca cacacacacc acaccacaca cacagaaaata cacacagaca    24000
tacacacatg cacttatgct tgggtcagtt tggctttat catcccagag agtctcttcc    24060
```

```
catgtcagca actccagatt cacttcctct cctaatatag gacagtcaca tgtctctatt   24120
ccagcaaaac aatctcaggg aaggtatctc attggcctgg cttgggtcat tcaacttgaa   24180
gtacaagaag agaaaacagt attcttttat ttttatagat ttcctgtaaa atcagtggat   24240
aatggtaaaa atttcatgac agcaggtgtt ttaccttatt tatgtttact atctctagaa   24300
cccagtatga tagttcataa taaatgctta ctaaacaat tatcaaactg tacacttaaa   24360
aattaaaaga gtaaatttta agttgtgtat gttttaccac agtaaaacaa aataaaataa   24420
acctattatt gatcttattg tctatttctc aaaagtagca tacgtcataa tttcatgtga   24480
tttctaaagg agatcaatc tcaaacttag ttcttagagt aaaataaaag gttttggcaa    24540
tcatatacag cagtagactt taccttgaag atttaacaaa ggtttgaaag caaaatgcta   24600
tgatactgaa tatactaatg tttgagggct tgtgaaaagg tcttaatata ggaatcatat   24660
atcttctttt agattgtgtc ttggggaaca ttgggggtca gttttctat cagtgttagt    24720
atgtagtaag taatggcata catctaagct tgagattttg ctcatttctg tattcttagc   24780
acttatatat ccaacatata ataggtgttg gataatattt gttgaataaa tgactaaata   24840
aatgtcttgg catgagaatt atgccatcta caaaccgtc acttttaaaa aaaacaacaa    24900
agattttga acctgtagat ccagccagaa agcaagaaat atcttcacct ttccagactg    24960
acttattttt tggtctagct gtgtactatg catgagctgt caactttaat actttatttt   25020
ttaatgccta ggtctagtga gttacaatgt gatgtagact gattgaatta aaggcccaa    25080
tgttgtcctc tcttcattgt atccatgcct tttgtcatgt aactttgcag tgtcctctac   25140
tctaggtgtc cattcagctt atcctttgac tctggccttc ttctcctttg actctggctt   25200
tatccatgtg acttacttta gccaacaatc ataatgctgg caaacactga gaaaatgctt   25260
attagtgtct gcttagtctc ttgcttctct gcaattgcca tgagaaaatg cccaagctag   25320
tacactggag gatgagacat gtggggcaga agcaacctgt cccatttgtc ccagccaaca   25380
ccatcctaga ttaaccagat gagaccagag cagaagacat gttcagtgga gcccaaccca   25440
gctcacgaat aatatttctt catgagcatg tgagcaatgt gtaactaatg caccatgctc   25500
tttttattct gcacttccaa acatctctca gattgccctg ttgttttgct tttcagtagt   25560
catcaccttt gtccagaacc ttaattgtat ctgcattttg gcagtatcct gccaattttc   25620
cacatccagc tgttcacatt ctaatgcatt ctgcaatgga tgattttgag catatgactg   25680
atcatcactg tctcagaaat ttatgctaat ctattgtgac ctattctgtc aaatccaaat   25740
aactttacat tcaaaacttt tcatattctg gccccatact gtctattgta atcttatttt   25800
ctaaaagcca caaactatta atcctgtagc ctaattaggt tgatatcatc attttcacaa   25860
cacgttgggt aaattcttat atctgttcct ttaatcatag tttccatgct tagacactcc   25920
attgccctcc ctaagcacca gccagagtcc actatggggg gatattttaa aggctctttt   25980
cccctaaccc atctgcccca gaggtggcac aggctagaaa agatagtcca attatttggc   26040
ttaattattt ggatcttaca gttttttttgg gagagttcca gatgatttga tgaaatgcaa   26100
catggtcaaa aacattttgg tggagaataa tttaatcaac tagaccattt ggtgaaaaat   26160
aaatcccagt tactagactt cccagtatta ataattttgg tatgccagga attttaaaa    26220
catttctaac aaattttttc agaaatcaga atgactgaaa ggtataacaa taggaaatta   26280
ggaaatcaat aagtaatcat tgaaaagtga gtgattgaat tagttggaac aatctatgcc   26340
atccatcctg tgggggaaaa aatgaaaaca gctaaacaag cagagcagac atcatcaact   26400
```

```
tagaaaaaca atatagtaaa taatttgaac tagaaaattt tccaaaattg aaaattccag    26460
ttttaaaaaa tttgtgtttt cttattcaaa aagcaataca tatttcgtta cataaaagtc    26520
agaaaatcag agaagcagaa gaacataata aatgcccact gtcctactca atagagacta    26580
taactgctat ctctgtacaa atcctttaaa atcctgtctt atgtgtattt attttacatc    26640
tgtacatatg attccaaaat taggtaatac tgtacgtggt ctatctatag ctaactatag    26700
tttgtaattt aataagctat atttgtccat ggtgatcatt tattgctcat aaaattaata    26760
aattataatt tatttatcaa cactgatcat ttgttgctaa taatttattt catttaatgt    26820
cttattcctg ggttatttta actaatccct attgttagcc ctttaggttg tttcaactaa    26880
tttaagaatt ataaatggcc catagtagtt acttaataaa tatttgagtg aaaggataaa    26940
tgaatgaata attccacatt attggatgtt caagttgttt ccattcaact ttattgttgt    27000
gggggagtat aatacaatct tggtgaagag ccaccaactt aggaagaact atgaagaagc    27060
atgttattta ctcctgcttg tgggtggggt gcattgggaa aggaatgcct aaatgcacgt    27120
ggggagccaa acaagacttc acaggggaga tgggaattga gccaaatttg gaagaagtga    27180
gaattttcag ttgataattg gggaagatag tactaagagt aagtggggtt cattaggaac    27240
tacttcttag aagaggcaag tccagaacag aaggcagaaa gggatatgga tatgaaggaa    27300
aagtagaatg caacttcagg gctagtaggt tggcatccaa cgtaggtaca gccctggatg    27360
aggagtaatg agaaactgac ctggctgtag caaaacagct aggctgggaa gtgatgctgt    27420
ttacatttat atgcgattct actggtcttc ctgttacttt gtagaagact gtaaggcttg    27480
gtgctcagag ctagaaatgc aacttatttg atttgctaag aagtccaaag caggtagggg    27540
tgccaagctg ctgcctgttc acacatattc gtctaactgg gtgtcaggga agcagatat     27600 gagccccctt gcattggtta aatcctgagc aacttttaag gaactgcaca cagagactac    27660
tggctatttt ttgtggataa agttgtagat agttattttt gggaaattat ttatgtgttc    27720
tattaggtgg ttgttttgtg ggaggctgtt tgaaattctg tcttaaggaa ctgcagctta    27780
taaaccatag tgctgataga aataagagaa ataatttggt ctgcgagcac aaacatcagg    27840
ctagttggca tgcttatgta aacaccacac agtagcagtg acttttaagg aagtcctcag    27900
acaatgtaat cccaatactc ttcttgaagt tgaggtaata gggtgccaga agaaaaaga    27960 aaataaatct ctagtgcctt ctaaaatttt ttcaatcctt tgaccttttt gaaaacggtc    28020
acctttaatt cagaactaaa gtaacatctg gagggcccct ttcttagata gggagaagac    28080
ataaatgagc tatttgaatt attttctgct tatgggctgc atttcatttc ttccaccatt    28140
ggtctcagtc catttaatta agattatttg taggattaaa ttaatccttt aagaattatt    28200
ccatttcaat ttttaaaaaa tctaatgaat gatagataac aaaaagcggt ccattcagta    28260
ttacccctga acatatttg ggtgattggt gataccatcc atgtctctcc aacttcagct    28320
tcatatactc agctgagtac caggcatctt cattgaaagc tagacttgtg acctaaatag    28380
aacttgatcc cttcccttcc ccaactcctt attttttgtt ttctttgagt tccttgattc    28440
ctcttcccct cctcacatgc aacatgtaac atccaattca tcagcaggtt ctacagattc    28500
tgccttcaat aatagcctaa atctagccac ttgttactat cttttttggt ccaaaccatc    28560
atgatctttt gcctggacca ttgcaatagt tgtctaactg gtatccttgc tcccattttg    28620
tcctcctaga tcctatttc cacgtagtag ccactgattt ttggaaactt atcaatcatt    28680
acccagacac aatgagtaca tttacatagt tgtttgattc catttacata aagtcccaca    28740
atcactctat gtactgggaa tcacaacagt ggtctcctat gttgagaatt gattaagagt    28800
```

```
cacaaggaaa caaggagtaa tattccattg tattaacaga ccacactgtt catacattct    28860
cctgtaaatg gacatttatg ttgttttcag ttttttttgct attgtgatta aagctattag    28920
gttggtgcca aagtaattgc agttttttgcc attactttttt aaatggcaaa aactgcaatt    28980
actttggcac caacctaata ctgtaagtat ctttgaactt accaatcaaa cattactaca    29040
acacttgaat aagaaacact tccatagcat ttacaattct aagtgctttc catgtattga    29100
cttagttaat cctcacaagg atataaccat gaggtgctat tactatccct actttacaga    29160
tgaggaaata gaggcacaga cttcagataa tttgcccaag gtcccacagc taataagggg    29220
gcagaattag gaaagcctgg ctgagtctat gctctcatca cttgctcaac tctgcctgga    29280
atgcccttcc cgtaccctct accgcctctg cccaatcctc cgggttctct gctccttcca    29340
cacaccccca tctcaggtcc cagtcttttt tagcattctt cacttttttct gttacagatc    29400 ctcagacaat gcttccttga agaagacttg cctgtctaaa ctgccttccc atcccaatcc    29460 ctgttaccttt ctatccttttc tctgctttgt tttcatttgt tatctctctt cttcccaaga    29520
atgtaagctc cataagaaca ggatcatatt ttgaatcccc tagaaaagtg cctagtgtaa    29580
tatttgttga atgaatatga tccctgcaat taaaagctaa atatatatat ttttttaact    29640
aacagattac tgtagtagtt tcaaagatga atttatgttt cggagaaaat cagtattctc    29700
ttgccacata aattgtaggt aattatattt ctatacctga atagctttgc caatgactaa    29760
gatattaatc tattatatat ttattaatct atagatcttt aaaattgatg cacatgtttt    29820
ataagcaatt tgatgaattt tgatgactac atacacctgt atgtgtatgg atatctgtaa    29880
caaatatcca agtaaagata tagaatattc tcattacccc agaaagtttc tttgtgactt    29940
ctaatcaatt ctcacctccg taggaaaccg ctgttgtgat tcccatcacc acagactgat    30000
tttgggactt tatgtaaatg gaatcaaaca actctgtgaa tgtactctgt gtctgagttc    30060
tttcaatcta cacaatcttt ttgacattaa tccatattac tgcctagaag agtagttcac    30120
tctttgcatt aatgaatagt attccattgt ataaacaaac cacactgttt atacattctc    30180
ctgtgaatgg acatttgtgt tgttttcagt tttctgctat tgcgatttaa gctactataa    30240
gcattttttt ttaattgtga tggggtttcg ctcttgttcc ccaggctgga gtgcagtggc    30300
agcgatctca gctcactgca gcttctgcca cgtgggtcca agcgattctc ctgcctcagc    30360
ctcccgagta cctgggatta caggcatgtg ccaccacacc tggctaagtt tcgtattttc    30420
agtagagacg gggtttcacc atgttggtca ggctggtctc gaagtcctga cctcaggtga    30480
tccacccacc tcggcctccc aaagtgctgg gattacagtc ttgagccact gtgcccggcc    30540
agcatctttg aacatatcaa tttgtaagtt ttatcttaat attgtacaag tcttttgggg    30600
ggcttatgtt gtcattctct ttggtaaata cctaggtatg aacttgctag attatagaga    30660
aaatctatct ttaattttat aagaaactgt caaatagttt tccaaagtgg tggtactatt    30720
tatactccca ccatcaatgt atgaaatttc cgttgtttta cgtccttgcc agaatttgtt    30780
ggtagtcttt ttttttttttt gaggcagcat ctcactgtgt tgcccaggca tacaatggtg    30840
tgatctcggc tcactgcaac ctctgcctcc caggttcaag ggattttcat gcctcagcat    30900
cccaagcagc tgggactaca gaggcgtgcc accacaccca gctaattttt gtattttag    30960 tagagatggg gtttcaccat gttgcccaag ttggtctcga actcctggct tcaagtgatt    31020
cgcccgcctc agcctcccaa attgctggga ttataggcgt gagtcactgt acccagcctg    31080
ttgccagtat ttttagttgt aggcatctta gtgggtgtga gtgctcgttg gggttttaat    31140
```

```
ttgcattttc ctgatagtgt tgatgttgag gacatttcta tgtgtttact gagcattggt    31200
gaagattctc ttgtgaaata tctattcaaa tattttgctc atggtgggaa ggggagttat    31260
ttttctttta ctactgatag gtaggcttac gtatttattt cggatataat tattttgtca    31320
attatatact aatcataaac aaaaactgat aaattggacg acgtcaaaat taaaacctgc    31380
tcatcaaatg ttagcgaaat gtaaaggcaa atcacatact gagggagat attttaatat      31440 atgtatattt atatagtgct ttctgtgttc taagaagtat tttcctactc caagataaag    31500
agactattct cttacatttt gttctataag ttttatagtt ttagctttta gctttggatc    31560
tatgatctgt ctcaaatttt tatgcaagat tggggtttaa ttttttcata cacttttcca    31620
gttgtcaagg atcatttgtt gaaacgtctt tcctgttgcc acataattgc tttgatgcat    31680
tcgttagaaa tcagttggct gtgggtttat tttggaattt tctgttctgc tcctttgatg    31740
tatttgtcta tccttatgcc aatatcaccc tatattaaat aattatagct ttataataag    31800
tcttgaaatc aggtaatgtg aatgtttcaa ctgtgttttt ccttttttcta gttattttag    31860 ctgttttatg ttcttattgt atatatttta gaatcaactt attcatttct acaaaaagtt    31920
tattgggatt ctggatgaga tggtgttgat tcagtaggtc aatctgggga aatctgataa    31980
caatattgac tcttccaatc catgaaaatg gtatctcatt ctttatttac atattcttta    32040
atttctgtta gcaatgtgtt ataattgtag caaacttgca catctttgt taaattattt      32100 tctaagtatt ttacgatttt ggtaccactg taagtggcat tgtatttaaa atttattttc    32160
tgtttgtttt ctgttcatat ataaatgcaa ttgattttct ttttttttt ttttttttt       32220 ttttttgag acagaggctt actttgtcac ccaggctgga gtgcagtggc gtgatcagca    32280
ctcactgcag acttgaactc ctgggctgaa gggagcctct cacctcagcc tcccaagtag    32340
ctgggactat gggtgtgagc cagtgttcct ggccaaatgc agctgatttt tgtattgaca    32400
ttgtattctg ccaacttgct aaattaactt attcgttta atagttttc tgttttttta      32460 aaaatcttag gatttctaca cagacaatca tgttttaat gaacaacaaa gtttgttttt      32520
ttgtttgttt gttttttccct tttcaatcaa catgcctttt atgtttttat ttgccttact    32580
gcactggcta ggacctccag tacaatttta atagcaatgg tgagagtgtt taaatgtact    32640
cctgtgtata ttttattctt ttggaactta ttataaatgg aattgttttc ttaattttct    32700
ttttggactt tcattgcta ttgtacagaa atacaactga ctattgtgtg ttgatcttgt      32760
accttgcaat tttgctgaaa tcgtttattt tttgcaatag attttttgtga attctttagg    32820 attttccata tgtagaatca tgttatctgt gaataggggat agttttactt cttttctaac    32880
ttggatagtt ttttccttcc taattgctct ggcaagaact tctagtacaa tgttagagag    32940
caatagtgaa agcaggcatc ttcctttcaa tcctgatgtt agggggtgaag ctctcagcct    33000 ttcactgtaa tgttggctgt ggattttcat aattttttgt ttgtttgttt ttttgtttga    33060
gacggagttt ctcttgttgc ctgggctgga gtgcagtggc gtgatctcgg ctcatcacaa    33120
cctctgcctc ctgggttcaa gcgattctcc tgcctcagcc tccagagtag ctgggattac    33180
aggtgcctgc caccacaccg actaattttg tatttttagt agagacgggg tttctcgatg    33240
ttggtcaggc tgctctcgaa ctcctgacct cagatgatcc gccgcctcg gcctcccaaa      33300 gtgctgggat tacaggcatg agccaccacg cccggcccat aaatgctttt cttaatcata    33360
ttaaggaagt tccttctag tcgtagtttt ctgagtgttt ttattatgaa agactttcag      33420 attttttgtaa aatgctttc ctgcgttaat tgagataatc atatgggttt tctccccctt     33480
tactctattg atgtaatgca ttacaacgat ttttttttaat gtttacccat ctttgcattc    33540
```

```
ctggaataaa tactagttga ttgtgctgta taattcttaa aatatgctgc tggatttgtt   33600
ttgttagtat ttggttgcat tcttttgcat ctatattcat aagggatatt gatctgtaac   33660
tattattttc ttgtggtggc tttatctggc tttggtatca agataatgct ggccacattg   33720
gctaagttag aaagtgttct ttcttctatt ttttgaagag cttgaaaaga gtcgtgttaa   33780
ttcttcttta aatatttggt acaattcact attaaagcca ctagtcctgg gcttttctta   33840
gtttgaaagt ttttgattac taattcaatc tcttttacac ctagattaga ttttgtattt   33900
tttccttagc cacttttggt aatgtgtgtg cttccgggaa tttggccagg tcatctctgt   33960
tatctaattt gctggcatcc aaatgttcat aatgttctct tgtaatcctt tttattatag   34020
aaatgatata cagaaaaggt cagttaccac tttctttttat gattgcatta atttgcttct   34080
tttctctttt tttctctagt cagtcttgct aaaggttggt ctgttttgtt gattttttc    34140 aaagaaccaa cttttgattt tgttgattct ataattttc tgctctgtat tttgtgtata    34200
tccattctaa ttttattag ttcctttatt ctgttagctg tgagtttagt tggctcttct    34260
tttttatttt cttaaggtgg aagactaagt tattgagata tatcttgttt tttttttga    34320 tgtaggtatt taaagctata aaatttcctc tgagcattgc ttttgctgca atttataagt   34380
attggtatgt tacatattca gttagttttt tatatacaca tttaagcttt tgctaatcta   34440
ccttgtgatt tcttcattga cttattgctt gtttgagtgt gtcaacaatt tccacgtatt   34500
tgtgaatatt ctagttttcc ttttgttatt gatttctagt ttcatttcat tgtggtaaga   34560
aacaatactt tttatgatct caacagttta aaatttatta agacttattt tctggtctaa   34620
catatgatct atcctggaaa atgtatcatg tgcacttgag aaaaatgtat attctgattt   34680
ttttaggtgg gtggcatgtt ctattaatat atatgtctgt tagctctagg tgaattatag   34740
tgatgttcaa agcctccatt ttgttattaa tataaccatg ccagattttt aatgctgtcc   34800
atttgcataa tatgtctctt tccattcttt ttcttttaca tgatcacttt atatttatag   34860
tatatttctt gcacacagaa tgtaattgaa acttactttt ctaaaatcta ctttcttttt   34920
tttttttttg agatggagtc ttgctctgtt gcccaggctg gagtgcagtg gcacaatctt   34980
ggctcactgc aatctctgct tcccgggttc aagcaattct cctgtctcag cctcccgagt   35040
agctgggatt acaggcacct gtattttag tagagacggg gtttcaccat gttggtcagg    35100
ctggtcttga actcctgacc tcgtgatcca cctgccttgg cctcccaaag tgctgggatt   35160
acaggcgtga gccactgcac ccagccccta aaatctgctt tcatagcatc tgtcttgtac   35220
ttggaacatt tagtccatgt gtatttgaat atttattgat atgtttgggt ttatgtttac   35280
aatcctgcta tttgttttct ttttgttcca tgtgtttttt gttttttatt tctgcatctt   35340
ttggaaaaat cagattttt ggtaattcat tttcttatt ttattggctt tttagagaaa    35400
ccttttaata tctttgtgag ttttagggat tacattattt attcttatta ttattccatt   35460
tagaattaat attgttaatc ccattcaaaa atttgtttat ttcgcttttc agttctagaa   35520
ttttcatgtt ttcttcagtt gttgtttctc tgttgttatt ctccatttgt tcattatatc   35580
tatcttttct ttgaaatcct taaaaatatt tataatagct attttaaagt cctctgctaa   35640
tcccaatgtc tgggacatct tggcttctgt tgatattgaa tacttctttt tttccccttta   35700 attaagggtt tcatttttcct gcttttcac atatctagta gattttatt atgctctgtg    35760 tgctatgaat gagatattat aggaagcctg tcaatattg tctctttta aagggtgttg     35820 tatttagttc tgccaagaag ttaaattacc agatttactt gatgtggctt tagtctttgt   35880
```

```
tagagctggt ctattcctgc tttgttctta cttctcaggt aatgaccttc ctgagtttca    35940
gctggatgcc tgaagtgctc agctgcattt ttctactctg gctattctga aatgcaatat    36000
tttccagacc tacccaacct tggtattca  tctcccagac ctgtggctgc ttctctttgc    36060
tgagcctcac aaaatcttgt cctgtgcatg gacagccaag gatccttggg aaatctcatg    36120
cagacttcta ggtccttcct ttgtgtagat ttcttctctc cagtacgttg acctgcttca    36180
gagtcctcat cattgctttc ttcctttca  gctcagcaat actgctgtgt attgtgtggg    36240
cttcatttgc ctcagccata cctagaacac aacccaaggc agaaagctgg agtggacctg    36300
aggctcatca cctgtttcct tccacccacc atttaaaagc agcttatttg tgtgaaactt    36360
tttgttgggt tctgtggggg atacgtatag gcaaatgaca gggagcttat aatttagcca    36420
aagagaaaat gtctatatgt tctgtggaat tcagagtatt ttcctcgact tccaaaatta    36480
ttttcctcga cttccaaaat tggggctac  tagctagttg gtaggaagga attccagatc    36540
catttttctt ctagattttt ttcagactcc atgtttcaaa atctagatgg aaggtaagaa    36600
ggaagcaagg agggcatcac atacgagaga gacttatacc ccaaagtgga tcattagcac    36660
attatgagat aatatggtat tattctcaga ggcctgccat ataaaattcc ttctaattta    36720
ttttttaatg gtatgtgcct gaaagttttc tgtctttcat gatcttgaaa gcaaaataag    36780
aaccagagta gcttatgaga gagttttcct gcttcagccc agaaaaatgt tgcttctgtc    36840
ctagacccct tgatctggtt cttagtgcca gccttcattc ctctagatct gtttattgaa    36900
tactggctct gttgcagaga ctttgctaga atctgagaga taaaagactc aatgccttca    36960
aaacacctac aatccagaca cttaaataaa tgcaataata tatggttaag gtcttggata    37020
gaggaccatc atagaaacac atagaacaga catttagtcc atgctaggga gagggaagat    37080
gtcaaggaat gcttcctgga ggtggcgaca tctaagctga gttttaaagt gggtgtaaga    37140
gtgaaggaac tgggaatagg caaaacatac cttagagagc tgcacctcca aagcatggaa    37200
ggctagataa tcttagaact tcaagtgggg ttcaatgtgc ctgggacttg gatttcaggc    37260
agagaccata gggcaagttg gagaacaggt gggcagggtg agatgaagca gagacttta    37320 ataaccatca aacaggcctg ccatccaact gctatcagcc attttccctt tttgaatttt    37380 attttttttaa tctctagagc aatacatgtt tatggtagga aatgaaaaaa atatatagat    37440
gggtaaaatg aagtgaatta taccacccac aatcctgctg taaaacaggt tttaacaagt    37500
tataaatccc tccagatcaa agtgctacta aactctactt gctatttat  aaccttttc     37560 tgttcagagt attttagaaa cgttttaca  tgttaattga tattcttttg cattatcctg    37620
aataatggta tttctttagt tatactatca tgtattaaaa cattcataca tggtaaacat    37680
atttgaatat tagacatttc aattgttttc aatgtttggc tattaaaaat agtatttaga    37740
tgaatgttct tggccataca gttaataact tcactgagtc cttgtcaata actttattaa    37800
atcccaatct taagacaaca agcctataag attaacatac caggaataat tagaaagcat    37860
tgcaagacta tatgtaacca tctccctgtt aatcatcctt atttgttgca acatcctaaa    37920
tagcgacctt cccacactct gcctcataat atttaatctg tcaaatgtac catccgcaaa    37980
gggagtgaac tggctcgtga agaggtggtg aagctggttc aactcagttt aacagacaat    38040
gagggcctcc gtgtgccagg gagggagtga gggaactcca cagggagctc attctgggga    38100
gggatgcccc tcattatctg cagtaaatga tattagagaa gtatgtgtga gactcttggt    38160
gtccagagga ggggcatgca gcacagtatg ggggtccatg gggttgcagc gatttcttag    38220
agacggtgcc atgcctggga tgaccaccaa gttaggatgc tgtaaagagt aatcaaataa    38280
```

```
gtttcaacag ggttttggca tgaggtgagc agttaatcca aatgatatct gaaatgcttt    38340
ctaatgctgc aagtgtattc ctctgtaaaa taatcaacta cttaaaagac actctcactt    38400
gcattatgtc atttaatcct cacagtgtcc ctacgggaca atagatgtca ttcccacttg    38460
tacagagcag taagtgaggc tcacaccggt catagttaga ggagtaggga atctaaacct    38520
aagtctcttc tactccaaac cccaagtttt atcagtatgt cacatcgcta ctgtgggctg    38580
aattccttag caggggttgt ttcctccacc tgcaatattc ttccttttgg tttgttcatc    38640
ctctagagag agaagggata cgcattcatg gagatcctac tgttgcaaac tctgcattag    38700
gagttttaca tgaattgtct catttagtcc tcacaacagt cctgtgaggc acaggaaagt    38760
tagatttacc tgcccaaatt aaggaatgtg gccaactcaa gagtgacgaa ggccaggtgc    38820
ggtggctcat gcctgtaatc tcagcacttt gggaggctga ggtgggaggc tgaggatcgc    38880
ttgagcccag gagtttaaga ccagccaggg caacacagca agatttaatc tctactagaa    38940
ataaaaaaga aattagccag gtgcctgtag tcccagttac ttgggaggtt gaagtgggac    39000
gattgcttga gcctgggagg tagaggctgc agtgagccat gatcccatca cttcactcca    39060
gtcagggtga cagagtgaga cccagtctta aaacaaaaca aaacaaaaaa gagtgatgga    39120
gcaggaactt tatctgccat cagagaccat atatgtcttt ccttatggcc caggtcattt    39180
atcatgtcct tgctaaacct cctcctctga gccttgttaa agtcctcaag gttagaagag    39240
tggtctataa ttataaaaaa ttccattgta tgacttcagc tacctgcaaa actgaccgag    39300
attaatgcat tctttgtttg ctttcactct ttcattccct gttcagcgct tattctacag    39360
aaaggtgcct ggtagattta ggacatgact gttcataggc ctcaaatgcg gtcaaattag    39420
gaaagtcccc tggttttttgg tctcaagagg ttaattgctg agtactagcc tggactgctc    39480
aatggatttt atgtttaact gttgtgttta tttgtttgtt tgtttttgtt ttgtgagaca    39540
tatctttctc tgtcacctgg gctggaggtc agtggtgtga acatggctca ccgaagcctc    39600
catctcctgg gctcaagtga tcctcctgcc tcagccttcc tagtagctgg gactacaggc    39660
acacagcacc atgactggtt aagttttgga ttttttggta gaaatggggt ctcactcttt    39720
gcgcaggcta gttgtgaact cctggtatca agggattctc ccaatgtgct gggatttcgg    39780
cctcccaaag tgctgggact gcaggcatga gccatcatgc ccagcctctg tttaactgtt    39840
aacatcatga ggtttccttt caatgaggaa gggaggcctg gggaggtgtg atggggaaga    39900
tggagaaggg taggagacat cataaaactg acagaagtgt ggcacgatta agaccctggt    39960
ttcttagacc acataagcaa gtgccactat tcttttgatc aacatttgat tctctatttc    40020
cttcttagca tatagatagc tgcttcaggt cgtgaaaaaa tacatttagt gaaatgaaac    40080
atagtagata tgttcaccaa gaaactaaaa agaaaagtta gccacaaact atcttatttc    40140
attgaaatgt ttggctgaac ccataagaat gttgatgagg ccattcttgg atgcctgtac    40200
tgaaatgaac cacgagagga atatttagga tatgttgaag aggctgtttg gcttaatgaa    40260
caaaggagtt tctgcaggcc cagggagtgg aatgaaaatt ggcatgatca ttttggagaa    40320
tatatggagt caaacagaga atttgaatgg agttttcaaa gaggatatgt taggggaata    40380
aaggctgata aacaacactt gtatttgtag gaaataggga gagtaaatc aaggaattca    40440 aagagaaaga gaaactcact tcaagtaggg gagaaaaaac ccctataatt ttcactcttc    40500 cttgtaaaata aaaaggaaac aaatgaaaat aagatattag aagtcagtaa gaatttatgg    40560
gagtataaag ttggttttat ggatgcaaag ccctttttcac tgctgtacga aactcctggc    40620
```

```
tgcatgctaa caatggacaa ctgatttcct tgcagctgta ttttgctgtt ttttgctctt    40680
ggcttggacc tagcaccctg ggtctgtggg aaaccagaac tgtcccagag ttctggaggg    40740
taggccaagg ttagatgctg gagtgggttc tttaatttat tgtactgatt cttcttggga    40800
agaaagaaga ttgcttgtta gaattttagc tacgagagat gactatgaaa cagtaaatta    40860
actccaacga cctgagtcat tttgaaaact cccagtctca ggataaaaaa tataatccta    40920
tttagaaatt cctggtgtga tcacagatgt agcattggtt cttttcatga aacccgtaaa    40980
ttaaaaagta cataatccaa agtcaattaa atagtaagct attataacaa attctttttat   41040 ttcattagct tttcaaaatg tggataacta cacactcaac ccaaggaatc tacattttc     41100 cactgactgc taaagaccaa tggaaataac tctagtcccc gtagcacctc actgtggggt    41160
gacctacctt tgaaataatg tattggttct agctgatttt tatattgtta gtcattaagt    41220
taggcttgat gagaaacaga tataatctga tttggggatt caagtattat attgcatttc    41280
tcctcacaac tagagataaa tttgccatgg ttttctctt cataggctca tgccaaagtc     41340
tggcatctct acaatacttc tttccgtccc actcagggag gtcaggtgtc cattgcccta    41400
agctctcact ggatcaatcc tcgaagaatg accgaccaca gcatcaaaga atgtcaaaaa    41460
tctctggact ttgtactagg ttggtttgcc aaacccgtat ttattgatgg tgactatccc    41520
gagagcatga agaataacct ttcatctatt ctgcctgatt ttactgaatc tgagaaaaag    41580
ttcatcaaag gaactgctga ctttttgct ctttgctttg gacccacctt gagttttcaa     41640
cttttggacc ctcacatgaa gttccgccaa ttggaatctc ccaacctgag gcaactgctt    41700
tcctggattg accttgaatt taaccatcct caaatattta ttgtggaaaa tggctggttt    41760
gtctcaggga ccaccaagag agatgatgcc aaatatatgt attacctcaa aaagttcatc    41820
atggaaacct taaaaggtat gattgtgggt aaagttctca tttcctgcca aaatcttctg    41880
gaaaaaaatc tctaagatta tctaacataa atgatgtgaa tttatatttt taaatcctaa    41940
tggagacatt cattttggca atagtagaat gcattcattt aacacctttc tcatttggag    42000
tcttgaggaa cttgaattaa tttttaaaaa cccatttgta aatgagaaac tgggttataa    42060
tatttgtaat tacttaactt tcagttatta atctagattt ttagattaaa ttgaacataa    42120
aacaaatccc aggatatcta gctctctgca catgtttttc agttcttgtt attttggttg    42180
aataaaacac tttaaagaaa aaggaatgtc catgttttct agagaaaata gtataaatag    42240
atcatgcttt taaagccttc atttatttat ttattgcatc agacacaaag ctgggtgtct    42300
aggatggaaa gtggtacaag acatctttcc agccctgtag aatatctatt ataaataagg    42360
aactattttt tcaaggtgct cagaaatcca aaaaacatat tagataggcc aattttgagg    42420
gcatttattt gtagagttat ataggtttga ttagagtctt tcgtcaagaa gaaaaatcat    42480
tggcttacca aacgagaagc attacacttt atttatttaa gtaggaaacg ctcagctgct    42540
cttgaaccat gatgcaagtg cccagcgaag ggtcatgttg ctcttgtccc ctcttccctt    42600
tgcagccatc aagctggatg gggtggatgt catcgggtat accgcatggt ccctcatgga    42660
tggtttcgag tggcacagag gttacagcat caggcgtgga ctcttctatg ttgactttct    42720
aagccaggac aagatgttgt tgccaaagtc ttcagccttg ttctaccaaa agctgataga    42780
gaaaaatggc ttccctcctt tacctgaaaa tcagcccta gaagggacat ttccctgtga      42840
ctttgcttgg ggagttgttg acaactacat tcaagtaagt cagctgacaa aaccaatcag    42900
cagtctcacc aagccctatc actagtaagt agtgcttcct tcctaggctg attgtcatgg    42960
cacattgtcc gttctttgag ccaaaaacaa ttccttatga gtacactaag ggcacaattt    43020
```

```
ggaatgctgc accCttctct ccaaaactct tccaatcttc atcttgttta agttagatcc   43080
aaagataaat aaatttaaag catatcaata tttaagatcc gattaagaca gtaaaaagat   43140
aaaacactct cttttcatac tgtggttttt gatccttttt aaggcagttg agttttttca   43200
tgaacaggat ctaacacaga actccaaagc ctctgagttt cagtggtgct gctgagactg   43260
aggcaggaac attaggcaga gtcctccaga ggcacaactg tgggctccac aaatgtgcag   43320
aaataccCta agaagtaaa ccctagatcc aatgattcac tggtcagaat gtctttttta   43380
gcaatagtca ttgaaatgat acgaaatttc ttcagaatga tcaaccaata tttattgagc   43440
atcttctcag tagtaagccc ttaacattct ttcagcttc ctaaattttg aaggggcttg   43500
ttttccagca tttgactgga tactctagta agcacttatt ggatgtctag tgtgtccgaa   43560
gccttgtgtt agttgctcgg gtcgcttggt taaggggagt gcaggtagag ggtatactga   43620
gatgagtaag ggtaacCttt gctttcaaag gagcaaagga gtctactgag cgaaaacaat   43680
gtatgcacaa atgatgcaat ggagtgaagc gggcatggtg gtaagtaaca agggcggggc   43740
tgggggattg ctgctgatag agtcccaagt gtgaaaatag ccctcaagac agagacagag   43800
ttcagtgtcc atagacaagc agttggcttt gacatgttgg gttatggtag ccaattaatt   43860
ggttctgcaa atcacagctt gaaaggaaac acttggaaga atgtgaaatg ggttgctgtt   43920
ttcttgtaaa tatccaattg aaatcttta tttataagga aataaattaa caccatcctt   43980
agtacatttt ttgctggttg ggattattct tcttttcag accacccagt tcattttaca   44040
ggcagtctca gacttaaacc ctcgccttcc atttaaaaga tgactggctc acgcctgtaa   44100
tcccagcact tgggaggcc gaggcgggcg gatcatgagg tcaggagatc aagaccatcc   44160
tgaataacac ggtgaaaccc cgtctctact aaaaatacaa aaaaaaaaa aaaaattatc   44220 cgggtgtggt ggcgggcacc tgtagtccca gctactctgg aggctgggc aggagaatgg   44280 catgaaccca ggaggcggag cttgcagtga gccgagattg cgccactgca ctccagcctg   44340
ggtgacagag caagagtccg tctcttaaaa aaaaaaatga ctggatgtgt catcttttat   44400
gccaggatat gtgagcccag gagaaaggct tctgagctcc ctcctgctcg gtgtgcaatt   44460
ttctgccctg ccccgactct ctccttctct cccagcctcc tgctatttga aatctcctta   44520
tcctaatttc cctcctcaga gtggattcca ctgtggggtt cagagaggat ctgaggtggg   44580
agaagtgagg ctggtgagga agaaggggag gagaaaggga agaagacctc cgtagccttc   44640
cttcctcctc ctctttactg gggttgggga tagatcggat ggtccctggt ccttgttcta   44700
tctcttgacc ttctgcctgc tccctgctga gcacggatct ctgatagcag cctgagtctg   44760
gcaggttcag tcctttgtat gcggcacaat ctcccagcca gcattgctgt gcagatcatg   44820
ggaacgaatg cagaacaaga gtgggggtgt cggagggagc cctacttctc ctgttctatt   44880
cctcatcagg gggctgtgcg ctggctttgg gaattggtaa atagtgagaa agtcttaagg   44940
gtacatccta tttccttgag ggagaagaga aaacgctggt cagaagcaat aagtatagca   45000
gtgaatagca agggagatgg gagataattc cttttcctac tacactctag aagctattgt   45060
tttagaatct gacctaaggt cagccactaa ttggccccag aggtctctct ctcagatcac   45120
acggtccttt tttcctcatc agcttgggga ccccaccccCt cctcctggca gtctcctcct   45180
gtgcagaacc caacaaacac aaaattaagt cactctcaaa cccacagcag atgagagctt   45240
ctctggaagc tccctggtgg ggaaaggctg caattgctat tttcttcttc tggttttcac   45300
ctcaggcttt gtgttatatt gacagtaccc ttctcaagct aactccctaa ctgacctgac   45360
```

```
gtagtcaaaa taagttcttt gtatgtcagt tctgaggtgt gtgtgttttc acttacaaac   45420
agtactctac agctttaaga cattatatta aagtcctgag aagtgatttt taaaccactg   45480
aacttcatct tttccctcct ggctagtatt tcagactttc agtgtttgag gcatgcattt   45540
cacctgaaca acttgaaaaa taatatccta agaagcacac aacctgactt taggctcatt   45600
cacatggatt gtcactttac ttggacccac tttctcggct gagaggtttg ttttcccata   45660
accacggatg ctcatagtta atataaatat tgaactcact atgtagtgag gacatagagc   45720
ctctttaaca ttggtccctg ttaggagaaa gtttctccca taacatacta aatacatgtt   45780
ttaatagccg ttccttctga aaggtccaac ttcactattt tatttttta gtaaaatctt   45840 agttaacaaa ttaatggagg ttaggtggaa ttttgcccca aaagtcctgt attttctttt   45900 ttttttttc ttttttttg acagagtctt gctctgtcgc ccaggctgga gtgcagtggc   45960
gtgatctcgg ctcactgcaa gctccgcctc ctaaggtcac gccattctcc tgcctcagcc   46020
tcctgagtag ctgggctac aggtgcccgc caccgcaccc ggctaatttt ttgtattttt   46080
agtagagacc gggtttcact gtgttagcca ggatggtctc aatctcctga cctcgggatc   46140
cacccacctc ggcctcccaa agtgctggga ttacaggcgt gagccaccat gcccggcctg   46200
tcctgtattt tcaagaaact tttttttcc tccagaaatg atacCctagt ctttcatatt   46260
tgttttcaga tggactgaat aaaagctgtt gttttggaac aatcacggtt aaaaaaaaa   46320 gttatgaatt tagtcaactc agagctctat aaaaataatc caaaaaattc ttcaaactc   46380 tgaacgcttc aaaagagcgt gcaaatattc tgtccttcaa agctaaggaa acatgatttg   46440
tggggtgcat cacagtggaa aaatactctg acagcattcc cacagcatta ggggaagtgc   46500
atgtgtgggt gttctgcaag ggacaattct ccagaaaagg caatttccct ttgacatgct   46560
gtttttaatg acttttcttt ataaacacac ttatctctcc agagaaatag cagtgcattt   46620
gcaacaggcc cgtaaaatgc aacaaaacct ctgctatggt ttctgacccc tgcttttata   46680
cagagcatca gaccaaggaa cctgttctaa caggattatt tcagagggga acacaggctt   46740
agggtgcaga tcttccagct ggattttttca ctttgcattc cctccacagc agacacatga   46800
aggaatgatt ttgtgatttt gatttatat tttgcacact tttcctaaat actttttta   46860 aattttattt tgggaggatt ttatagcata tgattgagaa ctataatcat catcattgtt   46920
acagaagaat aatttagaaa aattttttaa ctacgttaaa aattccacta tgggtggatg   46980
acaatattgt tctttccttc cacattctcc ctccttagac tttcttttct ttttttctat   47040
tttttttttg agatgaagtc tcgctctgtc actcaggctg gagtgcagtg ccatgatcct   47100
ggctcactgc aacctctgcc tcccgggttc aagtgattct cccgcctcag cttcctgagt   47160
agctgggatt acaggtgtgc accaccacac ctggctactt tttgtatttt tagtagagat   47220
ggggtttcac catgttggtc aggctggtct caaactcctg atctcatgat ctgcccgcct   47280
tggccccgca aagtgccggg attacaggcg tgagccactg cgcctggcct ctctctcgga   47340 cttctctacca tcagtcagat tgaatttgtt aaattctgtc actgaccta aacccaacaa   47400 aaggcaagag ttatgtttat ttagcacttc ctctacctat agcaaacctc aatttagagc   47460
gtaattttaa gcacaattta attataaata tcttttcatt ttcttactta actcactcag   47520
ttttttaaat cttctttttt gagacaagat cttgctctgt cactgaggcc gatgtacagt   47580
gatgtgatca tgacttactg cagccttgac ctcccaggct taggtgatcc tcatacctca   47640
gcctcccgag caactaggac tacaggcccg tgccaccatg ccgggccaag acggggtttg   47700
gacgtgttgc cccagctggt ctccaactcc tggcctcaag tgaccctccc gcctcggcct   47760
```

```
ctcaaagtgc tgggattata ggcatgagcc accgcacctg gccaactcac tcacatttta   47820
agttttttct tttttcatc tagttttttt tcttttaaa tttgaaagcc tcatgacatt    47880
aatgatttct tacattaaaa gaaaaacacc caaaaatact ctgcttacat aacaccgaca   47940
agtagtgtgc aagactcatt agcatttgtc atctgaagtg accaaatcca gactttgg    48000 ggtcacatta aagaaacagt tgaagagtta gaactatggg taaagcgagt gtgcatatca   48060
gaaagtggaa tattgtcttc ctcaggagct gacaatttat gaaaaatagt tcacattctc   48120
agctagaaag gcttctattt ttgctcatat tcctggctag ttttgctgaa ataattgctt   48180
tgaattactt cctcaggact gcccaggtga cgctaatgtt tactctgccc ttcacaggta   48240
gataccactc tgtctcagtt taccgacctg aatgtttacc tgtgggatgt ccaccacagt   48300
aaaaggctta ttaaagtgga tggggttgtg accaagaaga ggaaatccta ctgtgttgac   48360
tttgctgcca tccagcccca gatcgcttta ctccaggaaa tgcacgttac acattttcgc   48420
ttctccctgg actgggccct gattctccct ctgggtaacc agtcccaggt gaaccacacc   48480
atcctgcagt actatcgctg catggccagc gagcttgtcc gtgtcaacat caccccagtg   48540
gtggccctgt ggcagcctat ggccccgaac caaggactgc cgcgcctcct ggccaggcag   48600
ggcgcctggg agaacccta cactgccctg cctttgcag agtatgcccg actgtgcttt    48660
caagagctcg gccatcacgt caagctttgg ataacgatga atgagccgta tacaaggaat   48720
atgacataca gtgctggcca caaccttctg aaggcccatg ccctggcttg gcatgtgtac   48780
aatgaaaagt ttaggcatgc tcagaatggg aaaatatcca tagccttgca ggctgattgg   48840
atagaacctg cctgcccttt ctcccaaaag gacaaagagg tggctgagag agttttggaa   48900
tttgacattg gctggctggc tgagcccatt ttcggctctg gagattatcc atgggtgatg   48960
agggactggc tgaaccaaag aaacaatttt cttcttcctt atttcactga agatgaaaaa   49020
aagctaatcc agggtaccctt tgactttttg gctttaagcc attataccac catccttgta   49080
gactcagaaa aagaagatcc aataaaatac aatgattacc tagaagtgca agaaatgacc   49140
gacatcacgt ggctcaactc ccccagtcag gtggcggtag tgccctgggg gttgcgcaaa   49200
gtgctgaact ggctgaagtt caagtacgga gacctcccca tgtacataat atccaatgga   49260
atcgatgacg ggctgcatgc tgaggacgac cagctgaggg tgtattatat gcagaattac   49320
ataaacgaag ctctcaaagg taaggagccc tagctgcggc tatctcctga aggttatgtc   49380
accagagggc atgacacttg attaaatctc caacatcaac acacactgcc acccttggaa   49440
tggagggcta tccattttgt gcctcactga acagtccaa gagatatcta gcatttcccc   49500
aaggataaag gagtgtagct aaaagtagaa gaccagaaat ccctagcccc tactctggat   49560
ctatgcaagc ctagattctt gtcttccatc ttggatggct ccacagcagt cttaactgtt   49620
tcatgtacat aaagcagtac ataaagattt aaccttgctg ggcatggtgg ctcacacctg   49680
taatcccagc attttggaag gccaaggcag gaggattgct tgagcctaga gtttgagac    49740 cagcctgggc aacatagtga gaccttgtct ctactaaaaa tcacaaaaat tagctgggca   49800
cggtggcata tacgcctgca gattcagtta cttgggagga gaggcgggag gattgcttga   49860
gcttgggagg tccagctgca gtgaatcatg atcacagcac tgcaatctgg cctgggtgac   49920
agagcaagac actatttcaa aaaaaaaaag accaagcatg gtggctcatg cctgtaatcc   49980
cagcactttg ggaggctgag gcaggtggat catctgaggt cagaagttca agaccagcct   50040
gaccaacatg gtgaaacccc gtctctactg aaaatacgaa aattatccag gtgtagtgat   50100
```

```
gcacacctgt aatctcagct actcgggagg ctgaggcaga agaatcactt gaactgggga      50160
cgtggaggct gcagtgagcc aagattgcac cattgcactc cagcctgggt gacagagcaa      50220
gactccatct caaaaaaaaa aaaaaaaaaa aaaggattta acccaagtat atcatagtag      50280
attgaattat gtaaaacacc catttaacaa ccaggtccag gtttgttctc tctgtgtagt      50340
aaatcaatca ctgtgacaca ggttttgcaa agagaaaag atttatttgt aagggggacca     50400 agcgaggggg tgggagaata acttccaatc ctgcctctct gaagacaagg cttaggaata      50460
tgtatgggtt agggaatggg tggtctaagg catggtgaag agtgattggc aggggggggaa     50520 aatgaagtaa caggttagac acatgcacag aaaatggtgg tgttagcatg atctgagggc      50580
agagttttgg gccctctgac gtcaaaagac cacctctcag gcacttgtgc aggcccagtg      50640
gaagggtcag tggtcttaac tagtttgaac tggacaggag ctgccccaag ttcttggaaa      50700
aacaactgaa gtgaccattg ccatggtaac ctatgaatgt catcagtaaa gtagccagtg      50760
aaggttaagt ttcagcatac aatgggacaa ccttcagctt catggaaaaa ggaaaaaaaa      50820
aaaacacata cacacacgaa aagcaagtga ccaaaagcaa gcaggacagg cagacctgat      50880
ccaattaacc cctgggtttc aaccctgcta aatgcagctc aatatttgtc ttgataattt      50940
gcctatttgg ctttacataa aataaagcct tttctgatga aatctaattg agtctgaagt      51000
tgtattaaat ggtatcggaa acttcccagc aggaaggcta cgtaaaagtg gccgggcgtg      51060
gtgactcacg cctgtaatcc cagcactttg ggaggctgag gcaggcagat cacaaggtca      51120
agaaatcgag accatcctgg ccaacatggc gaaatcccat ctctactaaa aaaaaaaata      51180
caaaaatttg ccaggtgtgg tggtgctcac ctgtagtccc agctactcag gaggctgagg      51240
caggagaatc tgttgaacct gggaggcgga ggttgcagtg agtcaagatg gtgccattgc      51300
actccagcct gtgtgacaga gcaagactcc gtctcaaaaa aaaaaaaaag tgatgtgttg      51360
tgtgcaaaat acgtaataac tactctccta tccttttgtt tttccagccc acatactgga      51420
tggtatcaat ctttgcggat actttgctta ttcgtttaac gaccgcacag ctccgaggtt      51480
tggcctctat cgttatgctg cagatcagtt tgagcccaag gcatccatga acattacag      51540 gaaaattatt gacagcaatg gtttcccggg cccagaaact ctggaaagat tttgtccaga      51600
agaattcacc gtgtgtactg agtgcagttt ttttcacacc cgaaagtctt tactggcttt      51660
catagctttt ctattttttg cttctattat ttctctctcc cttatatttt actactcgaa      51720
gaaaggcaga agaagttaca aatag                                            51745

<210> SEQ ID NO 20
<211> LENGTH: 51745
<212> TYPE: DNA
<213> ORGANISM: Homo sapiens

<400> SEQUENCE: 20
ctatttgtaa cttcttctgc ctttcttcga gtagtaaaat ataagggaga gagaaataat       60
agaagcaaaa aatagaaaag ctatgaaagc cagtaaagac tttcgggtgt gaaaaaaact      120
gcactcagta cacacggtga attcttctgg acaaaatctt tccagagttt ctgggcccgg      180
gaaaccattg ctgtcaataa ttttcctgta atgtttcatg gatgccttgg gctcaaactg      240
atctgcagca taacgataga ggccaaacct cggagctgtg cggtcgttaa acgaataagc      300
aaagtatccg caaagattga taccatccag tatgtgggct ggaaaaacaa aaggatagga      360
gagtagttat tacgtatttt gcacacaaca catcactttt ttttttttt gagacggagt      420 cttgctctgt cacacaggct ggagtgcaat ggcaccatct tgactcactg caacctccgc      480
```

```
ctcccaggtt caacagattc tcctgcctca gcctcctgag tagctgggac tacaggtgag      540
caccaccaca cctggcaaat ttttgtattt ttttttttag tagagatggg atttcgccat      600
gttggccagg atggtctcga tttcttgacc ttgtgatctg cctgcctcag cctcccaaag      660
tgctgggatt acaggcgtga gtcaccacgc ccggccactt ttacgtagcc ttcctgctgg      720
gaagtttccg ataccattta atacaacttc agactcaatt agatttcatc agaaaaggct      780
ttattttatg taaagccaaa taggcaaatt atcaagacaa atattgagct gcatttagca      840
gggttgaaac ccaggggtta attggatcag gtctgcctgt cctgcttgct tttggtcact      900
tgcttttcgt gtgtgtatgt gtttttttt tttccttttt ccatgaagct gaaggttgtc      960
ccattgtatg ctgaaactta accttcactg gctactttac tgatgacatt cataggttac     1020
catggcaatg tcacttcag ttgttttcc aagaacttgg ggcagctcct gtccagttca      1080
aactagttaa gaccactgac ccttccactg gcctgcaca agtgcctgag aggtggtctt     1140
ttgacgtcag agggcccaaa actctgccct cagatcatgc taacaccacc attttctgtg     1200
catgtgtcta acctgttact tcattttccc cccctgccaa tcactcttca ccatgcctta     1260
gaccacccat tccctaaccc atacatattc ctaagccttg tcttcagaga ggcaggattg     1320
gaagttattc tcccaccccc tcgcttggtc cccttacaaa taaatctttt ctcttttgca     1380
aaacctgtgt cacagtgatt gatttactac acagagagaa caaacctgga cctggttgtt     1440
aaatgggtgt tttacataat tcaatctact atgatatact tgggttaaat ccttttttt     1500 tttttttttt ttttgagatg gagtcttgct ctgtcaccca ggctggagtg caatggtgca     1560
atcttggctc actgcagcct ccacgtcccc agttcaagtg attcttctgc ctcagcctcc     1620
cgagtagctg agattacagg tgtgcatcac tacacctgga taattttcgt attttcagta     1680
gagacggggt ttcaccatgt tggtcaggct ggtcttgaac ttctgacctc agatgatcca     1740
cctgcctcag cctcccaaag tgctgggatt acaggcatga gccaccatgc ttggtctttt     1800 ttttttgaa atagtgtctt gctctgtcac ccaggccaga ttgcagtgct gtgatcatga     1860
ttcactgcag ctggacctcc caagctcaag caatcctccc gcctctcctc ccaagtaact     1920
gaatctgcag gcgtatatgc caccgtgccc agctaatttt tgtgattttt agtagagaca     1980
aggtctcact atgttgccca ggctggtctc aaacttctag gctcaagcaa tcctcctgcc     2040
ttggccttcc aaaatgctgg gattacaggt gtgagccacc atgcccagca aggttaaatc     2100
tttatgtact gctttatgta catgaaacag ttaagactgc tgtggagcca tccaagatgg     2160
aagacaagaa tctaggcttg catagatcca gagtaggggc tagggatttc tggtcttcta     2220
cttttagcta cactccttta tccttgggga aatgctagat atctcttgga ctgtttcagt     2280
gaggcacaaa atggatagcc ctccattcca agggtggcag tgtgtgttga tgttggagat     2340
ttaatcaagt gtcatgccct ctggtgacat aaccttcagg agatagccgc agctagggct     2400
ccttaccttt gagagcttcg tttatgtaat tctgcatata atacaccctc agctggtcgt     2460
cctcagcatg cagcccgtca tcgattccat tggatattat gtacatgggg aggtctccgt     2520
acttgaactt cagccagttc agcactttgc gcaaccccca gggcactacc gccacctgac     2580
tgggggagtt gagccacgtg atgtcggtca tttcttgcac ttctaggtaa tcattgtatt     2640
ttattggatc ttcttttct gagtctacaa ggatggtggt ataatggctt aaagccaaaa     2700
agtcaaaggt accctggatt agcttttttt catcttcagt gaaataagga agaagaaaat     2760
tgtttctttg gttcagccag tccctcatca cccatggata atctccagag ccgaaaatgg     2820
```

```
gctcagccag ccagccaatg tcaaattcca aaactctctc agccacctct tgtccttttt    2880
gggagaaagg gcaggcaggt tctatccaat cagcctgcaa ggctatggat attttcccat    2940
tctgagcatg cctaaacttt tcattgtaca catgccaagc cagggcatgg ccttcagaa     3000
ggttgtggcc agcactgtat gtcatattcc ttgtatacgg ctcattcatc gttatccaaa    3060
gcttgacgtg atggccgagc tcttgaaagc acagtcgggc atactctgca aaggccaggg    3120
cagtgtaggg gttctcccag gcgccctgcc tggccaggag gcgcggcagt ccttggttcg    3180
gggccatagg ctgccacagg gccaccactg gggtgatgtt gacacggaca agctcgctgg    3240
ccatgcagcg atagtactgc aggatggtgt ggttcacctg ggactggtta cccagaggga    3300
gaatcagggc ccagtccagg gagaagcgaa aatgtgtaac gtgcatttcc tggagtaaag    3360
cgatctgggg ctggatggca gcaaagtcaa cacagtagga tttcctcttc ttggtcacaa    3420
ccccatccac tttaataagc ctttttactgt ggtggacatc ccacaggtaa acattcaggt   3480
cggtaaactg agacagagtg gtatctacct gtgaagggca gagtaaacat tagcgtcacc    3540
tgggcagtcc tgaggaagta attcaaagca attatttcag caaaactagc caggaatatg    3600
agcaaaaata gaagcctttc tagctgagaa tgtgaactat ttttcataaa ttgtcagctc    3660
ctgaggaaga caatattcca cttttctgata tgcacactcg ctttacccat agttctaact    3720
cttcaactgt ttctttaatg taccccccaa aagtctggat ttggtcactt cagatgacaa    3780
atgctaatga gtcttgcaca ctacttgtcg gtgttatgta agcagagtat ttttgggtgt    3840
ttttctttta atgtaagaaa tcattaatgt catgaggctt tcaaatttaa aaagaaaaaa    3900
aactagatga aaaaaagaaa aaacttaaaa tgtgagtgag ttggccaggt gcggtggctc    3960
atgcctataa tcccagcact ttgagaggcc gaggcgggag ggtcacttga ggccaggagt    4020
tggagaccag ctggggcaac acgtccaaac cccgtcttgg cccggcatgg tggcacgggc    4080
ctgtagtcct agttgctcgg gaggctgagg tatgaggatc acctaagcct gggaggtcaa    4140
ggctgcagta agtcatgatc acatcactgt acatcggcct cagtgacaga gcaagatctt    4200
gtctcaaaaa agaagattta aaaaactgag tgagttaagt aagaaaatga aaagatattt    4260
ataattaaat tgtgcttaaa attacgctct aaattgaggt ttgctatagg tagaggaagt    4320
gctaaataaa cataactctt gccttttgtt gggtttaggg tcagtgacag aatttaacaa    4380
attcaatctg actgatggta gaaagtccga gagagaggcc aggcgcagtg gctcacgcct    4440
gtaatcccgg cactttgcgg ggccaaggcg ggcagatcat gagatcagga gtttgagacc    4500
agcctgacca acatggtgaa accccatctc tactaaaaat acaaaaagta gccaggtgtg    4560
gtggtgcaca cctgtaatcc cagctactca ggaagctgag gcgggagaat cacttgaacc    4620
cgggaggcag aggttgcagt gagccaggat catggcactg cactccagcc tgagtgacag    4680
agcgagactt catctcaaaa aaaaaataga aaaaagaaa agaaagtcta aggagggaga     4740
atgtggaagg aaagaacaat attgtcatcc acccatagtg aattttaa cgtagttaaa      4800
aaattttct aaattattct tctgtaacaa tgatgatgat tatagttctc aatcatatgc     4860
tataaaatcc tcccaaataa aaatttaaaa aaagtattta ggaaaagtgt gcaaattata   4920
aaatcaaaat cacaaaatca ttccttcatg tgtctgctgt ggagggaatg caaagtgaaa   4980
aatccagctg gaagatctgc accctaagcc tgtgttcccc tctgaaataa tcctgttaga    5040
acaggttcct tggtctgatg ctctgtataa aagcaggggt cagaaaccat agcagaggtt    5100
ttgttgcatt ttacgggcct gttgcaaatg cactgctatt tctctggaga gataagtgtg    5160
tttataaaga aaagtcatta aaaacagcat gtcaaaggga aattgccttt tctggagaat    5220
```

```
tgtcccttgc agaacaccca cacatgcact tccccctaatg ctgtgggaat gctgtcagag    5280
tatttttcca ctgtgatgca ccccacaaat catgtttcct tagctttgaa ggacagaata    5340
tttgcacgct cttttgaagc gttcagagtt tgaaggaatt ttttggatta tttttataga    5400
gctctgagtt gactaaattc ataacttttt tttttaaccg tgattgttcc aaaacaacag    5460
cttttattca gtccatctga aaacaaatat gaaagactag ggtatcattt ctggaggaaa    5520
aaaaaagttt cttgaaaata caggacaggc cgggcatggt ggctcacgcc tgtaatccca    5580
gcactttggg aggccgaggt gggtggatcc cgaggtcagg agattgagac catcctggct    5640
aacacagtga aacccggtct ctactaaaaa tacaaaaaat tagccgggtg cggtggcggg    5700
cacctgtagc cccagctact caggaggctg aggcaggaga atggcgtgac cttaggaggc    5760
ggagcttgca gtgagccgag atcacgccac tgcactccag cctgggcgac agagcaagac    5820
tctgtcaaaa aaaagaaaa aaaaaaaag aaaatacagg acttttgggg caaaattcca    5880
cctaacctcc attaatttgt taactaagat tttactaaaa aaataaaata gtgaagttgg    5940
acctttcaga aggaacggct attaaaacat gtatttagta tgttatggga gaaactttct    6000
cctaacaggg accaatgtta aagaggctct atgtcctcac tacatagtga gttcaatatt    6060
tatattaact atgagcatcc gtggttatgg gaaaacaaac ctctcagccg agaaagtggg    6120
tccaagtaaa gtgacaatcc atgtgaatga gcctaaagtc aggttgtgtg cttcttagga    6180
tattattttt caagttgttc aggtgaaatg catgcctcaa acactgaaag tctgaaatac    6240
tagccaggag ggaaaagatg aagttcagtg gtttaaaaat cacttctcag gactttaata    6300
taatgtctta aagctgtaga gtactgtttg taagtgaaaa cacacacacc tcagaactga    6360
catacaaaga acttattttg actacgtcag gtcagttagg gagttagctt gagaagggta    6420
ctgtcaatat aacacaaagc ctgaggtgaa aaccagaaga agaaaatagc aattgcagcc    6480
tttccccacc agggagcttc cagagaagct ctcatctgct gtgggtttga gagtgactta    6540
attttgtgtt tgttgggttc tgcacaggag gagactgcca ggaggagggg tggggtcccc    6600
aagctgatga ggaaaaaagg accgtgtgat ctgagagaga gacctctggg gccaattagt    6660
ggctgacctt aggtcagatt ctaaaacaat agcttctaga gtgtagtagg aaaaggaatt    6720
atctcccatc tcccttgcta ttcactgcta tacttattgc ttctgaccag cgttttctct    6780
tctccctcaa ggaaatagga tgtacccctta agactttctc actatttacc aattcccaaa    6840
gccagcgcac agcccctga tgaggaatag aacaggagaa gtagggctcc ctccgacacc    6900
cccactcttg ttctgcattc gttcccatga tctgcacagc aatgctggct gggagattgt    6960
gccgcataca aaggactgaa cctgccagac tcaggctgct atcagagatc cgtgctcagc    7020
agggagcagg cagaaggtca agagatagaa caaggaccag ggaccatccg atctatcccc    7080
aaccccagta agaggagga ggaaggaagg ctacggaggt cttcttccct ttctcctccc    7140
cttcttcctc accagcctca cttctcccac ctcagatcct ctctgaaccc cacagtggaa    7200
tccactctga ggagggaaat taggataagg agatttcaaa tagcaggagg ctgggagaga    7260
aggagagagt cggggcaggg cagaaaattg cacaccgagc aggagggagc tcagaagcct    7320
ttctcctggg ctcacatatc ctggcataaa agatgacaca tccagtcatt ttttttttta    7380
agagacggac tcttgctctg tcacccaggc tggagtgcag tggcgcaatc tcggctcact    7440
gcaagctccg cctcctgggt tcatgccatt tccctgcccc agcctccaga gtagctggga    7500
ctacaggtgc ccgccaccac acccggataa ttttttttttt ttttttttgta tttttagtag    7560
```

```
agacggggtt tcaccgtgtt attcaggatg gtcttgatct cctgacctca tgatccgccc    7620
gcctcggcct cccaaagtgc tgggattaca ggcgtgagcc agtcatcttt taaatggaag    7680
gcgagggttt aagtctgaga ctgcctgtaa aatgaactgg gtggtctgaa aaagaagaat    7740
aatcccaacc agcaaaaaat gtactaagga tggtgttaat ttatttcctt ataaataaaa    7800
gatttcaatt ggatatttac aagaaaacag caacccattt cacattcttc caagtgtttc    7860
ctttcaagct gtgatttgca gaaccaatta attggctacc ataacccaac atgtcaaagc    7920
caactgcttg tctatggaca ctgaactctg tctctgtctt gagggctatt ttcacacttg    7980
ggactctatc agcagcaatc ccccagcccc gcccttgtta cttaccacca tgcccgcttc    8040
actccattgc atcatttgtg catacattgt tttcgctcag tagactcctt tgctcctttg    8100
aaagcaaagg ttacccttac tcatctcagt atacccctcta cctgcactcc ccttaaccaa    8160
gcgacccgag caactaacac aaggcttcgg acacactaga catccaataa gtgcttacta    8220
gagtatccag tcaaatgctg gaaaacaagc cccttcaaaa tttaggaagt ctgaaagaat    8280
gttaagggct tactactgag aagatgctca ataaatattg gttgatcatt ctgaagaaat    8340
ttcgtatcat ttcaatgact attgctaaaa aagacattct gaccagtgaa tcattggatc    8400
tagggtttac tttcttaggg tatttctgca catttgtgga gcccacagtt gtgcctctgg    8460
aggactctgc ctaatgttcc tgcctcagtc tcagcagcac cactgaaact cagaggcttt    8520
ggagttctgt gttagatcct gttcatgaaa aaactcaact gccttaaaaa ggatcaaaaa    8580
ccacagtatg aaaagagagt gttttatctt tttactgtct taatcggatc ttaaatattg    8640
atatgcttta aatttattta tctttggatc taacttaaac aagatgaaga ttggaagagt    8700
tttggagaga agggtgcagc attccaaatt gtgcccttag tgtactcata aggaattgtt    8760
tttggctcaa agaacggaca atgtgccatg acaatcagcc taggaaggaa gcactactta    8820
ctagtgatag ggcttggtga gactgctgat tggttttgtc agctgactta cttgaatgta    8880
gttgtcaaca actccccaag caaagtcaca gggaaatgtc ccttctaggg gctgattttc    8940
aggtaaagga gggaagccat ttttctctat cagcttttgg tagaacaagg ctgaagactt    9000
tggcaacaac atcttgtcct ggcttagaaa gtcaacatag aagagtccac gcctgatgct    9060
gtaacctctg tgccactcga aaccatccat gagggaccat gcggtatacc cgatgacatc    9120
caccccatcc agcttgatgg ctgcaaaggg aagaggggac aagagcaaca tgacccttcg    9180
ctgggcactt gcatcatggt tcaagagcag ctgagcgttt cctacttaaa taaataaagt    9240
gtaatgcttc tcgtttggta agccaatgat ttttcttctt gacgaaagac tctaatcaaa    9300
cctatataac tctacaaata aatgccctca aaattggcct atctaatatg tttttggat    9360
ttctgagcac cttgaaaaaa tagttcctta tttataatag atattctaca gggctggaaa    9420
gatgtcttgt accactttcc atcctagaca cccagctttg tgtctgatgc aataaataaa    9480
taaatgaagg cttaaaaagc atgatctatt tatactattt tctctagaaa acatggacat    9540
tcctttttct ttaaagtgtt ttattcaacc aaaataacaa gaactgaaaa acatgtgcag    9600
agagctagat atcctgggat ttgttttatg ttcaatttaa tctaaaaatc tagattaata    9660
actgaaagtt aagtaattac aaatattata acccagtttc tcatttacaa atgggttttt    9720
aaaaattaat tcaagttcct caagactcca aatgagaaag gtgttaaatg aatgcattct    9780
actattgcca aaatgaatgt ctccattagg atttaaaaat ataaattcac atcatttatg    9840
ttagataatc ttagagattt ttttccagaa gattttggca ggaaatgaga actttaccca    9900
caatcatacc ttttaaggtt tccatgatga acttttttgag gtaatacata tatttggcat    9960
```

```
catctctctt ggtggtccct gagacaaacc agccattttc cacaataaat atttgaggat    10020
ggttaaattc aaggtcaatc caggaaagca gttgcctcag gttgggagat tccaattggc    10080
ggaacttcat gtgagggtcc aaaagttgaa aactcaaggt gggtccaaag caaagagcaa    10140
aaaagtcagc agttcctttg atgaactttt tctcagattc agtaaaatca ggcagaatag    10200
atgaaaggtt attcttcatg ctctcgggat agtcaccatc aataaatacg ggtttggcaa    10260
accaacctag tacaaagtcc agagattttt gacattcttt gatgctgtgg tcggtcattc    10320
ttcgaggatt gatccagtga gagcttaggg caatggacac ctgacctccc tgagtgggac    10380
ggaaagaagt attgtagaga tgccagactt tggcatgagc ctatgaagag aaaaaccatg    10440
gcaaatttat ctctagttgt gaggagaaat gcaatataat acttgaatcc ccaaatcaga    10500
ttatatctgt ttctcatcaa gcctaactta atgactaaca atataaaaat cagctagaac    10560
caatacatta tttcaaaggt aggtcacccc acagtgaggt gctacgggga ctagagttat    10620
ttccattggt ctttagcagt cagtggaaaa atgtagattc cttgggttga gtgtgtagtt    10680
atccacattt tgaaaagcta atgaaataaa agaatttgtt ataatagctt actatttaat    10740
tgactttgga ttatgtactt tttaatttac gggtttcatg aaaagaacca atgctacatc    10800
tgtgatcaca ccaggaattt ctaaatagga ttatattttt tatcctgaga ctgggagttt    10860
tcaaaatgac tcaggtcgtt ggagttaatt tactgtttca tagtcatctc tcgtagctaa    10920
aattctaaca agcaatcttc tttcttccca agaagaatca gtacaataaa ttaaagaacc    10980
cactccagca tctaaccttg gcctaccctc cagaactctg ggacagttct ggtttcccac    11040
agacccaggg tgctaggtcc aagccaagag caaaaaacag caaaatacag ctgcaaggaa    11100
atcagttgtc cattgttagc atgcagccag gagtttcgta cagcagtgaa aagggctttg    11160
catccataaa accaacttta tactcccata aattcttact gacttctaat atcttatttt    11220
catttgtttc cttttatttt acaaggaaga gtgaaaatta tagggttttt ttctcccta    11280 cttgaagtga gtttctcttt ctctttgaat tccttgattt actctcccta ttttcctaca    11340
aatacaagtg ttgtttatca gcctttattc ccctaacata tcctctttga aaactccatt    11400
caaattctct gtttgactcc atatattctc caaaatgatc atgccaattt tcattccact    11460
ccctgggcct gcagaaactc ctttgttcat taagccaaac agcctcttca acatatccta    11520
aatattcctc tcgtggttca tttcagtaca ggcatccaag aatggcctca tcaacattct    11580
tatgggttca gccaaacatt tcaatgaaat aagatagttt gtggctaact tttcttttta    11640
gtttcttggt gaacatatct actatgtttc atttcactaa atgtattttt tcacgacctg    11700
aagcagctat ctatatgcta agaaggaaat agagaatcaa atgttgatca aaagaatagt    11760
ggcacttgct tatgtggtct aagaaaccag ggtcttaatc gtgccacact tctgtcagtt    11820
ttatgatgtc tcctacccTt ctccatcttc cccatcacac ctccccaggc ctcccttcct    11880
cattgaaagg aaacctcatg atgttaacag ttaaacagag gctgggcatg atggctcatg    11940
cctgcagtcc cagcactttg ggaggccgaa atcccagcac attgggagaa tcccttgata    12000
ccaggagttc acaactagcc tgcgcaaaga gtgagacccc atttctacca aaaaatccaa    12060
aacttaacca gtcatggtgc tgtgtgcctg tagtcccagc tactaggaag gctgaggcag    12120
gaggatcact tgagcccagg agatggaggc ttcggtgagc catgttcaca ccactgacct    12180
ccagcccagg tgacagagaa agatatgtct cacaaaacaa aaacaaacaa acaaataaac    12240
acaacagtta aacataaaat ccattgagca gtccaggcta gtactcagca attaacctct    12300
```

```
tgagaccaaa aaccagggga ctttcctaat ttgaccgcat ttgaggccta tgaacagtca    12360
tgtcctaaat ctaccaggca cctttctgta gaataagcgc tgaacaggga atgaaagagt    12420
gaaagcaaac aaagaatgca ttaatctcgg tcagttttgc aggtagctga agtcatacaa    12480
tggaattttt tataattata gaccactctt ctaaccttga ggactttaac aaggctcaga    12540
ggaggaggtt tagcaaggac atgataaatg acctgggcca taaggaaaga catatatggt    12600
ctctgatggc agataaagtt cctgctccat cactcttttt tgttttgttt tgttttaaga    12660
ctgggtctca ctctgtcacc ctgactggag tgaagtgatg ggatcatggc tcactgcagc    12720
ctctacctcc caggctcaag caatcgtccc acttcaacct cccaagtaac tgggactaca    12780
ggcacctggc taatttcttt tttatttcta gtagagatta aatcttgctg tgttgccctg    12840
gctggtctta aactcctggg ctcaagcgat cctcagcctc ccacctcagc ctcccaaagt    12900
gctgagatta caggcatgag ccaccgcacc tggccttcgt cactcttgag ttggccacat    12960
tccttaattt gggcaggtaa atctaacttt cctgtgcctc acaggactgt tgtgaggact    13020
aaatgagaca attcatgtaa aactcctaat gcagagtttg caacagtagg atctccatga    13080
atgcgtatcc cttctctctc tagaggatga acaaaccaaa aggaagaata ttgcaggtgg    13140
aggaaacaac ccctgctaag gaattcagcc cacagtagcg atgtgacata ctgataaaac    13200
ttggggtttg gagtagaaga gacttaggtt tagattccct actcctctaa ctatgaccgg    13260
tgtgagcctc acttactgct ctgtacaagt gggaatgaca tctattgtcc cgtagggaca    13320
ctgtgaggat taaatgacat aatgcaagtg agagtgtctt ttaagtagtt gattattta    13380 cagaggaata cacttgcagc attagaaagc atttcagata tcatttggat taactgctca    13440
cctcatgcca aaaccctgtt gaaacttatt tgattactct ttacagcatc ctaacttggt    13500
ggtcatccca ggcatggcac cgtctctaag aaatcgctgc aacccatgg acccccatac    13560 tgtgctgcat gcccctcctc tggacaccaa gagtctcaca catacttctc taatatcatt    13620
tactgcagat aatgagggc atccctcccc agaatgagct ccctgtggag ttccctcact    13680
ccctccctgg cacacggagg ccctcattgt ctgttaaact gagttgaacc agcttcacca    13740
cctcttcacg agccagttca ctccctttgc ggatggtaca tttgacagat taaatattat    13800
gaggcagagt gtgggaaggt cgctatttag gatgttgcaa caaataagga tgattaacag    13860
ggagatggtt acatatagtc ttgcaatgct ttctaattat tcctggtatg ttaatcttat    13920
aggcttgttg tcttaagatt gggatttaat aaagttattg acaaggactc agtgaagtta    13980
ttaactgtat ggccaagaac attcatctaa atactatttt taatagccaa acattgaaaa    14040
caattgaaat gtctaatatt caaatatgtt taccatgtat gaatgtttta atacatgata    14100
gtataactaa agaaatacca ttattcagga taatgcaaaa gaatatcaat taacatgtaa    14160
aaacgtttct aaaatactct gaacagaaaa aggttataaa atagcaagta gagtttagta    14220
gcactttgat ctggagggat ttataacttg ttaaaacctg ttttacagca ggattgtggg    14280
tggtataatt cacttcattt tacccatcta tatatttttt tcatttccta ccataaacat    14340
gtattgctct agagattaaa aaaataaaat tcaaaaggg aaaatggctg atagcagttg    14400
gatggcaggc ctgtttgatg gttattaaaa gtctctgctt catctcaccc tgcccacctg    14460
ttctccaact tgccctatgg tctctgcctg aaatccaagt cccaggcaca ttgaacccca    14520
cttgaagttc taagattatc tagccttcca tgctttggag gtgcagctct ctaaggtatg    14580
ttttgcctat tcccagttcc ttcactctta caccoactttt aaaactcagc ttagatgtcg    14640
ccacctccag gaagcattcc ttgacatctt ccctctccct agcatggact aaatgtctgt    14700
```

```
tctatgtgtt tctatgatgg tcctctatcc aagaccttaa ccatatatta ttgcatttat   14760
ttaagtgtct ggattgtagg tgttttgaag gcattgagtc ttttatctct cagattctag   14820
caaagtctct gcaacagagc cagtattcaa taaacagatc tagaggaatg aaggctggca   14880
ctaagaacca gatcaaaggg tctaggacag aagcaacatt tttctgggct gaagcaggaa   14940
aactctctca taagctactc tggttcttat tttgctttca agatcatgaa agacagaaaa   15000
ctttcaggca cataccatta aaaataaat tagaaggaat tttatatggc aggcctctga    15060
gaataatacc atattatctc ataatgtgct aatgatccac tttggggtat aagtctctct   15120
cgtatgtgat gccctccttg cttccttctt accttccatc tagattttga acatggagt    15180 ctgaaaaaaa tctagaagaa aaatggatct ggaattcctt cctaccaact agctagtagc   15240
cccaaatttt ggaagtcgag gaaaataatt ttggaagtcg aggaaaatac tctgaattcc   15300
acagaacata tagacatttt ctctttggct aaattataag ctccctgtca tttgcctata   15360
cgtatccccc acagaaccca acaaaaagtt tcacacaaat aagctgcttt taaatggtgg   15420
gtggaaggaa acaggtgatg agcctcaggt ccactccagc tttctgcctt gggttgtgtt   15480
ctaggtatgg ctgaggcaaa tgaagcccac acaatacaca gcagtattgc tgagctgaaa   15540
aggaagaaag caatgatgag gactctgaag caggtcaacg tactggagag aagaaatcta   15600
cacaaaggaa ggacctagaa gtctgcatga gatttcccaa ggatccttgg ctgtccatgc   15660
acaggacaag attttgtgag gctcagcaaa gagaagcagc cacaggtctg ggagatgaat   15720
accaaaggtt gggtaggtct ggaaaatatt gcatttcaga atagccagag tagaaaaatg   15780
cagctgagca cttcaggcat ccagctgaaa ctcaggaagg tcattacctg agaagtaaga   15840
acaaagcagg aatagaccag ctctaacaaa gactaaagcc acatcaagta aatctggtaa   15900
tttaacttct tggcagaact aaatacaaca ccctttaaaa agagacaata ttgaccaggc   15960
ttcctataat atctcattca tagcacacag agcataataa aaatctacta gatatgtgaa   16020
aaagcaggaa aatgaaaccc ttaattaagg ggaaaaaaag aagtattcaa tatcaacaga   16080
agccaagatg tcccagacat tgggattagc agaggacttt aaaatagcta ttataaatat   16140
ttttaaggat ttcaaagaaa agatagatat aatgaacaaa tggagaataa caacagagaa   16200
acaacaactg aagaaaacat gaaaattcta gaactgaaaa gcgaaataaa caaattttg    16260 aatgggatta caatattaa ttctaaatgg aataataata agaataaata atgtaatccc    16320
taaaactcac aaagatatta aaaggtttct ctaaaaagcc aataaaataa gaaaatgaa    16380 ttaccaaaaa atctgatttt tccaaaagat gcagaaataa aaaacaaaaa acacatgaa    16440 caaaagaaa acaaatagca ggattgtaaa cataaaccca aacatatcaa taaatattca    16500
aatacacatg gactaaatgt tccaagtaca agacagatgc tatgaaagca gatttttaggg  16560 gctgggtgca gtggctcacg cctgtaatcc cagcactttg ggaggccaag gcaggtggat   16620
cacgaggtca ggagttcaag accagcctga ccaacatggt gaaacccgt ctctactaaa    16680 aatacaggtg cctgtaatcc cagctactcg ggaggctgag acaggagaat tgcttgaacc   16740
cgggaagcag agattgcagt gagccaagat tgtgccactg cactccagcc tgggcaacag   16800
agcaagactc catctcaaaa aaaaaaaaaa gaaagtagat tttagaaaag taagtttcaa   16860
ttacattctg tgtgcaagaa atatactata aatataaagt gatcatgtaa aagaaaaaga   16920
atggaaagag acatattatg caaatggaca gcattaaaaa tctggcatgg ttatattaat    16980
aacaaaatgg aggctttgaa catcactata attcacctag agctaacaga catatatatt   17040
```

```
aatagaacat gccacccacc taaaaaaatc agaatataca tttttctcaa gtgcacatga   17100 tacatttttcc aggatagatc atatgttaga ccagaaaata agtcttaata aattttaaac   17160
tgttgagatc ataaaaagta ttgtttctta ccacaatgaa atgaaactag aaatcaataa   17220
caaaaggaaa actagaatat tcacaaatac gtggaaattg ttgacacact caaacaagca   17280
ataagtcaat gaagaaatca caaggtagat tagcaaaagc ttaaatgtgt atataaaaaa   17340
ctaactgaat atgtaacata ccaatactta taaattgcag caaaagcaat gctcaggga    17400 aattttatag ctttaaatac ctcatcaaa aaaaaaaca agatatatct caataactta     17460
gtcttccacc ttaagaaaat aaaaaagaag agccaactaa actcacagct aacagaataa   17520
aggaactaat aaaaattaga atggatatac acaaaataca gagcagaaaa attatagaat   17580
caacaaaatc aaaagttggt tctttgaaaa aaatcaacaa aacagaccaa cctttagcaa   17640
gactgactag agaaaaaaag agaaaagaag caaattaatg caatcataaa agaaagtggt   17700
aactgacctt ttctgtatat catttctata ataaaaagga ttacaagaga acattatgaa   17760
catttggatg ccagcaaatt agataacaga gatgacctgg ccaaattccc ggaagcacac   17820
acattaccaa aagtggctaa ggaaaaaata caaaatctaa tctaggtgta aaagagattg   17880
aattagtaat caaaaacttt caaactaaga aaagcccagg actagtggct ttaatagtga   17940
attgtaccaa atatttaaag aagaattaac acgactcttt tcaagctctt caaaaaatag   18000 aagaagaac actttctaac ttagccaatg tggccagcat tatcttgata ccaaagccag    18060
ataaagccac cacaagaaaa taatagttac agatcaatat cccttatgaa tatagatgca   18120
aaagaatgca accaaatact aacaaaacaa atccagcagc atattttaag aattatacag   18180
cacaatcaac tagtatttat tccaggaatg caaagatggg taaacattaa aaaaaatcgt   18240
tgtaatgcat tacatcaata gagtaaaggg ggagaaaacc catatgatta tctcaattaa   18300
cgcaggaaaa gcattttaca aaaatctgaa agtctttcat aataaaaaca ctcagaaaac   18360
tacgactaga aaggaacttc cttaatatga ttaagaaaag catttatggg ccgggcgtgg   18420
tggctcatgc ctgtaatccc agcactttgg gaggccgagg cgggcggatc atctgaggtc   18480
aggagttcga gagcagcctg accaacatcg agaaaccccg tctctactaa aaatacaaaa   18540
ttagtcggtg tggtggcagg cacctgtaat cccagctact ctggaggctg aggcaggaga   18600
atcgcttgaa cccaggaggc agaggttgtg atgagccgag atcacgccac tgcactccag   18660
cccaggcaac aagagaaact ccgtctcaaa caaaaaaaca aacaaacaaa aaattatgaa   18720
aatccacagc caacattaca gtgaaaggct gagagcttca cccctaacat caggattgaa   18780
aggaagatgc ctgctttcac tattgctctc taacattgta ctagaagttc ttgccagagc   18840
aattaggaag gaaaaaacta tccaagttag aaaagaagta aaactatccc tattcacaga   18900
taacatgatt ctacatatgg aaaatcctaa agaattcaca aaaatctatt gcaaaaaata   18960
aacgatttca gcaaaattgc aaggtacaag atcaacacac aatagtcagt tgtatttctg   19020
tacaatagca atgaacagtc caaaagaaa attaagaaaa caattccatt tataataagt   19080
tccaaaagaa taaaatatac acaggagtac atttaaacac tctcaccatt gctattaaaa   19140
ttgtactgga ggtcctagcc agtgcagtaa ggcaaataaa acataaaag gcatgttgat    19200 tgaaaaggga aaacaaaca aacaaaaaaa caaactttgt tgttcattaa aaacatgatt    19260
gtctgtgtag aaatcctaag atttttaaaa aaacagaaaa actattaaaa cgaataagtt   19320
aatttagcaa gttggcagaa tacaatgtca atacaaaaat cagctgcatt tggccaggaa   19380
cactggctca cacccatagt cccagctact tgggaggctg aggtgagagg ctcccttcag   19440
```

```
cccaggagtt caagtctgca gtgagtgctg atcacgccac tgcactccag cctgggtgac   19500
aaagtaagcc tctgtctcaa aaaaaaaaaa aaaaaaaaaa aaaaaagaaa atcaattgca   19560
tttatatatg aacagaaaac aaacagaaaa taaattttaa atacaatgcc acttacagtg   19620
gtaccaaaat cgtaaaatac ttagaaaata atttaacaaa agatgtgcaa gtttgctaca   19680
attataacac attgctaaca gaaattaaag aatatgtaaa taagaatga gataccattt    19740 tcatggattg gaagagtcaa tattgttatc agatttcccc agattgacct actgaatcaa   19800
caccatctca tccagaatcc caataaactt tttgtagaaa tgaataagtt gattctaaaa   19860
tatatacaat aagaacataa aacagctaaa ataactagaa aaaggaaaaa cacagttgaa   19920
acattcacat tacctgattt caagacttat tataaagcta taattattta atatagggtg   19980
atattggcat aaggatagac aaatacatca aaggagcaga acagaaaatt ccaaaataaa   20040
cccacagcca actgatttct aacgaatgca tcaaagcaat tatgtggcaa caggaaagac   20100
gtttcaacaa atgatccttg acaactggaa aagtgtatga aaaaattaaa ccccaatctt   20160
gcataaaaat ttgagacaga tcatagatcc aaagctaaaa gctaaaacta taaaacttat   20220
agaacaaaat gtaagagaat agtctcttta tcttggagta ggaaaatact tcttagaaca   20280
cagaaagcac tatataaata tacatatatt aaaatatctc ccctcagtat gtgatttgcc   20340
tttacatttc gctaacattt gatgagcagg ttttaatttt gacgtcgtcc aatttatcag   20400
tttttgttta tgattagtat ataattgaca aaataattat atccgaaata aatacgtaag   20460
cctacctatc agtagtaaaa gaaaaataac tccccttccc accatgagca aaatatttga   20520
atagatattt cacaagagaa tcttcaccaa tgctcagtaa acacatagaa atgtcctcaa   20580
catcaacact atcaggaaaa tgcaaattaa accccaacg agcactcaca cccactaaga    20640
tgcctacaac taaaaatact ggcaacaggc tgggtacagt gactcacgcc tataatccca   20700
gcaatttggg aggctgaggc gggcgaatca cttgaagcca ggagttcgag accaacttgg   20760
gcaacatggt gaaaccccat ctctactaaa aatacaaaaa ttagctgggt gtggtggcac   20820
gcctctgtag tcccagctgc ttgggatgct gaggcatgaa aatcccttga acctgggagg   20880
cagaggttgc agtgagccga gatcacacca ttgtatgcct gggcaacaca gtgagatgct   20940
gcctcaaaaa aaaaaaaga ctaccaacaa attctggcaa ggacgtaaaa caacggaaat   21000
ttcatacatt gatggtggga gtataaatag taccaccact ttggaaaact atttgacagt   21060
ttcttataaa attaaagata gatttttctct ataatctagc aagttcatac ctaggtattt   21120
accaagagaa atgacaacat aagcccccca aaagacttgt acaatattaa gataaaactt   21180
acaaattgat atgttcaaag atgctggccg ggcacagtgg ctcaagactg taatcccagc   21240
actttgggag gccgaggtgg gtggatcacc tgaggtcagg acttcgagac cagcctgacc   21300
aacatggtga aaccccgtct ctactgaaaa tacgaaactt agccaggtgt ggtggcacat   21360
gcctgtaatc ccaggtactc gggaggctga ggcaggagaa tcgcttggac ccacgtggca   21420
gaagctgcag tgagctgaga tcgctgccac tgcactccag cctggggaac aagagcgaaa   21480
ccccatcaca attaaaaaaa aatgcttata gtagcttaaa tcgcaatagc agaaaactga   21540
aaacaacaca aatgtccatt cacaggagaa tgtataaaca gtgtggtttg tttatacaat   21600
ggaatactat tcattaatgc aaagagtgaa ctactcttct aggcagtaat atggattaat   21660
gtcaaaaaga ttgtgtagat tgaaagaact cagacacaga gtacattcac agagttgttt   21720
gattccattt acataaagtc ccaaaatcag tctgtggtga tgggaatcac aacagcggtt   21780
```

```
tcctacggag gtgagaattg attagaagtc acaaagaaac tttctggggt aatgagaata    21840
ttctatatct ttacttggat atttgttaca gatatccata cacatacagg tgtatgtagt    21900
catcaaaatt catcaaattg cttataaaac atgtgcatca attttaaaga tctatagatt    21960
aataaatata taatagatta atatcttagt cattggcaaa gctattcagg tatagaaata    22020
taattaccta caatttatgt ggcaagagaa tactgatttt ctccgaaaca taaattcatc    22080
tttgaaacta ctacagtaat ctgttagtta aaaaaatata tatatttagc tttttaattgc   22140 agggatcata ttcattcaac aaatattaca ctaggcactt ttctagggga ttcaaaatat    22200
gatcctgttc ttatggagct acattcttg ggaagaagag agataacaaa tgaaaacaaa     22260
gcagagaaag gatagaaggt aacagggatt gggatgggaa ggcagtttag acaggcaagt    22320
cttcttcaag gaagcattgt ctgaggatct gtaacagaaa aagtgaagaa tgctaaaaaa    22380
gactgggacc tgagatgggg gtgtgtggaa ggagcagaga acccggagga ttgggcagag    22440
gcggtagagg gtacgggaag ggcattccag gcagagttga gcaagtgatg agagcataga    22500
ctcagccagg ctttcctaat tctgccccct tattagctgt gggaccttgg gcaaattatc    22560
tgaagtctgt gcctctattt cctcatctgt aaagtaggga tagtaatagc acctcatggt    22620
tatatccttg tgaggattaa ctaagtcaat acatggaaag cacttagaat tgtaaatgct    22680
atggaagtgt ttcttattca agtgttgtag taatgtttga ttggtaagtt caaagatact    22740
tacagtatta ggttggtgcc aaagtaattg cagttttgc catttaaaaa gtaatggcaa     22800
aaactgcaat tactttggca ccaacctaat agctttaatc acaatagcaa aaaaactgaa    22860
aacaacataa atgtccattt acaggagaat gtatgaacag tgtggtctgt taatacaatg    22920
gaatattact ccttgtttcc ttgtgactct taatcaattc tcaacatagg agaccactgt    22980
tgtgattccc agtacataga gtgattgtgg gactttatgt aaatggaatc aaacaactat    23040
gtaaatgtac tcattgtgtc tgggtaatga ttgataagtt tccaaaaatc agtggctact    23100
acgtggaaaa taggatctag gaggacaaaa tgggagcaag gataccagtt agacaactat    23160
tgcaatggtc caggcaaaag atcatgatgg tttggaccaa aaaagatagt aacaagtggc    23220
tagatttagg ctattattga aggcagaatc tgtagaacct gctgatgaat tggatgttac    23280
atgttgcatg tgaggagggg aagaggaatc aaggaactca aagaaaacaa aaaataagga    23340
gttggggaag ggaagggatc aagttctatt taggtcacaa gtctagcttt caatgaagat    23400
gcctggtact cagctgagta tatgaagctg aagttggaga gacatggatg gtatcaccaa    23460
tcacccaaat atgtttcagg ggtaaactg aatggaccgc ttttttgttat ctatcattca    23520 ttagattttt taaaaattga aatggaataa ttcttaaagg attaatttaa tcctacaaat    23580
aatcttaatt aaatggactg agaccaatgg tggaagaaat gaaatgcagc ccataagcag    23640
aaaataattc aaatagctca tttatgtctt ctccctatct aagaaaaggg ccctccagat    23700
gttactttag ttctgaatta aaggtgaccg ttttcaaaaa ggtcaaagga ttgaaaaaat    23760
tttagaaggc actagagatt tattttctt ttctttctgg caccctatta cctcaacttc     23820
aagaagagta ttgggattac attgtctgag gacttcctta aaagtcactg ctactgtgtg    23880
gtgtttacat aagcatgcca actagcctga tgtttgtgct cgcagaccaa attatttctc    23940
ttatttctat cagcactatg gtttataagc tgcagttcct taagacagaa tttcaaacag    24000
cctcccacaa acaaccacc taatagaaca cataaataat ttcccaaaaa taactatcta    24060
caactttatc cacaaaaaat agccagtagt ctctgtgtgc agttcctaa aagttgctca     24120 ggatttaacc aatgcaaggg ggctcatatc tgctttccct gacacccagt tagacgaata    24180
```

```
tgtgtgaaca ggcagcagct tggcacccct acctgctttg gacttcttag caaatcaaat   24240
aagttgcatt tctagctctg agcaccaagc cttacagtct tctacaaagt aacaggaaga   24300
ccagtagaat cgcatataaa tgtaaacagc atcacttccc agcctagctg ttttgctaca   24360
gccaggtcag tttctcatta ctcctcatcc agggctgtac ctacgttgga tgccaaccta   24420
ctagccctga agttgcattc tactttcct tcatatccat atcctttct gccttctgtt     24480 ctggacttgc ctcttctaag aagtagttcc taatgaaccc cacttactct tagtactatc   24540
ttccccaatt atcaactgaa aattctcact tcttccaaat ttggctcaat tcccatctcc   24600
cctgtgaagt cttgtttggc tcccacgtg catttaggca ttccttcccc aatgcacccc    24660
acccacaagc aggagtaaat aacatgcttc ttcatagttc ttcctaagtt ggtggctctt   24720
caccaagatt gtattatact cccccacaac aataaagttg aatggaaaca acttgaacat   24780
ccaataatgt ggaattattc attcatttat cctttcactc aaatatttat taagtaacta   24840
ctatgggcca tttataattc ttaaattagt tgaaacaacc taaagggcta acaataggga   24900
ttagttaaaa taacccagga ataagacatt aaatgaaata aattattagc aacaaatgat   24960
cagtgttgat aaataaatta taatttatta attttatgag caataaatga tcaccatgga   25020
caaatatagc ttattaaatt acaaactata gttagctata gatagaccac gtacagtatt   25080
acctaatttt ggaatcatat gtacagatgt aaaataaata cacataagac aggattttaa   25140
aggatttgta cagagatagc agttatagtc tctattgagt aggacagtgg gcatttatta   25200
tgttcttctg cttctctgat tttctgactt ttatgtaacg aaatatgtat tgctttttga   25260
ataagaaaac acaaatttt taaaactgga attttcaatt ttggaaaatt ttctagttca    25320
aattatttac tatattgttt ttctaagttg atgatgtctg ctctgcttgt ttagctgttt   25380
tcattttttc ccccacagga tggatggcat agattgttcc aactaattca atcactcact   25440
tttcaatgat tacttattga tttcctaatt tcctattgtt ataccttca gtcattctga    25500 tttctgaaaa aatttgttag aaatgtttta aaaattcctg gcataccaaa attattaata   25560
ctgggaagtc tagtaactgg gatttatttt tcaccaaatg gtctagttga ttaaattatt   25620
ctccaccaaa atgtttttga ccatgttgca tttcatcaaa tcatctggaa ctctcccaaa   25680
aaaactgtaa gatccaaata attaagccaa ataattggac tatctttct agcctgtgcc    25740 acctctgggg cagatgggtt aggggaaaag agcctttaaa atatccccc atagtggact    25800 ctggctggtg cttagggagg gcaatggagt gtctaagcat ggaaactatg attaaaggaa   25860
cagatataag aatttaccca acgtgttgtg aaaatgatga tatcaaccta attaggctac   25920
aggattaata gtttgtggct tttagaaaat aagattacaa tagacagtat ggggccagaa    25980
tatgaaaagt tttgaatgta aagttatttg gatttgacag aataggtcac aatagattag   26040
cataaatttc tgagacagtg atgatcagtc atatgctcaa aatcatccat gcagaatgc    26100 attagaatgt gaacagctgg atgtggaaaa ttggcaggat actgccaaaa tgcagataca   26160
attaaggttc tggacaaagg tgatgactac tgaaaagcaa acaacaggg caatctgaga    26220 gatgtttgga agtgcagaat aaaaagagca tggtgcatta gttacacatt gctcacatgc   26280
tcatgaagaa atattattcg tgagctgggt tgggctccac tgaacatgtc ttctgctctg   26340
gtctcatctg gttaatctag gatggtgttg gctgggacaa atgggacagg ttgcttctgc   26400
cccacatgtc tcatcctcca gtgtactagc ttgggcattt tctcatggca attgcagaga   26460
agcaagagac taagcagaca ctaataagca ttttctcagt gtttgccagc attatgattg   26520
```

```
ttggctaaag taagtcacat ggataaagcc agagtcaaag gagaagaagg ccagagtcaa  26580
aggataagct gaatggacac ctagagtaga ggacactgca aagttacatg acaaaaggca  26640
tggatacaat gaagagagga caacattggg gcctttaatt caatcagtct acatcacatt  26700
gtaactcact agacctaggc attaaaaaat aaagtattaa agttgacagc tcatgcatag  26760
tacacagcta gaccaaaaaa taagtcagtc tggaaaggtg aagatatttc ttgctttctg  26820
gctggatcta caggttcaaa atctttgtt gttttttta aaagtgacgg ttttgtagat  26880
ggcataattc tcatgccaag acatttattt agtcatttat tcaacaaata ttatccaaca  26940
cctattatat gttggatata taagtgctaa gaatacagaa atgagcaaaa tctcaagctt  27000
agatgtatgc cattacttac tacatactaa cactgataga aaaactgacc cccaatgttc  27060
cccaagacac aatctaaaag aagatatatg attcctatat taagacctt tcacaagccc  27120 tcaaacatta gtatattcag tatcatagca ttttgctttc aaacctttgt taaatcttca  27180
aggtaaagtc tactgctgta tatgattgcc aaaaccttt atttactct aagaactaag  27240 tttgagatta gatctccttt agaaatcaca tgaaattatg acgtatgcta cttttgagaa  27300
atagacaata agatcaataa taggtttatt ttatttgtt ttactgtggt aaaacataca  27360
caacttaaaa tttactcttt taatttttaa gtgtacagtt tgataattgt tttagtaagc  27420
atttattatg aactatcata ctgggttcta gagatagtaa acataaataa ggtaaaacac  27480
ctgctgtcat gaaattttta ccattatcca ctgatttac aggaaatcta taaaaataaa  27540
agaatactgt tttctcttct tgtacttcaa gttgaatgac ccaagccagg ccaatgagat  27600
accttccctg agattgtttt gctggaatag agacatgtga ctgtcctata ttaggagagg  27660
aagtgaatct ggagttgctg acatgggaag agactctctg ggatgataaa agccaaactg  27720
acccaagcat aagtgcatgt gtgtatgtct gtgtgtattt ctgtgtgtgt ggtgtggtgt  27780
gtgtgtggtg tgtgtgcatg tgtgtggtat gtatgtggta tgtgtatgtg tgtgtggtgt  27840
gtgtgcatgt gtttagtgag ggagaaggag aacccacctt gacagtaatg gttactttag  27900
tgacaaatac agttgttaac atctaaagtc cctggagttc ttcttcaatc ctttgtcctt  27960
gtcgtaaagt ccccttttctt ccttaagctt gttttagtta gggctggtca aatgcaaata  28020
tagagttcct taatacaaat ataaccaaac ttgagattct ataagaatcc gtttagttaa  28080
aagtacactg taacaaccag gcaagacaaa ggtcagggta gttttttgaaa atcatgttgt  28140 aattttggag ttttgttact taagattgtt ttatctggac ttttccaaag taggtgacaa  28200
taaagggctt atttatttgt atttaaataa aaacttcctt caaatgaaat aaaaagatt  28260 tcataactta cactgggtaa atacatcaat aaatcagaga ttgagcttct tgcttcatta  28320
atttatctgt acagaactaa ttaacattag ttaaatcatt ctattcaata ctaaatcatg  28380
ctgcggtgaa aatcattcca agtcattgac gctaggttgt taacaaaata tccagcttgt  28440
gaccagaatc catctaaccc attaatcaca gaattattac tggagacaca gaggggttcc  28500
aattcctggt ttttgtatct ctgttttct aatagcaaca aaatgagaac catgagggaa  28560
caggtaggga ggcataggct agatgagaaa aaagagacaa gaagataagg aactcagata  28620
agtgatgttt tccacaaggt cagcaaaagt attccatggt tcatcagtca ataggattt  28680 tttcagtaaa catctattag tataattgcc aataattcca caatacccctc atgaaagagc  28740 tactctccaa tatcaacaaa actgagacaa gcagttttc ctctataatg gtcacttta  28800 ttttctaaac attctacttc tgcctcctta tctaattctc ctgctttaag ttatcaacag  28860
cagatgccaa cagactctcc ttgagacttt ctttaacagg ctcatttata gctctttgct  28920
```

```
tttgaaataa ctcaattcat cttgcagtag agaacgcttt tcacccaaag aaaaagtggc    28980
atgtgagtgt gtgaggattt ctacatcatt gaacaggata caattacagg aaaatgaaat    29040
atgctttatg gagtggtgga tagcggaaag tcatcggcct gctctttccc ccttctttcg    29100
catttgcctt tttgtggtag cagtttcgac atggtgttaa gtcaaagttt ttcataacac    29160
aaactccact tgtgaaatca acctatgagt agcctcagca attttgaaaa tcaaaataga    29220
agagattagg aaatatcaca gtgcactgcc tgtaataatg gtaagttttt tctgtgaaaa    29280
ttttgtttca atggtgtata ttcaacatgg aaaatgcctt tcttactatg ggtcaagatc    29340
aaaaaagttt ggaactcact ggtctaagtg gaggggggatt tcattccag aagtatttat    29400 tgagcatcta ttgtgtgcct ggcatgattc tagcactttg gggcacaaca gggaacaaat    29460
caaagaaaaa cccgtgccct cacggagatt ccattttagc aggaggagcg acaaccaaca    29520
acaaacataa taaatgtaaa ttataaagaa tgttctaagg caataagtgc tatgaagaaa    29580
tagagtgagg taaggaaggc ctggggtgcc acggagagga gatacatttt atttattttt    29640
ttttttggtg gcactcacaa gagtctttat tttccttca ttaaatgtgt tgtgattttc    29700
atcttttcat ttacatctct acagaacaaa atccgtttgt gtccctatta ggcaagaatc    29760
cttcccatcg ctatcagttt tctacaagtt aaaaactacc cttacagaat ttaaaatgcc    29820
ctaatccatg gtaagcagca aattgaacaa aggtgcactg ccttcttcac ccccagagaa    29880
tgaggatagg agaatgggat taactaggca ggcctgcctg aggcctcagt ccagatggac    29940
accaataatc ctgcctcatt tccaagtcta ggaaaatttt ctgtacagtc tcccttgtg    30000 atcataaata atctccaaag attatatttt atcacacaga aaaacctggt ttccttgagc    30060
tttagccaga ttcatttaca aatgtttgac aagggtgtt aattaacact ctataagcct    30120
cttggctcta cagtgtacag catattaaat tcaaagaaac agcttctgtc tggggatttc    30180
ataaggaatc tcagattgcc ttttcaaaag aaggcaatct gagggtgtgt gttcatcttt    30240
tttaaaaaaa aatgctttta tactagaggg tttgtgtttg tctgtttta tctttttaa    30300 aaaaatgatc ttattggttc ttctattcag aagctaaaaa aacaagccca ataaattcat    30360
tatcacacag tttcatccac agcacctgta aatttggtga cttcctgtct cctcgaggcc    30420
cccagaagta gtcagtcttc tccgctgctc gtaaagtggg ttgctggaag tagagaagac    30480
tagttccggg ggcctccagg agacaggaag tcaccaaatg ggggtggtta gaggtgtgcc    30540
tcctttgaga aggagcttgt gaccatagac ttaaggaaag tgaagggttg gttctgtggc    30600
tatggcggta gggcaggttg ggaagaacct tccaggcagg gagaagagta aaaaaaata    30660 atgccccaag gcacaaatgc aagaccttca gtgtggctgg atggcgtggg gcagcggggc    30720
aggagtcaga gttgagacaa aatgtgttga aacacctttg agagtgtttc cagaacaggg    30780
aactgcagcg ttaactgctg cttgatcccc tgtgacgaaa gggaaatttt taaaacggca    30840
aggcttaaac gtgaaaggaa aagataaaaa gcttttttaat caaattgtaa atgacatggt    30900
ttttcactct cccatctccc gtatttctca ctgagtagca gtaaacacag gaaacagcca    30960
cgcataagtt atactgtaac tcctcataaa ggatcctctg gcttctttca tttttcggaa    31020
atgagaattg tgaaggaaga aaaagagag atctgaattg aaatgcactt tttcaggact    31080
gctatttgag ttatcatgta atgattattt cattaagcaa atatttactc aatagacaaa    31140
ttattatgct gggcatcgtg aggggtcaaa cataggtaca tagaataatt acagtataag    31200
tctgaaagtg aaaacgccag aagatggatt tttttttta tgcaatggcg attcagagga    31260
```

```
aggaaagatt ctttcttgct gagggaaatc aaggaagtct tcctgtagga ggtagtttct    31320
aaaccttata ttgaaagatg tagatcctgg agagacggaa aaaggcattc caggcagatc    31380
actgtgagct ggaaagccag tgatgctgtg gcaaaatgta ttttttacag aaaatagatg    31440
ggtatctccc atgccccatg atcttttacg atataacctg gctgttcctc ccattggcgg    31500
atctgtggac cctcccctt gaatctgtgg gcatgtgact gctctgatag aaatgaagct    31560
acatgatatc aagaataagt gaaagaagaa agaagaagaa gaaagaagt ccataccact    31620 tcctcctagt tctcttggga tgcttgccgg gagggaagct agtttccatg tacagaggct    31680
actaatctga gaccacttgt gtaagcgagg ccaacagaga tgctctggtc cacagccagg    31740
ctcaaccgcg gatcacatgt gtgagccgtc ttgcatgccc caccccgttc aagcttcaga    31800
tgactgcgga ccagagaaaa actgcgtggg tgagccctcc cctaatcctg acccataagt    31860
ttgtaaacca aataaaatgg ttatttaaag caattaagtc tgggggaatt acgcagaaat    31920
agtaatggga acagatgtat ctgggttagt gttttttgtaa tgatgtaatg atgcactct    31980 cagatgtcaa ttaaggttaa agacgttagt ggcaagtcat gactaacatt cttgtccatt    32040
tcagatgctg atgtggacga ggatggtcta ggcatttgct agcacacccc tagatgtaac    32100
ctgtgcaatg cgggaggcag cctggagtca tggaatgtac actgggaata ggggttcaga    32160
aaacctgagt tttgacccca gctctgaccc ttggtaccca caggaaagtc agctaaactc    32220
tctgggtctc tcaatgaatt tacctgcccc aaaatacaaa aaaaaggac tctagaaatt    32280 atcaagcatt atccagtggt atgggttttt taaattactt taaattaata aatgcattta    32340
tatagtttaa aatcaaatag taccaaaggc ttatcatgaa aacagtaagc atctcccca    32400 atcccgtctc taaccctcac tcctgctccc cactggcaac cttttagctc tttcttctcg    32460
taataactat catatttcta aatactatgc tattgtgaaa tttaataatt cattaggata    32520
atgaggagtt agctcttta catgccccat tttcttccct tattttccga aatgtctgtt    32580
cttatttaaa tcattgttag tatttacatg aagattccta tataaatgtt cattttagag    32640
ccaaataggg cactataaca tttccctttt ctaaacagct tttaattttc ccttgaataa    32700
ataatgacct cattattaag cgtgcagaat attctatatg tgatttttc aatgtgttag    32760 tgattctcta tcatgttttc tatgatcgta tctattctgt tgagtctact ttttcaccca    32820
gagctcttcc ttccctgcta gaagtttcca gcctccaagt ccagtttgga ctagatgctg    32880
tcaagagctg ctctcgtcct gggagttttcc tttatttctt atggattgaa accatacttt    32940
ttctatatac tatttcttcc tatgtattta ctacaatttt gctggtgcat atcttccatt    33000
agcttcttag gaaacatgac actgaaggtg aactttcaat acccttacat gtctatacat    33060
tcattgagct aggaactcag tcggctcttt aaagttaaaa gctcatgttc ttcagttctg    33120 gggcattta ttatattatt tctttacaaa tttcctgacc tgtatttcct tattctctct    33180
ttccagaact tctattagtc tgatgttgga tctttatgaa tatcctttaa atcttttcc    33240 cttttcaaaaa tgtgttctat ttctttatca tcttgtacta cttttacagc attgctttga    33300
ccttactttt caaatatttt actaaatatt ttgtttcaac tattgtgtta ctgatgttca    33360 agaattttt tatgttctg atggttcctg tttcagtttg tgtatgtgtt taattcctgc    33420
ataatttatt ttccctggtt tgcttttctg tttattttat tctgtttcat gttgatagct    33480
ttcctcaaat gtctttcacc agcattgtca ccccttgccc ttctgttgta cctgctccct    33540
tttaagcctg ggttcctgat tattgcagga gacaagactc ctgatgtcgg gagtctgcat    33600
gccattccaa attcatcatc tccaagtgtg gtctagcaaa ataatttgca cttatgatca    33660
```

```
tgcaacagcc atcagttact ttgagagatt atagaaaata aggcgcttga agaatgaaaa   33720
ttttctcaac tttaaaaggg aagataatgt gaatttcaga aataatagac tcaagcaaaa   33780
ttaggtaatg gttaacaaaa atgcatcagt actatggaag ggaagataac taggagacaa   33840
catggattcc tagaataaat ttaccaaact tagctcagaa aatttttatt gtattatatg   33900
gtgctatgat ttgaatgctt gcccctccaa aactcatgtt gaaatttaat tgccattgta   33960
atagtattaa gcgagacctt taagaggtct cactttaggc caattaggca atgaggtctc   34020
tgtcctcatc aatgaattaa tgctgttatc atagaagtgg gttcaatatc tcaggcatgg   34080
gttccttgta aaaggatgag ttcagcctcc ttttgtctct ctcttgccct ctcaccttcc   34140
accatgggag aaagcagcaa gaagtctctc accagatgcc agagacttgc ccttggactt   34200
cccagccaac agaactgtga ggaaataaat tcctttaaaa aaaaaaaaaa tagggccagg   34260
cgcggtggct cacgcctgta atcccagcac tttgggaggc cgaggtgagt ggatcacaag   34320
gtcaggagat cgagaccatc ccgactaaca cggtgaaacc ccgtctctac taaaaataca   34380
aaaaattagc caggcatggc ggcaggtgcc tgtagtccca gctactcggg aggctgaggc   34440
aggagaatgg cgtgaacctg ggaggcggag cttggagtga ccgagattg tgccactgca    34500 ctccagcctg gcaacacag caagactccg tctcaaaaaa taaataaata aataaataaa    34560
taacctagtc tcagctactc ttatagctgt acaaaatgaa ctaagacata cagcatatct   34620
gagaacacaa tagtcatctc tgtatgtaat aatcttgaca gttgctaaac attttttgtga   34680 cattcttagg gtcaaaaaga aaagtagagt gcaaataaga tagtactgtt gccacttgaa   34740
aaaatatatt ttaagagtat tcattggttc aacaaaaact tactcgttgc ttattaagta   34800
tcaaatgctg gtcaatgttt gaaacattga ttcatgggac agatcgactt gagagaaggt   34860
gactaacaat atcccacaag gtttattcat aaccctattt ctttgtaact tgttatcatc   34920
aaagggatga aaactcacaa aggcattaat ctaaaacttt gaaaattctc caaaacttga   34980
atccaaaaga gctctacaga gtgtaatgct ataaatatgt gctataacta gcaaaattaa   35040
tatttaaagt gatagaaaaa atatttatgt cttttttaaaa ttaaaaatac aagtaatata   35100
tgttcatggt ttaaaatgtc agaacaactt acaagaaaaa tcacagttcc ctgtcctaca   35160
ttgccctaca attcccccag ttctctctag aggcaaccac ttttgactct taagacgttt   35220
tcttttggaa tttacatctc cacacatcca cacttcagga agtatccact gacttcctat   35280
tatgctagat aagggtttag ctctcttaca caggcaattt agttatacaa tagttttggg   35340
tttaaccgac atttggtatt gacattattc tgccaacatg aatatcattc acagctggac   35400
cttgtaatgt agtaagtaag actgttttcc ttcttatttt tgttttcttt gaagttcata   35460
attgcattgc ttttttgattg gctctgtttt ctttgggact gtggctaatt cttccctcaa   35520
tttccaatag cctctcagca gaaacttccc cagggaagtc acatgagcct ccaatatttt   35580 gggggggacac acttctggaa tctcccccat tctgcactgg ctgatcttag tctgctgcac   35640
atctgacatc atgggtctac agttcatcat ccttttcctg ggttagacct gccctttcat   35700
agatcccatg tcttcctcct tgtcttcctc atgttatgtg gcggttaccc tccaataact   35760
tcctgagaaa gggtttatgg aagatttatt ttttgggact ttgactctca tgaatgattg   35820
acagtttaga taagtatcaa attctaggct ggaaataatt ttcattccct tctctgaagg   35880
gcactcctca ctagtctttg tgatggccaa gaaatgcact gctcagtgtt cctgctataa   35940
ggagcacagt tgactgaggc catcagttgc taccccttg aatctgccat tgcagttgat    36000
```

```
cctaagatca tgattctcat cggctactcc cagatgacta acatggcag gggaactaat    36060 gcaggcccat ttcagcaaga tgtggactcc gccaatgggc aacattggct caaggcgtcc    36120
ccatcagcct atgcctgggt tgttctgaga cccacagtgc caactgaaac tcttcccagc    36180
ccatccttct ccctgcccac tctccttcat agttgttgga cacacatcat gatccaaagg    36240
ttcaatgcct cccctagctc cttcccctttt atccttcaca attctttccc caataaattt    36300
cttgtacatc taatcctatc ttgacattta cttctttcag gactcaaact aacacaagag    36360
gggttgggga accagctcat tcactttctg gaaagcaaag agaatgccat tctgagtgtt    36420
gtgtaggggc agatagtccc cttgcacaaa tggtgcttca attgctaaat atttcaacag    36480
cagtaacctg ggaaatatcc tggtggagaa tgtcattgta ggtgcaatga tttaggcatt    36540
ccctgcctac aaggagatgg aattgaatgc tttctgatat attgtattga gactctacag    36600
agagctaatg agaaactgag ggccaataac aaacagttaa aggctcaata taagagccac    36660
agccttctct cctacagtgg aagagtagaa aacttagca gcaggcctag gacctgatag    36720
acttgcagag atttagggat gtttaaatgc tcagccaagg cagatcagtt atgccaaggt    36780
caaggccccg gttggggaaa cctgggaata tttggagctt acagaggtgg cccattcttc    36840
cctagtaaga gatagcactt ctttatgctg aagaggcctc gtccctaaaa agcaacaggt    36900 gcaccctca ggagctgacc cggcactaac gaggattaaa tcctagtata acccacctgg    36960
agacagctgg gcctgataga gaagaaaaga tactatatcc caacattgct tcaagattga    37020
gcatgcactg caaatcctga ggagtagcgc tggggtcctt gaccaaggaa ctggaactta    37080
acacaggaca gaaataatt cattatctag ggaacacttt ctccggaagt atgttttcac    37140
gatccagcaa ggaccccagg agacgcggta aagttgctgc tagggtggct ctgagaagcc    37200
tgtaaaaagg gatgcccaat gctgagcagg cggaaatgcc tgacattgtt gccctaacag    37260
ctgataaaag aatcaagaag cagagagaag ctggcatgca agaaccagta tattatgtga    37320
ggtcaaacaa cccaccagag gacagtgttt cccagaagtc ccaagtaggg agaaagagca    37380
ttcactgcac cctcaggaat atgctcatgg gggtgccaat ctcactgaga cattcagtgg    37440
gggcaccgct ctccaggcca gggctgctgg tagcagaggt gtcacagagc tgggcttgtt    37500
gccacccacg gggatggtca gaagttgaaa ttacagaggc cagatagtga gtggtgctta    37560
actgccagaa gccagggagt tataaagatg gttcatagag catggctaca taaaagtga    37620 tgaccccttg tacagttccc cgacttagcc aatttccaa gctataattc actgactgaa    37680
gaggtgccta ggtccctagg agccaggacc ctgcaataac acagaggtat gacccccca    37740 ccccattctt cccattcaat atgaaaatgc atgtcctcca gctataggaa attttctgga    37800
attacttcat tgttccttt ccttttacgt cagttaccta ttgctgtgaa atagaccgcc    37860
cccaatttgg agaattgaac taataagaat ttattttttt cctcttgctt ctgtgagtta    37920
atgggggttg gctgggcaaa tccagtcttg agtatgcagc cagggaaggg acactgcaag    37980
ggaaaaggca ctggcaggga gaatgaagga cagaggctag agagagccca gtcccaccca    38040
tgaactatac agtaatcttt acatactttt tacatactta ttcatacaga agagacataa    38100
catgggctgc cttttaataa tcatacatca acatttaat aaccaattag tattccactg    38160
tataagcgta ccaacattcc tctaacggat taccttaaca catttagctg atgtccagtt    38220
ttaaagaata aaccaccatc agcggtaaac ttcctcttat ctttgcacat tggagatgaa    38280
atttaataag attgaaagtt tgaaaataaa ctaccaaaga gatgacaggg atgtttggct    38340
tcacagcaat tcacaagctg gggggaaaaa acctgagagg ttttagctga ctgcaaacta    38400
```

```
atttgagtcc gcggtaaggt gacagccaaa attgttaatg caatcttggg cggcatgaac   38460
aaaattcagt gtctaacaag aaatgtaatc gctgaagcct actctgaaca cctggggcac   38520
tgcttggttc tgcacagcaa atgttaagag aggccttgga aattcccagg ctttcttctt   38580
cagctcctca tcctttccca cctgacgctt cagccattca aaagacctca tgctgtggtg   38640
ggaatggcca cactgtctca cctgtactga cttttgcaagg gatgtttcct agaaaggcac   38700
aatgcccttc tcactttgtg tgcccagcaa gccaagccca gcagcagggc ccactaccta   38760
tttttgtaaa taaagttttta ttgaaacaca gctgtgccca ttcattaaca cattgcccat   38820
ggctgcattc atgctgcaac cacagaactg tgtaatagtt gcaacagaca ctgtaggatc   38880
tgcaaagtcc aaaacttagc cctctacaga aaaagattgc cagcctctga tcttacaagt   38940
attgctttcc ctgactgctc ccgtactacc tccccaaaac gctaacctat ctctcctttc   39000
ttgaaatagg ttcctaagca agtacttatt tctcttaagg catttataca ttttactgta   39060
attatttgac aattacctct cccctactaa tctgtgacat gagggcagga atcttacctt   39120
atccctcttt tctgacagtg cagaaacttg gaaatggcag ctctggccag gaaggagtaa   39180
aaaggccccc taggttagga gcccctcac agcccatgcc agatagatag gagaaaactg   39240
aatctctcgt gcagcccaag cagtatacct ttggtgagca atgtccacgc tgagttgtgt   39300
ttgactgcag acaatttctg ggagaatgta gttgagtcgg gagtgagacg ccctaccac   39360
tgtccccgca cctgtgcagg gctggcataa aggcctgatg ggaacaaggg gacacaggtc   39420
tctatggaag aacttgggac accgaagaga ggaaaaggca gaggaaagag gaccacatga   39480
tgagaaatca aagagaagag aggacaggcg gggaagagca gcatcccaa gaggctctga   39540
cagggcaacg ggcttgcctc ccatgccccc atcctcccct gcagctttgc agccgtcctc   39600
tggaccctca cgaaaagagc cctacaaata tgcctccttt gggagccagg gctctggact   39660
ctctacaggg tccggcacag ggagaactcc aaccactcgt cctcagtcct ctgcacccat   39720
cagcaggaca atggtgatgg atgatgagac agaggcaggt cccacagaca accctaaacc   39780
ctccccgctg gggagatagg tcgactttcc cctctcctct cctccacctt atcctgaaac   39840
gtcagaagac agagccacct gttcaaaggt tacattcata ttctcagaat caacattgc   39900
acctgcctgc cacagggtaa gctctcaaga aatgttcctg actaaatgtc cagtcacctc   39960
catgtcttct tggagcagac attagcatga aggagaaaat tctaggaaga acaaaacgta   40020
ctggtctttt caaatatgtg aaagatgtct tttcaaatat gtgaaagatg tcttgtcaaa   40080
aagtgacttg ctttattctt tgagatttag gaaggcaaag agacagtcac ggaggagtcc   40140
tgtgcagcag caggttcaat atgaaagaga aaatcaaggg ggcaacttga gtggaactga   40200
gttcctcctg cttcaaaggg tcaagcaaaa gctagctgac cccaggagag ccactgtaag   40260
gagttcgtcc tggagagaag tgtaacctgg gatttttccaa attccttctg attctaacat   40320
tctaattatc aaataaaatg cacttataga tatggaaata acatttgctt aaccattata   40380
tttaaaatta atgtacatca ctgctttcag tttgagtatt ttatcaagct ataatgatac   40440
cggttcatgg atgacgtgac atctgtactt caaacaaaaa atgttaataa aaaaatctat   40500
tgaaactggg gccacaaaag ttcaatcaat atttatctttt ggtttagtca atatataaag   40560
ttatatcagt cataaacttt agtatgtatc ttttttaccac caagctggat ccagaaagat   40620
atttgataat gtgttttatg taaaaatacg ttatttcaaa aatgatttga tagttttttgg   40680
tcaaatgcta ttgaaataat ttcaaagaag aggcaaatta agtagttaag tgaggctacc   40740
```

```
atgtctaatg catttgtatg attccttcta aacagctcaa gaggaccatt tctcaagtat    40800
tttgctatta ttactattat tattaatgat aaatttatag ctcacttttg tagagctttt    40860
tgtattttt  caaaacacgt tgacatatat aaggtgcttt taattctcac aatatgcctg    40920
ggagttaggc aatgtggtag agcctgctgg ttatcctaaa tgatctgttc ccatctgatt    40980
tcaacttaat agaatcattc actgagcacc cggctcctca ggggacaatt atttgcagac    41040
tccttttgac catgtgactg agttctgccc aagggacagt gataggtgca gcttccaggt    41100
caggcacttg agaggccacc ttttccctct tcctctcttt tcctgtccac tggatgaaat    41160
tgggatatta tgtgctctgg aaatcaacaa aggtcacata acgtatctgc ctaggaaaat    41220
ctttactgtt cttcctcact ctttaaaact ccttcccaga tattgtgtga gagcagactg    41280
caagcgcaat attccattta caagaaagaa tatggacacg ttgaaaccag aaatatgtat    41340
tttacctctc cacttatgcc tttattaaaa attgtatttc tttcctctgt gccaagcact    41400
gagataagca ctacaaattt tgaaataaat atgataggta gtctgtgctc ttaagagagc    41460
cacaactgag taaatgatcc attctacctg tggttattgc agaatgaaaa tatttgagtc    41520
aagtctctga agggtaagta agagtttacc ccaagataaa gagggaaaa  aggcatcctt    41580
caggttatct tcatactcag aatacatcaa aatagagcat ataaaagtca cattctgctt    41640
atctgtttaa atatagattt caagtataac tttgcatttc tggagaaaat gtggatctga    41700
gacaattcaa taagctgtgt gttttttactc acctattatt acttgtcctc ccagtaagca    41760
tgtattctat tctcctcctc cacctaaaat ttcctttatg cctcaaaaag acaacattca    41820
ttgaaagaaa gacaactttt gcacaaatta attataataa aattctagtt tagagcaatg    41880
atatttttga gaatataaga taattcagaa ggcttctatg tgcaaaagcc gtgattgcta    41940
catattcagc tggcacagtt aattgttcat tcatttgca  cctgagaagg tgcattgaca    42000
ttacttgaat gcatagttta cattttcctt cttttcttca actcaaaata attggcattg    42060
ttaaaacact gctatgattt tgaaatgatt tgattaattc ttttcctatt ttaaaatttt    42120
ttcttggact tgactgtaac cttcaaaaaa caatgtgttc aaaaaggagt gattcaagct    42180
gtttgggaga tattttaact atttctgact aaatgcacta ttgaattcag tagtattcta    42240
aaatttatat taactttcaa tccagttgat tattctagtt atgtacaaaa tacattttt     42300
tgagatggag tttcgctctt gttgctcagg atggagtgca atggtgcgat ctcagctcac    42360
tacaacctct gcctcccatg ttcaaacgat tctcctgcct cagcctccca agtagctggg    42420
attacaggca cctgccacca cgtctggtga attttccata ttttagtag  agacggggtt    42480
tcaccatgtt ggccaggctg ttctcaaact cctgatctca ggtgatccac ccgcctcagc    42540
ctcccaaagt gctgggatta caggtgtgag ccactcgcc  cggccccaaa tacatttta     42600
tgaaagaaaa acttgtaaag tatttctcaa aagtgcatag tatatgtaat ttgagcatat    42660
atacagtaga caaatcgctc atactaatta cttggggaat aaaaattcaa tcagctaaca    42720
aagccccttc aatatatac  tcctaaagct ggccaggaga ctttaccacc tgcccttatt    42780
ctgaaaactt cttcataatg ctgcatggtg actacagata gcttttaact ggacattttc    42840
acaatggaat catacatttg atgatgaacc ttaaattttc actgcagatg tcagagtctg    42900
ccacgttatg tttacctatt tttccttatc agattaggat ttggtagtct ctgttccatt    42960
ggaaagtggc tagaaagact gacaaggaga gaaaattcta gtagcatgag tttataaagg    43020
tgaaatcagg ctattcggta aaccagaagc caccttctga gcaccaaggg agggcaagat    43080
gccatttca  gagatacaga tgaagggaac aggattaccc cagatagcga aggggtaaaa    43140
```

```
tggagacaaa tggttaaata aagggaagag cgcgggagga ggcatctgag caaagcgaag    43200
tcctgtgcag gatgccatag aaggaagaga tggcattcag gcatgggcc caagggagcg    43260 tgttagctgg ctccagaaga acaggtggga tttgaaaaag caaggactct gtcttgtcca   43320
cacataatgt caccctgtag agcatccatc atggcacact gcaggggca aggcagaaat    43380 aagaacccca gcagtgaggc tgttcccatt acccaggcaa ggttggatgg tgtcttgcac   43440
ctccatcgta gtcatagata aggggagaag tggtttgatt ctggacacat cctggaggta   43500
ggtagagctg caggatttgt tgatggatta gaaacaagac atgaaaaagg ggagtagtta   43560
agattcgggg tccaacaact ggaagagtaa aaagtcatca taatagagaa ggggaagcag   43620
gggtttggtt tgggatgtgt tcgatgtgac atgcccatta gacatccacg tggagaaggc   43680
ggttgtctat gccagtctga tgctcgggga aacctgggtg gagactcaaa atctccagtc   43740
atcgggatgc agcagtattc aaagcaatgg cctggagtga atctagacag agccctgagc   43800
cctccactat ttacaggcaa ggtgaggagg aacaagcaaa ggagactaag agggaatcgc   43860
cagggagctg agaggagaag caagggagag ccagggcctg aaatccaagt tgaggaagga   43920
ttcaagggac aagaagtgat ggcttcaaca aacattgcag acagatgggc tgagacctgc   43980
acactgatgc taatgctcaa caatgcccag attaatatct cctagcccta cttccttacg   44040
tgaaagaagt cttttcaca ggttccttgc acaaatgttt gcaagaatct caggcggtga    44100
ggggagttga aggtgggaaa tgggaacacg tgtatttcca acttgattct aatcctctta   44160
gaacccatat acagaacaaa gactcagagg cactgctggg gctgaactcc ccaactacag   44220
tccctagtgc tgatttcagg ggacattaag aactttgttt caagagctgt gaaggctgag   44280
cagttggtct tcaagtccga gagaaaaggt gcatcctcct ggattacact caaatgagca   44340
aagcagcctg agctccaagc tctttgtagg agacctctct ctctctgtcc ctcctcccct   44400
ctcccctctt ctccttctct tctgtctcct ctctctctct ctctctctct ctcacacaca   44460
cacacacaca cacacaccat tttgccaag gctcactcca gtatgaggaa cccacaaaga    44520
acaccaagac ctccattctg agcagggcct ccattatttg tcctgctgtt tgtttgttct   44580
gcctcctgtc ctccaggcca tcaatgattc ttgactctct aggaggggtc aagcttccca   44640
tcatcccagg ggatctcctt agcccatttg taagttagtg gaaacacaga gggagtgagg   44700
gaagggtgct agccagtctt tatccttcac caacatcaga tcccggaaca caactggccc   44760
ctatatctgt acagcagcaa tatctaagcc ccagctaaaa tgccctttta tcaaaatctg   44820
cagaatgttt tatcttttc aggtaagctc aaattttct attctcgctt cccccaaccc    44880
ctatatacac accgagaaag gtcattgaaa acagaatgaa agtatctcat acaacaaaat   44940
taattcaaga tactttcttt gacaatggga actcgcttct aaataagata caagaatgac   45000
taaacaccaa accaaaagaa atgtgaaagc aaaattaata ctttacacca actaacagtt   45060
tgtttgcaac atcagcaaat ggagcattca cctgttacta atttccctaa atacaaagtc   45120
cactgcattt ctaggaagga tggttagtgt ttggcaaatt ttttgtgtaa gcattgaaaa   45180
atataactga gaagttaatc agagggccat gagtgggcaa aaagatctaa acatgttga    45240 ttatttaaaa caccagagca ccagagagca cgcaagtctt tatcttataa taaaatgatc   45300
ctataagtca ctataataac aattgactac tttgtatatg caagtttatc ctagggactc   45360
taaaaataga acttgtagga tttaaatcta aagtaaagat tttatgggca tgatctatta   45420
gatcctccag ctgatccatt tatttgcttc cagtatgaac tgataacttg cttatgtttt   45480
```

```
cttcaaaaag tgagaccatt cttcccatag ttttctatc accagccata cactggtggt    45540
ctttagagtt tttcagatcc ataaaaggat tgaaaaagta taagaatcac cgctctaaaa    45600
catccttatg aaagacata cataagtatg aaatcacaaa aatcacaatg tgtttccaaa    45660
caaatccaac attctttat ggccagtagc agcaaacagg ttttgtggaa ctgacataaa    45720
atctaattta gccattatta caacattacc agcagctcag agcactaagt cacctcaata    45780
acccagtact gctctgccca tattatctat ggctttaatt aaaagtgttt agaaatggtt    45840
ttagtactga ctttgttcag aatatgtggc tgaattctaa atttaaaaat aagtcttcca    45900
gtaggcccac aagtgatcag aattgggtac caaaagttgt acatttaaac acttttatta    45960
aaatgtttat acatgtacat aaaatatttt attgtgatac aaaactctgt acaaagtgta    46020
ctaacaactg acatgattat aaatgaatcc caaaacaat ggtgcctaaa tttgaacact    46080
aaggagaaaa aaggaggaag aaatacttga gacaacttta ccatggcata gcaatatttc    46140
ctgctgtcaa aattaataaa atattttgca caagggtgtt acaattaatt ttatcaggct    46200
aacaatgtca taagtgagga acccttcaa ctgtagagag cactgtggaa atatagatgt    46260
ggtagaacaa tctatatcac cctgcagttg tttctgtgtt tctatgacta gctttgtttg    46320
agattgtata agcggtctt cacaccccgg tgaataagat tggtggatgc agttccctgc    46380
cctgccgcag aagggacctc caaacacagt ttaaatctga ctctccggga gttgtgtttt    46440
gacactttca caacagtgtg aacttgtgcc acaagcaaga cagatcttat tggattaaca    46500
ctgaactcgt gacagctcca gagagtaatg ctatctgtgc ggcttaagaa caaacgtgtt    46560
tctttcatcc accctgctca ttctcttcct gcagttactc ctagcaaatc ctccccgccc    46620
tcacctctag gaattcctct acacccagag aaaggagttt cttttcctcac tgcggaaacc    46680 tatcaccgct tcctttccac agatggactc caaggggcac tcactcgtgt gcccactaag    46740
ggatttctct cctaattcca cgccttccaa gggaagtcag aactgctcag tttccccgg    46800 tgaccacata cacgtgtcca agtgaagcct cgtctggggg agactcagtt cccacacttc    46860
cccctggccc ctgtggaggc cctctgtctc cctgcgtgg ccctccgcct ggccctcgc    46920 actcaccagg aggaggttgt gcgccaccag gtacccgagc cgcgggctgc cccggatgcc    46980
gggggccagg cgcccggtgg cgtagccgtg ccaggccacc acgtagggt tgtcgatggt    47040 gatccagtac ttgacctgac cgccgaagtg gcggaagcag agctccgcgt aatccctgaa    47100
gtggtcggcc agggcgcggt tggcccagcc gccgtaggcg cctgcaggc gctggggcag    47160 gtcccagtgg tacagggtga ccacgggctg cacgccagc tcccgcagcc gctccagcag    47220
gcgccggtag tagcgcagcc cctcgcggtt ggggacgccc gcgctgccat tggggagcac    47280
tcgcgcccac gagatggaga agcggtagtg agtgaccccg agctcgcgca gcgcctccgt    47340
gtcgcggaag acgttgttgt agctgtcgct ggctacgtcc ccggtggcgg gctgcagcgg    47400
cgacggggcg cccaacggca gactggcgtt ccgggagtct cccggggtg ccaggggtg    47460 gtgggtgaac gtatcccaga tggacgcacc cttgccgtgc tgctgccagc cgccctcggt    47520
ctggtaggcg gcgctgccca cggcccagag gaagccgtcg gggaaggtgc cctggaagag    47580
gcccgcggcc tcggggcag gaggccgcga gaaacgggcc caggtctgcg cgccgtcgcc    47640
cggctccgca cgcaggcggc ggccgcccag gcccagcagc accagcagca gcgacagcga    47700
ccggcggcgg ggccgcgggc ggcggcggcgg ggcgctggcg ggcatgctgc gcgggagcca    47760
ggctccgggg ccccgcgccg cgcccctta tgcccgcgcc ccgccgcgcc cgcccgccca    47820
ccgccggcgc gcccacccc gctccccggc gggctccgct ggcaataatt acctgcgagc    47880
```

```
cgggactgcc tccgccctgg cactgggggt gggggcaggg gcgccgaggg cgagggg tgc    47940
ccgggagggg cgcggcagcg ggcaaggtgc ggcaggcgtc gcccgcggac gtcggagaaa    48000
ggcacctgtt cctcccagct cccgggagcc gtgcaggacg tttcgtggac gctcaggttc    48060
attctctttg cctgccgcgc gtcctctgag agcagccctg gagcggcttc gtcgggagaa    48120
aaaggcgccg accaactttc cccgacttgg gggcgggatc ctgccgggcc ctagcggagc    48180
gcgccgctgg ggaagcacct gctctcactt ttctcccact cggaggccca agaagctcc     48240
ggctggacat tgctggagcc aattagggac tggccgaaat cctagaggga ctgccaggtg    48300
ggacagccga gggggaactt cgccgtgcgc tgaaagggat tccccct tag gtgagatgct    48360
cgcggggaga cgcgcccacc cgcgcccctc tttcgaggaa gacaaagtag atttatgggt    48420
tgcgttggga ctgggttttt gctctccctt ttactgttac cttttaataa tttcaaacca    48480
gcactctatc tttgattaga tctctcagaa taccctggtg aacttcaaat cacagtcgtt    48540
gattgttctc ctgaaaaacc aaacaccaag tttccaattt tgagtaaatc tcattcacct    48600
ttattatcct ttggcatctg tgttaccttt cggctctgac ttagcaggta atctgtgcaa    48660
agttgtgcgc acaggtctgc tggagcggga ggtccctggg tcgcacattt gccatctgag    48720
ctgtggaggg aaaggggagg gagaatttag ccggaacacc cattcccatc ctctacaata    48780
caatggagcc atgacgtttt tcctgttgcc aaagagccct tttgacagaa gttgcagagc    48840
cacggtgtcc atttggatgt gggtagatag gattgtggct aaccgaaata cagttggtgg    48900
agactgagaa ggtctaggct ccacctttgt gatttgggc aggaaacctc tgtaagccta    48960
agttttttcc tctataaaat aaggatgtcc tgtctgccct gccgcctcag aggcttgtga    49020
agtccagtga aaactgcgc aaaggtgact caaagacaga aagcccagac aagtgaagga    49080
tcttgctaat atccctacct ccctacccag taagtcgtgc cttagtttcc tcacccgtac    49140
acgtgtgttg aatgaccaag atcctcacag aggtgcatcc attctcccc agtgatctat     49200
cctccctgca ttatttaata caaatttaaa ggcaataaca ttttaaatgt tgcagatgaa    49260
ggtgcttta ttaattcccc tgaaatataa gcacaaattt attccagtat tttatgaaat     49320
attcccaact ccagccagca tatattacca tgattagtaa gattaagtct tcagattgaa    49380
acagagttac tgccattctg ttaaatatag catttacatt ttttcaataa atacgaaata    49440
gcaaaccatg acacttcagc aattttaaaa aattacagca cacaacttca ctgtcacgct    49500
gtcttccagc taaatttaaa aagctacgtc tacatggagt atcacatttc ccttctagaa    49560
gtgaagattg gagtgtctgt tgggttgtag cttgttaagt ttcaattaga aatgcttcat    49620
gggtctcatg gaaaatcgct taagctaagt attcatttat tgatgtatgg tctgtttgct    49680
cagggcagat tttatctatt gctatttta cttgaccagc agcatttttt aaatttaaa     49740
gcagtgatta aaaagcaaga ccaagttaac taaacgtttc acatttgaaa tttgtctgcc    49800
acataggcac atgcatctca aagctttaag cattccaaga catgttccca gatgattgtt    49860
catttaaccc agtgataaag attgcatgat gattaaactt tatttccaga actttctgtt    49920
tattaaggtt ctgttcatgg ttactaagtt ctggggttcca caagtgtgag acggagtctc    49980
actctgtcgc ccaggctgga gtgcagtggc atggtctctg ctcactgcaa cctctgcctc    50040
ccaggttcaa gcaattctcc tgtctcagcc ccccagtagc tgggattata agggcacacc    50100
accacacctg gctaattttt gtattttttag tagagacagg gtttcaccat gctgaccagg    50160
ctggtctcaa actcctgatc tcctgtgatc cacccacctc ggtctcctaa aatgctggga   50220
```

-continued

```
ttacaggtgt gagacactgt gcccggccta gtgctgctgc ttatttattt tggctttatt    50280
ttggtttttta ttttttacaa ccaccttcaa acatctgaaa cttgggtttc aaatgcaaat    50340
aagagattaa ttacttgctg tgctttgaac aggaaggtga agttattgat gcattgaaga    50400
aaaggacatt gtaaatttat ttactgactt tgattttggt gacaatttca acactgaaag    50460
ttgtcaacaa tctgatcaac ttttcctcca ttctccacat tccttcatcc agtgccttcc    50520
cacctgttct ctttcctatt gtgttcccag gacgatggga gccttttaac accaatggag    50580
caggagatgc actgattcac atgcactcaa atacaacacc aaccccacaa gctctcggct    50640
caccagtcac agacatcacc ttctacggac atattttttat ttcactgagc tacaactacg    50700
ggcaaggcaa cgatgagctg tgtggagact caaaacata gaggacaacc tctgccctca    50760
aagacaacat ccaactgaag aaaggatcaa gaaagatgaa aataaataag ttgtttgatt    50820
atgctgtgtt aataaatgac ccatagaata attgtcagag aaattcagaa gaagaagaaa    50880
ttaccctatt ttgagttgtt tggaaaagtt taacagagaa aaatatgaca atatctgggg    50940
tttaaagagt aaaactcgca caaagacctg gagggaagga atcaagagat gccaacactg    51000
aagaaaaaaa catgttcata gtgtattcgt ggtgaaaaga aagggttttt gtgcgcaagg    51060
aagtaatgga ccaaaatgca gtagtcccag tgcctagaat catgctgagc acaaaacaag    51120
tatttgttta atgagcaaat gaaagtagag tttcatttgt ccagttaaca aaatacacaa    51180
gtattccctg ccctcctctt tttaaaatta attaattaat taattttaa cagacaaaaa    51240
attatatata tttctcatgta cagcatgtta ttttaaaata tatacacatt gtagagtgg    51300
ctaaattgag ctaataaacg tatgtattac ctcacatact tattttttt gtggtaagaa    51360
gacttaaaat ctggccgggc gtggtggctc acacctgtaa tcccagcact tgagaggcc    51420
gaggcaggtg gaccacctaa ggtcaggagt tcgagaccag cctggccaac atggtgaaac    51480
tcctgtctct actaaaaata caaaaattca ccaacatggt ggcaggcacc tgtaatccca    51540
gctactcagg aggctgaggc aggagaatca cttgaacccg ggaggcggag gttgcagtga    51600
gctgagatca caccactgta ctccagcttt ggcaacagag caagagtctg tttcaaaaaa    51660
gaaaaaagaa aagaaaagaa gaaaagaaag aaaaagaaga atacttaaaa tctactctga    51720
gattttcaaa aatacaatat attgt                                          51745
```

<210> SEQ ID NO 21
<211> LENGTH: 4392
<212> TYPE: DNA
<213> ORGANISM: Artificial Sequence
<220> FEATURE:
<223> OTHER INFORMATION: NLS-dCas9(D10A, H840A)-NLS-VP64

<400> SEQUENCE: 21

```
atgagcccca agaagaagag aaaggtggag gccagcgaca gaagtacag catcggcctg     60
gccatcggca ccaactctgt gggctgggcc gtgatcaccg acgagtacaa ggtgcccagc    120
aagaaattca aggtgctggg caacaccgac cggcacagca tcaagaagaa cctgatcgga    180
gccctgctgt tcgacagcgg cgaaacagcc gaggccaccc ggctgaagag aaccgccaga    240
agaagataca ccagacggaa gaaccggatc tgctatctgc aagagatctt cagcaacgag    300
atggccaagg tggacgacag cttcttccac agactggaag agtccttcct ggtggaagag    360
gataagaagc acgagcggca ccccatcttc ggcaacatcg tggacgaggt ggcctaccac    420
gagaagtacc caccatcta ccacctgaga aagaaactgg tggacagcac cgacaaggcc    480
gacctgcggc tgatctatct ggccctggcc cacatgatca agttccgggg ccacttcctg    540
```

```
atcgagggcg acctgaaccc cgacaacagc gacgtggaca agctgttcat ccagctggtg      600
cagacctaca accagctgtt cgaggaaaac cccatcaacg ccagcggcgt ggacgccaag      660
gccatcctgt ctgccagact gagcaagagc agacggctgg aaaatctgat cgcccagctg      720
cccggcgaga agaagaatgg cctgttcggc aacctgattg ccctgagcct gggcctgacc      780
cccaacttca gagcaacttc gacctggcc gaggatgcca aactgcagct gagcaaggac      840
acctacgacg acgacctgga caacctgctg gcccagatcg cgaccagta cgccgacctg      900 tttctggccg ccaagaacct gtccgacgcc atcctgctga gcgacatcct gagagtgaac      960
accgagatca ccaaggcccc cctgagcgcc tctatgatca agatacga cgagcaccac     1020 caggacctga ccctgctgaa agctctcgtg cggcagcagc tgcctgagaa gtacaaagag     1080 atttcttcg accagagcaa gaacggctac gccggctaca ttgacggcgg agccagccag     1140
gaagagttct acaagttcat caagcccatc ctggaaaaga tggacggcac cgaggaactg     1200
ctcgtgaagc tgaacagaga ggacctgctg cggaagcagc ggaccttcga caacggcagc     1260
atcccccacc agatccacct gggagagctg cacgccattc tgcggcggca ggaagatttt     1320
tacccattcc tgaaggacaa ccgggaaaag atcgagaaga tcctgacctt ccgcatcccc     1380
tactacgtgg cccctctggc caggggaaac agcagattcg cctggatgac cagaaagagc     1440
gaggaaacca tcacccctg aacttcgag gaagtggtgg acaagggcgc ttccgcccag     1500
agcttcatcg agcggatgac caacttcgat aagaacctgc ccaacgagaa ggtgctgccc     1560
aagcacagcc tgctgtacga gtacttcacc gtgtataacg agctgaccaa agtgaaatac     1620
gtgaccgagg gaatgagaaa gcccgccttc ctgagcggcg agcagaaaaa ggccatcgtg     1680
gacctgctgt tcaagaccaa ccggaaagtg accgtgaagc agctgaaaga ggactacttc     1740
aagaaaatcg agtgcttcga ctccgtggaa atctccggcg tggaagatcg gttcaacgcc     1800
tccctgggca cataccacga tctgctgaaa attatcaagg acaaggactt cctggacaat     1860
gaggaaaacg aggacattct ggaagatatc gtgctgaccc tgacactgtt tgaggacaga     1920
gagatgatcg aggaacggct gaaaacctat gcccacctgt tcgacgacaa agtgatgaag     1980
cagctgaagc ggcggagata caccggctgg ggcaggctga gccggaagct gatcaacggc     2040
atccgggaca gcagtccgg caagacaatc ctggatttcc tgaagtccga cggcttcgcc     2100
aacagaaact tcatgcagct gatccacgac gacagcctga cctttaaaga ggacatccag     2160
aaagcccagg tgtccggcca gggcgatagc ctgcacgagc acattgccaa tctggccggc     2220
agccccgcca ttaagaaggg catcctgcag acagtgaagg tggtggacga gctcgtgaaa     2280
gtgatgggcc ggcacaagcc cgagaacatc gtgatcgaaa tggccagaga aaccagacc     2340 acccagaagg acagaagaa cagccgcgag agaatgaagc ggatcgaaga gggcatcaaa     2400
gagctgggca gccagatcct gaaagaacac cccgtggaaa acacccagct gcagaacgag     2460
aagctgtacc tgtactacct gcagaatggg cgggatatgt acgtggacca ggaactggac     2520
atcaaccggc tgtccgacta cgatgtggac gctatcgtgc ctcagagctt tctgaaggac     2580
gactccatcg acaacaaggt gctgaccaga agcgacaaga ccggggcaa gagcgacaac     2640 gtgcccteg aagaggtcgt gaagaagatg aagaactact ggcggcagct gctgaacgcc     2700
aagctgatta cccagagaaa gttcgacaat ctgaccaagg ccgagagagg cggcctgagc     2760
gaactggata aggccggctt catcaagaga cagctggtgg aaacccggca gatcacaaag     2820
cacgtggcac agatcctgga ctcccggatg aacactaagt acgacgagaa tgacaagctg     2880
```

| | |
|---|---|
| atccgggaag tgaaagtgat caccctgaag tccaagctgg tgtccgattt ccggaaggat | 2940 |
| ttccagtttt acaaagtgcg cgagatcaac aactaccacc acgcccacga cgcctacctg | 3000 |
| aacgccgtcg tgggaaccgc cctgatcaaa aagtaccota agctggaaag cgagttcgtg | 3060 |
| tacggcgact acaaggtgta cgacgtgcgg aagatgatcg ccaagagcga gcaggaaatc | 3120 |
| ggcaaggcta ccgccaagta cttcttctac agcaacatca tgaactttt caagaccgag | 3180 |
| attaccctgg ccaacggcga gatccggaag cggcctctga tcgagacaaa cggcgaaacc | 3240 |
| ggggagatcg tgtgggataa gggccgggat tttgccaccg tgcggaaagt gctgagcatg | 3300 |
| ccccaagtga atatcgtgaa aaagaccgag gtgcagacag gcggcttcag caaagagtct | 3360 |
| atcctgccca agaggaacag cgataagctg atcgccagaa agaaggactg ggaccctaag | 3420 |
| aagtacggcg cttcgacag ccccaccgtg gcctattctg tgctggtggt ggccaaagtg | 3480 |
| gaaagggca agtccaagaa actgaagagt gtgaagagc tgctggggat caccatcatg | 3540 |
| gaaagaagca gcttcgagaa gaatcccatc gactttctgg aagccaaggg ctacaaagaa | 3600 |
| gtgaaaaagg acctgatcat caagctgcct aagtactccc tgttcgagct ggaaaacggc | 3660 |
| cggaagagaa tgctggcctc tgccggcgaa ctgcagaagg gaaacgaact ggccctgccc | 3720 |
| tccaaatatg tgaacttcct gtacctggcc agccactatg agaagctgaa gggctccccc | 3780 |
| gaggataatg agcagaaaca gctgtttgtg aacagcaca agcactacct ggacgagatc | 3840 |
| atcgagcaga tcagcgagtt ctccaagaga gtgatcctgg ccgacgctaa tctggacaaa | 3900 |
| gtgctgtccg cctacaacaa gcaccgggat aagcccatca gagagcaggc cgagaatatc | 3960 |
| atccacctgt ttaccctgac caatctggga gcccctgccg ccttcaagta ctttgacacc | 4020 |
| accatcgacc ggaagaggta caccagcacc aaagaggtgc tggacgccac cctgatccac | 4080 |
| cagagcatca ccggcctgta cgagacacgg atcgacctgt ctcagctggg aggcgacagc | 4140 |
| gctggaggag gtggaagcgg aggaggagga agcggaggag gaggtagcgg acctaagaaa | 4200 |
| aagaggaagg tggcggccgc tggatccgga cgggctgacg cattggacga tttttgatctg | 4260 |
| gatatgctgg gaagtgacgc cctcgatgat tttgaccttg acatgcttgg ttcggatgcc | 4320 |
| cttgatgact ttgaccctcga catgctcggc agtgacgccc ttgatgattt cgacctggac | 4380 |
| atgctgatta ac | 4392 |

<210> SEQ ID NO 22
<211> LENGTH: 4743
<212> TYPE: DNA
<213> ORGANISM: Artificial Sequence
<220> FEATURE:
<223> OTHER INFORMATION: dCas9(D10A, H840A)-NLS-P65

<400> SEQUENCE: 22

| | |
|---|---|
| gacaagaagt acagcatcgg cctggccatc ggcaccaact ctgtgggctg ggccgtgatc | 60 |
| accgacgagt acaaggtgcc cagcaagaaa ttcaaggtgc tgggcaacac cgaccggcac | 120 |
| agcatcaaga gaacctgat cggagccctg ctgttcgaca cggcgaaac agccgaggcc | 180 |
| acccggctga agagaaccgc cagaagaaga tacaccagac ggaagaaccg gatctgctat | 240 |
| ctgcaagaga tcttcagcaa cgagatggcc aaggtggacg acagcttctt ccacagactg | 300 |
| gaagagtcct tcctggtgga agaggataag aagcacgagc ggcacccat cttcggcaac | 360 |
| atcgtggacg aggtggccta ccacgagaag taccccacca tctaccacct gagaagaaa | 420 |
| ctggtggaca gcaccgacaa ggccgacctg cggctgatct atctggccct ggcccacatg | 480 |
| atcaagttcc ggggccactt cctgatcgag ggcgacctga accccgacaa cagcgacgtg | 540 |

```
gacaagctgt tcatccagct ggtgcagacc tacaaccagc tgttcgagga aaacccatc    600 aacgccagcg gcgtggacgc caaggccatc ctgtctgcca gactgagcaa gagcagacgg   660
ctggaaaatc tgatcgccca gctgcccggc gagaagaaga atggcctgtt cggcaacctg   720
attgccctga gctgggcct gacccccaac ttcaagagca acttcgacct ggccgaggat    780
gccaaactgc agctgagcaa ggacacctac gacgacgacc tggacaacct gctggcccag   840
atcggcgacc agtacgccga cctgtttctg gccgccaaga acctgtccga cgccatcctg   900
ctgagcgaca tcctgagagt gaacaccgag atcaccaagg ccccctgag cgcctctatg    960 atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga tttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg cgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga agaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc   2280 gaaatggcca gagagaacca gaccacccag aagggacaga agaacagccg cgagagaatg   2340
aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggacgctatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga aaagttcga caatctgacc   2700 aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
```

```
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga atcggcaag gctaccgcca agtacttctt ctacagcaac    3120
atcatgaact ttttcaagac cgagattacc ctggccaacg gcgagatccg gaagcggcct    3180
ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga acagcgataa gctgatcgcc    3360
agaaagaagg actgggaccc taagaagtac ggcggcttcg acagcccac cgtggcctat    3420 tctgtgctgg tggtggccaa agtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtggaacag    3780 cacaagcact acctggacga gatcatcgag cagatcagcg agttctccaa gagagtgatc    3840
ctggccgacg ctaatctgga caaagtgctg tccgcctaca acaagcaccg ggataagccc    3900
atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggcga cagcgctgga ggaggtggaa gcggaggagg aggaagcgga    4140
ggaggaggta gcggacctaa gaaaaagagg aaggtggcgg ccgctggatc cccttcaggg    4200
cagatcagca accaggccct ggctctggcc cctagtcccg ctccagtgct ggcccagact    4260
atggtgccct ctagtgctat ggtgcctctg gcccagccac tgctccagc ccctgtgctg    4320 accccaggac cacccagtc actgagcgct ccagtgccca gtctacaca ggccggcgag    4380 gggactctga gtgaagctct gctgcacctg cagttcgacg ctgatgagga cctgggagct    4440
ctgctgggga acagcaccga tcccggagtg ttcacagatc tggcctccgt ggacaactct    4500
gagtttcagc agctgctgaa tcagggcgtg tccatgtctc atagtacagc cgaaccaatg    4560
ctgatggagt accccgaagc cattacccgg ctggtgaccg gcagccagcg gccccccgac    4620
cccgctccaa ctcccctggg aaccagcggc ctgcctaatg gctgtccgg agatgaagac    4680 ttctcaagca tcgctgatat ggacttagt gccctgctgt cacagatttc ctctagtggg    4740
cag                                                                 4743
```

<210> SEQ ID NO 23
<211> LENGTH: 645
<212> TYPE: DNA
<213> ORGANISM: Artificial Sequence
<220> FEATURE:
<223> OTHER INFORMATION: MS2-NLS-VP64

<400> SEQUENCE: 23

```
atggcttcaa actttactca gttcgtgctc gtggacaatg gtgggacagg ggatgtgaca      60
gtggctcctt ctaatttcgc taatgggtg gcagagtgga tcagtccaa ctcacggagc     120 caggcctaca aggtgacatg cagcgtcagg cagtctagtg cccagaagag aaagtatacc     180
```

```
atcaaggtgg aggtccccaa agtggctacc cagacagtgg gcggagtcga actgcctgtc      240
gccgcttgga ggtcctacct gaacatggag ctcactatcc aattttcgc  taccaattct      300 gactgtgaac tcatcgtgaa ggcaatgcag gggctcctca agacggtaa  tcctatccct      360 tccgccatcg ccgctaactc aggtatctac agcgctggag gaggtggaag cggaggagga      420
ggaagcggag gaggaggtag cggacctaag aaaagagga aggtggcggc cgctggatcc       480
ggacgggctg acgcattgga cgattttgat ctggatatgc tgggaagtga cgccctcgat      540
gattttgacc ttgacatgct tggttcggat gcccttgatg actttgacct cgacatgctc      600
ggcagtgacg cccttgatga tttcgacctg gacatgctga ttaac                     645

<210> SEQ ID NO 24
<211> LENGTH: 1032
<212> TYPE: DNA
<213> ORGANISM: Artificial Sequence
<220> FEATURE:
<223> OTHER INFORMATION: MS2-NLS-P65

<400> SEQUENCE: 24
atggcttcaa actttactca gttcgtgctc gtggacaatg gtgggacagg ggatgtgaca       60
gtggctcctt ctaatttcgc taatgggtg  gcagagtgga tcagctccaa ctcacggagc      120
caggcctaca aggtgacatg cagcgtcagg cagtctagtg cccagaagag aaagtatacc      180
atcaaggtgg aggtccccaa agtggctacc cagacagtgg gcggagtcga actgcctgtc      240
gccgcttgga ggtcctacct gaacatggag ctcactatcc aattttcgc  taccaattct      300 gactgtgaac tcatcgtgaa ggcaatgcag gggctcctca agacggtaa  tcctatccct      360 tccgccatcg ccgctaactc aggtatctac agcgctggag gaggtggaag cggaggagga      420
ggaagcggag gaggaggtag cggacctaag aaaagagga aggtggcggc cgctggatcc       480
ccttcagggc agatcagcaa ccaggccctg gctctggccc ctagctccgc tccagtgctg      540
gcccagacta tggtgccctc tagtgctatg gtgcctctgg cccagccacc tgctccagcc      600
cctgtgctga ccccaggacc accccagtca ctgagcgctc cagtgcccaa gtctacacag      660
gccggcgagg ggactctgag tgaagctctg ctgcacctgc agttcgacgc tgatgaggac      720 ctggagctc  tgctggggaa cagcaccgat cccggagtgt tcacagatct ggcctccgtg      780
gacaactctg agtttcagca gctgctgaat cagggcgtgt ccatgtctca gtacagcc       840 gaaccaatgc tgatggagta ccccgaagcc attacccggc tggtgaccgg cagccagcgg      900 cccccccgacc ccgctccaac tcccctggga accagcggcc tgcctaatgg gctgtccgga     960
gatgaagact ctctcaagcat cgctgatatg gactttagtg ccctgctgtc acagatttcc    1020
tctagtgggc ag                                                        1032

<210> SEQ ID NO 25
<211> LENGTH: 1419
<212> TYPE: DNA
<213> ORGANISM: Artificial Sequence
<220> FEATURE:
<223> OTHER INFORMATION: MS2-NLS-P65-HSF1

<400> SEQUENCE: 25
atggcttcaa actttactca gttcgtgctc gtggacaatg gtgggacagg ggatgtgaca       60
gtggctcctt ctaatttcgc taatgggtg  gcagagtgga tcagctccaa ctcacggagc      120
caggcctaca aggtgacatg cagcgtcagg cagtctagtg cccagaagag aaagtatacc      180
```

```
atcaaggtgg aggtccccaa agtggctacc cagacagtgg gcggagtcga actgcctgtc    240
gccgcttgga ggtcctacct gaacatggag ctcactatcc aattttcgc taccaattct     300 gactgtgaac tcatcgtgaa ggcaatgcag gggctcctca agacggtaa tcctatccct    360 tccgccatcg ccgctaactc aggtatctac agcgctggag gaggtggaag cggaggagga    420
ggaagcggag gaggaggtag cggacctaag aaaaagagga aggtggcggc cgctggatcc    480
ccttcagggc agatcagcaa ccaggccctg gctctggccc ctagctccgc tccagtgctg    540
gcccagacta tggtgccctc tagtgctatg gtgcctctgg cccagccacc tgctccagcc    600
cctgtgctga ccccaggacc accccagtca ctgagcgctc cagtgcccaa gtctacacag    660
gccggcgagg ggactctgag tgaagctctg ctgcacctgc agttcgacgc tgatgaggac    720
ctgggagctc tgctggggaa cagcaccgat cccggagtgt tcacagatct ggcctccgtg    780
gacaactctg agtttcagca gctgctgaat cagggcgtgt ccatgtctca tagtacagcc    840
gaaccaatgc tgatggagta ccccgaagcc attacccggc tggtgaccgg cagccagcgg    900
ccccccgacc ccgctccaac tcccctggga accagcggcc tgcctaatgg gctgtccgga    960
gatgaagact tctcaagcat cgctgatatg gactttagtg ccctgctgtc acagatttcc    1020
tctagtgggc agggaggagg tggaagcggc ttcagcgtgg acaccagtgc cctgctggac    1080
ctgttcagcc cctcggtgac cgtgcccgac atgagcctgc tgaccttga cagcagcctg    1140 gccagtatcc aagagctcct gtctccccag gagcccccca ggcctcccga ggcagagaac    1200
agcagcccgg attcagggaa gcagctggtg cactacacag cgcagccgct gttcctgctg    1260
gaccccggct ccgtgacac cgggagcaac gacctgccgg tgctgtttga gctgggagag    1320
ggctcctact tctccgaagg ggacggcttc gccgaggacc ccaccatctc cctgctgaca    1380
ggctcggagc tccccaaagc caaggacccc actgtctcc                          1419

<210> SEQ ID NO 26
<211> LENGTH: 1236
<212> TYPE: DNA
<213> ORGANISM: Artificial Sequence
<220> FEATURE:
<223> OTHER INFORMATION: MS2-NLS-P65-MyoD1

<400> SEQUENCE: 26
atggcttcaa actttactca gttcgtgctc gtggacaatg gtgggacagg ggatgtgaca     60
gtggctcctt ctaatttcgc taatggggtg gcagagtgga tcagctccaa ctcacggagc    120
caggcctaca aggtgacatg cagcgtcagg cagtctagtg cccagaagag aaagtatacc    180
atcaaggtgg aggtccccaa agtggctacc cagacagtgg gcggagtcga actgcctgtc    240
gccgcttgga ggtcctacct gaacatggag ctcactatcc aattttcgc taccaattct     300 gactgtgaac tcatcgtgaa ggcaatgcag gggctcctca agacggtaa tcctatccct    360 tccgccatcg ccgctaactc aggtatctac agcgctggag gaggtggaag cggaggagga    420
ggaagcggag gaggaggtag cggacctaag aaaaagagga aggtggcggc cgctggatcc    480
ccttcagggc agatcagcaa ccaggccctg gctctggccc ctagctccgc tccagtgctg    540
gcccagacta tggtgccctc tagtgctatg gtgcctctgg cccagccacc tgctccagcc    600
cctgtgctga ccccaggacc accccagtca ctgagcgctc cagtgcccaa gtctacacag    660
gccggcgagg ggactctgag tgaagctctg ctgcacctgc agttcgacgc tgatgaggac    720
ctgggagctc tgctggggaa cagcaccgat cccggagtgt tcacagatct ggcctccgtg    780
gacaactctg agtttcagca gctgctgaat cagggcgtgt ccatgtctca tagtacagcc    840
```

```
gaaccaatgc tgatggagta ccccgaagcc attacccggc tggtgaccgg cagccagcgg      900
ccccccgacc ccgctccaac tcccctggga accagcggcc tgcctaatgg gctgtccgga      960
gatgaagact tctcaagcat cgctgatatg gactttagtg ccctgctgtc acagatttcc     1020
tctagtgggc agggaggagg tggaagcatg gagcttcttt ctcctcctct gcgggatgtt     1080
gacctgactg cgcccgacgg ctctctttgc tccttcgcca caaccgacga cttctacgat     1140
gatccatgtt ttgacagccc cgatctcagg ttctttgagg atctcgatcc tagactgatg     1200
cacgtgggcg cactgctcaa acctgaggaa catagc                              1236

<210> SEQ ID NO 27
<211> LENGTH: 8
<212> TYPE: PRT
<213> ORGANISM: Artificial Sequence
<220> FEATURE:
<223> OTHER INFORMATION: SV40 NLS

<400> SEQUENCE: 27

Pro Pro Lys Lys Lys Arg Lys Val
1               5

<210> SEQ ID NO 28
<211> LENGTH: 34
<212> TYPE: DNA
<213> ORGANISM: Artificial Sequence
<220> FEATURE:
<223> OTHER INFORMATION: MS2 stem loop

<400> SEQUENCE: 28
ggccaacatg aggatcaccc atgtctgcag ggcc                                   34

<210> SEQ ID NO 29
<211> LENGTH: 34
<212> TYPE: DNA
<213> ORGANISM: Artificial Sequence
<220> FEATURE:
<223> OTHER INFORMATION: MS2 stem loop (variant)

<400> SEQUENCE: 29
ggccagcatg aggatcaccc atgcctgcag ggcc                                   34

<210> SEQ ID NO 30
<211> LENGTH: 25
<212> TYPE: DNA
<213> ORGANISM: Artificial Sequence
<220> FEATURE:
<223> OTHER INFORMATION: sgRNA1 sense primer

<400> SEQUENCE: 30
caccgggcat aaaggggcgc ggcgc                                             25

<210> SEQ ID NO 31
<211> LENGTH: 25
<212> TYPE: DNA
<213> ORGANISM: Artificial Sequence
<220> FEATURE:
<223> OTHER INFORMATION: sgRNA1 antisense primer

<400> SEQUENCE: 31
aaacgcgccg cgccccttta tgccc                                             25

<210> SEQ ID NO 32
<211> LENGTH: 25
```

<212> TYPE: DNA
<213> ORGANISM: Artificial Sequence
<220> FEATURE:
<223> OTHER INFORMATION: sgRNA2 sense primer

<400> SEQUENCE: 32
caccgcggcg gggcgcgggc ataaa                                              25

<210> SEQ ID NO 33
<211> LENGTH: 25
<212> TYPE: DNA
<213> ORGANISM: Artificial Sequence
<220> FEATURE:
<223> OTHER INFORMATION: sgRNA2 antisense primer

<400> SEQUENCE: 33
aaactttatg cccgcgcccc gccgc                                              25

<210> SEQ ID NO 34
<211> LENGTH: 25
<212> TYPE: DNA
<213> ORGANISM: Artificial Sequence
<220> FEATURE:
<223> OTHER INFORMATION: sgRNA3 sense primer

<400> SEQUENCE: 34
caccggtgcc tttctccgac gtccg                                              25

<210> SEQ ID NO 35
<211> LENGTH: 25
<212> TYPE: DNA
<213> ORGANISM: Artificial Sequence
<220> FEATURE:
<223> OTHER INFORMATION: sgRNA3 antisense primer

<400> SEQUENCE: 35
aaaccggacg tcggagaaag gcacc                                              25

<210> SEQ ID NO 36
<211> LENGTH: 25
<212> TYPE: DNA
<213> ORGANISM: Artificial Sequence
<220> FEATURE:
<223> OTHER INFORMATION: sgRNA4 sense primer

<400> SEQUENCE: 36
caccggaaac gtcctgcacg gctcc                                              25

<210> SEQ ID NO 37
<211> LENGTH: 25
<212> TYPE: DNA
<213> ORGANISM: Artificial Sequence
<220> FEATURE:
<223> OTHER INFORMATION: sgRNA4 antisense primer

<400> SEQUENCE: 37
aaacggagcc gtgcaggacg tttcc                                              25

<210> SEQ ID NO 38
<211> LENGTH: 37
<212> TYPE: DNA
<213> ORGANISM: Artificial Sequence
<220> FEATURE:
<223> OTHER INFORMATION: SV40 enhancer forward primer

<400> SEQUENCE: 38

```
aaatcgataa ggatccgatg gagcggagaa tgggcgg                              37
```

<210> SEQ ID NO 39
<211> LENGTH: 35
<212> TYPE: DNA
<213> ORGANISM: Artificial Sequence
<220> FEATURE:
<223> OTHER INFORMATION: SV40 enhancer reverse primer

<400> SEQUENCE: 39

```
atacgcaaac ggatccgctg tggaatgtgt gtcag                                35
```

<210> SEQ ID NO 40
<211> LENGTH: 37
<212> TYPE: DNA
<213> ORGANISM: Artificial Sequence
<220> FEATURE:
<223> OTHER INFORMATION: Forward primer for 2.2 kb KL promoter insert

<400> SEQUENCE: 40

```
ctcgctagcc tcgagatcta tagtgccaca tggtgac                              37
```

<210> SEQ ID NO 41
<211> LENGTH: 38
<212> TYPE: DNA
<213> ORGANISM: Artificial Sequence
<220> FEATURE:
<223> OTHER INFORMATION: Reverse primer for 2.2 kb KL promoter insert

<400> SEQUENCE: 41

```
agtatcacat ttccttcta gaagtgaaga ttggagtg                              38
```

<210> SEQ ID NO 42
<211> LENGTH: 23
<212> TYPE: DNA
<213> ORGANISM: Artificial Sequence
<220> FEATURE:
<223> OTHER INFORMATION: Forward primer for vector

<400> SEQUENCE: 42

```
gggaaatgtg atactccatg tag                                             23
```

<210> SEQ ID NO 43
<211> LENGTH: 25
<212> TYPE: DNA
<213> ORGANISM: Artificial Sequence
<220> FEATURE:
<223> OTHER INFORMATION: Reverse primer for vector

<400> SEQUENCE: 43

```
ctcgaggcta gcgagctcag gtacc                                           25
```

<210> SEQ ID NO 44
<211> LENGTH: 25
<212> TYPE: DNA
<213> ORGANISM: Artificial Sequence
<220> FEATURE:
<223> OTHER INFORMATION: gRNA pair 1 sense primer

<400> SEQUENCE: 44

```
caccggtctc actggcatct tgttg                                           25
```

<210> SEQ ID NO 45
<211> LENGTH: 25
<212> TYPE: DNA
<213> ORGANISM: Artificial Sequence

```
<220> FEATURE:
<223> OTHER INFORMATION: gRNA pair 1 antisense primer

<400> SEQUENCE: 45
aaaccaacaa gatgccagtg agacc                                           25

<210> SEQ ID NO 46
<211> LENGTH: 25
<212> TYPE: DNA
<213> ORGANISM: Artificial Sequence
<220> FEATURE:
<223> OTHER INFORMATION: gRNA pair 2 sense primer

<400> SEQUENCE: 46
caccgcaggg acacagggtt tagac                                           25

<210> SEQ ID NO 47
<211> LENGTH: 25
<212> TYPE: DNA
<213> ORGANISM: Artificial Sequence
<220> FEATURE:
<223> OTHER INFORMATION: gRNA pair 2 antisense primer

<400> SEQUENCE: 47
aaacgtctaa accctgtgtc cctgc                                           25

<210> SEQ ID NO 48
<211> LENGTH: 25
<212> TYPE: DNA
<213> ORGANISM: Artificial Sequence
<220> FEATURE:
<223> OTHER INFORMATION: pcDNA3.1 forward primer

<400> SEQUENCE: 48
ctcgagtcta gagggcccgc ggttc                                           25

<210> SEQ ID NO 49
<211> LENGTH: 30
<212> TYPE: DNA
<213> ORGANISM: Artificial Sequence
<220> FEATURE:
<223> OTHER INFORMATION: pcDNA3.1 reverse primer

<400> SEQUENCE: 49
aagcttcgta tatctggccc gtacatcgcg                                      30

<210> SEQ ID NO 50
<211> LENGTH: 39
<212> TYPE: DNA
<213> ORGANISM: Artificial Sequence
<220> FEATURE:
<223> OTHER INFORMATION: KL 2710 forward primer

<400> SEQUENCE: 50
agatatacga agcttcccac atactggatg gtatcaatc                            39

<210> SEQ ID NO 51
<211> LENGTH: 39
<212> TYPE: DNA
<213> ORGANISM: Artificial Sequence
<220> FEATURE:
<223> OTHER INFORMATION: KL 3700 reverse primer

<400> SEQUENCE: 51
agtagctccg cttccgacag gacctcaaaa atcatataa                            39
```

```
<210> SEQ ID NO 52
<211> LENGTH: 25
<212> TYPE: DNA
<213> ORGANISM: Artificial Sequence
<220> FEATURE:
<223> OTHER INFORMATION: P2A NLuc forward primer

<400> SEQUENCE: 52
ggaagcggag ctactaactt cagcc                                        25

<210> SEQ ID NO 53
<211> LENGTH: 24
<212> TYPE: DNA
<213> ORGANISM: Artificial Sequence
<220> FEATURE:
<223> OTHER INFORMATION: P2A NLuc reverse primer

<400> SEQUENCE: 53
ttagacgttg atgcgagctg aagc                                         24

<210> SEQ ID NO 54
<211> LENGTH: 39
<212> TYPE: DNA
<213> ORGANISM: Artificial Sequence
<220> FEATURE:
<223> OTHER INFORMATION: KL 3743 forward primer

<400> SEQUENCE: 54
cgcatcaacg tctaattgag ggccttgcac ataggaaac                         39

<210> SEQ ID NO 55
<211> LENGTH: 40
<212> TYPE: DNA
<213> ORGANISM: Artificial Sequence
<220> FEATURE:
<223> OTHER INFORMATION: KL 4978 reverse primer

<400> SEQUENCE: 55
ccctctagac tcgagattat gaaagaaggc aaaaagttgc                        40

<210> SEQ ID NO 56
<211> LENGTH: 25
<212> TYPE: DNA
<213> ORGANISM: Artificial Sequence
<220> FEATURE:
<223> OTHER INFORMATION: Klotho intron 4 forward primer

<400> SEQUENCE: 56
gtgttgtgtg caaaatacgt aataa                                        25

<210> SEQ ID NO 57
<211> LENGTH: 22
<212> TYPE: DNA
<213> ORGANISM: Artificial Sequence
<220> FEATURE:
<223> OTHER INFORMATION: NLuc reverse primer

<400> SEQUENCE: 57
tgacatggat gtcgatcttc ag                                           22

<210> SEQ ID NO 58
<211> LENGTH: 20
<212> TYPE: RNA
<213> ORGANISM: Artificial sequence
<220> FEATURE:
<223> OTHER INFORMATION: synthetic oligonucleotide
```

```
<400> SEQUENCE: 58
gugccuuucu ccgacguccg                                                       20

<210> SEQ ID NO 59
<211> LENGTH: 28
<212> TYPE: RNA
<213> ORGANISM: Artificial sequence
<220> FEATURE:
<223> OTHER INFORMATION: synthetic oligonucleotide

<400> SEQUENCE: 59
gugccuuucu ccgacguccg guuuuaga                                              28

<210> SEQ ID NO 60
<211> LENGTH: 15
<212> TYPE: RNA
<213> ORGANISM: Artificial sequence
<220> FEATURE:
<223> OTHER INFORMATION: synthetic oligonucleotide

<400> SEQUENCE: 60
aacaugagga ucacc                                                            15

<210> SEQ ID NO 61
<211> LENGTH: 33
<212> TYPE: RNA
<213> ORGANISM: Artificial sequence
<220> FEATURE:
<223> OTHER INFORMATION: synthetic oligonucleotide

<400> SEQUENCE: 61
caugucugca gggccuagca aguuaaaaua agg                                        33

<210> SEQ ID NO 62
<211> LENGTH: 22
<212> TYPE: RNA
<213> ORGANISM: Artificial sequence
<220> FEATURE:
<223> OTHER INFORMATION: synthetic oligonucleotide

<400> SEQUENCE: 62
cuaguccguu aucaacuugg cc                                                    22

<210> SEQ ID NO 63
<211> LENGTH: 40
<212> TYPE: RNA
<213> ORGANISM: Artificial sequence
<220> FEATURE:
<223> OTHER INFORMATION: synthetic oligonucleotide

<400> SEQUENCE: 63
caugucugca gggccaagug gcaccgaguc ggugcuuuuu                                 40
```

COMPOSITIONS AND METHODS FOR MODULATING GENE EXPRESSION

RELATED APPLICATIONS

This application claims the benefit of U.S. Provisional Application No. 62/595,410 filed Dec. 6, 2017; U.S. Provisional Application No. 62/617,328 filed Jan. 15, 2018; and U.S. Provisional Application No. 62/753,531 filed Oct. 31, 2018, all of which are incorporated herein in their entirety by reference.

GOVERNMENT SUPPORT

This invention was made with government support under Contract Nos. 5R44 AG053084 and R56 AG051638 awarded by the National Institute of Health. The government has certain rights in the invention.

FIELD OF THE DISCLOSURE

The present disclosure relates to compositions and methods for modulating gene expression and in particular to compositions and methods for increasing expression of Klotho.

INCORPORATION BY REFERENCE OF SEQUENCE LISTING

This application contains a Sequence Listing in computer readable form filename: 190349PCTUS_ST25; 319,136 bytes ASCII text file; created Jun. 8, 2023), which is incorporated herein by reference in its entirety and forms part of the disclosure.

BACKGROUND OF THE DISCLOSURE

Any discussion of the prior art throughout the specification should in no way be considered as an admission that such prior art is widely known or forms part of the common general knowledge in the field.

The single copy gene Klotho plays important roles in ageing, cognition, anti-oxidative stress, neurological protection and development, and kidney health. Klotho is a Type I transmembrane protein which is mainly expressed in the brain, kidney and reproductive organs (Masuda et al., 2005. *Mech. Ageing Dev.* 126(21): 1274-1283). It is also shed by proteolytic cleaving resulting in a soluble form that is detectable in serum and cerebrospinal fluid (CSF) (Bloch et al., 2009. *FEBS Lett.* 583(19): 3221-3224; Chen et al., 2007. *Proc. Natl Acad. Sci. USA.* 104(50): 19796-19801; Matsumura et al., 1998. *Biochem. Biophys. Res. Commun.* 242(3): 626-630). A third form of Klotho, found mainly in the brain, results from differential mRNA splicing and is secreted from the cell into the blood and CSF (Masso et al., 2015. *PLoS One.* 10(11): e0143623). Both the transmembrane and soluble forms of Klotho have important functions in many homeostatic processes.

Klotho promotes oligodendrocyte maturation, and it protects neurons from oxidative stress by increasing expression of antioxidant factors. It also induces re-myelination in vivo in the cuprizone-induced demyelination model of multiple sclerosis (Zeldich et al., 2015. *J. Mol. Neurosci.* 57(2): 185-196). Studies have shown that Klotho overexpression reduces cognitive deficits in a mouse model of Alzheimer's disease, and that it enhances cognition in humans and mice (Dubal et al., 2014. *Cell Rep.* 7(4): 1065-1076; Dubal et al., 2015. *Off. J. Socr. Neuroscience.* 35(6): 2358-2371).

Despite efforts to modulate the activity of Klotho, or the activity of factors regulated by Klotho, there remains a need for compositions and methods for modulating Klotho activity, and preferably for increasing Klotho activity in humans.

SUMMARY OF THE DISCLOSURE

In a first aspect, the present disclosure provides a method of increasing expression of a Klotho gene in a human cell the method comprising introducing into the cell: a CRISPR enzyme; and a guide RNA comprising a guide sequence that is substantially complementary to a target sequence within or near the Klotho gene, wherein the guide RNA associates with a transcriptional activation domain in the cell to thereby increase expression of the Klotho gene.

In certain examples, the method further comprises introducing into the cell an adapter protein capable of binding to the guide RNA wherein the adapter protein comprises or is attached to the transcriptional activation domain.

In some examples, the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. The adapter protein may bind to a tetra-loop and/or a stem loop 2 of the guide RNA.

The target sequence may be located within a region between the Klotho gene translation start site and 4000 nucleotides upstream of the Klotho gene translation start site.

The guide sequence may be substantially complementary to a nucleotide sequence set forth in SEQ ID NO. 9 or SEQ ID NO. 10.

The target sequence may be located within a region between 200 nucleotides and 4000 nucleotides upstream of the Klotho gene translation start site.

In certain examples, the guide sequence is substantially complementary to a nucleotide sequence set forth in SEQ ID NO. 11 or SEQ ID NO. 12.

The target sequence may be located within a region between 200 nucleotides and 300 nucleotides upstream of the Klotho gene translation start site. For example, the target sequence may be located within a region between 240 nucleotides and 300 nucleotides upstream of the Klotho gene translation start site.

In some examples, the guide sequence is substantially complementary to a nucleotide sequence set forth in SEQ ID NO. 13 or SEQ ID NO. 14.

In certain examples, the guide sequence is between 14 nucleotides and 25 nucleotides in length.

The guide sequence may comprise at least 14 contiguous nucleotides which are identical to a nucleotide sequence set forth in any one of SEQ ID NOs 1 to 4. In certain examples, the guide sequence comprises at least 14 contiguous nucleotides which are identical to a nucleotide sequence set forth in SEQ ID NO. 3 or SEQ ID NO. 4. The guide sequence may be at least 90% identical to a nucleotide sequence set forth in any one of SEQ ID NOs 1 to 4. The guide sequence may be at least 90% identical to a nucleotide sequence set forth in SEQ ID NO. 3 or SEQ ID NO. 4.

In certain examples, the guide sequence is selected from a nucleotide sequence set forth in any one of SEQ ID NOs 1 to 4. The guide sequence may be selected from a nucleotide sequence set forth in SEQ ID NO. 3 and SEQ ID NO. 4.

In certain examples, the guide RNA is at least 90% identical to a nucleotide sequence set forth in any one of SEQ ID NOs 5 to 8. The guide RNA may be at least 90% identical to a nucleotide sequence set forth in SEQ ID NO. 7 or SEQ ID NO. 8. In some examples, the guide RNA comprises a nucleotide sequence set forth in any one of SEQ ID NOs 5 to 8. The guide RNA may comprise a nucleotide sequence set forth in SEQ ID NO. 7 or SEQ ID NO. 8.

In certain examples, the guide RNA is a single-molecule guide RNA (sgRNA).

The guide RNA may be between about 100 nucleotides and 200 nucleotides in length.

In certain examples, the method comprises introducing into the cell more than one guide RNA. For example, the method may comprise introducing into the cell two guide RNAs, wherein each guide RNA is independently as defined herein.

In some examples, the transcriptional activation domain is selected from the group consisting of VP16, or a plurality thereof, VP64, VP160, p65, MyoD1, HSF1, RTA, TET3CD, p300 and SET7/9.

In some examples, the CRISPR enzyme comprises or is attached to a second transcriptional activation domain. The second transcriptional activation domain may be selected from the group consisting of VP16, or a plurality thereof, VP64, VP160, p65, MyoD1, HSF1, RTA, TET3CD, p300 and SET7/9.

In some examples, the CRISPR enzyme comprises a mutation which abolishes or reduces its nuclease activity. The CRISPR enzyme may be Cas9. For example, the CRISPR enzyme may be dead Cas9 (dCas9).

In certain examples, the cell is a neuronal cell or a kidney cell. The cell may be inside a human body.

In a second aspect, the present disclosure provides a method of increasing expression of a Klotho gene in a human cell the method comprising introducing into the cell: a guide RNA comprising a guide sequence that is substantially complementary to a target sequence within or near the Klotho gene; and a CRISPR enzyme, wherein the CRISPR enzyme comprises or is attached to a transcriptional activation domain.

In certain examples, the target sequence is located within a region between the Klotho gene translation start site and 4000 nucleotides upstream of the Klotho gene translation start site.

The guide sequence may be substantially complementary to a nucleotide sequence set forth in SEQ ID NO. 9 or SEQ ID NO. 10.

The target sequence may be located within a region between 200 nucleotides and 4000 nucleotides upstream of the Klotho gene translation start site.

The guide sequence may be substantially complementary to a nucleotide sequence set forth in SEQ ID NO. 11 or SEQ ID NO. 12.

In certain examples, the target sequence is located within a region between 200 nucleotides and 300 nucleotides upstream of the Klotho gene translation start site. For example, the target sequence may be located within a region between 240 nucleotides and 300 nucleotides upstream of the Klotho gene translation start site.

In some examples, the guide sequence is substantially complementary to a nucleotide sequence set forth in SEQ ID NO. 13 or SEQ ID NO. 14.

In some examples, the guide sequence is between 14 nucleotides and 25 nucleotides in length.

In some examples, the guide sequence comprises at least 14 contiguous nucleotides which are identical to a nucleotide sequence set forth in any one of SEQ ID NOs 1 to 4. The guide sequence may comprise at least 14 contiguous nucleotides which are identical to a nucleotide sequence set forth in SEQ ID NO. 3 or SEQ ID NO. 4.

In certain examples, the guide sequence is at least 90% identical to a nucleotide sequence set forth in any one of SEQ ID NOs 1 to 4. For example, the guide sequence may be at least 90% identical to a nucleotide sequence set forth in SEQ ID NO. 3 or SEQ ID NO. 4.

In some examples, the guide sequence is selected from a nucleotide sequence set forth in any one of SEQ ID NOs 1 to 4. For example, the guide sequence may be selected from a nucleotide sequence set forth in SEQ ID NO. 3 and SEQ ID NO. 4.

In some examples, the guide RNA is at least 90% identical to a nucleotide sequence set forth in any one of SEQ ID NOs 5 to 8. For example, the guide RNA may be at least 90% identical to a nucleotide sequence set forth in SEQ ID NO. 7 or SEQ ID NO. 8. In certain examples, the guide RNA comprises a nucleotide sequence set forth in any one of SEQ ID NOs 5 to 8. For example, the guide RNA may comprise a nucleotide sequence set forth in SEQ ID NO. 7 or SEQ ID NO. 8.

Preferably, the guide RNA is a single-molecule guide RNA (sgRNA).

The guide RNA may be between about 100 nucleotides and about 200 nucleotides in length.

In certain examples, the method comprises introducing into the cell more than one guide RNA. For example, the method may comprise introducing into the cell two guide RNAs, wherein each guide RNA is independently as defined herein.

In some examples, the transcriptional activation domain is selected from the group consisting of VP16, or a plurality thereof, VP64, VP160, p65, MyoD1, HSF1, RTA, TET3CD, p300 and SET7/9.

In some examples, the CRISPR enzyme comprises a mutation which abolishes or reduces its nuclease activity. The CRISPR enzyme may be Cas9. For example, the CRISPR enzyme may be dead Cas9 (dCas9).

In certain examples, the cell is a neuronal cell or a kidney cell. The cell may be inside a human body.

In a third aspect, the present disclosure provides a method of treating cancer in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In certain examples, the cancer is selected from the group consisting of colon cancer, prostate cancer, lung cancer, cervical cancer, pancreatic cancer, ovarian cancer and breast cancer.

In a fourth aspect, the present disclosure provides a method of treating a muscle disorder in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In certain examples, the muscle disorder is selected from the group consisting of muscle atrophy and muscular dystrophy such as duchene muscular dystrophy.

In a fifth aspect, the present disclosure provides a method of treating a kidney disorder in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In certain examples, the kidney disorder is selected from the group consisting of renal dysfunction, acute kidney injury and kidney disease such as chronic kidney disease.

In a sixth aspect, the present disclosure provides a method of enhancing cognition in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In an seventh aspect, the present disclosure provides a method of treating a neurological disorder in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In certain examples, the neurological disorder is selected from the group consisting of memory loss, stress, biopolar disorder, epilepsy, dementia, Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress and neurodegeneration.

In certain examples, the method further comprises administering to the subject an adapter protein capable of binding to the guide RNA wherein the adapter protein comprises or is attached to the transcriptional activation domain.

In some examples, the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. The adapter protein may bind to a tetra-loop and/or a stem loop 2 of the guide RNA.

The target sequence may be located within a region between the Klotho gene translation start site and 4000 nucleotides upstream of the Klotho gene translation start site.

The guide sequence may be substantially complementary to a nucleotide sequence set forth in SEQ ID NO. 9 or SEQ ID NO. 10.

The target sequence may be located within a region between 200 nucleotides and 4000 nucleotides upstream of the Klotho gene translation start site.

The guide sequence may be substantially complementary to a nucleotide sequence set forth in SEQ ID NO. 11 or SEQ ID NO. 12.

In some examples, the target sequence is located within a region between 200 nucleotides and 300 nucleotides upstream of the Klotho gene translation start site. For example, the target sequence may be located within a region between 240 nucleotides and 300 nucleotides upstream of the Klotho gene translation start site.

The guide sequence may be substantially complementary to a nucleotide sequence set forth in SEQ ID NO. 13 or SEQ ID NO. 14.

In certain examples, the guide sequence is between 14 nucleotides and 25 nucleotides in length.

In some examples, the guide sequence comprises at least 14 contiguous nucleotides which are identical to a nucleotide sequence set forth in any one of SEQ ID NOs 1 to 4. For example, the guide sequence may comprise at least 14 contiguous nucleotides which are identical to a nucleotide sequence set forth in SEQ ID NO. 3 or SEQ ID NO. 4. In some examples, the guide sequence is at least 90% identical to a nucleotide sequence set forth in any one of SEQ ID NOs 1 to 4. For example, the guide sequence may be at least 90% identical to a nucleotide sequence set forth in SEQ ID NO. 3 or SEQ ID NO. 4.

In some examples, the guide sequence is selected from a nucleotide sequence set forth in any one of SEQ ID NOs 1 to 4. For example, the guide sequence may be selected from a nucleotide sequence set forth in SEQ ID NO. 3 and SEQ ID NO. 4.

In some examples, the guide RNA is at least 90% identical to a nucleotide sequence set forth in any one of SEQ ID NOs 5 to 8. For example, the guide RNA may be at least 90% identical to a nucleotide sequence set forth in SEQ ID NO. 7 or SEQ ID NO. 8. In some examples, the guide RNA comprises a nucleotide sequence set forth in any one of SEQ ID NOs 5 to 8. For example, the guide RNA may comprise a nucleotide sequence set forth in SEQ ID NO. 7 or SEQ ID NO. 8.

Preferably, the guide RNA is a single-molecule guide RNA (sgRNA).

In certain examples, the guide RNA is between about 100 nucleotides and 200 nucleotides in length.

In certain examples, the method comprises introducing into the cell more than one guide RNA. For example, the method may comprise introducing into the cell two guide RNAs, wherein each guide RNA is independently as defined herein.

In some examples, the transcriptional activation domain is selected from the group consisting of VP16, or a plurality thereof, VP64, VP160, p65, MyoD1, HSF1, RTA, TET3CD, p300 and SET7/9.

In certain examples, the CRISPR enzyme comprises or is attached to a second transcriptional activation domain. The second transcriptional activation domain may be selected from the group consisting of VP16, or a plurality thereof, VP64, VP160, p65, MyoD1, HSF1, RTA, TET3CD, p300 and SET7/9.

In certain examples, the CRISPR enzyme comprises a mutation which abolishes or reduces its nuclease activity. The CRISPR enzyme may be Cas9. For example, the CRISPR enzyme may be dead Cas9 (dCas9).

In an eighth aspect, the present disclosure provides a method of treating cancer in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In certain examples, the cancer is selected from the group consisting of colon cancer, prostate cancer, lung cancer, cervical cancer, pancreatic cancer, ovarian cancer and breast cancer.

In a ninth aspect, the present disclosure provides a method of treating a muscle disorder in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In certain examples, the muscle disorder is selected from the group consisting of muscle atrophy and muscular dystrophy such as duchene muscular dystrophy.

In an tenth aspect, the present disclosure provides a method of treating a kidney disorder in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In certain examples, the kidney disorder is selected from the group consisting of renal dysfunction, acute kidney injury and kidney disease such as chronic kidney disease.

In a eleventh aspect, the present disclosure provides a method of enhancing cognition in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In a twelfth aspect, the present disclosure provides a method of treating a neurological disorder in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In some examples, the neurological disorder is selected from the group consisting of memory loss, stress, biopolar disorder, epilepsy, dementia, Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress and neurodegeneration.

In some examples, the target sequence is located within a region between the Klotho gene translation start site and 4000 nucleotides upstream of the Klotho gene translation start site.

The guide sequence may be substantially complementary to a nucleotide sequence set forth in SEQ ID NO. 9 or SEQ ID NO. 10.

The target sequence may be located within a region between 200 nucleotides and 4000 nucleotides upstream of the Klotho gene translation start site.

The guide sequence may be substantially complementary to a nucleotide sequence set forth in SEQ ID NO. 11 or SEQ ID NO. 12.

The target sequence may be located within a region between 200 nucleotides and 300 nucleotides upstream of the Klotho gene translation start site. For example, the target sequence may be located within a region between 240 nucleotides and 300 nucleotides upstream of the Klotho gene translation start site.

The guide sequence may be substantially complementary to a nucleotide sequence set forth in SEQ ID NO. 13 or SEQ ID NO. 14.

In certain examples, the guide sequence is between 14 nucleotides and 25 nucleotides in length.

In some examples, the guide sequence comprises at least 14 contiguous nucleotides which are identical to a nucleotide sequence set forth in any one of SEQ ID NOs 1 to 4. For example, the guide sequence may comprise at least 14 contiguous nucleotides which are identical to a nucleotide sequence set forth in SEQ ID NO. 3 or SEQ ID NO. 4.

In some examples, the guide sequence is at least 90% identical to a nucleotide sequence set forth in any one of SEQ ID NOs 1 to 4. For example, the guide sequence may be at least 90% identical to a nucleotide sequence set forth in SEQ ID NO. 3 or SEQ ID NO. 4.

In some examples, the guide sequence is selected from a nucleotide sequence set forth in any one of SEQ ID NOs 1 to 4. For example, the guide sequence may be selected from a nucleotide sequence set forth in SEQ ID NO. 3 and SEQ ID NO. 4.

In some examples, the guide RNA is at least 90% identical to a nucleotide sequence set forth in any one of SEQ ID NOs 5 to 8. For example, the guide RNA may be at least 90% identical to a nucleotide sequence set forth in SEQ ID NO. 7 or SEQ ID NO. 8.

In some examples, the guide RNA comprises a nucleotide sequence set forth in any one of SEQ ID NOs 5 to 8. For example, the guide RNA may comprise a nucleotide sequence set forth in SEQ ID NO. 7 or SEQ ID NO. 8.

Preferably, the guide RNA is a single-molecule guide RNA (sgRNA).

The guide RNA may be between about 100 nucleotides and about 200 nucleotides in length.

In certain examples, the method comprises introducing into the cell more than one guide RNA. For example, the method may comprise introducing into the cell two guide RNAs, wherein each guide RNA is independently as defined herein.

In some examples, the transcriptional activation domain is selected from the group consisting of VP16, or a plurality thereof, VP64, VP160, p65, MyoD1, HSF1, RTA, TET3CD, p300 and SET7/9.

In some examples, the CRISPR enzyme comprises a mutation which abolishes or reduces its nuclease activity. The CRISPR enzyme may be Cas9. For example, the CRISPR enzyme may be dead Cas9 (dCas9).

In a thirteenth aspect, the present disclosure provides a guide RNA comprising a guide sequence wherein the guide sequence is substantially complementary to a target sequence within or near a human Klotho gene.

The guide RNA may further comprise at least one protein binding sequence for binding to an adapter protein. The protein binding sequence may comprise an aptamer.

In certain examples, the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

In some examples, the guide RNA comprises two protein binding sequences.

In some examples, the target sequence is located within a region between the Klotho gene translation start site and 4000 nucleotides upstream of the Klotho gene translation start site.

The guide sequence may be substantially complementary to a nucleotide sequence set forth in SEQ ID NO. 9 or SEQ ID NO. 10.

The target sequence may be located within a region between 200 nucleotides and 4000 nucleotides upstream of the Klotho gene translation start site.

The guide sequence may be substantially complementary to a nucleotide sequence set forth in SEQ ID NO. 11 or SEQ ID NO. 12.

In some examples, the target sequence is located within a region between 200 nucleotides and 300 nucleotides upstream of the Klotho gene translation start site. For example, the target sequence may be located within a region between 240 nucleotides and 300 nucleotides upstream of the Klotho gene translation start site.

In some examples, the guide sequence is substantially complementary to a nucleotide sequence set forth in SEQ ID NO. 13 or SEQ ID NO. 14.

The guide sequence may be between 14 nucleotides and 25 nucleotides in length.

In some examples, the guide sequence comprises at least 14 contiguous nucleotides which are identical to a nucleotide sequence set forth in any one of SEQ ID NOs 1 to 4. For example, the guide sequence may comprise at least 14 contiguous nucleotides which are identical to a nucleotide sequence set forth in SEQ ID NO. 3 or SEQ ID NO. 4.

In some examples, the guide sequence is at least 90% identical to a nucleotide sequence set forth in any one of SEQ ID NOs 1 to 4. For example, the guide sequence may be at least 90% identical to a nucleotide sequence set forth in SEQ ID NO. 3 or SEQ ID NO. 4.

In some examples, the guide sequence is selected from a nucleotide sequence set forth in any one of SEQ ID NOs 1 to 4. For example, the guide sequence may be selected from a nucleotide sequence set forth in SEQ ID NO. 3 and SEQ ID NO. 4.

In some examples, the guide RNA is at least 90% identical to a nucleotide sequence set forth in any one of SEQ ID NOs 5 to 8. For example, the guide RNA may be at least 90% identical to a nucleotide sequence set forth in SEQ ID NO. 7 or SEQ ID NO. 8.

In some examples, the guide RNA comprises a nucleotide sequence set forth in any one of SEQ ID NOs 5 to 8. For example, the guide RNA may comprise a nucleotide sequence set forth in SEQ ID NO. 7 or SEQ ID NO. 8.

Preferably, the guide RNA is a single-molecule guide RNA (sgRNA).

In certain examples, the guide RNA is between about 100 nucleotides and 200 nucleotides in length.

In a fourteenth aspect, the present disclosure provides an isolated or recombinant nucleic acid molecule encoding the guide RNA of the thirteenth aspect.

In a fifteenth aspect, the present disclosure provides a vector encoding the guide RNA of the thirteenth aspect.

The vector may be an adeno-associated viral (AAV) vector, an adenoviral vector (AdV) or a lentiviral (LV) vector.

In certain examples, the vector further encodes a CRISPR enzyme, an adapter protein or a transcriptional activation domain.

The CRISPR enzyme may comprise a mutation which abolishes or reduces its nuclease activity. In certain examples, the CRISPR enzyme is Cas9. For example, the CRISPR enzyme may be dead Cas9 (dCas9).

In certain examples, the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

In certain examples, the transcriptional activation domain is selected from the group consisting of VP16, or a plurality thereof, VP64, VP160, p65, MyoD1, HSF1, RTA, TET3CD, p300 and SET7/9.

In a sixteenth aspect, the present disclosure provides a ribonucleoprotein complex comprising: a CRISPR enzyme; and a guide RNA comprising a guide sequence that is substantially complementary to a target sequence within or near a human Klotho gene, wherein the guide RNA comprises at least one protein binding sequence for binding to an adapter protein.

The protein binding sequence may comprise an aptamer.

In some examples, the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

In some examples, the guide RNA comprises two protein binding sequences.

The target sequence may be located within a region between the Klotho gene translation start site and 4000 nucleotides upstream of the Klotho gene translation start site.

The guide sequence may be substantially complementary to a nucleotide sequence set forth in SEQ ID NO. 9 or SEQ ID NO. 10.

In some examples, the target sequence is located within a region between 200 nucleotides and 4000 nucleotides upstream of the Klotho gene translation start site.

In some examples, the guide sequence is substantially complementary to a nucleotide sequence set forth in SEQ ID NO. 11 or SEQ ID NO. 12.

In some examples, the target sequence is located within a region between 200 nucleotides and 300 nucleotides upstream of the Klotho gene translation start site. For example the target sequence may be located within a region between 240 nucleotides and 300 nucleotides upstream of the Klotho gene translation start site.

In some examples, the guide sequence is substantially complementary to a nucleotide sequence set forth in SEQ ID NO. 13 or SEQ ID NO. 14.

In some examples, the guide sequence is between 14 nucleotides and 25 nucleotides in length.

In some examples, the guide sequence comprises at least 14 contiguous nucleotides which are identical to a nucleotide sequence set forth in any one of SEQ ID NOs 1 to 4.

In some examples, the guide sequence comprises at least 14 contiguous nucleotides which are identical to a nucleotide sequence set forth in SEQ ID NO. 3 or SEQ ID NO. 4.

In some examples, the guide sequence is at least 90% identical to a nucleotide sequence set forth in any one of SEQ ID NOs 1 to 4. For example, the guide sequence may be at least 90% identical to a nucleotide sequence set forth in SEQ ID NO. 3 or SEQ ID NO. 4.

In some examples, the guide sequence is selected from a nucleotide sequence set forth in any one of SEQ ID NOs 1 to 4. For example, the guide sequence may be selected from a nucleotide sequence set forth in SEQ ID NO. 3 and SEQ ID NO. 4.

In some examples, the guide RNA is at least 90% identical to a nucleotide sequence set forth in any one of SEQ ID NOs 5 to 8. For example, the guide RNA may be at least 90% identical to a nucleotide sequence set forth in SEQ ID NO. 7 or SEQ ID NO. 8.

In some examples, the guide RNA comprises a nucleotide sequence set forth in any one of SEQ ID NOs 5 to 8. For example, the guide RNA may comprise a nucleotide sequence set forth in SEQ ID NO. 7 or SEQ ID NO. 8.

In some examples, the guide RNA is a single-molecule guide RNA (sgRNA).

In some examples, the guide RNA is between about 100 nucleotides and 200 nucleotides in length.

In some examples, the guide RNA is bound to the adapter protein.

In some examples, the adapter protein comprises or is attached to a transcriptional activation domain. The transcriptional activation domain may be selected from the group consisting of VP16, or a plurality thereof, VP64, VP160, p65, MyoD1, HSF1, RTA, TET3CD, p300 and SET7/9.

In some examples, the CRISPR enzyme comprises a mutation which abolishes or reduces its nuclease activity.

In some examples, the CRISPR enzyme is Cas9. For example, the CRISPR enzyme may be dCas9.

In a seventeenth aspect, the present disclosure provides a ribonucleoprotein complex comprising: a guide RNA comprising a guide sequence that is substantially complementary to a target sequence within or near a human Klotho gene; and a CRISPR enzyme, wherein the CRISPR enzyme comprises or is attached to a transcriptional activation domain.

In some examples, the target sequence is located within a region between the Klotho gene translation start site and 4000 nucleotides upstream of the Klotho gene translation start site.

In some examples, the guide sequence is substantially complementary to a nucleotide sequence set forth in SEQ ID NO. 9 or SEQ ID NO. 10.

In some examples, the target sequence is located within a region between 200 nucleotides and 4000 nucleotides upstream of the Klotho gene translation start site.

In some examples, the guide sequence is substantially complementary to a nucleotide sequence set forth in SEQ ID NO. 11 or SEQ ID NO. 12.

In some examples, the target sequence is located within a region between 200 nucleotides and 300 nucleotides upstream of the Klotho gene translation start site. For example, the target sequence may be located within a region between 240 nucleotides and 300 nucleotides upstream of the Klotho gene translation start site.

In some examples, the guide sequence is substantially complementary to a nucleotide sequence set forth in SEQ ID NO. 13 or SEQ ID NO. 14.

In some examples, the guide sequence is between 14 nucleotides and 25 nucleotides in length.

In some examples, the guide sequence comprises at least 14 contiguous nucleotides which are identical to a nucleotide sequence set forth in any one of SEQ ID NOs 1 to 4. For example, the guide sequence may comprise at least 14 contiguous nucleotides which are identical to a nucleotide sequence set forth in SEQ ID NO. 3 or SEQ ID NO. 4.

In some examples, the guide sequence is at least 90% identical to a nucleotide sequence set forth in any one of SEQ ID NOs 1 to 4. For example, the guide sequence may be at least 90% identical to a nucleotide sequence set forth in SEQ ID NO. 3 or SEQ ID NO. 4.

In some examples, the guide sequence is selected from a nucleotide sequence set forth in any one of SEQ ID NOs 1 to 4. For example, the guide sequence may be selected from a nucleotide sequence set forth in SEQ ID NO. 3 and SEQ ID NO. 4.

In some examples, the guide RNA is at least 90% identical to a nucleotide sequence set forth in any one of SEQ ID NOs 5 to 8. For example, the guide RNA may be at least 90% identical to a nucleotide sequence set forth in SEQ ID NO. 7 or SEQ ID NO. 8.

In some examples, the guide RNA comprises a nucleotide sequence set forth in any one of SEQ ID NOs 5 to 8. For example, the guide RNA may comprise a nucleotide sequence set forth in SEQ ID NO. 7 or SEQ ID NO. 8.

In some examples, the guide RNA is a single-molecule guide RNA (sgRNA).

In some examples, the guide RNA is between about 100 nucleotides and about 200 nucleotides in length.

In some examples, the transcriptional activation domain is selected from the group consisting of VP16, or a plurality thereof, VP64, VP160, p65, MyoD1, HSF1, RTA, TET3CD, p300 and SET7/9.

In some examples, the CRISPR enzyme comprises a mutation which abolishes or reduces its nuclease activity.

In some examples, the CRISPR enzyme is Cas9. For example, the CRISPR enzyme may be dCas9.

DETAILED DESCRIPTION

Definitions

Figure 1:
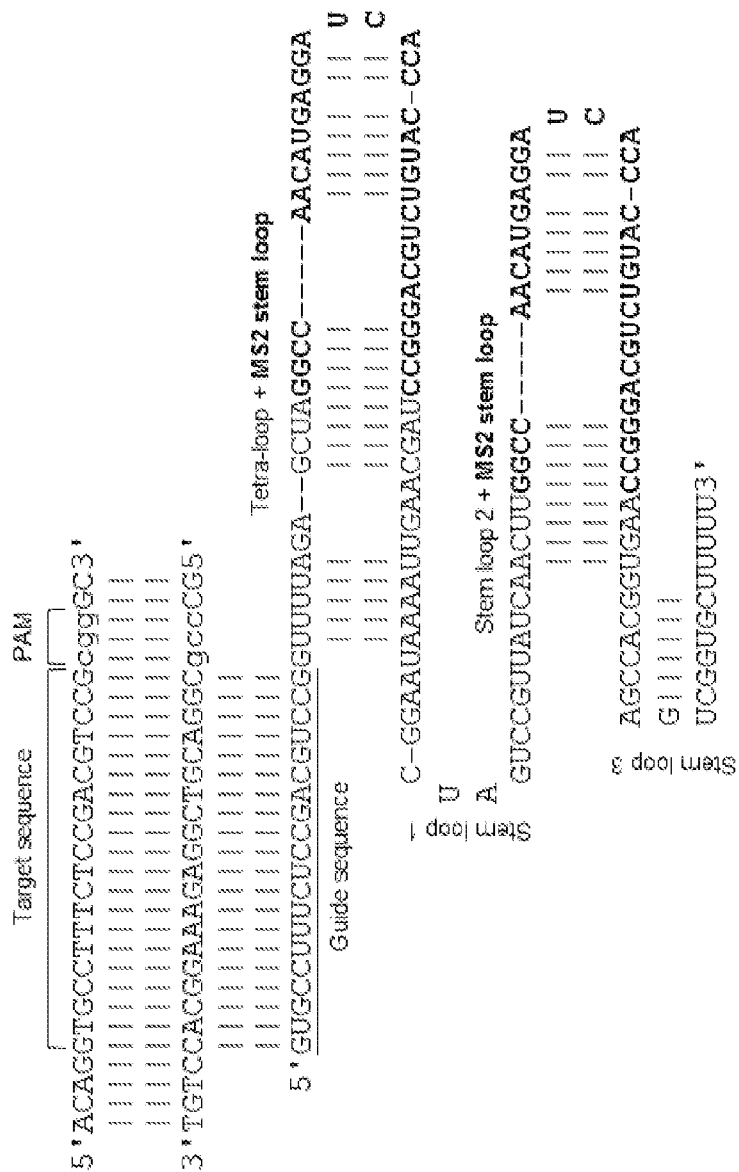
FIG. 1. Representation of sgRNA3 (SEQ ID NO: 7) hybridised to a target sequence in the Klotho promoter.

In the context of this specification, the terms "a" and "an" are used herein to refer to one or to more than one (ie, to at least one) of the grammatical object of the article. By way of example, "an element" means one element or more than one element.

The term "about" is understood to refer to a range of +/−10%, preferably +/−5% or +/−1% or, more preferably, +/−0.1%.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and preferably together in the same formulation.

The terms "comprise", "comprises", "comprised" or "comprising", "including" or "having" and the like in the present specification and claims are used in an inclusive sense, ie, to specify the presence of the stated features but not preclude the presence of additional or further features.

The term "substantially complementary" when used to describe a first nucleotide sequence in relation to a second nucleotide sequence, refers to the ability of an oligonucleotide or polynucleotide comprising the first nucleotide sequence to hybridize to, and form a duplex structure with, an oligonucleotide or polynucleotide comprising the second nucleotide sequence. It will be understood that the sequence of a nucleic acid need not be 100% complementary to that of its target. Conditions under which hybridisation occurs may be stringent, such as 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can also apply. Substantial complementarity allows the relevant function of the nucleic acid to proceed, eg, guide RNA hybridisation and CRISPR-mediated gene activation. The skilled person will be able to determine the set of conditions most appropriate for a test of complementarity of two sequences in accordance with the ultimate application of the hybridized nucleotides.

The term "identity" refers to a relationship between the sequences of two or more polypeptide molecules or two or more nucleic acid molecules, as determined by aligning and comparing the sequences. The percent identity between two sequences is a function of the number of identical positions shared by the sequences when the sequences are optimally aligned (ie, % homology=# of identical positions/total # of positions ×100), with optimal alignment determined taking into account the number of gaps, and the length of each gap, which need to be introduced for optimal alignment of the two sequences. The comparison of sequences and determination of percent identity between two sequences can be accomplished using a mathematical algorithm.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4: 11-17 (1989)) which has been incorporated into the ALIGN program, using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The term "isolated" as used herein refers to material that is substantially or essentially free from components that normally accompany it in its native state. For example, an "isolated polynucleotide" as used herein refers to a polynucleotide which has been purified from the sequences which flank it in a naturally-occurring state, eg, a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell, ie, it is not associated with in vivo substances.

The term "pharmaceutically acceptable" as used herein refers to substances that do not cause substantial adverse allergic or immunological reactions when administered to a subject. A "pharmaceutically acceptable carrier" includes, but is not limited to, solvents, coatings, dispersion agents, wetting agents, isotonic and absorption delaying agents and disintegrants.

The term "polynucleotide variant" refers to polynucleotides displaying substantial sequence identity with a reference polynucleotide sequence or polynucleotides that hybridize with a reference sequence under stringent conditions. The term also encompasses polynucleotides that are distinguished from a reference polynucleotide by the addition, deletion or substitution of at least one nucleotide. Accordingly, the term "polynucleotide variant" includes polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The term "polynucleotide variant" also includes naturally occurring allelic variants. The terms "peptide variant" and "polypeptide variant" and the like refer to peptides and polypeptides that are distinguished from a reference peptide or polypeptide by the addition, deletion or substitution of at least one amino acid residue. In certain examples, a peptide or polypeptide variant is distinguished from a reference peptide or polypeptide by one or more substitutions, which may be conservative or non-conservative. In certain examples, the peptide or polypeptide variant comprises conservative substitutions and, in this regard, it is well understood in the art that some amino acids may be changed to others with broadly similar properties without changing the nature of the activity of the peptide or polypeptide. Peptide and polypeptide variants also encompass peptides and polypeptides in which one or more amino acids have been added or deleted, or replaced with different amino acid residues.

"Prevention" includes reduction of risk, incidence and/or severity of a condition or disorder. The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

The term "recombinant polypeptide" as used herein refers to a polypeptide made using recombinant techniques, ie, through the expression of a recombinant polynucleotide.

A "therapeutically effective amount" is at least the minimum concentration or amount required to effect a measurable improvement of a particular disease or condition. A therapeutically effective amount herein may vary according to factors such as the disease state, age, sex, and weight of the patient. A therapeutically effective amount is also one in which any toxic or detrimental effects are outweighed by the therapeutically beneficial effects.

Klotho

Human Klotho plays important regulatory and protective roles in, inter alia, memory loss, stress, synaptic plasticity, biopolar disorder, epilepsy, Alzheimer's disease, Parkinson's disease, multiple sclerosis, myelin-related disease, neurogenic decline, neurodegeneration and kidney dysfunction (Vo et al., 2018. *Brain Plast.* 3: 183-194).

The human Klotho gene is located on chromosome 13 and comprises five exons. The Klotho protein primarily exists in one of three forms. Transmembrane Klotho is an approximately 130 kDa, glycosylated, Type I transmembrane protein. The transmembrane Klotho can be shed from the cell surface by ADAM10/17 metalloproteinases into a soluble form that is detectable in serum and cerebrospinal fluid (CSF) (Bloch et al., 2009. *FEBS Lett.* 583(19): 3221-3224; Chen et al., 2007. *Proc. Natl Acad. Sci. USA.* 104(50): 19796-19801; Matsumura et al., 1998. *Biochem. Biophys. Res. Commun.* 242(3): 626-630). A third, secreted form of Klotho is generated by alternative splicing of exon 3 to produce a 70 kDa protein which is detectable in blood and CSF (Masso et al., 2015. *PLoS One.* 10(11): e0143623). Both the transmembrane and soluble forms of Klotho have important functions in many homeostatic processes.

The present disclosure relates to methods and compositions for modulating Klotho expression. Table 1 lists various Klotho sequences relevant to the present disclosure. However, those skilled in the art will understand that several different Klotho alleles exist among humans, and all of those alleles are envisaged by the present disclosure. Skilled persons will also understand that greater levels of sequence variation may exist in genomic regions which do not directly encode amino acids.

TABLE 1

| SEQ ID NO. | Description |
|---|---|
| 9 | 4,000 nt genomic region extending upstream of Klotho translation start site (−4,000 to +1) (sense) |
| 10 | 4,000 nt genomic region extending upstream of Klotho translation start site (−4,000 to +1) (antisense) |
| 11 | Genomic region between 200 nt and 4,000 nt upstream of Klotho translation start site (−4,000 to −200) (sense) |
| 12 | Genomic region between 200 nt and 4,000 nt upstream of Klotho translation start site (−4,000 to −200) (antisense) |
| 13 | Genomic region between 200 nt and 300 nt upstream of Klotho translation start site (−300 to −200) (sense) |
| 14 | Genomic region between 200 nt and 300 nt upstream of Klotho translation start site (−300 to −200) (antisense) |
| 15 | Klotho coding sequence |
| 16 | Klotho mRNA sequence |
| 17 | Genomic sequence of Klotho from translation start site to translation stop site (sense) |
| 18 | Genomic sequence of Klotho from translation start site to translation stop site (antisense) |
| 19 | Genomic region extending from 4,000 nt upstream of Klotho translation start site to Klotho translation stop site (sense) |
| 20 | Genomic region extending from 4,000 nt upstream of Klotho translation start site to Klotho translation stop site (antisense) |

Genome Editing

Genome editing generally refers to the process of modifying the nucleotide sequence of a genome in a precise or pre-determined manner. The genome of an organism may be edited using site-directed nucleases to cut DNA at precise target locations, thereby creating single-strand or double-strand DNA breaks. In some instances, the DNA breaks are repaired by natural, endogenous cellular processes, such as homology-directed repair (HDR) and non-homologous end joining (NHEJ). NHEJ directly joins the DNA ends resulting from a double-strand break, sometimes with the loss or addition of a nucleotide sequence. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism, referred to as microhomology-mediated end joining (MMEJ), or "Alternative NHEJ", is similar to NHEJ in that small deletions and insertions can occur at the cleavage site. MMEJ can make use of homologous sequences of a few base pairs flanking the DNA break site to drive a more favored DNA end joining repair outcome. In some instances, it may be possible to predict likely repair outcomes based on analysis of potential microhomologies at the site of the DNA break.

A CRISPR (Clustered Regularly Interspaced Short Palindromic Repeats) genomic locus can be found in the genomes of many prokaryotes. In prokaryotes, the CRISPR locus encodes products that function as a type of immune system to help defend against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary structures (e.g., hairpins) and/or comprise unstructured single-stranded sequences. The repeats usually occur in clusters and frequently diverge between species. The repeats are regularly interspaced with unique intervening sequences referred to as "spacers" resulting in a repeat-spacer-repeat locus architecture. The spacers (sometimes referred to as "guide sequences") are identical to, or have high homology with, foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence may be located at the 5' or 3' end of the crRNA.

A CRISPR locus also comprises polynucleotide sequences encoding CRISPR-associated (Cas) genes. Cas genes encode endonucleases involved in the biogenesis and the interference stages of crRNA function in prokaryotes. Some Cas genes comprise homologous secondary and/or tertiary structures.

Type II CRISPR Systems crRNA biogenesis in a Type II CRISPR system in nature requires a trans-activating CRISPR RNA (tracrRNA). The tracrRNA can be modified by endogenous RNaseIII, before hybridizing to a crRNA repeat in the pre-crRNA array. Endogenous RNaseIII can be recruited to cleave the pre-crRNA. Cleaved crRNAs can be subjected by exoribonuclease trimming to produce the mature crRNA form (e.g., 5' trimming). The tracrRNA can remain hybridized to the crRNA, and the tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid can activate Cas9 for targeted nucleic acid cleavage. The region of DNA targeted by a Type II CRISPR system includes a protospacer adjacent motif (PAM). In nature, the PAM facilitates binding of a CRISPR enzyme (e.g., Cas9) to the target nucleic acid.

Type II systems (also referred to as Nmeni or CASS4) are further subdivided into Type II-A (CASS4) and II-B (CASS4a). Jinek et al., *Science*, 337(6096):816-821 (2012) showed that the CRISPR/Cas9 system is useful for RNA-programmable genome editing, and international patent application publication number WO2013/176772 provides numerous examples and applications of the CRISPR/Cas endonuclease system for site-specific gene editing.

Type V CRISPR Systems

Type V CRISPR systems differ from Type II systems in many respects. For example, Cpf1 is a single RNA-guided endonuclease that, in contrast to Type II systems, lacks tracrRNA. Cpf1-associated CRISPR arrays can be processed into mature crRNAs without the requirement of an additional trans-activating tracrRNA. The Type V CRISPR array can be processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems can start with 20-24 nucleotides of spacer sequence followed by about 22 nucleotides of direct repeat. Also, Cpf1 can utilize a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point adjacent the PAM. In addition, in contrast to Type II systems, Cpf1 cleaves DNA via a staggered DNA double-stranded break with a 4- or 5-nucleotide 5' overhang. Type II systems on the other hand cleave via a blunt double-stranded break. Similar to Type II systems, Cpf1 contains a predicted RuvC-like endonuclease domain, but lacks a second HNH endonuclease domain, which is in contrast to Type II systems.

CRISPR Enzymes

CRISPR enzymes are enzymes which can bind to a guide RNA and to a complementary target DNA sequence. CRISPR enzymes may have nuclease activity or they may be rendered nuclease inactive, for example, by mutation of their nuclease domain(s). The term "CRISPR enzyme" will be used herein in reference to both nuclease active and nuclease inactive enzymes.

Naturally-occurring wild-type Cas9 enzymes comprise two nuclease domains, a HNH nuclease domain and a RuvC domain. Herein, the term "Cas9" refers to both naturally occurring and recombinant Cas9. Cas9 enzymes contemplated herein can comprise a HNH or HNH-like nuclease domain, and/or a RuvC or RuvC-like nuclease domain. The Cas9 enzymes may also lack nuclease activity, or have reduced nuclease activity, due to mutations or modifications within one or both of its nuclease domains. HNH or HNH-like domains comprise a McrA-like fold. HNH or HNH-like domains comprise two antiparallel β-strands and an α-helix. HNH or HNH-like domains also comprise a metal binding site (e.g., a divalent cation binding site). HNH or HNH-like domains can cleave one strand of a target nucleic acid (e.g., the complementary strand of the crRNA targeted strand). RuvC or RuvC-like domains comprise an RNaseH or RNaseH-like fold. The RNaseH domain comprises 5 β-strands surrounded by a plurality of α-helices. RuvC/RNaseH or RuvC/RNaseH-like domains comprise a metal binding site (e.g., a divalent cation binding site). RuvC/RNaseH or RuvC/RNaseH-like domains can cleave one strand of a target nucleic acid (e.g., the non-complementary strand of a double-stranded target DNA).

Non-limiting examples of Cas9 orthologs from other bacterial strains include but are not limited to, Cas proteins identified in *Acaryochloris marina* MBIC11017; *Acetohalobium arabaticum* DSM 5501; *Acidithiobacillus caldus*; *Acidithiobacillus ferrooxidans* ATCC 23270; *Alicyclobacillus acidocaldarius* LAA1; *Alicyclobacillus acidocaldarius* subsp. *acidocaldarius* DSM 446; *Allochromatium vinosum* DSM 180; *Ammonifex degensii* KC4; *Anabaena variabilis* ATCC 29413; *Arthrospira maxima* CS-328; *Arthrospira platensis* str. *Paraca*; *Arthrospira* sp. PCC 8005; *Bacillus pseudomycoides* DSM 12442; *Bacillus selenitireducens* MLS10; *Burkholderiales bacterium* 1_1_47; *Caldicelulosiruptor becscii* DSM 6725; *Candidatus Desulforudis audaxviator* MP104C; *Caldicellulosiruptor hydrothermalis*_108; *Clostridium phage* c-st; *Clostridium botulinum* A3 str. *Loch Maree*; *Clostridium botulinum* Ba4 str. 657; *Clostridium difficile* QCD-63q42; *Crocosphaera watsonii* WH 8501; *Cyanothece* sp. ATCC 51142; *Cyanothece* sp. CCY0110; *Cyanothece* sp. PCC 7424; *Cyanothece* sp. PCC 7822; *Exiguobacterium sibiricum* 255-15; *Finegoldia magna* ATCC 29328; *Ktedonobacter racemifer* DSM 44963; *Lactobacillus delbrueckii* subsp. *bulgaricus* PB2003/044-T3-4; *Lactobacillus salivarius* ATCC 11741; *Listeria innocua*; *Lyngbya* sp. PCC 8106; *Marinobacter* sp. ELB17; *Methanohalobium evestigatum* Z-7303; *Microcystis phage* Ma-LM M01; *Microcystis aeruginosa* NI ES-843; *Microscilla marina* ATCC 23134; *Microcoleus chthonoplastes* PCC 7420; *Neisseria meningitidis*; *Nitrosococcus halophilus* Nc4; *Nocardiopsis dassonvillei* subsp. *dassonvillei* DSM 43111; *Nodularia spumigena* CCY9414; *Nostoc* sp. PCC 7120; *Oscillatoria* sp. PCC 6506; *Pelotomaculum thermopropionicum* SI; *Petrotoga mobilis* SJ95; *Polaromonas naphthalenivorans* CJ2; *Polaromonas* sp. JS666; *Pseudoalteromonas haloplanktis* TAC125; *Streptomyces pristinaespiralis* ATCC 25486; *Streptomyces pristinaespiralis* ATCC 25486; *Streptococcus thermophilus*; *Streptomyces viridochromogenes* DSM 40736; *Streptosporangium roseum* DSM 43021; *Synechococcus* sp. PCC 7335; and *Thermosipho africanus* TCF52B (Chylinski et al., *RNA Biol.*, 2013; 10(5): 726-737.

Other examples of Cas enzymes include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 and homologues thereof.

CRISPR enzymes, if nuclease-active, can introduce double-strand breaks or single-strand breaks in genomic DNA. The double-strand break can stimulate a cell's endogenous DNA-repair pathways (e.g., HDR, NHEJ or MMEJ). In some cases, homologous recombination can be used to insert an exogenous polynucleotide sequence at the target cleavage site. An exogenous polynucleotide sequence may be termed a donor polynucleotide (or donor or donor sequence). The donor polynucleotide can be an exogenous polynucleotide sequence, i.e., a sequence that does not naturally occur at the target nucleic acid cleavage site.

The CRISPR enzyme may comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99% or 100% amino acid sequence identity to a wild-type exemplary CRISPR enzyme [e.g., Cas9 from *S. pyogenes*, US2014/0068797 Sequence ID No. 8 or Sapranauskas et al., *Nucleic Acids Res*, 39(21): 9275-9282 (2011)], and various other site-directed polypeptides. The CRISPR enzyme may comprise one or more mutations that reduces or abolishes its nucleic acid-cleaving activity. For example, the CRISPR enzyme may comprise a mutation such that it can induce a single-stranded break (SSB) on a target nucleic acid (e.g., by cutting only one of the sugar-phosphate backbones of a double-strand target nucleic acid). The mutation may result in less than 90%, less than 80%, less than 70%, less than 60%, less than 50%, less than 40%, less than 30%, less than 20%, less than 10%, less than 5%, or less than 1% of the nucleic acid-cleaving activity in one or more of the nucleic acid-cleaving domains of the wild-type CRISPR enzyme (e.g., Cas9 from *S. pyogenes*, supra). The mutation may result in one or more of the nucleic acid-cleaving domains retaining the ability to cleave the complementary strand of the target nucleic acid, but reducing its ability to cleave the non-complementary strand of the target nucleic acid. The mutation may result in one or more of the nucleic acid-cleaving domains retaining the ability to cleave the non-complementary strand of the target nucleic acid, but reducing its ability to cleave the complementary strand of the target nucleic acid. For example, residues in the wild-type exemplary *S. pyogenes* Cas9 polypeptide, such as Asp10, His840, Asn854 and Asn856 may be mutated to inactivate one or more of the nucleic acid-cleaving domains. Non-limiting examples of mutations include D10A, H840A, N854A or N856A. N580A in Sa Cas9 may also be employed. Mutations other than alanine substitutions may also be suitable. Site-directed polypeptides that comprise one substantially inactive nuclease domain are referred to as "nickases".

Nickase variants of CRISPR enzymes, for example Cas9, can be used to increase the specificity of CRISPR-mediated genome editing. Wild type Cas9 is typically guided by a single guide RNA designed to hybridize with an approximately 20 nucleotide target sequence. However, several mismatches can be tolerated between the guide sequence and the target locus, effectively reducing the length of required homology in the target site to, for example, as little as 13 nt of homology. This can increase the potential for binding and double-strand nucleic acid cleavage by the CRISPR/Cas9 complex elsewhere in the target genome—also known as "off-target" cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—bind in close proximity and on opposite strands of the target nucleic acid. This requirement essentially doubles the minimum length of homology needed for the double-strand break to occur, thereby reducing the likelihood that a double-strand cleavage event will occur elsewhere in the genome.

A Cas9 whose nuclease activity is abolished is often referred to as a "dead Cas9" or "dCas9". A combination of D10A and H840A mutations or D10A and N863A mutations may render a Cas9 catalytically inactive. In some examples, the CRISPR enzyme of the present disclosure is dCas9.

A high fidelity CRISPR/Cas9 variant with reduced off-targeting was described by Kleinstiver et al. 2016. Nature.

529 (7587): 490-495. In certain examples, the CRISPR enzyme is a high fidelity Cas9 or a high fidelity dead Cas9 such as a Cas9 comprising mutations D10A, H840A, Y450A, N497A, R661A, Q695A and Q926A.

In certain examples, the CRISPR enzyme is truncated, for example to reduce the size of the CRISPR enzyme. In some examples, the CRISPR enzyme is a chimer, comprising amino acid stretches from more than one distinct CRISPR enzyme.

In addition to, or instead of, mutations which reduce or abolish the nuclease activity of a CRISPR enzyme, guide RNAs may be designed in such a way as to enable hybridisation between the guide sequence and the target sequence, but without enabling nuclease activity of the CRISPR enzyme. For example, a guide sequence which is 14 nucleotides or 15 nucleotides in length may be capable of guiding Cas9 to a target locus without enabling cleavage of the target locus, even if the Cas9 comprises functional nuclease domains. Such guide RNAs may be referred to as "dead guide RNAs" (dgRNAs). In certain examples, the guide RNA of the present disclosure is a dead guide RNA. The guide RNA may comprise a guide sequence that is no greater than 15 nucleotides in length, or no greater than 14 nucleotides in length.

The CRISPR enzyme may also be modified to comprise, or associate with, a transcriptional activation domain. For example, the CRISPR enzyme may be fused to a transcriptional activation domain as a single polypeptide. In such examples, a flexible linker may fuse the CRISPR enzyme to the transcriptional activation domain. For example, GlySer linkers (eg, GGGGS) may be used. They may be repeats of 3 ((GGGGS)$_3$), 6, 9, 12 or more, to provide suitable lengths as desired. The linker may also be rigid such as an Ala (GluAlaAlaAlaLys)Ala linker. Alternatively, the CRISPR enzyme may bind to a separate protein which comprises a transcriptional activation domain. The transcriptional activation domain may enhance transcription of nearby genes, for example, by recruiting transcription factors and or chromatin remodelling complexes. Indeed, the transcriptional activation domain may itself contribute to chromatin remodelling. Suitable transcriptional activation domains may include VP16, or a plurality thereof, VP64, VP160, p65, MyoD1, HSF1, RTA, SET7/9 as well as domains from chromatin-remodelling enzymes such as DNA demethylases and histone acetyltransferases. For example, members of the ten-eleven translocation (TET) family of zinc finger proteins catalyze the oxidation of methylated cytosine residues which leads to the replaced of methylated cytosine residues with naked cytosines and ultimately an increase in transcriptional activity. In certain examples, the transcriptional activation domain of the present disclosure is a TET catalytic domain (CD) such as the catalytic domain of TET1, TET2 or TET3. In some examples, the transcriptional activation domain is an acetyltransferase such as p300.

A CRISPR enzyme such as Cas9, and preferably dCas9, may comprise or associate with a transcriptional activation domain in many different ways. For example, dCas9-VP64 comprises dCas9 and four copies of the VP16 transcriptional activation domain fused to the C-terminus of the dCas9. dCas9-VPR comprises dCas9 fused to the activation domains VP64, p65 and RTA, with each activation domain optionally separated by a short amino acid linker, thereby resulting in six transcriptional activation domains fused to the C-terminus of dCas9. Suntag comprises a dCas9 and a chain of 10 peptide epitopes called GCN4 fused repetitively to the C-terminus of the dCas9. Single chain antibodies with specificity to the GCN4 epitope and fused to VP64 can then be co-administered (eg, co-expressed) with the dCas9 fusion. P300 is the catalytic core of the human acetyltransferase p300 protein directly fused to dCas9. VP160 comprises 10 repeats of VP16 fused to the C-terminus of dCas9. VP64-dCas9-BFP-VP64 is dCas9 with VP64 fused to the N-terminus and BFP-VP64 fused to the C-terminus resulting in eight transcriptional activation domains. Vectors encoding such fusions are commercially available, for example, from Addgene.

In certain examples, the present disclosure provides a method of increasing expression of a Klotho gene in a human cell the method comprising introducing into the cell: a single-molecule guide RNA comprising a guide sequence that is substantially complementary to a nucleotide sequence set forth in SEQ ID NO. 9 or SEQ ID NO. 10, and preferably to a nucleotide sequence set forth in SEQ ID NO. 11 or SEQ ID NO. 12; and a CRISPR enzyme, wherein the CRISPR enzyme comprises or is attached to a transcriptional activation domain. In some examples, the present disclosure provides a method of increasing expression of a Klotho gene in a human cell the method comprising introducing into the cell: a single-molecule guide RNA comprising a guide sequence that is substantially complementary to a target sequence located within a region between 200 nucleotides and 300 nucleotides upstream of the Klotho gene translation start site; and a CRISPR enzyme, wherein the CRISPR enzyme comprises or is attached to a transcriptional activation domain. In some examples, the present disclosure provides a method of increasing expression of a Klotho gene in a human cell the method comprising introducing into the cell: a single-molecule guide RNA comprising a guide sequence that is substantially complementary to a nucleotide sequence set forth in SEQ ID NO. 13 or SEQ ID NO. 14; and a CRISPR enzyme, wherein the CRISPR enzyme comprises or is attached to a transcriptional activation domain. In some examples, the present disclosure provides a method of increasing expression of a Klotho gene in a human cell the method comprising introducing into the cell: a single-molecule guide RNA comprising a guide sequence that is at least 90% identical to a nucleotide sequence set forth in any one of SEQ ID NOs 1 to 4, such as to a nucleotide sequence set forth in SEQ ID NO. 3 or SEQ ID NO. 4; and a CRISPR enzyme, wherein the CRISPR enzyme comprises or is attached to a transcriptional activation domain. In some examples, the present disclosure provides a method of increasing expression of a Klotho gene in a human cell the method comprising introducing into the cell: a single-molecule guide RNA comprising a guide sequence that is substantially complementary to a nucleotide sequence set forth in SEQ ID NO. 13 or SEQ ID NO. 14; and a CRISPR enzyme, wherein the CRISPR enzyme comprises or is attached to a transcriptional activation domain, wherein the transcriptional activation domain is selected from the group consisting of VP16, or a plurality thereof, VP64, VP160, p65, MyoD1, HSF1, RTA, TET3CD, p300 and SET7/9. In some examples, the present disclosure provides a method of increasing expression of a Klotho gene in a human cell the method comprising introducing into the cell: a single-molecule guide RNA comprising a guide sequence that is substantially complementary to a target sequence located within a region between 200 nucleotides and 300 nucleotides upstream of the Klotho gene translation start site; and a CRISPR enzyme, wherein the CRISPR enzyme is fused to VP64, and wherein the CRISPR enzyme is dead Cas9 (dCas9). In some examples, the present disclosure provides a method of increasing expression of a Klotho gene in a human cell the method comprising introducing into the cell: a single-molecule guide RNA comprising a guide sequence that is substantially complementary to a target sequence located within a region between 200 nucleotides and 300 nucleotides upstream of the Klotho gene translation start site; and a CRISPR enzyme, wherein the CRISPR enzyme is attached to VP64 via a GCN4 fusion, and wherein the CRISPR enzyme is dead Cas9 (dCas9). In some examples, the present disclosure provides a method of increasing expression of a Klotho gene in a human cell the method comprising introducing into the cell: a single-molecule guide RNA comprising a guide sequence that is substantially complementary to a target sequence located within a region between 200 nucleotides and 300 nucleotides upstream of the Klotho gene translation start site; and a CRISPR enzyme, wherein the CRISPR enzyme is fused to VP64, p65 and RTA, and wherein the CRISPR enzyme is dead Cas9 (dCas9).

Table 2 provides exemplary sequences of a dCas9 fused to an NLS and a transcriptional activation domain.

TABLE 2

| SEQ | Description | Sequence |
|---|---|---|
| 21 | NLS-dCas9 (D10A, H840A)-NLS-VP64 dCas9 underlined NLS lowercase VP64 highlighted | ATGAGCcccaagaagaagagaaaggtgGAGGCCAGCGACAAGAAGTACAGCATCGGCCTGGCCATCGGCA<br>CCAACTCTGTGGGCTGGGCCGTGATCACCGACGAGTACAAGGTGCCCAGCAAGAAATTCAAGGTGCTGGG<br>CAACACCGACCGGCACAGCATCAAGAAGAACCTGATCGGAGCCCTGCTGTTCGACAGCGGCGAAACAGCC<br>GAGGCCACCCGGCTGAAGAGAACCGCCAGAAGAAGATACACCAGACGGAAGAACCGGATCTGCTATCTGC<br>AAGAGATCTTCAGCAACGAGATGGCCAAGGTGGACGACAGCTTCTTCCACAGACTGGAAGAGTCCTTCCT<br>GGTGGAAGAGGATAAGAAGCACGAGCGGCACCCCATCTTCGGCAACATCGTGGACGAGGTGGCCTACCAC<br>GAGAAGTACCCCACCATCTACCACCTGAGAAAGAAACTGGTGGACAGCACCGACAAGGCCGACCTGCGGC<br>TGATCTATCTGGCCCTGGCCCACATGATCAAGTTCCGGGGCCACTTCCTGATCGAGGGCGACCTGAACCC<br>CGACAACAGCGACGTGGACAAGCTGTTCATCCAGCTGGTGCAGACCTACAACCAGCTGTTCGAGGAAAAC<br>CCCATCAACGCCAGCGGCGTGGACGCCAAGGCCATCCTGTCTGCCAGACTGAGCAAGAGCAGACGGCTGG<br>AAAATCTGATCGCCCAGCTGCCCGGCGAGAAGAAGAATGGCCTGTTCGGCAACCTGATTGCCCTGAGCCT<br>GGGCCTGACCCCCAACTTCAAGAGCAACTTCGACCTGGCCGAGGATGCCAAACTGCAGCTGAGCAAGGAC<br>ACCTACGACGACGACCTGGACAACCTGCTGGCCCAGATCGGCGACCAGTACGCCGACCTGTTTCTGGCCG<br>CCAAGAACCTGTCCGACGCCATCCTGCTGAGCGACATCCTGAGAGTGAACACCGAGATCACCAAGGCCCC<br>CCTGAGCGCCTCTATGATCAAGAGATACGACGAGCACCACCAGGACCTGACCCTGCTGAAAGCTCTCGTG<br>CGGCAGCAGCTGCCTGAGAAGTACAAAGAGATTTTCTTCGACCAGAGCAAGAACGGCTACGCCGGCTACA<br>TTGACGGCGGAGCCAGCCAGGAAGAGTTCTACAAGTTCATCAAGCCCATCCTGGAAAAGATGGACGGCAC<br>CGAGGAACTGCTCGTGAAGCTGAACAGAGAGGACCTGCTGCGGAAGCAGCGGACCTTCGACAACGGCAGC<br>ATCCCCCACCAGATCCACCTGGGAGAGCTGCACGCCATTCTGCGGCGGCAGGAAGATTTTTACCCATTCC<br>TGAAGGACAACCGGGAAAAGATCGAGAAGATCCTGACCTTCCGCATCCCCTACTACGTGGGCCCTCTGGC<br>CAGGGGAAACAGCAGATTCGCCTGGATGACCAGAAAGAGCGAGGAAACCATCACCCCCTGGAACTTCGAG<br>GAAGTGGTGGACAAGGGCGCTTCCGCCCAGAGCTTCATCGAGCGGATGACCAACTTCGATAAGAACCTGC<br>CCAACGAGAAGGTGCTGCCCAAGCACAGCCTGCTGTACGAGTACTTCACCGTGTATAACGAGCTGACCAA<br>AGTGAAATACGTGACCGAGGGAATGAGAAAGCCCGCCTTCCTGAGCGGCGAGCAGAAAAAGGCCATCGTG<br>GACCTGCTGTTCAAGACCAACCGGAAAGTGACCGTGAAGCAGCTGAAAGAGGACTACTTCAAGAAAATCG<br>AGTGCTTCGACTCCGTGGAAATCTCCGGCGTGGAAGATCGGTTCAACGCCTCCCTGGGCACATACCACGA<br>TCTGCTGAAAATTATCAAGGACAAGGACTTCCTGGACAATGAGGAAAACGAGGACATTCTGGAAGATATC<br>GTGCTGACCCTGACACTGTTTGAGGACAGAGAGATGATCGAGGAACGGCTGAAAACCTATGCCCACCTGT<br>TCGACGACAAAGTGATGAAGCAGCTGAAGCGGCGGAGATACACCGGCTGGGGCAGGCTGAGCCGGAAGCT<br>GATCAACGGCATCCGGGACAAGCAGTCCGGCAAGACAATCCTGGATTTCCTGAAGTCCGACGGCTTCGCC<br>AACAGAAACTTCATGCAGCTGATCCACGACGACAGCCTGACCTTTAAAGAGGACATCCAGAAAGCCCAGG<br>TGTCCGGCCAGGGCGATAGCCTGCACGAGCACATTGCCAATCTGGCCGGCAGCCCCGCCATTAAPAAGGG<br>CATCCTGCAGACAGTGAAGGTGGTGGACGAGCTCGTGAAAGTGATGGGCCGGCACAAGCCCGAGAACATC<br>GTGATCGAAATGGCCAGAGAGAACCAGACCACCCAGAAGGGACAGAAGAACAGCCGCGAGAGAATGAAGC<br>GGATCGAAGAGGGCATCAAAGAGCTGGGCAGCCAGATCCTGAAAGAACACCCCGTGGAAAACACCCAGCT<br>GCAGAACGAGAAGCTGTACCTGTACTACCTGCAGAATGGGCGGGATATGTACGTGGACCAGGAACTGGAC<br>ATCAACCGGCTGTCCGACTACGATGTGGACCATATCGTGCCTCAGAGCTTTCTGAAGGACGACTCCATCG<br>ACAACAAGGTGCTGACCAGAAGCGACAAGAACCGGGGCAAGAGCGACAACGTGCCCTCCGAAGAGGTCGT<br>GAAGAAGATGAAGAACTACTGGCGGCAGCTGCTGAACGCCAAGCTGATTACCCAGAGAAAGTTCGACAAT<br>CTGACCAAGGCCGAGAGAGGCGGCCTGAGCGAACTGGATAAGGCCGGCTTCATCAAGAGACAGCTGGTGG<br>AAACCCGGCAGATCACAAAGCACGTGGCACAGATCCTGGACTCCCGGATGAACACTAAGTACGACGAGAA<br>TGACAAGCTGATCCGGGAAGTGAAAGTGATCACCCTGAAGTCCAAGCTGGTGTCCGATTTCCGGAAGGAT<br>TTCCAGTTTTACAAAGTGCGCGAGATCAACAACTACCACCACGCCCACGACGCCTACCTGAACGCCGTCG<br>TGGGAACCGCCCTGATCAAAAAGTACCCTAAGCTGGAAAGCGAGTTCGTGTACGGCGACTACAAGGTGTA<br>CGACGTGCGGAAGATGATCGCCAAGAGCGAGCAGGAAATCGGCAAGGCTACCGCCAAGTACTTCTTCTAC<br>AGCAACATCATGAACTTTTTCAAGACCGAGATTACCCTGGCCAACGGCGAGATCCGGAAGCGGCCTCTGA<br>TCGAGACAAACGGCGAAACCGGGGAGATCGTGTGGGATAAGGGCCGGGATTTTGCCACCGTGCGGAAAGT<br>GCTGAGCATGCCCCAAGTGAATATCGTGAAAAAGACCGAGGTGCAGACAGGCGGCTTCAGCAAAGAGTCT<br>ATCCTGCCCAAGAGGAACAGCGATAAGCTGATCGCCAGAAAGAAGGACTGGGACCCTAAGAAGTACGGCG<br>GCTTCGACAGCCCCACCGTGGCCTATTCTGTGCTGGTGGTGGCCAAAGTGGAAAAGGGCAAGTCCAAGAA<br>ACTGAAGAGTGTGAAAGAGCTGCTGGGGATCACCATCATGGAAAGAAGCAGCTTCGAGAAGAATCCCATC<br>GACTTTCTGGAAGCCAAGGGCTACAAAGAGGTGAAAAAGGACCTGATCATCAAGCTGCCTAAGTACTCCC<br>TGTTCGAGCTGGAAAACGGCCGGAAGAGAATGCTGGCCTCTGCCGGCGAACTGCAGAAGGGAAACGAACT<br>GGCCCTGCCCTCCAAATATGTGAACTTCCTGTACCTGGCCAGCCACTATGAGAAGCTGAAGGGCTCCCCC<br>GAGGATAATGAGCAGAAACAGCTGTTTGTGGAACAGCACAAGCACTACCTGGACGAGATCATCGAGCAGA<br>TCAGCGAGTTCTCCAAGAGAGTGATCCTGGCCGACGCTAATCTGGACAAAGTGCTGTCCGCCTACAACAA<br>GCACCGGGATAAGCCCATCAGAGAGCAGGCCGAGAATATCATCCACCTGTTTACCCTGACCAATCTGGGA<br>GCCCCTGCCGCCTTCAAGTACTTTGACACCACCATCGACCGGAAGAGGTACACCAGCACCAAAGAGGTGC<br>TGGACGCCACCCTGATCCACCAGAGCATCACCGGCCTGTACGAGACACGGATCGACCTGTCTCAGCTGGG<br>AGGCGACAGCGCTGGAGGAGGTGGAAGCGGAGGAGGAGGAAGCGGAGGAGGAGGTAGCggacctaagaaa<br>aagaggaaggtggcggccgctGGATCC<mark>GGACGGGCTGACGCATTGGACGATTTGATCTGGATATGCTGG<br>GAAGTGACGCCCTCGATGATTTTGAGCCTTGACATGCTTGGTTCGGATGCCCTTGATGACTTTGACCTCGA<br>CATGCTCGGCAGTGACGCCCTTGATGATTTCGACCTGGACATGCTGATTAAC</mark> |

TABLE 2-continued

| SEQ | Description | Sequence |
|---|---|---|
| 22 | dCas9 (D10A, H840A)-NLS-p-65 dCas9 underlined NLS lowercase p65 highlighted | GACAAGAAGTACAGCATCGGCCTGGCCATCGGCACCAACTCTGTGGGCTGGGCCGTGATCACCGACGAGT<br>ACAAGGTGCCCAGCAAGAAATTCAAGGTGCTGGGCAACACCGACCGGCACAGCATCAAGAAGAACCTGAT<br>CGGAGCCCTGCTGTTCGACAGCGGCGAAACAGCCGAGGCCACCCGGCTGAAGAGAACCGCCAGAAGAAGA<br>TACACCAGACGGAAGAACCGGATCTGCTATCTGCAAGAGATCTTCAGCAACGAGATGGCCAAGGTGGACG<br>ACAGCTTCTTCCACAGACTGGAAGAGTCCTTCCTGGTGGAAGAGGATAAGAAGCACGAGCGGCACCCCAT<br>CTTCGGCAACATCGTGGACGAGGTGGCCTACCACGAGAAGTACCCCACCATCTACCACCTGAGAAAGAAA<br>CTGGTGGACAGCACCGACAAGGCCGACCTGCGGCTGATCTATCTGGCCCTGGCCCACATGATCAAGTTCC<br>GGGGCCACTTCCTGATCGAGGGCGACCTGAACCCCGACAACAGCGACGTGGACAAGCTGTTCATCCAGCT<br>GGTGCAGACCTACAACCAGCTGTTCGAGGAAAACCCCATCAACGCCAGCGGCGTGGACGCCAAGGCCATC<br>CTGTCTGCCAGACTGAGCAAGAGCAGACGGCTGGAAAATCTGATCGCCCAGCTGCCCGGCGAGAAGAAGA<br>ATGGCCTGTTCGGCAACCTGATTGCCCTGAGCCTGGGCCTGACCCCCAACTTCAAGAGCAACTTCGACCT<br>GGCCGAGGATGCCAAACTGCAGCTGAGCAAGGACACCTACGACGACGACCTGGACAACCTGCTGGCCCAG<br>ATCGGCGACCAGTACGCCGACCTGTTTCTGGCCGCCAAGAACCTGTCCGACGCCATCCTGCTGAGCGACA<br>TCCTGAGAGTGAACACCGAGATCACCAAGGCCCCCCTGAGCGCCTCTATGATCAAGAGATACGACGAGCA<br>CCACCAGGACCTGACCCTGCTGAAAGCTCTCGTGCGGCAGCAGCTGCCTGAGAAGTACAAAGAGATTTTC<br>TTCGACCAGAGCAAGAACGGCTACGCCGGCTACATTGACGGCGGAGCCAGCCAGGAAGAGTTCTACAAGT<br>TCATCAAGCCCATCCTGGAAAAGATGGACGGCACCGAGGAACTGCTCGTGAAGCTGAACAGAGAGGACCT<br>GCTGCGGAAGCAGCGGACCTTCGACAACGGCAGCATCCCCCACCAGATCCACCTGGGAGAGCTGCACGCC<br>ATTCTGCGCGGCAGGAAGATTTTTACCCATTCCTGAAGGACAACGGGAAAAGATCGAGAAGATCCTGA<br>CCTTCCGCATCCCCTACTACGTGGGCCCTCTGGCCAGGGGAAACAGCAGATTCGCCTGGATGACCAGAAA<br>GAGCGAGGAAACCATCACCCCCTGGAACTTCGAGGAAGTGGTGGACAAGGGCGCTTCCGCCCAGAGCTTC<br>ATCGAGCGGATGACCAACTTCGATAAGAACCTGCCCAACGAGAAGGTGCTGCCCAAGCACAGCCTGCTGT<br>ACGAGTACTTCACCGTGTATAACGAGCTGACCAAAGTGAAATACGTGACCGAGGGAATGAGAAAGCCCGC<br>CTTCCTGAGCGGCGAGCAGAAAAAGGCCATCGTGGACCTGCTGTTCAAGACCAACCGGAAAGTGACCGTG<br>AAGCAGCTGAAAGAGGACTACTTCAAGAAAATCGAGTGCTTCGACTCCGTGGAAATCTCCGGCGTGGAAG<br>ATCGGTTCAACGCCTCCCTGGGCACATACCACGATCTGCTGAAAATTATCAAGGACAAGGACTTTCTGGA<br>CAATGAGGAAAACGAGGACATTCTGGAAGATATCGTGCTGACCCTGACACTGTTTGAGGACAGAGAGATG<br>ATCGAGGAACGGCTGAAAACCTATGCCCACCTGTTCGACGACAAAGTGATGAAGCAGCTGAAGCGGCGGA<br>GATACACCGGCTGGGGCAGGCTGAGCCGGAAGCTGATCAACGGCATCCGGGACAAGCAGTCCGGCAAGAC<br>AATCCTGGATTTCCTGAAGTCCGACGGCTTCGCCAACAGAAACTTCATGCAGCTGATCCACGACGACAGC<br>CTGACCTTTAAAGAGGACATCCAGAAAGCCCAGGTGTCCGGACAGGGCGATAGCCTGCACGAGCACATTG<br>CCAATCTGGCCGGCAGCCCCGCCATTAAGAAGGGCATCCTGCAGACAGTGAAGGTGGTGGACGAGCTCGT<br>GAAAGTGATGGGCCGGCACAAGCCCGAGAACATCGTGATCGAAATGGCCAGAGAGAACCAGACCACCCAG<br>AAGGGACAGAAGAACAGCCGCGAGAGAATGAAGCGGATCGAAGAGGGCATCAAAGAGCTGGGCAGCCAGA<br>TCCTGAAAGAACACCCCGTGGAAAACACCCAGCTGCAGAACGAGAAGCTGTACCTGTACTACCTGCAGAA<br>TGGGCGGGATATGTACGTGGACCAGGAACTGGACATCAACCGGCTGTCCGACTACGATGTGGACGCTATC<br>GTGCCTCAGAGCTTTCTGAAGGACGACTCCATCGACAACAAGGTGCTGACCAGAAGCGACAAGAACCGGG<br>GCAAGAGCGACAACGTGCCCTCCGAAGAGGTCGTGAAGAAGATGAAGAACTACTGGCGGCAGCTGCTGAA<br>CGCCAAGCTGATTACCCAGAGAAAGTTCGACAATCTGACCAAGGCCGAGAGAGGCGGCCTGAGCGAACTG<br>GATAAGGCCGGCTTCATCAAGAGACAGCTGGTGGAAACCCGGCAGATCACAAAGCACGTGGCACAGATCC<br>TGGACTCCCGGATGAACACTAAGTACGACGAGAATGACAAGCTGATCCGGGAAGTGAAAGTGATCACCCT<br>GAAGTCCAAGCTGGTGTCCGATTTCCGGAAGGATTTCCAGTTTTACAAAGTGCGCGAGATCAACAACTAC<br>CACCACGCCCACGACGCCTACCTGAACGCCGTCGTGGGAACCGCCCTGATCAAAAAGTACCCTAAGCTGG<br>AAAGCGAGTTCGTGTACGGCGACTACAAGGTGTACGACGTGCGGAAGATGATCGCCAAGAGCGAGCAGGA<br>AATCGGCAAGGCTACCGCCAAGTACTTCTTCTACAGCAACATCATGAACTTTTTCAAGACCGAGATTACC<br>CTGGCCAACGGCGAGATCCGGAAGCGGCCTCTGATCGAGACAAACGGCGAAACCGGGGAGATCGTGTGGG<br>ATAAGGGCCGGGATTTTGCCACCGTGCGGAAAGTGCTGAGCATGCCCCAAGTGAATATCGTGAAAAAGAC<br>CGAGGTGCAGACAGGCGGCTTCAGCAAAGAGTCTATCCTGCCCAAGAGGAACAGCGATAAGCTGATCGCC<br>AGAAAGAAGGACTGGGACCCTAAGAAGTACGGCGGCTTCGACAGCCCCACCGTGGCCTATTCTGTGCTGG<br>TGGTGGCCAAAGTGGAAAAGGGCAAGTCCAAGAAACTGAAGAGTGTGAAAGAGCTGCTGGGGATCACCAT<br>CATGGAAAGAAGCAGCTTCGAGAAGAATCCCATCGACTTTCTGGAAGCCAAGGGCTACAAAGAAGTGAAA<br>AAGGACCTGATCATCAAGCTGCCTAAGTACTCCCTGTTCGAGCTGGAAAACGGCCGGAAGAGAATGCTGG<br>CCTCTGCCGGCGAACTGCAGAAGGGAAACGAACTGGCCCTGCCCTCCAAATATGTGAACTTCCTGTACCT<br>GGCCAGCCACTATGAGAAGCTGAAGGGCTCCCCCGAGGATAATGAGCAGAAACAGCTGTTTGTGGAACAG<br>CACAAGCACTACCTGGACGAGATCATCGAGCAGATCAGCGAGTTCTCCAAGAGAGTGATCCTGGCCGACG<br>CTAATCTGGACAAAGTGCTGTCCGCCTACAACAAGCACCGGGATAAGCCCATCAGAGAGCAGGCCGAGAA<br>TATCATCCACCTGTTTACCCTGACCAATCTGGGAGCCCCTGCCGCCTTCAAGTACTTTGACACCACCATC<br>GACCGGAAGAGGTACACCAGCACCAAAGAGGTGCTGGACGCCACCCTGATCCACCAGAGCATCACCGGCC<br>TGTACGAGACACGGATCGACCTGTCTCAGCTGGGAGGCGACAGCGCTGGAGGAGGTGGAAGCGGAGGAGG<br>AGGAAGCGGAGGAGGAGGTAGCggacctaagaaaaagaggaaggtggcggccgctGGATCCCCTTCAGGG<br>CAGATCAGCAACCAGGCCCTGGCTCTGGCCCCTAGCTCCGCTCCAGTGCTGGCCCAGACTATGGTGCCCT<br>CTAGTGCTATGGTGCCTCTGGCCCAGCCACCTGCTCCAGCCCCTGTGCTGACCCCAGGACCACCCCAGTC<br>ACTGAGCGGCTCCAGTGCCCAAGTCTACACAGGCCGGCGAGGGGACTCTGAGTGAAGCTCTGCTGCACCTG<br>CAGTTCGACGCTGATGAGGACCTGGGAGCTCTGCTGGGAACAGCACCGATCCCGGAGTGTTCACAGATC<br>TGGCCTCCGTGGACAACTCTGAGTTTCAGCAGCTGCTGAATCAGGGCGTGTCCATGTCTCATAGTACAGC<br>CGAACCAATGCTGATGGAGTACCCCGAAGCCATTACCCGGCTGGTGACCGGCAGCCAGCGGCCCCCCGAC<br>CCCGCTCCAACTCCCCTGGAACCAGCGGCCTGCCTAATGGGCTGTCCGGAGATGAAGCTTCTCAAGCA<br>TCGCTGATATGGACTTTAGTGCCCTGCTGTCACAGATTTCCTCTAGTGGGCAG |

It will be understood that in examples where the CRISPR enzyme comprises or associates with a transcriptional activation domain, expression of the Klotho gene may be enhanced in the absence of an adapter protein. Accordingly, the present disclosure provides methods of increasing expression of a Klotho gene in a human cell the method comprising introducing into the cell: a guide RNA comprising a guide sequence that is substantially complementary to a target sequence within or near the Klotho gene; and a CRISPR enzyme, wherein the CRISPR enzyme comprises or is attached to a transcriptional activation domain.

In certain examples, the CRISPR enzyme is modified to include a nuclear localisation signal (NLS). For example, the CRISPR enzyme may be flanked at its N-terminus, its C-terminus, or both the N-terminus and C-terminus by one or more NLSs. For example, a Cas9 endonuclease can be flanked by two NLSs, one NLS located at the N-terminus and the second NLS located at the C-terminus. The NLS can be any NLS known in the art, such as a SV40 NLS. A non-limiting example of an SV40 NLS is set forth in SEQ ID NO. 27.

Guide RNA, Adapter Proteins and Transcriptional Activation Domains

A guide RNA (gRNA) can comprise at least a guide (also called a "spacer") sequence, which is the sequence of the guide RNA that hybridizes to a target nucleic acid sequence of interest, and a CRISPR repeat sequence. The term guide sequence is not to be construed as referring to the sequence of the entire guide RNA, but rather, the portion of the guide RNA that hybridizes to the target sequence. In wild type Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex can bind a CRISPR enzyme, such that the guide RNA and the CRISPR enzyme form a complex. The guide RNA provides target specificity to the complex by virtue of its association with the CRISPR enzyme.

A double-molecule guide RNA can comprise two strands of RNA. The first strand comprises in the 5' to 3' direction, an optional spacer extension sequence, a guide sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) comprises only one strand of RNA. The sgRNA may comprise a guide sequence fused to a tracr sequence. Without wishing to be bound to any particular arrangement of sequences or structure, a sgRNA in a Type II system may comprise, in a 5' to 3' direction, an optional spacer extension sequence, a guide sequence (also referred to as a spacer sequence), a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

The length of the guide sequence may vary from between 10 nucleotides to 40 nucleotides and is generally located at the 5' end of the guide RNA. In certain examples, the guide sequence is less than 40 nucleotides in length such as less than 25 nucleotides. The guide sequence may be 24 nucleotides, 23 nucleotides, 22 nucleotides, 21 nucleotides, 20 nucleotides, 19 nucleotides, 18 nucleotides, 17 nucleotides, 16 nucleotides, 15 nucleotides, 14 nucleotides, 13 nucleotides, 12, nucleotides, 11 nucleotides or 10 nucleotides in length.

The length of the guide RNA may vary from 50 nucleotides to more than 300 nucleotides. For example, the guide RNA of the present disclosure may be between about 50 nucleotides and 300 nucleotides in length, such as between about 70 nucleotides and 250 nucleotides in length, or between about 80 nucleotides and 225 nucleotides in length, or between about 90 nucleotides and 215 nucleotides in length, or between about 100 nucleotides and 200 nucleotides in length, or between about 110 nucleotides and 190 nucleotides in length, or between about 125 nucleotides and 170 nucleotides in length, or between about 140 nucleotides and 165 nucleotides in length.

In a CRISPR/Cas system, the guide sequence can be designed to hybridize to a target nucleic acid that is located immediately upstream (5') of a PAM of the Cas9 enzyme used in the system. The guide sequence can be perfectly complementary with the target sequence or it can have mismatches. Each Cas9 enzyme has a particular PAM sequence that it recognizes in a target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

In certain examples, the guide RNA of the present disclosure comprises a guide sequence that is substantially complementary to a target sequence within or near the Klotho gene. A target sequence will be considered "near" the Klotho gene if, despite not being located within the Klotho gene, the target sequence is sufficiently close to the Klotho gene such that when the target sequence is bound by a guide RNA of the present disclosure along with a CRISPR enzyme and a transcriptional activation domain (optionally via an adapter protein), expression of the Klotho gene is increased relative to an absence of such binding.

In some examples, the percent complementarity between the guide sequence and the target sequence is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99% or 100%. In some examples, the percent complementarity between the guide sequence and the target nucleic acid is 100% over the six contiguous 5-most nucleotides of the target sequence of the complementary strand of the target nucleic acid. The percent complementarity between the guide sequence and the target nucleic acid can be at least 60%, such as at least 65%, at least 75%, at least 80%, at least 85%, at least 90%, at least 95% or 100% over about 20 contiguous nucleotides. The length of the guide sequence and the target nucleic acid can differ by 1 to 6 nucleotides, the difference in length may result in a bulge or bulges. In certain examples, the guide sequence is at least about 80% identical to a nucleotide sequence set forth in any one of SEQ ID NOs 1 to 4, such as at least about 85%, at least about 90%, at least about 95% or about 100% identical to a nucleotide sequence set forth in any one of SEQ ID NOs 1 to 4. In certain examples, the guide sequence comprises at least 10 contiguous nucleotides which are identical to a nucleotide sequence set forth in any one of SEQ ID NOs 1 to 4. For example, the guide sequence may comprises at least 11 contiguous nucleotides, or at least 12 contiguous nucleotides, or at least 13 contiguous nucleotides, or at least 14 contiguous nucleotides, or at least 15 contiguous nucleotides, or at least 16 contiguous nucleotides, or at least 17 contiguous nucleotides, or at least 18 contiguous nucleotides, or at least 19 contiguous nucleotides or at least 20 contiguous nucleotides which are identical to a nucleotide sequence set forth in any one of SEQ ID NOs 1 to 4.

The target sequence may be located anywhere within or near the Klotho gene such that binding of a guide RNA of the present disclosure to the target sequence, along with a CRISPR enzyme and a transcriptional activation domain (optionally via an adapter protein), enhances transcription of Klotho. In certain examples, the target sequence is located within a region between the Klotho gene translation start site and about 5 kb upstream of the Klotho translation start site. In other words, the target sequence may be located within a window starting from the translation initiation site and extending 5 kb upstream. In some examples, the target sequence may be located within a region extending about 4.5 kb upstream of the Klotho translation start site, or about 4 kb upstream of the Klotho translation start site, or about 3.5 kb upstream of the Klotho translation start site, or about 3 kb upstream of the Klotho translation start site, or about 2.5 kb upstream of the Klotho translation start site, or about 2 kb upstream of the Klotho translation start site, or about 1.5 kb upstream of the Klotho translation start site, or about 1 kb upstream of the Klotho translation start site, or about 0.5 kb upstream of the Klotho translation start site. In certain examples, the target sequence is located within a region between about 100 nucleotides and 5000 nucleotides upstream of the Klotho translation start site, such as within a region between about 150 nucleotides and 5000 nucleotides upstream of the Klotho translation start site, or within a region between about 200 nucleotides and 5000 nucleotides upstream of the Klotho translation start site, or within a region between about 200 nucleotides and 4500 nucleotides upstream of the Klotho translation start site, or within a region between about 200 nucleotides and 4000 nucleotides upstream of the Klotho translation start site, or within a region between about 200 nucleotides and 3500 nucleotides upstream of the Klotho translation start site, or within a region between about 200 nucleotides and 3000 nucleotides upstream of the Klotho translation start site, or within a region between about 200 nucleotides and 2500 nucleotides upstream of the Klotho translation start site, or within a region between about 200 nucleotides and 2000 nucleotides upstream of the Klotho translation start site, or within a region between about 200 nucleotides and 1500 nucleotides upstream of the Klotho translation start site, or within a region between about 200 nucleotides and 1000 nucleotides upstream of the Klotho translation start site, or within a region between about 200 nucleotides and 500 nucleotides upstream of the Klotho translation start site, within a region between about 200 nucleotides and 300 nucleotides upstream of the Klotho translation start site, within a region between about 210 nucleotides and 300 nucleotides upstream of the Klotho translation start site, within a region between about 220 nucleotides and 300 nucleotides upstream of the Klotho translation start site, within a region between about 230 nucleotides and 300 nucleotides upstream of the Klotho translation start site, or within a region between about 240 nucleotides and 300 nucleotides upstream of the Klotho translation start site.

In certain examples, the target sequence is located within a regulatory element of the Klotho gene such as a promoter or an enhancer. Expression of eukaryotic protein-coding genes generally is regulated through multiple cis-acting transcription-control regions. Some control elements are located close to the start site (promoter-proximal elements), whereas others lie more distal (enhancers and silencers). Promoters determine the site of transcription initiation and direct binding of RNA polymerase II. They may extend a few hundred base pairs to several kilobases upstream of a transcription start site. Enhancers may be 100 to 200 base pairs in length and may be located a hundred base pairs up to tens of kilobases upstream or down stream of a promoter. Promoters of highly expressed genes often comprise a TATA box. CpG islands are characteristic of transcribed genes.

For the purposes of the present disclosure, a target sequence will be considered "within" a region if it is entirely within that region or partially within that region. For example, the target sequence may be located entirely within a region between 200 nucleotides and 300 nucleotides upstream of the Klotho gene translation start site, or alternatively, only a part of the target sequence may be located with that region. In either case, the target sequence is deemed to be "within" a region between 200 nucleotides and 300 nucleotides upstream of the Klotho gene translation start site.

The sgRNA of the present disclosure may comprise no uracil at the 3' end of the sgRNA. Alternatively, the sgRNA may comprise 1 uracil (U) at the 3' end of the sgRNA. The sgRNA may comprise 2 uracil (UU) at the 3' end of the sgRNA. The sgRNA may comprise 3 uracil (UUU) at the 3' end of the sgRNA. The sgRNA may comprise 4 uracil (UUUU) at the 3' end of the sgRNA. The sgRNA may comprise 5 uracil (UUUUU) at the 3' end of the sgRNA. The sgRNA may comprise 6 uracil (UUUUUU) at the 3' end of the sgRNA. The sgRNA may comprise 7 uracil (UUUUUUU) at the 3' end of the sgRNA. The sgRNA may comprise 8 uracil (UUUUUUUU) at the 3' end of the sgRNA.

The guide sequence may be designed or chosen using a computer program. The computer program may use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more positions as a result of mismatch, insertion or deletion), methylation status, presence of SNPs, and the like.

The guide RNA of the present disclosure preferably associates with a transcriptional activation domain. The guide RNA may associate with a transcriptional activation domain via the CRISPR enzyme which may be modified to comprise, or bind to, a transcriptional activation domain. Alternatively, or additionally, the guide RNA may associate with a transcriptional activation domain by way of an adapter protein which is capable of binding to the guide RNA and which comprises, or binds to, a transcriptional activation domain.

The sgRNA may comprise multiple loop structures owing to self-complementarity within the sgRNA molecule. Two of those loops, namely the tetra-loop and step loop 2 have been shown to protrude outside of the Cas9-sgRNA ribonucleoprotein complex, with the distal four base pairs of each stem free of interactions with Cas9 amino acid side chains (Nishimasu et al. (2014) *Cell* 156: 935-949). Those loops may be engineered to include a protein-binding sequence, such as an RNA aptamer, thus enabling the guide RNA to bind to one or more adapter proteins as well as to the CRISPR enzyme. The adapter protein may comprise or attach to a transcriptional activation domain. Those skilled in the art will be able to identify suitable locations within a particular guide RNA for insertion of a protein-binding sequence, such as at the tetra-loop and/or stem loop 2 which may be modified, altered or replaced to include the protein-binding sequence. Suitable guide RNAs comprising protein-binding sequences are described herein. Konermann et al. (*Nature* (2015) 517: 583-588) have also described guide RNAs comprising protein-binding sequences.

The exposed or extraneous portion of the guide (when the guide-Cas9-DNA complex is formed) is preferably a 4 (four) nucleotide stretch. In some examples, the stretch may be in the tetra-loop as described. In some examples, the stretch may be in the stem loop 2 as described. In some examples, stretches in both the tetra-loop and the stem loop 2 are envisaged. This stretch may be modified, altered or entirely replaced. It is not generally preferred to reduce the number of nucleotides in the exposed stretch to less than 4 for stearic reasons as this could affect the secondary structure of the rest of the guide RNA and thus affect formation of the Cas9-guide-DNA complex or the exposure of the stretch. It may be modified or altered in that all four of the original 4 nucleotides in the stretch are retained and additions (or further nucleotides) are made between 1 and 2, 2 and 3, or 3 and 4. It is also envisaged that additions may be made immediately 5' to 1 or 3' immediately to 4. The stem may be flexible, but it is preferred that it is largely self-complementary throughout.

Unafold is a software tool that can be used to help predict RNA secondary structure in the guide and so assist the skilled person to determine what changes to the guide RNA may be acceptable within the framework discussed herein.

In some examples, one or more GC tracts may replace the stem portion of stem loop 2 and/or the tetra-loop. Preferably, the loop feature should be retained but protein binding section of the distinct RNA added to the guide may determine this. The non-loop ends abutting the edge of the enzyme should preferably be retained in the sense that they should be present, but the primary sequence of the original guide can be changed, for example by insertion of one or more GC tract(s). Preferably, this should be done at the non-loop (non-protein-binding end) of the distinct RNA added, which may be extended. The secondary structure of the non-protein-binding region of the distinct RNA preferably forms a stem.

FIG. 1 shows an exemplary guide RNA of the present disclosure (sgRNA3; SEQ ID NO: 3) hybridised to a target sequence in the Klotho promoter. The secondary structure of the guide RNA is also indicated including the tetra-loop and the stem loop 2 which have been engineered to include a MS2 binding sequence.

Synergistic activation mediator (SAM) comprises dCas9-VP64 with a guide RNA that associates with the fusion polypeptide MS2-p65-HSF1 (sometimes referred to as MCP-p65-HSF1 where MCP is an abbreviation for MS2 coat protein). The guide RNA of the SAM system typically comprises two MS2 binding sequences at the tetraloop and stem loop 2, and are used to recruit MS2-p65-HSF1. MS2-p65-HSF1 binds to the MS2 binding loops as a dimer, thereby resulting in four sets of the activation domains p65 and HSF1 being recruited. Together with the VP64 component, 12 transcriptional activation domains may be involved in a SAM complex.

Scaffold comprises a dCas9 component and a guide RNA wherein the guide RNA comprises an MS2 binding loop, which associates with a dimer of MS2-VP4 (sometimes referred to as MCP-VP64), and an F6 aptamer, which associates with two MS2-VP64 fusions resulting in the recruitment of 16 transcriptional activation domains. Vectors encoding such fusions are commercially available, for example, from Addgene.

Suitable adapter proteins for binding to guide RNAs of the present disclosure may include bacteriophage coat proteins such as Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. In preferred examples, the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. A suitable protein binding sequence may include the MS2-binding loop ggccAACAT-GAGGATCACCCATGTCTGCAGggcc (SEQ ID NO: 28) or ggccAGCATGAGGATCACCCATGCCTGCAGggcc (SEQ ID NO: 29), or the F6 aptamer. Accordingly, in certain examples, the guide RNA of the present disclosure is a sgRNA which is capable of binding to an adapter protein.

The guide RNA may comprise more than one protein binding sequence, and each protein binding sequence may bind the same or different adapter proteins. The adapter protein may comprise a nuclear localisation signal (NLS) such as that from SV40.

A PP7 variant may be used in some examples. For example, the PP7 Pseudomonas bacteriophage coat protein (with amino acids 68-69 mutated to SG and amino acids 70-75 deleted from the wild type protein as described in Wu et al. *Biophysical Journal*. 102.1 (2012): 2936-2944 and Chao and Singer, *Nature Structural & Molecular Biology* 15.1 (2007): 103-105 may be desirable.

An MS2 variant may also be used, such as the N55 mutant, particularly the N55K mutant. This is the N55K mutant of the MS2 bacteriophage coat protein (shown to have higher binding affinity than wild type MS2 in Lim et al. *Journal of Biological Chemistry* 269.12 (1994): 9006-9010).

The adapter protein may itself comprise a transcriptional activation domain or it may be fused to the transcriptional activation domain of another protein. For example, GlySer linkers (eg, GGGGS) may be used. They may be repeats of 3 ((GGGGS)$_3$), 6, 9, 12 or more, to provide suitable lengths as desired. Alternatively, the adapter protein may bind to another protein which comprises a transcriptional activation domain. In further examples, the adapter protein may bind to a further adapter such as an antibody which then binds to a protein which comprises a transcriptional activation domain. The transcriptional activation domain may enhance transcription of nearby genes, for example, by recruiting transcription factors and or chromatin remodelling complexes. Indeed, the transcriptional activation domain may itself contribute to chromatin remodelling. Suitable transcriptional activation domains may include VP16, or a plurality thereof, VP64, VP160, p65, MyoD1, HSF1, RTA, SET7/9 as well as domains from chromatin-remodelling enzymes such as DNA demethylases and histone acetyltransferases. In certain examples, the transcriptional activation domain is a TET catalytic domain such as the catalytic domain of TET1, TET2 or TET3. In other examples, the transcriptional activation domain is an acetyltransferase such as p300.

Table 3 provides exemplary sequences of an adapter protein (MS2) fused to an NLS and one or more transcriptional activation domains.

TABLE 3

| SEQ | Description | Sequence |
|---|---|---|
| 23 | MS2-NLS-VP64<br>MS2 underlined<br>NLS lowercase<br>VP64 highlighted | ATGGCTTCAAACTTTACTCAGTTCGTGCTCGTGGACAATGGTGGGACAGGGGAT<br>GTGACAGTGGCTCCTTCTAATTTCGCTAATGGGGTGGCAGAGTGGATCAGCTCC<br>AACTCACGGAGCCAGGCCTACAAGGTGACATGCAGCGTCAGGCAGTCTAGTGCC<br>CAGAAGAGAAAGTATACCATCAAGGTGGAGGTCCCCAAAGTGGCTACCCAGACA<br>GTGGGCGGAGTCGAACTGCCTGTCGCCGCTTGGAGGTCCTACCTGAACATGGAG<br>CTCACTATCCCAATTTTCGCTACCAATTCTGACTGTGAACTCATCGTGAAGGCA<br>ATGCAGGGGCTCCTCAAAGACGGTAATCCTATCCCTTCCGCCATCGCCGCTAAC<br>TCAGGTATCTACAGCGCTGGAGGAGGTGGAAGCGGAGGAGGAGGAAGCGGAGGA<br>GGAGGTAGCggacctaagaaaaagaggaaggtggcggccgctGGATCCGGACGG<br>GCTGACGCATTGGACGATTTTGATCTGGATATGCTGGGAAGTGACGCCCTCGAT<br>GATTTTGACCTTGACATGCTTGGTTCGGATGCCCTTGATGACTTTGACCTCGAC<br>ATGCTCGGCAGTGACGCCCTTGATGATTTCGACCTGGACATGCTGATTAAC |
| 24 | MS2-NLS-P65<br>MS2 underlined<br>NLS lowercase<br>P65 highlighted | ATGGCTTCAAACTTTACTCAGTTCGTGCTCGTGGACAATGGTGGGACAGGGGAT<br>GTGACAGTGGCTCCTTCTAATTTCGCTAATGGGGTGGCAGAGTGGATCAGCTCC<br>AACTCACGGAGCCAGGCCTACAAGGTGACATGCAGCGTCAGGCAGTCTAGTGCC<br>CAGAAGAGAAAGTATACCATCAAGGTGGAGGTCCCCAAAGTGGCTACCCAGACA<br>GTGGGCGGAGTCGAACTGCCTGTCGCCGCTTGGAGGTCCTACCTGAACATGGAG<br>CTCACTATCCCAATTTTCGCTACCAATTCTGACTGTGAACTCATCGTGAAGGCA<br>ATGCAGGGGCTCCTCAAAGACGGTAATCCTATCCCTTCCGCCATCGCCGCTAAC<br>TCAGGTATCTACAGCGCTGGAGGAGGTGGAAGCGGAGGAGGAGGAAGCGGAGGA<br>GGAGGTAGCggacctaagaaaaagaggaaggtggcggccgctGGATCCCCTTCA<br>GGGCAGATCAGCAACCAGGCCCTGGCTCTGGCCCCTAGCTCCGCTCCAGTGCTG<br>GCCCAGACTATGGTGCCCTCTAGTGCTATGGTGCCTCTGGCCCAGCCACCTGCT<br>CCAGCCCCTGTGCTGACCCCAGGACCACCCCAGTCACTGAGCGCTCCAGTGCCC<br>AAGTCTACACAGGCCGGCGAGGGGACTCTGAGTGAAGCTCTGCTGCACCTGCAG<br>TTCGACGCTGATGAGGACCTGGGAGCTCTGCTGGGGAACAGCACCGATCCCGGA<br>GTGTTCACAGATCTGGCCTCCGTGGACAACTCTGAGTTTCAGCAGCTGCTGAAT<br>CAGGGCGTGTCCATGTCTCATAGTACAGCCGAACCAATGCTGATGGAGTACCCC<br>GAAGCCATTACCCGGCTGGTGACCGGCAGCCAGCGGCCCCCCGACCCCGCTCCA<br>ACTCCCCTGGGAACCAGCGGCCCTGCCTAATGGGCTGTCCGGAGATGAAGACTTC<br>TCAAGCATCGCTGATATGGACTTTAGTGCCCTGCTGTCACAGATTTCCTCTAGT<br>GGGCAG |
| 25 | MS2-NLS-P65-HSF1<br>MS2 underlined<br>NLS lowercase<br>P65 highlighted<br>HSF1 bold | ATGGCTTCAAACTTTACTCAGTTCGTGCTCGTGGACAATGGTGGGACAGGGGAT<br>GTGACAGTGGCTCCTTCTAATTTCGCTAATGGGGTGGCAGAGTGGATCAGCTCC<br>AACTCACGGAGCCAGGCCTACAAGGTGACATGCAGCGTCAGGCAGTCTAGTGCC<br>CAGAAGAGAAAGTATACCATCAAGGTGGAGGTCCCCAAAGTGGCTACCCAGACA<br>GTGGGCGGAGTCGAACTGCCTGTCGCCGCTTGGAGGTCCTACCTGAACATGGAG<br>CTCACTATCCCAATTTTCGCTACCAATTCTGACTGTGAACTCATCGTGAAGGCA<br>ATGCAGGGGCTCCTCAAAGACGGTAATCCTATCCCTTCCGCCATCGCCGCTAAC<br>TCAGGTATCTACAGCGCTGGAGGAGGTGGAAGCGGAGGAGGAGGAAGCGGAGGA<br>GGAGGTAGCggacctaagaaaaagaggaaggtggcggccgctGGATCCCCTTCA<br>GGGCAGATCAGCAACCAGGCCCTGGCTCTGGCCCCTAGCTCCGCTCCAGTGCTG<br>GCCCAGACTATGGTGCCCTCTAGTGCTATGGTGCCTCTGGCCCAGCCACCTGCT<br>CCAGCCCCTGTGCTGACCCCAGGACCACCCCAGTCACTGAGCGCTCCAGTGCCC<br>AAGTCTACACAGGCCGGCGAGGGGACTCTGAGTGAAGCTCTGCTGCACCTGCAG<br>TTCGACGCTGATGAGGACCTGGGAGCTCTGCTGGGGAACAGCACCGATCCCGGA<br>GTGTTCACAGATCTGGCCTCCGTGGACAACTCTGAGTTTCAGCAGCTGCTGAAT<br>CAGGGCGTGTCCATGTCTCATAGTACAGCCGAACCAATGCTGATGGAGTACCCC<br>GAAGCCATTACCCGGCTGGTGACCGGCAGCCAGCGGCCCCCCGACCCCGCTCCA<br>ACTCCCCTGGGAACCAGCGGCCCTGCCTAATGGGCTGTCCGGAGATGAAGACTTC<br>TCAAGCATCGCTGATATGGACTTTAGTGCCCTGCTGTCACAGATTTCCTCTAGT<br>GGGCAGGGAGGAGGTGGAAGCGGCTTCAGCGTGGACACCAGTGCCCTGCTGGAC |

TABLE 3-continued

| SEQ | Description | Sequence |
|---|---|---|
| | | CTGTTCAGCCCCTCGGTGACCGTGCCCGACATGAGCCTGCCTGACCTTGACAGC<br>AGCCTGGCCAGTATCCAAGAGCTCCTGTCTCCCCAGGAGCCCCCCAGGCCTCCC<br>GAGGCAGAGAACAGCAGCCCGGATTCAGGGAAGCAGCTGGTGCACTACACAGCG<br>CAGCCGCTGTTCCTGCTGGACCCCGGCTCCGTGGACACCGGGAGCAACGACCTG<br>CCGGTGCTGTTTGAGCTGGGAGAGGGCTCCTACTTCTCCGAAGGGGACGGCTTC<br>GCCGAGGACCCCACCATCTCCCTGCTGACAGGCTCGGAGCCTCCCAAAGCCAAG<br>GACCCCACTGTCTCC |
| 26 | MS2-NLS-P65-<br>MyoD1<br>MS2 underlined<br>NLS lowercase<br>P65<br>highlighted<br>MyoD1 bold | ATGGCTTCAAACTTTACTCAGTTCGTGCTCGTGGACAATGGTGGGACAGGGGAT<br>GTGACAGTGGCTCCTTCTAATTTCGCTAATGGGGTGGCAGAGTGGATCAGCTCC<br>AACTCACGGAGCCAGGCCTACAAGGTGACATGCAGCGTCAGGCAGTCTAGTGCC<br>CAGAAGAGAAAGTATACCATCAAGGTGGAGGTCCCCAAAGTGGCTACCCAGACA<br>GTGGGCGGAGTCGAACTGCCTGTCGCCGCTTGGAGGTCCTACCTGAACATGGAG<br>CTCACTATCCCAATTTTCGCTACCAATTCTGACTGTGAACTCATCGTGAAGGCA<br>ATGCAGGGGCTCCTCAAAGACGGTAATCCTATCCCTTCCGCCATCGCCGCTAAC<br>TCAGGTATCTACAGCGCTGGAGGAGGTGGAAGCGGAGGAGGAGGAAGCGGAGGA<br>GGAGGTAGCggacctaagaaaaagaggaaggtggcggccgctGGATCCCCTTCA<br>GGGCAGATCAGCAACCAGGCCCTGGCTCTGGCCCCTAGCTCCGCTCCAGTGCTG<br>GCCCAGACTATGGTGCCCTCTAGTGCTATGGTGCCTCTGGCCCAGCCACCTGCT<br>CCAGCCCCTGTGCTGACCCCAGGACCACCCCAGTCACTGAGCGCTCCAGTGCCC<br>AAGTCTACACAGGCCGGCGAGGGGACTCTGAGTGAAGCTCTGCTGCACCTGCAG<br>TTCGACGCTGATGAGGACCTGGGAGCTCTGCTGGGGAACAGCACCGATCCCGGA<br>GTGTTCACAGATCTGGCCTCCGTGGACAACTCTGAGTTTCAGCAGCTGCTGAAT<br>CAGGGCGTGTCCATGTCTCATAGTACAGCCGAACCAATGCTGATGGAGTACCCC<br>GAAGCCATTACCCGGCTGGTGACCGGCAGCCAGCGGCCCCCCGACCCCGCTCCA<br>ACTCCCCTGGGAACCAGCGGCCTGCCTAATGGGCTGTCCGGAGATGAAGACTTC<br>TCAAGCATCGCTGATATGGACTTTAGTGCCCTGCTGTCACAGATTTCCTCTAGT<br>GGGCAGGGAGGAGGTGGAAGCATGGAGCTTCTTTCTCCTCCTCTGCGGGATGTT<br>GACCTGACTGCGCCCGACGGCTCTCTTTGCTCCTTCGCCACAACCGACGACTTC<br>TACGATGATCCATGTTTTGACAGCCCCGATCTCAGGTTCTTTGAGGATCTCGAT<br>CCTAGACTGATGCACGTGGGCGCACTGCTCAAACCTGAGGAACATAGC |

In certain examples, the present disclosure provides a method of increasing expression of a Klotho gene in a human cell the method comprising introducing into the cell: a CRISPR enzyme; a single-molecule guide RNA comprising a guide sequence that is substantially complementary to a target sequence within or near the Klotho gene; and an adapter protein capable of binding to the guide RNA wherein the adapter protein comprises or is attached to a transcriptional activation domain. In some examples, the present disclosure provides a method of increasing expression of a Klotho gene in a human cell the method comprising introducing into the cell: a CRISPR enzyme; a single-molecule guide RNA comprising a guide sequence that is substantially complementary to a nucleotide sequence set forth in SEQ ID NO. 11 or SEQ ID NO. 12; and an adapter protein capable of binding to the guide RNA wherein the adapter protein comprises or is attached to a transcriptional activation domain. In certain examples, the present disclosure provides a method of increasing expression of a Klotho gene in a human cell the method comprising introducing into the cell: a CRISPR enzyme; a single-molecule guide RNA comprising a guide sequence that is substantially complementary to a nucleotide sequence set forth in SEQ ID NO. 13 or SEQ ID NO. 14; and an adapter protein capable of binding to the guide RNA wherein the adapter protein comprises or is attached to a transcriptional activation domain. In certain examples, the present disclosure provides a method of increasing expression of a Klotho gene in a human cell the method comprising introducing into the cell: a CRISPR enzyme; a single-molecule guide RNA comprising a guide sequence that is substantially complementary to a target sequence located within a region between 200 nucleotides and 300 nucleotides upstream of the Klotho gene translation start site; and an adapter protein capable of binding to the guide RNA wherein the adapter protein comprises or is attached to a transcriptional activation domain. In some examples, the present disclosure provides a method of increasing expression of a Klotho gene in a human cell the method comprising introducing into the cell: a CRISPR enzyme; a single-molecule guide RNA comprising a guide sequence that is substantially complementary to a nucleotide sequence set forth in SEQ ID NO. 11 or SEQ ID NO. 12; and an adapter protein capable of binding to the guide RNA wherein the adapter protein comprises or is attached to a transcriptional activation domain. In certain examples, the present disclosure provides a method of increasing expression of a Klotho gene in a human cell the method comprising introducing into the cell: a CRISPR enzyme; a single-molecule guide RNA comprising a guide sequence that is substantially complementary to a target sequence located within a region between 200 nucleotides and 300 nucleotides upstream of the Klotho gene translation start site; and an adapter protein capable of binding to the guide RNA wherein the adapter protein comprises or is attached to a transcriptional activation domain. In certain examples, the present disclosure provides a method of increasing expression of a Klotho gene in a human cell the method comprising introducing into the cell: a CRISPR enzyme; a single-molecule guide RNA comprising a guide sequence that is substantially complementary to a nucleotide sequence set forth in SEQ ID NO. 13 or SEQ ID NO. 14; and an adapter protein capable of binding to the guide RNA wherein the adapter protein comprises or is attached to a transcriptional activation domain. In some examples, the present disclosure provides a method of increasing expression of a Klotho gene in a human cell the method comprising introducing into the cell: a CRISPR enzyme; a single-molecule guide RNA comprising a guide sequence that is substantially complementary to a nucleotide sequence set forth in SEQ ID NO. 11 or SEQ ID NO. 12; and an adapter protein capable of binding to the guide RNA wherein the adapter protein comprises or is attached to a transcriptional activation domain. In certain examples, the present disclosure provides a method of increasing expression of a Klotho gene in a human cell the method comprising introducing into the cell: a CRISPR enzyme; a single-molecule guide RNA comprising a guide sequence that is at least 90% identical to a nucleotide sequence set forth in any one of SEQ ID NOs 1 to 4, preferably at least 90% identical to a nucleotide sequence set forth in SEQ ID NO. 3 or SEQ ID NO. 4; and an adapter protein capable of binding to the guide RNA wherein the adapter protein comprises or is attached to a transcriptional activation domain. In some examples, the present disclosure provides a method of increasing expression of a Klotho gene in a human cell the method comprising introducing into the cell: a CRISPR enzyme; a single-molecule guide RNA comprising a guide sequence that is substantially complementary to a nucleotide sequence set forth in SEQ ID NO. 11 or SEQ ID NO. 12; and an adapter protein capable of binding to the guide RNA wherein the adapter protein comprises or is attached to a transcriptional activation domain. In certain examples, the present disclosure provides a method of increasing expression of a Klotho gene in a human cell the method comprising introducing into the cell: a CRISPR enzyme; a single-molecule guide RNA comprising a guide sequence that is at least 90% identical to a nucleotide sequence set forth in any one of SEQ ID NOs 1 to 4, preferably at least 90% identical to a nucleotide sequence set forth in SEQ ID NO. 3 or SEQ ID NO. 4; and an adapter protein capable of binding to the guide RNA wherein the adapter protein comprises or is attached to a transcriptional activation domain, wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1, and wherein the transcriptional activation domain is selected from the group consisting of VP16, or a plurality thereof, VP64, VP160, p65, MyoD1, HSF1, RTA, TET3CD, p300 and SET7/9. In certain examples, the present disclosure provides a method of increasing expression of a Klotho gene in a human cell the method comprising introducing into the cell: a CRISPR enzyme; a single-molecule guide RNA comprising a guide sequence that is substantially complementary to a target sequence located within a region between 200 nucleotides and 300 nucleotides upstream of the Klotho gene translation start site; and an adapter protein capable of binding to the guide RNA wherein the adapter protein is MS2 fused to p65 and HSF1. In certain examples, the present disclosure provides a method of increasing expression of a Klotho gene in a human cell the method comprising introducing into the cell: a CRISPR enzyme; a single-molecule guide RNA comprising a guide sequence that is substantially complementary to a target sequence located within a region between 200 nucleotides and 300 nucleotides upstream of the Klotho gene translation start site; and an adapter protein capable of binding to the guide RNA wherein the adapter protein is MS2 fused to p65 and HSF1, and wherein the CRISPR enzyme is fused to VP64, and wherein the CRISPR enzyme is dead Cas9 (dCas9).

In certain examples, the present disclosure provides a guide RNA comprising a guide sequence wherein the guide sequence is substantially complementary to a nucleotide sequence set forth in SEQ ID NO. 9 or SEQ ID NO. 10. In some examples, the present disclosure provides a single-molecule guide RNA comprising a guide sequence wherein the guide sequence is substantially complementary to a nucleotide sequence set forth in SEQ ID NO. 11 or SEQ ID NO. 12. In some examples, the present disclosure provides a single-molecule guide RNA comprising a guide sequence wherein the guide sequence is substantially complementary to a target sequence located within a region between 200 nucleotides and 300 nucleotides upstream of the Klotho gene translation start site. In some examples, the present disclosure provides a single-molecule guide RNA comprising a guide sequence wherein the guide sequence is substantially complementary to a nucleotide sequence set forth in SEQ ID NO. 13 or SEQ ID NO. 14. In some examples, the present disclosure provides a single-molecule guide RNA comprising a guide sequence wherein the guide sequence is substantially complementary to a target sequence located within a region between 200 nucleotides and 300 nucleotides upstream of the Klotho gene translation start site, and wherein the guide RNA is between about 100 nt and 200 nt in length. In some examples, the present disclosure provides a single-molecule guide RNA comprising a guide sequence wherein the guide sequence is substantially complementary to a nucleotide sequence set forth in SEQ ID NO. 13 or SEQ ID NO. 14, wherein the guide RNA is between about 100 nt and 200 nt in length. In some examples, the present disclosure provides a single-molecule guide RNA comprising a guide sequence wherein the guide sequence comprises at least 14 contiguous nucleotides which are identical to a nucleotide sequence set forth in any one of SEQ ID NOs 1 to 4, preferably to a nucleotide sequence set forth in SEQ ID NO. 3 or SEQ ID NO. 4. In some examples, the present disclosure provides a single-molecule guide RNA comprising a guide sequence wherein the guide sequence is selected from a nucleotide sequence set forth in any one of SEQ ID NOs 1 to 4.

In certain examples, the present disclosure provides a single-molecule guide RNA comprising: a guide sequence that is substantially complementary to a target sequence within or near a human Klotho gene; and at least one protein binding sequence for binding to an adapter protein, wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. In some examples, the present disclosure provides a single-molecule guide RNA comprising: a guide sequence that is substantially complementary to a nucleotide sequence set forth in SEQ ID NO. 9 or SEQ ID NO. 10; and at least one protein binding sequence for binding to an adapter protein, wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. In some examples, the present disclosure provides a single-molecule guide RNA comprising: a guide sequence that is substantially complementary to a nucleotide sequence set forth in SEQ ID NO. 11 or SEQ ID NO. 12; and at least one protein binding sequence for binding to an adapter protein, wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. In some examples, the present disclosure provides a single-molecule guide RNA comprising: a guide sequence that is substantially complementary to a target sequence located within a region between 200 nucleotides and 300 nucleotides upstream of the Klotho gene translation start site; and at least one protein binding sequence for binding to an adapter protein, wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1, preferably MS2. In some examples, the present disclosure provides a single-molecule guide RNA comprising: a guide sequence that is substantially complementary to a nucleotide sequence set forth in SEQ ID NO. 13 or SEQ ID NO. 14; and at least one protein binding sequence for binding to an adapter protein, wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. In some examples, the present disclosure provides a single-molecule guide RNA comprising: a guide sequence that comprises at least 14 contiguous nucleotides which are identical to a nucleotide sequence set forth in any one of SEQ ID NOs 1 to 4; and at least one protein binding sequence for binding to an adapter protein, wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. In some examples, the present disclosure provides a single-molecule guide RNA comprising: a guide sequence that is at least 90% identical to a nucleotide sequence set forth in any one of SEQ ID NOs 1 to 4, preferably to a nucleotide sequence set forth in SEQ ID NO. 3 or SEQ ID NO. 4; and at least one protein binding sequence for binding to an adapter protein, wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1, wherein the guide RNA is between about 100 nucleotides and about 200 nucleotides in length. In some examples, the present disclosure provides a single-molecule guide RNA comprising: a guide sequence that is at least 90% identical to a nucleotide sequence set forth in any one of SEQ ID NOs 1 to 4, preferably to a nucleotide sequence set forth in SEQ ID NO. 3 or SEQ ID NO. 4; and at least one protein binding sequence for binding to MS2, wherein the guide RNA is between about 100 nucleotides and about 200 nucleotides in length.

Nucleic Acid Modifications

In some cases, polynucleotides introduced into cells can comprise one or more modifications that can be used individually or in combination, for example, to enhance activity, stability or specificity, alter delivery, reduce innate immune responses in host cells, or for other enhancements, as further described herein and known in the art.

Modifications of guide RNAs may be used to enhance the initiation, stability or kinetics of interactions between the CRISPR enzyme and the target sequence in the genome, and can be used, for example, to enhance on-target activity. Modifications of guide RNAs can also or alternatively be used to enhance specificity, e.g., the relative rates of on-targeting as compared to off-targeting. Modifications may also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in aspects in which a CRISPR enzyme is introduced into a cell via an RNA that needs to be translated in order to generate the CRISPR enzyme, because increasing the half-life of guide RNAs introduced at the same time as the RNA encoding the CRISPR enzyme can be used to increase the time that the guide RNAs and the encoded CRISPR enzyme co-exist in the cell.

Modifications may also or alternatively be used to decrease the likelihood or degree to which RNAs introduced into cells elicit innate immune responses. Such responses tend to be associated with reduced half-life of the RNA and/or the elicitation of cytokines or other factors associated with immune responses.

One or more types of modifications can also be made to RNAs encoding a CRISPR enzyme that are introduced into a cell, including, without limitation, modifications that enhance the stability of the RNA, modifications that enhance translation of the resulting product (i.e. the CRISPR enzyme), and/or modifications that decrease the likelihood or degree to which the RNAs introduced into cells elicit innate immune responses.

By way of illustration of various types of modifications, especially those used frequently with smaller chemically synthesized RNAs, modifications can comprise one or more nucleotides modified at the 2' position of the sugar, in some aspects a 2'-O-alkyl, 2'-O-alkyl-O-alkyl, or 2'-fluoro-modified nucleotide. In some examples, RNA modifications can comprise 2'-fluoro, 2'-amino or 2'-O-methyl modifications on the ribose of pyrimidines, abasic residues, or an inverted base at the 3' end of the RNA. Such modifications can be routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide. These modified oligos survive intact for a longer period of time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, CH, ~N($CH_3$)—O—$CH_2$ (known as a methylene(methylimino) or MMI backbone), $CH_2$—O—N ($CH_3$)—$CH_2$, $CH_2$—N($CH_3$)—N ($CH_3$)—$CH_2$ and O—N($CH_3$)—$CH_2$—$CH_2$ backbones, wherein the native phosphodiester backbone is represented as O— P— O— CH); amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3-5' linkages, 2'-5' linked analogs of these, and those having inverted polarity wherein the adjacent pairs of nucleoside units are linked 3'-5' to 5-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41(14): 4503-4510 (2002); Genesis, Volume 30, Issue 3, (2001); Heasman, Dev. Biol., 243: 209-214 (2002); Nasevicius et al., Nat. Genet., 26:216-220 (2000); Lacerra et al., Proc. Natl. Acad. Sci., 97: 9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

One or more substituted sugar moieties can also be included, e.g., one of the following at the 2' position: OH, SH, $SCH_3$, F, OCN, $OCH_3$ $OCH_3$, $OCH_3O(CH_2)n$ $CH_3$, $O(CH_2)n$ $NH_2$, or $O(CH_2)n$ $CH_3$, where n is from 1 to about 10; C1 to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some aspects, a modification includes 2'-methoxyethoxy (2'-O—$CH_2CH_2OCH_3$, also known as 2'-O-(2-methoxyethyl)) (Martin et al, Helv. Chim. Acta, 1995, 78, 486). Other modifications include 2'-methoxy (2'-O—$CH_3$), 2'-propoxy (2'-$OCH_2$ $CH_2CH_3$) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some examples, both a sugar and an internucleoside linkage, i.e., the backbone, of the nucleotide units can be replaced with novel groups. The base units can be maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide can be replaced with an amide containing backbone, for example, an aminoethylglycine backbone. The nucleobases can be retained and bound directly or indirectly to aza nitrogen atoms of the amide portion of the backbone. Representative U.S. patents that teach the preparation of PNA compounds comprise, but are not limited to, U.S. Pat. Nos. 5,539,082; 5,714,331; and 5,719,262. Further teaching of PNA compounds can be found in Nielsen et al, Science, 254: 1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases that are not found, or found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino) adenine, 2-(imidazolylalkyl)adenine, 2-(aminoalklyamino) adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl) adenine, and 2,6-diaminopurine. Kornberg, A., DNA Replication, W. H. Freeman & Co., San Francisco, pp. 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases can comprise those disclosed in U.S. Pat. No. 3,687,808, those disclosed in 'The Concise Encyclopedia of Polymer Science and Engineering', pages 858-859, Kroschwitz, J. I., ed. John Wley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of oligomeric compounds. These include 5-substituted pyrimidines, 6-azapyrimidines and N-2, N-6 and O-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are aspects of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and U.S. Patent Application Publication 2003/0158403.

Thus, the term "modified" refers to a non-natural sugar, phosphate, or base that is incorporated into a nucleic acid such as a guide RNA or a nucleic acid encoding a CRISPR enzyme. It is not necessary for all positions in a given nucleic acid molecule to be uniformly modified, and in fact more than one of the aforementioned modifications can be incorporated in a nucleic acid molecule, or even in a single nucleoside within an oligonucleotide.

The guide RNAs and/or the RNA or DNA encoding a CRISPR enzyme may be chemically linked to one or more moieties or conjugates that enhance the activity, cellular distribution, or cellular uptake. Such moieties comprise, but are not limited to, lipid moieties such as a cholesterol moiety [Letsinger et al., Proc. Natl. Acad. Sci. USA, 86: 6553-6556 (1989)]; cholic acid [Manoharan et al., Bioorg. Med. Chem. Let., 4: 1053-1060 (1994)]; a thioether, e.g., hexyl-S-tritylthiol [Manoharan et al, Ann. N. Y. Acad. Sci., 660: 306-309 (1992) and Manoharan et al., Bioorg. Med. Chem. Let., 3: 2765-2770 (1993)]; a thiocholesterol [Oberhauser et al., Nucl. Acids Res., 20: 533-538 (1992)]; an aliphatic chain, e.g., dodecandiol or undecyl residues [Kabanov et al., FEBS Lett., 259: 327-330 (1990) and Svinarchuk et al., Biochimie, 75: 49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36: 3651-3654 (1995) and Shea et al., Nucl. Acids Res., 18: 3777-3783 (1990)]; a polyamine or a polyethylene glycol chain [Mancharan et al., Nucleosides & Nucleotides, 14: 969-973 (1995)]; adamantane acetic acid [Manoharan et al., Tetrahedron Lett., 36: 3651-3654 (1995)]; a palmityl moiety [(Mishra et al., Biochim. Biophys. Acta, 1264: 229-237 (1995)]; or an octadecylamine or hexylamino-carbonyl-t oxycholesterol moiety [Crooke et al., J. Pharmacol. Exp. Ther., 277: 923-937 (1996)]. See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., Protein Pept Lett. 21(10):1025-30 (2014). Other systems known in the art and regularly developed can be used to target biomolecules of use in the present case and/or complexes thereof to particular target cells of interest. These targeting moieties or conjugates can include conjugate groups covalently bound to functional groups, such as primary or secondary hydroxyl groups. Conjugate groups of the present disclosure include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this present disclosure, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present disclosure. Representative conjugate groups are disclosed in International Patent Application No. PCT/US92/09196, filed Oct. 23, 1992 (published as WO1993007883), and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium I,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9. Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al. and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7(5):618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs such as (m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNAs used in RNA interference (RNAi), including small-interfering RNAs (siRNAs). siRNAs present particular challenges in vivo because their effects on gene silencing via RNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g., the reviews by Angart et al., Pharmaceuticals (Basel) 6(4): 440-468 (2013); Kanasty et al., Molecular Therapy 20(3): 513-524 (2012); Burnett et al., Biotechnol J. 6(9):1130-46 (2011); Judge and MacLachlan, Hum Gene Ther 19(2):111-24 (2008).

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2: 77-96 (2011); Gaglione and Messere, Mini Rev Med Chem, 10(7):578-95 (2010); Chernolovskaya et al, Curr Opin Mol Ther., 12(2):158-67 (2010); Deleavey et al., Curr Protoc Nucleic Acid Chem Chapter 16: Unit 16.3 (2009); Behlke, Oligonucleotides 18(4):305-19 (2008); Fucini et al., Nucleic Acid Ther 22(3): 205-210 (2012); Bremsen et al., Front Genet 3:154 (2012).

There are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013).

Target Sequence Selection

Many endonuclease systems have rules or criteria that can guide the initial selection of potential target sites for cleavage, such as the requirement of a PAM sequence in a particular position adjacent the DNA cleavage site in the case of CRISPR Type II or Type V enzymes.

The frequency of off-target activity can be assessed relative to the frequency of on-target activity. In some cases, cells that have been correctly targeted at the desired locus can have a selective advantage relative to other cells. Illustrative, but non-limiting, examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly targeted at the desired locus can be positively selected for by one or more screening methods used to identify, sort or otherwise select for cells that have been correctly targeted. In some cases, cells can be targeted two or more times in order to select or purify the intended population of cells. Such a second targeting could be created by adding a second gRNA for a selectable or screenable marker. DNA or RNA sequencing such as whole genome sequencing can be used to detect off-target activity.

The occurrence of off-target activity can be influenced by a number of factors including similarities and dissimilarities between the target site and various off-target sites, as well as the particular CRISPR enzyme used. Bioinformatics tools such as MIT's CRISPR design tool (http://crispr.mit.edu; Ran et al. 2013. *Nat. Protoc.* 8(11): 2281-2308) are available to assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities.

Nucleic Acids Encoding System Components

Those skilled in the art will understand that RNA molecules of the present disclosure (eg, guide RNA) may be introduced into a cell directly or via a DNA molecule which is transcribed to produce the RNA. In either case, the RNA is considered to be introduced into the cell. Similarly, proteins such as a CRISPR enzyme or an adapter protein may be delivered to a cell directly or as an RNA molecule which is translated or as a DNA molecule which is transcribed to produce an RNA molecule which is subsequently translated.

The nucleic acids of the present disclosure may include a vector (eg, a recombinant expression vector). The term "vector" refers to a nucleic acid capable of transporting another nucleic acid to which it has been linked. One type of vector is a "plasmid", which refers to a circular double-stranded DNA loop into which additional nucleic acid segments can be ligated. Another type of vector is a viral vector; wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, Calif. (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3. Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., *Molecular Therapy—Nucleic Acids* 3, el 61 (2014) doi:10.1038/mtna.2014.12.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

A polynucleotide encoding a CRISPR enzyme of the disclosure, an adapter protein of the disclosure, a transcriptional activation domain of the disclosure (or a protein comprising a transcriptional activation domain) and/or any proteinaceous molecule necessary to carry out the aspects of the methods of the disclosure can be codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Delivery and Treatments

The present disclosure provides methods for increasing expression of a Klotho gene in a human cell the method comprising introducing into the cell: a CRISPR enzyme; and a guide RNA comprising a guide sequence that is substantially complementary to a target sequence within or near the Klotho gene, wherein the guide RNA associates with a transcriptional activation domain in the cell to thereby increase expression of the Klotho gene. The methods may comprise introducing into the cell an adapter protein capable of binding to the guide RNA wherein the adapter protein comprises or is attached to the transcriptional activation domain. It will be understood that the guide RNA may be delivered directly into the cell, or as a DNA vector which is transcribed in the cell to thereby produce the guide RNA. Likewise, the CRISPR enzyme and the adapter protein may be introduced into the cell directly, or one or both may be introduced as a DNA or RNA molecule which is transcribed (in the case of a DNA molecule) and translated to thereby produce the CRISPR enzyme and/or the adapter protein.

Guide RNA polynucleotides (RNA or DNA) and/or polynucleotides encoding a CRISPR enzyme of the disclosure, an adapter protein of the disclosure, a transcriptional activation domain of the disclosure (or a protein comprising a transcriptional activation domain) and/or any proteinaceous molecule necessary to carry out the aspects of the methods of the disclosure can be delivered by viral or non-viral delivery vehicles known in the art. Alternatively, CRISPR enzyme polypeptides, adapter proteins and activation domain polypeptides can be delivered by viral or non-viral delivery vehicles known in the art, such as electroporation or lipid nanoparticles. In further alternative aspects, the CRISPR enzyme polypeptides, adapter proteins and activation domain polypeptides can be delivered as one or more polypeptides, either alone or pre-complexed with one or more guide RNAs.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011) (which focuses on non-viral delivery vehicles for siRNA that are also useful for delivery of other polynucleotides).

Polynucleotides, such as guide RNA, sgRNA, and mRNA, can be delivered to a cell or a patient by a lipid nanoparticle (LNP). A LNP has a diameter of less than about 1000 nm, about 500 nm, about 250 nm, about 200 nm, about 150 nm, about 100 nm, about 75 nm, about 50 nm, or about 25 nm. Alternatively, a nanoparticle can range in size from about 1-1000 nm, about 1-500 nm, about 1-250 nm, about 25-200 nm, about 25-100 nm, about 35-75 nm, or about 25-60 nm. LNPs can be made from cationic, anionic or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses. LNPs can also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20. The lipids can be combined in any number of molar ratios to produce a LNP. In addition, the polynucleotide(s) can be combined with lipid(s) in a wide range of molar ratios to produce a LNP.

The CRISPR enzyme, the adapter protein and guide RNA can each be administered separately to a cell or a patient. On the other hand, the CRISPR enzyme and/or the adapter protein can be pre-complexed with one or more guide RNAs. The pre-complexed material can then be administered to a cell or a patient. Such pre-complexed material is known as a ribonucleoprotein particle (RNP). RNPs can provide the advantage of reducing undesirable nucleic acid interactions, and protecting the RNA from degradation.

Adeno-Associated Virus (AAV)

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are known in the art. Production of rAAV typically prefers that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes described herein. Production of pseudotyped rAAV is disclosed in, for example, international patent application publication number WO 01/83692.

AAV particles packaging polynucleotides encoding compositions of the present disclosure, e.g., CRISPR enzyme, adapter protein or RNA guide molecules can comprise or be derived from any natural or recombinant AAV serotype. According to the present disclosure, the AAV particles can utilize or be based on a serotype selected from any of the following serotypes, and variants thereof including but not limited to AAV1, AAV10, AAV106.1/hu.37, AAV11, AAV114.3/hu.40, AAV12, AAV127.2/hu.41, AAV127.5/hu.42, AAV128.1/hu.43, AAV128.3/hu.44, AAV130.4/hu.48, AAV145.1/hu.53, AAV145.5/hu.54, AAV145.6/hu.55, AAV16.12/hu.11, AAV16.3, AAV16.8/hu.10, AAV161.10/hu.60, AAV161.6/hu.61, AAV1-7/rh.48, AAV1-8/rh.49, AAV2, AAV2.5T, AAV2-15/rh.62, AAV223.1, AAV223.2, AAV223.4, AAV223.5, AAV223.6, AAV223.7, AAV2-3/rh.61, AAV24.1, AAV2-4/rh.50, AAV2-5/rh.51, AAV27.3, AAV29.3/bb.1, AAV29.5/bb.2, AAV2G9, AAV-2-pre-miRNA-101, AAV3, AAV3.1/hu.6, AAV3.1/hu.9, AAV3-11/rh.53, AAV3-3, AAV33.12/hu.17, AAV33.4/hu.15, AAV33.8/hu.16, AAV3-9/rh.52, AAV3a, AAV3b, AAV4, AAV4-19/rh.55, AAV42.12, AAV42-10, AAV42-11, AAV42-12, AAV42-13, AAV42-15, AAV42-1 b, AAV42-2, AAV42-3a, AAV42-3b, AAV42-4, AAV42-5a, AAV42-5b, AAV42-6b, AAV42-8, AAV42-aa, AAV43-1, AAV43-12, AAV43-20, AAV43-21, AAV43-23, AAV43-25, AAV43-5, AAV4-4, AAV44.1, AAV44.2, AAV44.5, AAV46.2/hu.28, AAV46.6/hu.29, AAV4-8/r11.64, AAV4-8/rh.64, AAV4-9/rh.54, AAV5, AAV52.1/hu.20, AAV52/hu.19, AAV5-22/rh.58, AAV5-3/rh.57, AAV54.1/hu.21, AAV54.2/hu.22, AAV54.4R/hu.27, AAV54.5/hu.23, AAV54.7/hu.24, AAV58.2/hu.25, AAV6, AAV6.1, AAV6.1.2, AAV6.2, AAV7, AAV7.2, AAV7.3/hu.7, AAV8, AAV-8b, AAV-8h, AAV9, AAV9.11, AAV9.13, AAV9.16, AAV9.24, AAV9.45, AAV9.47, AAV9.61, AAV9.68, AAV9.84, AAV9.9, AAVA3.3, AAVA3.4, AAVA3.5, AAVA3.7, AAV-b, AAVC1, AAVC2, AAVC5, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAV-DJ, AAV-DJ8, AAVF3, AAVF5, AAV-h, AAVH-1/hu.1, AAVH2, AAVH-5/hu.3, AAVH6, AAVhE1.1, AAVhER1.14, AAVhEr1.16, AAVhEr1.18, AAVhER1.23, AAVhEr1.35, AAVhEr1.36, AAVhEr1.5, AAVhEr1.7, AAVhEr1.8, AAVhEr2.16, AAVhEr2.29, AAVhEr2.30, AAVhEr2.31, AAVhEr2.36, AAVhEr2.4, AAVhEr3.1, AAVhu.1, AAVhu.10, AAVhu.11, AAVhu.11, AAVhu.12, AAVhu.13, AAVhu.14/9, AAVhu.15, AAVhu.16, AAVhu.17, AAVhu.18, AAVhu.19, AAVhu.2, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.3, AAVhu.31, AAVhu.32, AAVhu.34, AAVhu.35, AAVhu.37, AAVhu.39, AAVhu.4, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.5, AAVhu.51, AAVhu.52, AAVhu.53, AAVhu.54, AAVhu.55, AAVhu.56, AAVhu.57, AAVhu.58, AAVhu.6, AAVhu.60, AAVhu.61, AAVhu.63, AAVhu.64, AAVhu.66, AAVhu.67, AAVhu.7, AAVhu.8, AAVhu.9, AAVhu.t 19, AAVLG-10/rh.40, AAVLG-4/rh.38, AAVLG-9/hu.39, AAVLG-9/hu.39, AAV-LK01, AAV-LK02, AAVLK03, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK17, AAV-LK18, AAV-LK19, AAVN721-8/rh.43, AAV-PAEC, AAV-PAEC11, AAV-PAEC12, AAV-PAEC2, AAV-PAEC4, AAV-PAEC6, AAV-PAEC7, AAV-PAEC8, AAVpi.1, AAVpi.2, AAVpi.3, AAVrh.10, AAVrh.12, AAVrh.13, AAVrh.13R, AAVrh.14, AAVrh.17, AAVrh.18, AAVrh.19, AAVrh.2, AAVrh.20, AAVrh.21, AAVrh.22, AAVrh.23, AAVrh.24, AAVrh.25, AAVrh.2R, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.43, AAVrh.44, AAVrh.45, AAVrh.46, AAVrh.47, AAVrh.48, AAVrh.48, AAVrh.48.1, AAVrh.48.1.2, AAVrh.48.2, AAVrh.49, AAVrh.50, AAVrh.51, AAVrh.52, AAVrh.53, AAVrh.54, AAVrh.55, AAVrh.56, AAVrh.57, AAVrh.58, AAVrh.59, AAVrh.60, AAVrh.61, AAVrh.62, AAVrh.64, AAVrh.64R1, AAVrh.64R2, AAVrh.65, AAVrh.67, AAVrh.68, AAVrh.69, AAVrh.70, AAVrh.72, AAVrh.73, AAVrh.74, AAVrh.8, AAVrh.8R, AAVrh8R, AAVrh8R A586R mutant, AAVrh8R R533A mutant, BAAV, BNP61 AAV, BNP62 AAV, BNP63 AAV, bovine AAV, caprine AAV, Japanese AAV 10, true type AAV (ttAAV), UPENN AAV 10, AAV-LK16, AAAV, AAV Shuffle 100-1, AAV Shuffle 100-2, AAV Shuffle 100-3, AAV Shuffle 100-7, AAV Shuffle 10-2, AAV Shuffle 10-6, AAV Shuffle 10-8, AAV SM 100-10, AAV SM 100-3, AAV SM 10-1, AAV SM 10-2, and/or AAV SM 10-8.

In some examples, the AAV serotype can be, or have, a mutation in the AAV9 sequence as described by N Pulicherla et al. (Molecular Therapy 19(6):1070-1078 (2011), such as but not limited to, AAV9.9, AAV9.11, AAV9.13, AAV9.16, AAV9.24, AAV9.45, AAV9.47, AAV9.61, AAV9.68, AAV9.84.

In some examples, the AAV serotype can be, or have, a sequence as described in U.S. Pat. No. 6,156,303, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some examples, the serotype can be AAVDJ or a variant thereof, such as AAVDJ8 (or AAV-DJ8), as described by Grimm et al. (Journal of Virology 82(12): 5887-5911 (2008)). The amino acid sequence of AAVDJ8 can comprise two or more mutations in order to remove the heparin binding domain (HBD). As a non-limiting example, the AAV-DJ sequence described as SEQ ID NO: 1 in U.S. Pat. No. 7,588,772, can comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, can comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some examples, the AAV serotype can be, or have, a sequence as described in International Publication No. WO2015121501, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present disclosure, AAV capsid serotype selection or use can be from a variety of species. In one example, the AAV can be an avian AAV (AAAV). The AAAV serotype can be, or have, a sequence as described in U.S. Pat. No. 9,238,800, such as, but not limited to, AAAV (SEQ ID NO: 1, 2, 4, 6, 8, 10, 12, and 14 of U.S. Pat. No. 9,238,800), or variants thereof.

In some examples, the AAV can be a bovine AAV (BAAV). The BAAV serotype can be, or have, a sequence as described in U.S. Pat. No. 9,193,769, such as, but not limited to, BAAV (SEQ ID NO: 1 and 6 of U.S. Pat. No. 9,193,769), or variants thereof. The BAAV serotype can be or have a sequence as described in U.S. Pat. No. 7,427,396, such as, but not limited to, BAAV (SEQ ID NO: 5 and 6 of U.S. Pat. No. 7,427,396), or variants thereof.

In some examples, the AAV can be a caprine AAV. The caprine AAV serotype can be, or have, a sequence as described in U.S. Pat. No. 7,427,396, such as, but not limited to, caprine AAV (SEQ ID NO: 3 of U.S. Pat. No. 7,427,396), or variants thereof.

In other examples the AAV can be engineered as a hybrid AAV from two or more parental serotypes. In one example, the AAV can be AAV2G9 which comprises sequences from AAV2 and AAV9. The AAV2G9 AAV serotype can be, or have, a sequence as described in United States Patent Publication No. US20160017005.

In some examples, the AAV can be a serotype generated by the AAV9 capsid library with mutations in amino acids 390-627 (VP1 numbering) as described by Pulicherla et al. (Molecular Therapy 19(6):1070-1078 (2011). The serotype and corresponding nucleotide and amino acid substitutions can be, but is not limited to, AAV9.1 (G1594C; D532H), AAV6.2 (T1418A and T1436X; V473D and I479K), AAV9.3 (T1238A; F413Y), AAV9.4 (T12500 and A1617T; F417S), AAV9.5 (A1235G, A1314T, A1642G, 01760T; Q412R, T548A, A587V), AAV9.6 (T1231A; F4111), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T4921, H527N), AAV.59 (T1336C; Y446H), AAV9.61 (A1493T; N4981), AAV9.64 (C1531A, A1617T; L511I), AAV9.65 (C1335T, T1530C, C1568A; A523D), AAV9.68 (C1510A; P504T), AAV9.80 (G1441A, G481R), AAV9.83 (C1402A, A1500T; P4681, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, A1712T, G1732A, A1744T, A1832T; S425G, Q474R, Q546H, P571L, G578R, T582S, D611V), AAV9.94 (A16751; M559L) and AAV9.95 (T1605A; F535L).

In some examples, the AAV can be a serotype comprising at least one AAV capsid CD8+ T-cell epitope. As a non-limiting example, the serotype can be AAV1, AAV2 or AAV8.

In some examples, the AAV can be a variant, such as PHP.A or PHP.B as described in Deverman. 2016. Nature Biotechnology. 34(2): 204-209.

A method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Viral., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others:

TABLE 4

| Tissue/Cell Type | Serotype |
| --- | --- |
| Liver | AAV3, AA5, AAV8, AAV9 |
| Skeletal muscle | AAV1, AAV7, AAV6, AAV8, AAV9 |
| Central nervous system | AAV1, AAV4, AAV5, AAV8, AAV9 |
| RPE | AAV5, AAV4, AAV2, AAV8, AAV9 AAVrh8r |
| Photoreceptor cells | AAV5, AAV8, AAV9, AAVrh8R |
| Lung | AAV9, AAV5 |
| Heart | AAV8 |
| Pancreas | AAV8 |
| Kidney | AAV2, AAV8 |

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirusr, poxvirus, vaccinia virus, and herpes simplex virus.

In some cases, the components of the present disclosure (eg, gRNA, CRISPR enzyme and adapter protein) are each separately formulated into lipid nanoparticles, or are all co-formulated into one lipid nanoparticle. In some cases, the CRISPR enzyme is formulated in a lipid nanoparticle, while the gRNA is delivered in a viral vector such as an AAV vector. A range of non-viral delivery methods also exist that can deliver each of these components, or non-viral and viral methods can be employed in tandem.

Lentivirus

In some examples, lentiviral vectors or particles can be used as delivery vehicles. Lentiviruses are subgroup of the Retroviridae family of viruses. Lentiviral particles are able to integrate their genetic material into the genome of a target/host cell. Examples of lentivirus include the Human Immunodeficiency Viruses: HIV-1 and HIV-2, Jembrana Disease Virus (JDV), equine infectious anemia virus (EIAV), equine infectious anemia virus, visna-maedi and caprine arthritis encephalitis virus (CAEV), the Simian Immunodeficiency Virus (SIV), feline immunodeficiency virus (FIV), bovine immunodeficiency virus (BIV). LV's are capable of infecting both dividing and non-dividing cells due to their unique ability to pass through a target cell's intact nuclear membrane Greenberg et al., University of Berkeley, Calif.; 2006). Lentiviral particles that form the gene delivery vehicle are replication defective and are generated by attenuating the HIV virulence genes. For example, the genes Vpu, Vpr, Nef, Env, and Tat are excised making the vector biologically safe. Lentiviral vehicles, for example, derived from HIV-1/HIV-2 can mediate the efficient delivery, integration and long-term expression of transgenes into non-dividing cells.

In order to produce a lentivirus that is capable of infecting host cells, three types of vectors should be co-expressed in virus producing cells: a backbone vector containing the transgene of interests and self-inactivating 3'-LTR regions, one construct expressing viral structure proteins, and one vector encoding vesicular stomatitis virus glycoprotein (VSVG) for encapsulation (Naldini, L. et al., Science 1996; 272, 263-267). Separation of the Rev gene from other structural genes further increases the biosafety by reducing the possibility of reverse recombination. Cell lines that can be used to produce high-titer lentiviral particles may include, but are not limited to 293T cells, 293FT cells, and 293SF-3F6 cells (Witting et al., Human Gene Therapy, 2012; 23: 243-249; Ansorge et al., Journal of Genetic Medicine, 2009; 11: 868-876).

Methods for generating recombinant lentiviral particles are discussed in the art, for example, WO 2013076309 (PCT/EP2012/073645); WO 2009153563 (PCT/GB2009/001527); U.S. Pat. Nos. 7,629,153; and 6,808,905.

Guide RNA Formulation

Guide RNAs of the present disclosure can be formulated with pharmaceutically acceptable excipients such as carriers, solvents, stabilizers, adjuvants, diluents, etc., depending upon the particular mode of administration and dosage form. Guide RNA compositions can be formulated to achieve a physiologically compatible pH, and range from a pH of about 3 to a pH of about 11, for example, from about pH 3 to about pH 7, depending on the formulation and route of administration. In some cases, the pH can be adjusted to a range from about pH 5 to about pH 8. In some cases, the compositions can comprise a therapeutically effective amount of at least one compound as described herein, together with one or more pharmaceutically acceptable excipients.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Administration and Efficacy

In some examples, the compositions of the present disclosure are administered via a route such as, but not limited to, enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration, which is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis and spinal.

Modes of administration include injection, infusion, instillation, and/or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be made.

In addition, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). The release system material can be selected so that components having different molecular weights are released by diffusion or through degradation of the material. Representative synthetic, biodegradable polymers include, for example: polyamides such as poly (amino acids) and poly(peptides); polyesters such as poly (lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof. Poly(lactide-co-glycolide) microspheres can also be used.

Dosages may vary with the type and severity of the condition to be treated, and may include single or multiple dosses. Specific dosage regimens may be adjusted over time according to the individual need and the professional judgment of the practitioner administering the composition. When administered to a human subject, the dosage regimen may vary depending on a variety of factors including the type and severity of the condition, the age, sex, weight or medical condition of the subject and the route of administration.

The compositions described herein may be administered over a period of hours, days, weeks, or months, depending on several factors, including the severity of the condition being treated, whether a recurrence is considered likely, etc. The administration may be constant, eg, constant infusion over a period of hours, days, weeks, months, etc. Alternatively, the administration may be intermittent, eg, once per day over a period of days, once per hour over a period of hours, or any other such schedule as deemed suitable.

Treatments

The present disclosure provides methods of treating a neurological disorder in a subject the method comprising administering to the subject: a CRISPR enzyme; and a guide RNA comprising a guide sequence that is substantially complementary to a target sequence within or near the Klotho gene of the subject, wherein the guide RNA associates with a transcriptional activation domain in a cell of the subject and thereby increases expression of the Klotho gene. The neurological disorder may be associated with memory loss, psychological dysfunction, stress, biopolar disorder, epilepsy, dementia (eg, post stroke dementia, post-traumatic dementia, senile dementia), Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress, neurogenic decline or neurodegeneration. Symptoms of neurological disorders may include memory loss, anxiety, depression, insomnia, disorientation, irrational fear, decline of motor skills or locomotor activity, neophobia, apathy, agitation, tremors, loss of balance, irritability or agoraphobia.

In certain examples, the present disclosure provides a method of treating a neurological disorder in a human subject the method comprising administering to the subject: a CRISPR enzyme; a single-molecule guide RNA comprising a guide sequence that is substantially complementary to a target sequence within or near a Klotho gene of the subject; and an adapter protein capable of binding to the guide RNA wherein the adapter protein comprises or is attached to a transcriptional activation domain. In certain examples, the present disclosure provides a method of treating a neurological disorder in a human subject the method comprising administering to the subject: a CRISPR enzyme; a single-molecule guide RNA comprising a guide sequence that is substantially complementary to a nucleotide sequence set forth in SEQ ID NO. 9 or SEQ ID NO. 10, such as to a nucleotide sequence set forth in SEQ ID NO. 11 or SEQ ID NO. 12; and an adapter protein capable of binding to the guide RNA wherein the adapter protein comprises or is attached to a transcriptional activation domain. In certain examples, the present disclosure provides a method of treating a neurological disorder in a human subject the method comprising increasing expression of a Klotho gene of the subject by administering to the subject: a CRISPR enzyme; a single-molecule guide RNA comprising a guide sequence that is substantially complementary to a target sequence located within a region between 200 nucleotides and 300 nucleotides upstream of the Klotho gene translation start site; and an adapter protein capable of binding to the guide RNA wherein the adapter protein comprises or is attached to a transcriptional activation domain. In certain examples, the present disclosure provides a method of treating a neurological disorder in a human subject the method comprising administering to the subject: a CRISPR enzyme; a single-molecule guide RNA comprising a guide sequence that is substantially complementary to a nucleotide sequence set forth in SEQ ID NO. 13 or SEQ ID NO. 14; and an adapter protein capable of binding to the guide RNA wherein the adapter protein comprises or is attached to a transcriptional activation domain. In certain examples, the present disclosure provides a method of treating a neurological disorder in a human subject the method comprising administering to the subject: a CRISPR enzyme; a single-molecule guide RNA comprising a guide sequence that is at least 90% identical to a nucleotide sequence set forth in any one of SEQ ID NOs 1 to 4; and an adapter protein capable of binding to the guide RNA wherein the adapter protein comprises or is attached to a transcriptional activation domain. In certain examples, the present disclosure provides a method of treating a neurological disorder in a human subject the method comprising administering to the subject: a CRISPR enzyme; a single-molecule guide RNA comprising a guide sequence that is substantially complementary to a nucleotide sequence set forth in SEQ ID NO. 13 or SEQ ID NO. 14; and an adapter protein capable of binding to the guide RNA wherein the adapter protein comprises or is attached to a transcriptional activation domain, wherein the neurological disorder is selected from the group consisting of memory loss, stress, biopolar disorder, epilepsy, dementia, Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress and neurodegeneration. In certain examples, the present disclosure provides a method of treating a neurological disorder in a human subject the method comprising increasing expression of a Klotho gene of the subject by administering to the subject: a CRISPR enzyme; a single-molecule guide RNA comprising a guide sequence that is substantially complementary to a target sequence located within a region between 200 nucleotides and 300 nucleotides upstream of the Klotho gene translation start site; and an adapter protein capable of binding to the guide RNA wherein the adapter protein is MS2 fused to p65 and HSF1, and wherein the CRISPR enzyme is fused to VP64, and wherein the CRISPR enzyme is dead Cas9 (dCas9).

In certain examples, the present disclosure provides a method of treating a neurological disorder in a human subject the method comprising administering to the subject: a single-molecule guide RNA comprising a guide sequence that is substantially complementary to a target sequence located within a region between 200 nucleotides and 300 nucleotides upstream of the Klotho gene translation start site; and a dead Cas9 (dCas9), wherein the dCas9 is attached to VP64 via a GCN4 fusion. In certain examples, the present disclosure provides a method of treating a neurological disorder in a human subject the method comprising administering to the subject: a single-molecule guide RNA comprising a guide sequence that is substantially complementary to a target sequence located within a region between 200 nucleotides and 300 nucleotides upstream of the Klotho gene translation start site; and a dead Cas9 (dCas9), wherein the dCas9 is fused to VP64. In certain examples, the present disclosure provides a method of treating a neurological disorder in a human subject the method comprising administering to the subject: a single-molecule guide RNA comprising a guide sequence that is substantially complementary to a target sequence located within a region between 200 nucleotides and 300 nucleotides upstream of the Klotho gene translation start site; and a dead Cas9 (dCas9), wherein the dCas9 is fused to VP64, p65 and RTA. In certain examples, the present disclosure provides a method of treating a neurological disorder in a human subject the method comprising administering to the subject: a single-molecule guide RNA comprising a guide sequence that is substantially complementary to a nucleotide sequence set forth in SEQ ID NO. 9 or SEQ ID NO. 10, such as to a nucleotide sequence set forth in SEQ ID NO. 11 or SEQ ID NO. 12; and a CRISPR enzyme, wherein the CRISPR enzyme comprises or is attached to a transcriptional activation domain. In certain examples, the present disclosure provides a method of treating a neurological disorder in a human subject the method comprising administering to the subject: a single-molecule guide RNA comprising a guide sequence that is at least 90% identical to a nucleotide sequence set forth in any one of SEQ ID NOs 1 to 4; and a CRISPR enzyme, wherein the CRISPR enzyme comprises or is attached to a transcriptional activation domain. In certain examples, the present disclosure provides a method of treating a neurological disorder in a human subject the method comprising administering to the subject: a single-molecule guide RNA comprising a guide sequence that is substantially complementary to a nucleotide sequence set forth in SEQ ID NO. 13 or SEQ ID NO. 14; and a CRISPR enzyme, wherein the CRISPR enzyme comprises or is attached to a transcriptional activation domain.

The method may further comprise administering to the subject an active agent suitable for the treatment of a neurological disorder such as donepezil hydrochloride, memantine, rivastigmine, ligustilide, aripiprazole, asenapine, cariprazine, clozapine, lurasidone, olanzapine, quetiapine, risperidone, ziprasidone, xenazine, tetrabenazine, baclofen, lioresal, kemstro, deutetrabenazine, austedo, cannabis extract, a cannabinoid or cannabinol, an antidepressant, memantine, a cholinesterase inhibitor, an antipsychotic, antioxidants, levodopa, carbidopa, trazodone or dibenzoylmethane. Those skilled in the art will be aware of other active agents that may be suitable for treatment of neurological disorders.

The present disclosure also provides a method of enhancing cognitive ability in a subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene. For example, the method may enhance memory or learning in the subject.

Klotho also plays important regulatory and protective roles in the kidney. In that regard, the present disclosure provides a method of treating renal dysfunction in a subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene. In certain examples, the renal dysfunction is associated with renal fibrosis. The present disclosure also provides a method of treating acute kidney injury or a kidney disease such as chronic kidney disease in a subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

Studies have also shown that Klotho plays important roles in regulating fertility. In that regard, the present disclosure provides a method of treating infertility in a subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

Klotho protein has been identified as a regulator of various tumorigenesis and cancer signalling pathways. In that regard, the present disclosure provides methods for treating cancer in a subject comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene. In certain examples the cancer is mediated by IGF-1, WNT, bFGF or TGF-β. The cancer may be colon cancer, prostate cancer, lung cancer, cervical cancer, pancreatic cancer, ovarian cancer or breast cancer. Further, non-limiting examples of cancer include leukemias (e.g., acute leukemia, acute lymphocytic leukemia, acute myelocytic leukemia, acute myeloblastic leukemia, acute promyclocytic leukemia, acute myclomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, Squamous cell carcinoma, basal cell carcinoma, adenocarcinoma, Sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, Small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, Schwannoma, meningioma, melanoma, neuroblastoma, and retinoblastoma). In some examples, the cancer is metastatic cancer.

The present disclosure also provides methods of suppressing tumorigenesis, such as breast tumorigenesis and pancreatic tumorigenesis in a subject comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

The present disclosure also provides methods for treating an age-related condition in a subject comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene. The age-related condition may be sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, memory loss, wrinkles, impaired kidney function or hearing loss.

The present disclosure also provides methods for treating a muscular disorder such as muscle atrophy and muscular dystrophy (eg, duchene muscular dystrophy) in a subject comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene. Muscle atrophy is associated with numerous neuromuscular, metabolic, immunological and neurological disorders and diseases as well as starvation, nutritional deficiency, metabolic stress, diabetes, aging, muscular dystrophy or myopathy. Symptoms include a decline in skeletal muscle tissue mass. In human males, muscle mass declines by one-third between the ages of 50 and 80. Some molecular features of muscle atrophy include the upregulation of ubiquitin ligases, and the loss of myofibrillar proteins (Furuno et al. 1990. J. Biol. Chem. 265: 8550-8557). The degradation of these proteins can be detected, eg, by measuring 3-methyl-histidine production, which is a specific component of actin, and in certain muscles of myosin. Release of creatine kinase can also be indicative.

The present disclosure also provides methods for treating a metabolic disorder in a subject comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene. In certain examples, the metabolic disorder is selected from Type II Diabetes, Metabolic Syndrome, hyperglycemia and obesity.

Methods and Compositions of the Disclosure

In a first method, Method 1, the present disclosure provides a method of increasing expression of a Klotho gene in a human cell the method comprising introducing into the cell: a CRISPR enzyme; and a guide RNA comprising a guide sequence that is substantially complementary to a target sequence within or near the Klotho gene, wherein the guide RNA associates with a transcriptional activation domain in the cell to thereby increase expression of the Klotho gene.

In another method, Method 2, the present disclosure provides the method of Method 1 further comprising introducing into the cell an adapter protein capable of binding to the guide RNA wherein the adapter protein comprises or is attached to the transcriptional activation domain.

In another method, Method 3, the present disclosure provides the method of Method 2 wherein the adapter protein is selected from the group consisting of MS2, PP7, Qβ, F2, GA, fr, JP501, M12, R17, BZ13, JP34, JP500, KU1, M11, MX1, TW18, VK, SP, FI, 102, NL95, TW19, AP205, φCb5, φCb8r, φCb12r, φCb23r, 7s and PRR1.

In another method, Method 4, the present disclosure provides the Method of Method 2 or Method 3 wherein the adapter protein binds to a tetra-loop and/or a stem loop 2 of the guide RNA.

In another method, Method 5, there is provided the method of any one of Methods 1 to 4 wherein the target sequence is located within a region between the Klotho gene translation start site and 4000 nucleotides upstream of the Klotho gene translation start site.

In another method, Method 6, there is provided the method of any one of Methods 1 to 5 wherein the guide sequence is substantially complementary to a nucleotide sequence set forth in SEQ ID NO. 9 or SEQ ID NO. 10.

In another method, Method 7, there is provided the method of any one of Methods 1 to 6 wherein the target sequence is located within a region between 200 nucleotides and 4000 nucleotides upstream of the Klotho gene translation start site.

In another method, Method 8, there is provided the method of any one of Methods 1 to 7 wherein the guide sequence is substantially complementary to a nucleotide sequence set forth in SEQ ID NO. 11 or SEQ ID NO. 12.

In another method, Method 9, there is provided the method of any one of Methods 1 to 8 wherein the target sequence is located within a region between 200 nucleotides and 300 nucleotides upstream of the Klotho gene translation start site.

In another method, Method 10, there is provided the method of any one of Methods 1 to 9 wherein the target sequence is located within a region between 240 nucleotides and 300 nucleotides upstream of the Klotho gene translation start site.

In another method, Method 11, there is provided the method of any one of Methods 1 to 10 wherein the guide sequence is substantially complementary to a nucleotide sequence set forth in SEQ ID NO. 13 or SEQ ID NO. 14.

In another method, Method 12, there is provided the method of any one of Methods 1 to 11 wherein the guide sequence is between 14 nucleotides and 25 nucleotides in length.

In another method, Method 13, there is provided the method of any one of Methods 1 to 6 wherein the guide sequence comprises at least 14 contiguous nucleotides which are identical to a nucleotide sequence set forth in any one of SEQ ID NOs 1 to 4.

In another method, Method 14, there is provided the method of any one of Methods 1 to 13 wherein the guide sequence comprises at least 14 contiguous nucleotides which are identical to a nucleotide sequence set forth in SEQ ID NO. 3 or SEQ ID NO. 4.

In another method, Method 15, there is provided the method of any one of Methods 1 to 6 wherein the guide sequence is at least 90% identical to a nucleotide sequence set forth in any one of SEQ ID NOs 1 to 4.

In another method, Method 16, there is provided the method of any one of Methods 1 to 15 wherein the guide sequence is at least 90% identical to a nucleotide sequence set forth in SEQ ID NO. 3 or SEQ ID NO. 4.

In another method, Method 17, there is provided the method of any one of Methods 1 to 6 wherein the guide sequence is selected from a nucleotide sequence set forth in any one of SEQ ID NOs 1 to 4.

In another method, Method 18, there is provided the method of any one of Methods 1 to 17 wherein the guide sequence is selected from a nucleotide sequence set forth in SEQ ID NO. 3 and SEQ ID NO. 4.

In another method, Method 19, there is provided the method of any one of Methods 1 to 6 wherein the guide RNA is at least 90% identical to a nucleotide sequence set forth in any one of SEQ ID NOs 5 to 8.

In another method, Method 20, there is provided the method of any one of Methods 1 to 19 wherein the guide RNA is at least 90% identical to a nucleotide sequence set forth in SEQ ID NO. 7 or SEQ ID NO. 8.

In another method, Method 21, there is provided the method of any one of Methods 1 to 6 wherein the guide RNA comprises a nucleotide sequence set forth in any one of SEQ ID NOs 5 to 8.

In another method, Method 22, there is provided the method of any one of Methods 1 to 21 wherein the guide RNA comprises a nucleotide sequence set forth in SEQ ID NO. 7 or SEQ ID NO. 8.

In another method, Method 23, there is provided the method of any one of Methods 1 to 22 wherein the guide RNA is a single-molecule guide RNA (sgRNA).

In another method, Method 24, there is provided the method of any one of Methods 1 to 23 wherein the guide RNA is between about 100 nucleotides and 200 nucleotides in length.

In another method, Method 25, there is provided the method of any one of Methods 1 to 24 wherein the transcriptional activation domain is selected from the group consisting of VP16, or a plurality thereof, VP64, VP160, p65, MyoD1, HSF1, RTA, TET3CD, p300 and SET7/9.

In another method, Method 26, there is provided the method of any one of Methods 1 to 25 wherein the CRISPR enzyme comprises or is attached to a second transcriptional activation domain.

In another method, Method 27, there is provided the method of Method 26 wherein the second transcriptional activation domain is selected from the group consisting of VP16, or a plurality thereof, VP64, VP160, p65, MyoD1, HSF1, RTA, TET3CD, p300 and SET7/9.

In another method, Method 28, there is provided the method of any one of Methods 1 to 27 wherein the CRISPR enzyme comprises a mutation which abolishes or reduces its nuclease activity.

In another method, Method 29, there is provided the method of any one of Methods 1 to 28 wherein the CRISPR enzyme is Cas9.

In another method, Method 30, there is provided the method of any one of Methods 1 to 29 wherein the cell is a neuronal cell or a kidney cell.

In another method, Method 31, there is provided the method of any one of Methods 1 to 30 wherein the cell is inside a human body.

In another method, Method 32, there is provided a method of increasing expression of a Klotho gene in a human cell the method comprising introducing into the cell: a guide RNA comprising a guide sequence that is substantially complementary to a target sequence within or near the Klotho gene; and a CRISPR enzyme, wherein the CRISPR enzyme comprises or is attached to a transcriptional activation domain.

In another method, Method 33, there is provided the method of Method 32 wherein the target sequence is located within a region between the Klotho gene translation start site and 4000 nucleotides upstream of the Klotho gene translation start site.

In another method, Method 34, there is provided the method of Method 32 or Method 33 wherein the guide sequence is substantially complementary to a nucleotide sequence set forth in SEQ ID NO. 9 or SEQ ID NO. 10.

In another method, Method 35, there is provided the method of any one of Methods 32 to 34 wherein the target sequence is located within a region between 200 nucleotides and 4000 nucleotides upstream of the Klotho gene translation start site.

In another method, Method 36, there is provided the method of any one of Methods 32 to 35 wherein the guide sequence is substantially complementary to a nucleotide sequence set forth in SEQ ID NO. 11 or SEQ ID NO. 12.

In another method, Method 37, there is provided the method of any one of Methods 32 to 36 wherein the target sequence is located within a region between 200 nucleotides and 300 nucleotides upstream of the Klotho gene translation start site.

In another method, Method 38, there is provided the method of any one of Methods 32 to 37 wherein the target sequence is located within a region between 240 nucleotides and 300 nucleotides upstream of the Klotho gene translation start site.

In another method, Method 39, there is provided the method of any one of Methods 32 to 38 wherein the guide sequence is substantially complementary to a nucleotide sequence set forth in SEQ ID NO. 13 or SEQ ID NO. 14.

In another method, Method 40, there is provided the method of any one of Methods 32 to 39 wherein the guide sequence is between 14 nucleotides and 25 nucleotides in length.

In another method, Method 41, there is provided the method of any one of Methods 32 to 34 wherein the guide sequence comprises at least 14 contiguous nucleotides which are identical to a nucleotide sequence set forth in any one of SEQ ID NOs 1 to 4.

In another method, Method 42, there is provided the method of any one of Methods 32 to 41 wherein the guide sequence comprises at least 14 contiguous nucleotides which are identical to a nucleotide sequence set forth in SEQ ID NO. 3 or SEQ ID NO. 4.

In another method, Method 43, there is provided the method of any one of Methods 32 to 34 wherein the guide sequence is at least 90% identical to a nucleotide sequence set forth in any one of SEQ ID NOs 1 to 4.

In another method, Method 44, there is provided the method of any one of Methods 32 to 43 wherein the guide sequence is at least 90% identical to a nucleotide sequence set forth in SEQ ID NO. 3 or SEQ ID NO. 4.

In another method, Method 45, there is provided the method of any one of Methods 32 to 34 wherein the guide sequence is selected from a nucleotide sequence set forth in any one of SEQ ID NOs 1 to 4.

In another method, Method 46, there is provided the method of any one of Methods 32 to 45 wherein the guide sequence is selected from a nucleotide sequence set forth in SEQ ID NO. 3 and SEQ ID NO. 4.

In another method, Method 47, there is provided the method of any one of Methods 32 to 34 wherein the guide RNA is at least 90% identical to a nucleotide sequence set forth in any one of SEQ ID NOs 5 to 8.

In another method, Method 48, there is provided the method of any one of Methods 32 to 47 wherein the guide RNA is at least 90% identical to a nucleotide sequence set forth in SEQ ID NO. 7 or SEQ ID NO. 8.

In another method, Method 49, there is provided the method of any one of Methods 32 to 34 wherein the guide RNA comprises a nucleotide sequence set forth in any one of SEQ ID NOs 5 to 8.

In another method, Method 50, there is provided the method of any one of Methods 32 to 49 wherein the guide RNA comprises a nucleotide sequence set forth in SEQ ID NO. 7 or SEQ ID NO. 8.

In another method, Method 51, there is provided the method of any one of Methods 32 to 50 wherein the guide RNA is a single-molecule guide RNA (sgRNA).

In another method, Method 52, there is provided the method of any one of Methods 32 to 51 wherein the guide RNA is between about 100 nucleotides and about 200 nucleotides in length.

In another method, Method 53, there is provided the method of any one of Methods 32 to 52 wherein the transcriptional activation domain is selected from the group consisting of VP16, or a plurality thereof, VP64, VP160, p65, MyoD1, HSF1, RTA, TET3CD, p300 and SET7/9.

In another method, Method 54, there is provided the method of any one of Methods 32 to 53 wherein the CRISPR enzyme comprises a mutation which abolishes or reduces its nuclease activity.

In another method, Method 55, there is provided the method of any one of Methods 32 to 54 wherein the CRISPR enzyme is Cas9.

In another method, Method 56, there is provided the method of any one of Methods 32 to 55 wherein the cell is a neuronal cell or a kidney cell.

In another method, Method 57, there is provided the method of any one of Methods 32 to 56 wherein the cell is inside a human body.

In another method, Method 58, there is provided a method of treating cancer in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In another method, Method 59, there is provided the method of Method 58 wherein the cancer is selected from the group consisting of colon cancer, prostate cancer, lung cancer, cervical cancer, pancreatic cancer, ovarian cancer and breast cancer.

In another method, Method 60, there is provided a method of treating a muscle disorder in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In another method, Method 61, there is provided the method of Method 60 wherein the muscle disorder is selected from the group consisting of muscle atrophy and muscular dystrophy such as duchene muscular dystrophy.

In another method, Method 62, there is provided a method of treating a kidney disorder in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In another method, Method 63, there is provided the method of Method 62 wherein the kidney disorder is selected from the group consisting of renal dysfunction, acute kidney injury and kidney disease such as chronic kidney disease.

In another method, Method 64, there is provided a method of enhancing cognition in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In another method, Method 65, there is provided a method of treating a neurological disorder in a human subject the method comprising administering to the subject: a CRISPR enzyme; and a guide RNA comprising a guide sequence that is substantially complementary to a target sequence within or near a Klotho gene of the subject, wherein the guide RNA associates with a transcriptional activation domain in a cell of the subject and thereby increases expression of the Klotho gene.

In another method, Method 66, there is provided the method of Method 65 wherein the neurological disorder is selected from the group consisting of memory loss, stress, biopolar disorder, epilepsy, dementia, Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress and neurodegeneration.

In another method, Method 67, there is provided the method of any one of Methods 58 to 66 further comprising administering to the subject an adapter protein capable of binding to the guide RNA wherein the adapter protein comprises or is attached to the transcriptional activation domain.

In another method, Method 68, there is provided the method of Method 67 wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

In another method, Method 69, there is provided the method of Method 67 or Method 68 wherein the adapter protein binds to a tetra-loop and/or a stem loop 2 of the guide RNA.

In another method, Method 70, there is provided the method of any one of Methods 58 to 69 wherein the target sequence is located within a region between the Klotho gene translation start site and 4000 nucleotides upstream of the Klotho gene translation start site.

In another method, Method 71, there is provided the method of any one of Methods 58 to 70 wherein the guide sequence is substantially complementary to a nucleotide sequence set forth in SEQ ID NO. 9 or SEQ ID NO. 10.

In another method, Method 72, there is provided the method of any one of Methods 58 to 71 wherein the target sequence is located within a region between 200 nucleotides and 4000 nucleotides upstream of the Klotho gene translation start site.

In another method, Method 73, there is provided the method of any one of Methods 58 to 72 wherein the guide sequence is substantially complementary to a nucleotide sequence set forth in SEQ ID NO. 11 or SEQ ID NO. 12.

In another method, Method 74, there is provided the method of any one of Methods 58 to 73 wherein the target sequence is located within a region between 200 nucleotides and 300 nucleotides upstream of the Klotho gene translation start site.

In another method, Method 75, there is provided the method of any one of Methods 58 to 74 wherein the target sequence is located within a region between 240 nucleotides and 300 nucleotides upstream of the Klotho gene translation start site.

In another method, Method 76, there is provided the method of any one of Methods 58 to 75 wherein the guide sequence is substantially complementary to a nucleotide sequence set forth in SEQ ID NO. 13 or SEQ ID NO. 14.

In another method, Method 77, there is provided the method of any one of Methods 58 to 76 wherein the guide sequence is between 14 nucleotides and 25 nucleotides in length.

In another method, Method 78, there is provided the method of any one of Methods 58 to 71 wherein the guide sequence comprises at least 14 contiguous nucleotides which are identical to a nucleotide sequence set forth in any one of SEQ ID NOs 1 to 4.

In another method, Method 79, there is provided the method of any one of Methods 58 to 78 wherein the guide sequence comprises at least 14 contiguous nucleotides which are identical to a nucleotide sequence set forth in SEQ ID NO. 3 or SEQ ID NO. 4.

In another method, Method 80, there is provided the method of any one of Methods 58 to 71 wherein the guide sequence is at least 90% identical to a nucleotide sequence set forth in any one of SEQ ID NOs 1 to 4.

In another method, Method 81, there is provided the method of any one of Methods 58 to 80 wherein the guide sequence is at least 90% identical to a nucleotide sequence set forth in SEQ ID NO. 3 or SEQ ID NO. 4.

In another method, Method 82, there is provided the method of any one of Methods 58 to 71 wherein the guide sequence is selected from a nucleotide sequence set forth in any one of SEQ ID NOs 1 to 4.

In another method, Method 83, there is provided the method of any one of Methods 58 to 82 wherein the guide sequence is selected from a nucleotide sequence set forth in SEQ ID NO. 3 and SEQ ID NO. 4.

In another method, Method 84, there is provided the method of any one of Methods 58 to 71 wherein the guide RNA is at least 90% identical to a nucleotide sequence set forth in any one of SEQ ID NOs 5 to 8.

In another method, Method 85, there is provided the method of any one of Methods 58 to 84 wherein the guide RNA is at least 90% identical to a nucleotide sequence set forth in SEQ ID NO. 7 or SEQ ID NO. 8.

In another method, Method 86, there is provided the method of any one of Methods 58 to 71 wherein the guide RNA comprises a nucleotide sequence set forth in any one of SEQ ID NOs 5 to 8.

In another method, Method 87, there is provided the method of any one of Methods 58 to 86 wherein the guide RNA comprises a nucleotide sequence set forth in SEQ ID NO. 7 or SEQ ID NO. 8.

In another method, Method 88, there is provided the method of any one of Methods 58 to 87 wherein the guide RNA is a single-molecule guide RNA (sgRNA).

In another method, Method 89, there is provided the method of any one of Methods 58 to 88 wherein the guide RNA is between about 100 nucleotides and 200 nucleotides in length.

In another method, Method 90, there is provided the method of any one of Methods 58 to 89 wherein the transcriptional activation domain is selected from the group consisting of VP16, or a plurality thereof, VP64, VP160, p65, MyoD1, HSF1, RTA, TET3CD, p300 and SET7/9.

In another method, Method 91, there is provided the method of any one of Methods 58 to 90 wherein the CRISPR enzyme comprises or is attached to a second transcriptional activation domain.

In another method, Method 92, there is provided the method of Method 91 wherein the second transcriptional activation domain is selected from the group consisting of VP16, or a plurality thereof, VP64, VP160, p65, MyoD1, HSF1, RTA, TET3CD, p300 and SET7/9.

In another method, Method 93, there is provided the method of any one of Methods 58 to 92 wherein the CRISPR enzyme comprises a mutation which abolishes or reduces its nuclease activity.

In another method, Method 94, there is provided the method of any one of Methods 58 to 93 wherein the CRISPR enzyme is Cas9.

In another method, Method 95, there is provided a method of treating cancer in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In another method, Method 96, there is provided the method of Method 95 wherein the cancer is selected from the group consisting of colon cancer, prostate cancer, lung cancer, cervical cancer, pancreatic cancer, ovarian cancer and breast cancer.

In another method, Method 97, there is provided a method of treating a muscle disorder in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In another method, Method 98, there is provided the method of Method 97 wherein the muscle disorder is selected from the group consisting of muscle atrophy and muscular dystrophy such as duchene muscular dystrophy.

In another method, Method 99, there is provided a method of treating a kidney disorder in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In another method, Method 100, there is provided the method of Method 99 wherein the kidney disorder is selected from the group consisting of renal dysfunction, acute kidney injury and kidney disease such as chronic kidney disease.

In another method, Method 101, there is provided a method of enhancing cognition in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In another method, Method 102, there is provided a method of treating a neurological disorder in a human subject the method comprising administering to the subject: a guide RNA comprising a guide sequence that is substantially complementary to a target sequence within or near a Klotho gene of the subject; and a CRISPR enzyme, wherein the CRISPR enzyme comprises or is attached to a transcriptional activation domain.

In another method, Method 103, there is provided the method of Method 102 wherein the neurological disorder is selected from the group consisting of memory loss, stress, biopolar disorder, epilepsy, dementia, Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress and neurodegeneration.

In another method, Method 104, there is provided the method of any one of Methods 95 to 103 wherein the target sequence is located within a region between the Klotho gene translation start site and 4000 nucleotides upstream of the Klotho gene translation start site.

In another method, Method 105, there is provided the method of any one of Methods 95 to 104 wherein the guide sequence is substantially complementary to a nucleotide sequence set forth in SEQ ID NO. 9 or SEQ ID NO. 10.

In another method, Method 106, there is provided the method of any one of Methods 95 to 105 wherein the target sequence is located within a region between 200 nucleotides and 4000 nucleotides upstream of the Klotho gene translation start site.

In another method, Method 107, there is provided the method of any one of Methods 95 to 106 wherein the guide sequence is substantially complementary to a nucleotide sequence set forth in SEQ ID NO. 11 or SEQ ID NO. 12.

In another method, Method 108, there is provided the method of any one of Methods 95 to 107 wherein the target sequence is located within a region between 200 nucleotides and 300 nucleotides upstream of the Klotho gene translation start site.

In another method, Method 109, there is provided the method of any one of Methods 95 to 108 wherein the target sequence is located within a region between 240 nucleotides and 300 nucleotides upstream of the Klotho gene translation start site.

In another method, Method 110, there is provided the method of any one of Methods 95 to 109 wherein the guide sequence is substantially complementary to a nucleotide sequence set forth in SEQ ID NO. 13 or SEQ ID NO. 14.

In another method, Method 111, there is provided the method of any one of Methods 95 to 110 wherein the guide sequence is between 14 nucleotides and 25 nucleotides in length.

In another method, Method 112, there is provided the method of any one of Methods 95 to 105 wherein the guide sequence comprises at least 14 contiguous nucleotides which are identical to a nucleotide sequence set forth in any one of SEQ ID NOs 1 to 4.

In another method, Method 113, there is provided the method of any one of Methods 95 to 112 wherein the guide sequence comprises at least 14 contiguous nucleotides which are identical to a nucleotide sequence set forth in SEQ ID NO. 3 or SEQ ID NO. 4.

In another method, Method 114, there is provided the method of any one of Methods 95 to 105 wherein the guide sequence is at least 90% identical to a nucleotide sequence set forth in any one of SEQ ID NOs 1 to 4.

In another method, Method 115, there is provided the method of any one of Methods 95 to 114 wherein the guide sequence is at least 90% identical to a nucleotide sequence set forth in SEQ ID NO. 3 or SEQ ID NO. 4.

In another method, Method 116, there is provided the method of any one of Methods 95 to 105 wherein the guide sequence is selected from a nucleotide sequence set forth in any one of SEQ ID NOs 1 to 4.

In another method, Method 117, there is provided the method of any one of Methods 95 to 116 wherein the guide sequence is selected from a nucleotide sequence set forth in SEQ ID NO. 3 and SEQ ID NO. 4.

In another method, Method 118, there is provided the method of any one of Methods 95 to 105 wherein the guide RNA is at least 90% identical to a nucleotide sequence set forth in any one of SEQ ID NOs 5 to 8.

In another method, Method 119, there is provided the method of any one of Methods 95 to 118 wherein the guide RNA is at least 90% identical to a nucleotide sequence set forth in SEQ ID NO. 7 or SEQ ID NO. 8.

In another method, Method 120, there is provided the method of any one of Methods 95 to 105 wherein the guide RNA comprises a nucleotide sequence set forth in any one of SEQ ID NOs 5 to 8.

In another method, Method 121, there is provided the method of any one of Methods 95 to 120 wherein the guide RNA comprises a nucleotide sequence set forth in SEQ ID NO. 7 or SEQ ID NO. 8.

In another method, Method 122, there is provided the method of any one of Methods 95 to 121 wherein the guide RNA is a single-molecule guide RNA (sgRNA).

In another method, Method 123, there is provided the method of any one of Methods 95 to 122 wherein the guide RNA is between about 100 nucleotides and about 200 nucleotides in length.

In another method, Method 124, there is provided the method of any one of Methods 95 to 123 wherein the transcriptional activation domain is selected from the group consisting of VP16, or a plurality thereof, VP64, VP160, p65, MyoD1, HSF1, RTA, TET3CD, p300 and SET7/9.

In another method, Method 125, there is provided the method of any one of Methods 95 to 124 wherein the CRISPR enzyme comprises a mutation which abolishes or reduces its nuclease activity.

In another method, Method 126, there is provided the method of any one of Methods 95 to 125 wherein the CRISPR enzyme is Cas9.

The present disclosure also provides a composition, Composition 1 which comprises a guide RNA comprising a guide sequence wherein the guide sequence is substantially complementary to a target sequence within or near a human Klotho gene.

In another composition, Composition 2, there is provided the composition of Composition 1 wherein the guide RNA further comprises at least one protein binding sequence for binding to an adapter protein.

In another composition, Composition 3, there is provided the composition of Composition 2 wherein the protein binding sequence comprises an aptamer.

In another composition, Composition 4, there is provided the composition of Composition 2 or Composition 3 wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

In another composition, Composition 5, there is provided the composition of any one of Compositions 2 to 4 wherein the guide RNA comprises two protein binding sequences.

In another composition, Composition 6, there is provided the composition of any one of Compositions 1 to 5 wherein the target sequence is located within a region between the Klotho gene translation start site and 4000 nucleotides upstream of the Klotho gene translation start site.

In another composition, Composition 7, there is provided the composition of any one of Compositions 1 to 6 wherein the guide sequence is substantially complementary to a nucleotide sequence set forth in SEQ ID NO. 9 or SEQ ID NO. 10.

In another composition, Composition 8, there is provided the composition of any one of Compositions 1 to 7 wherein the target sequence is located within a region between 200 nucleotides and 4000 nucleotides upstream of the Klotho gene translation start site.

In another composition, Composition 9, there is provided the composition of any one of Compositions 1 to 8 wherein the guide sequence is substantially complementary to a nucleotide sequence set forth in SEQ ID NO. 11 or SEQ ID NO. 12.

In another composition, Composition 10, there is provided the composition of any one of Compositions 1 to 9 wherein the target sequence is located within a region between 200 nucleotides and 300 nucleotides upstream of the Klotho gene translation start site.

In another composition, Composition 11, there is provided the composition of any one of Compositions 1 to 10 wherein the target sequence is located within a region between 240 nucleotides and 300 nucleotides upstream of the Klotho gene translation start site.

In another composition, Composition 12, there is provided the composition of any one of Compositions 1 to 11 wherein the guide sequence is substantially complementary to a nucleotide sequence set forth in SEQ ID NO. 13 or SEQ ID NO. 14.

In another composition, Composition 13, there is provided the composition of any one of Compositions 1 to 12 wherein the guide sequence is between 14 nucleotides and 25 nucleotides in length.

In another composition, Composition 14, there is provided the composition of any one of Compositions 1 to 7 wherein the guide sequence comprises at least 14 contiguous nucleotides which are identical to a nucleotide sequence set forth in any one of SEQ ID NOs 1 to 4.

In another composition, Composition 15, there is provided the composition of any one of Compositions 1 to 14 wherein the guide sequence comprises at least 14 contiguous nucleotides which are identical to a nucleotide sequence set forth in SEQ ID NO. 3 or SEQ ID NO. 4.

In another composition, Composition 16, there is provided the composition of any one of Compositions 1 to 7 wherein the guide sequence is at least 90% identical to a nucleotide sequence set forth in any one of SEQ ID NOs 1 to 4.

In another composition, Composition 17, there is provided the composition of any one of Compositions 1 to 16 wherein the guide sequence is at least 90% identical to a nucleotide sequence set forth in SEQ ID NO. 3 or SEQ ID NO. 4.

In another composition, Composition 18, there is provided the composition of any one of Compositions 1 to 7 wherein the guide sequence is selected from a nucleotide sequence set forth in any one of SEQ ID NOs 1 to 4.

In another composition, Composition 19, there is provided the composition of any one of Compositions 1 to 18 wherein the guide sequence is selected from a nucleotide sequence set forth in SEQ ID NO. 3 and SEQ ID NO. 4.

In another composition, Composition 20, there is provided the composition of any one of Compositions 1 to 7 wherein the guide RNA is at least 90% identical to a nucleotide sequence set forth in any one of SEQ ID NOs 5 to 8.

In another composition, Composition 21, there is provided the composition of any one of Compositions 1 to 20 wherein the guide RNA is at least 90% identical to a nucleotide sequence set forth in SEQ ID NO. 7 or SEQ ID NO. 8.

In another composition, Composition 22, there is provided the composition of any one of Compositions 1 to 7 wherein the guide RNA comprises a nucleotide sequence set forth in any one of SEQ ID NOs 5 to 8.

In another composition, Composition 23, there is provided the composition of any one of Compositions 1 to 22 wherein the guide RNA comprises a nucleotide sequence set forth in SEQ ID NO. 7 or SEQ ID NO. 8.

In another composition, Composition 24, there is provided the composition of any one of Compositions 1 to 23 wherein the guide RNA is a single-molecule guide RNA (sgRNA).

In another composition, Composition 25, there is provided the composition of any one of Compositions 1 to 24 wherein the guide RNA is between about 100 nucleotides and 200 nucleotides in length.

In another composition, Composition 26, there is provided an isolated or recombinant nucleic acid molecule encoding the guide RNA of any one of Compositions 1 to 25.

In another composition, Composition 27, there is provided a vector encoding the guide RNA of any one of Compositions 1 to 25.

In another composition, Composition 28, there is provided the composition of Composition 27 wherein the vector is an adeno-associated viral (AAV) vector, an adenoviral vector (AdV) or a lentiviral (LV) vector.

In another composition, Composition 29, there is provided the composition of Composition 27 or Composition 28 wherein the vector further encodes a CRISPR enzyme, an adapter protein or a transcriptional activation domain.

In another composition, Composition 30, there is provided the composition of Composition 29 wherein the transcriptional activation domain is selected from the group consisting of VP16, or a plurality thereof, VP64, VP160, p65, MyoD1, HSF1, RTA, TET3CD, p300 and SET7/9.

In another composition, Composition 31, there is provided the composition of Composition 29 or Composition 30 wherein the CRISPR enzyme comprises a mutation which abolishes or reduces its nuclease activity.

In another composition, Composition 32, there is provided the composition of any one of Compositions 29 to 31 wherein the CRISPR enzyme is Cas9.

In another composition, Composition 33, there is provided the composition of any one of Compositions 29 to 32 wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

In another composition, Composition 34, there is provided a ribonucleoprotein complex comprising: a CRISPR enzyme; and a guide RNA comprising a guide sequence that is substantially complementary to a target sequence within or near a human Klotho gene, wherein the guide RNA comprises at least one protein binding sequence for binding to an adapter protein.

In another composition, Composition 35, there is provided the composition of Composition 34 wherein the protein binding sequence comprises an aptamer.

In another composition, Composition 36, there is provided the composition of Composition 34 or Composition 35 wherein the adapter protein is selected from the group consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1.

In another composition, Composition 37, there is provided the composition of any one of Compositions 34 to 36 wherein the guide RNA comprises two protein binding sequences.

In another composition, Composition 38, there is provided the composition of any one of Compositions 34 to 37 wherein the target sequence is located within a region between the Klotho gene translation start site and 4000 nucleotides upstream of the Klotho gene translation start site.

In another composition, Composition 39, there is provided the composition of any one of Compositions 34 to 38 wherein the guide sequence is substantially complementary to a nucleotide sequence set forth in SEQ ID NO. 9 or SEQ ID NO. 10.

In another composition, Composition 40, there is provided the composition of any one of Compositions 34 to 39 wherein the target sequence is located within a region between 200 nucleotides and 4000 nucleotides upstream of the Klotho gene translation start site.

In another composition, Composition 41, there is provided the composition of any one of Compositions 34 to 40 wherein the guide sequence is substantially complementary to a nucleotide sequence set forth in SEQ ID NO. 11 or SEQ ID NO. 12.

In another composition, Composition 42, there is provided the composition of any one of Compositions 34 to 41 wherein the target sequence is located within a region between 200 nucleotides and 300 nucleotides upstream of the Klotho gene translation start site.

In another composition, Composition 43, there is provided the composition of any one of Compositions 34 to 42 wherein the target sequence is located within a region between 240 nucleotides and 300 nucleotides upstream of the Klotho gene translation start site.

In another composition, Composition 44, there is provided the composition of any one of Compositions 34 to 43 wherein the guide sequence is substantially complementary to a nucleotide sequence set forth in SEQ ID NO. 13 or SEQ ID NO. 14.

In another composition, Composition 45, there is provided the composition of any one of Compositions 34 to 44 wherein the guide sequence is between 14 nucleotides and 25 nucleotides in length.

In another composition, Composition 46, there is provided the composition of any one of Compositions 34 to 39 wherein the guide sequence comprises at least 14 contiguous nucleotides which are identical to a nucleotide sequence set forth in any one of SEQ ID NOs 1 to 4.

In another composition, Composition 47, there is provided the composition of any one of Compositions 34 to 46 wherein the guide sequence comprises at least 14 contiguous nucleotides which are identical to a nucleotide sequence set forth in SEQ ID NO. 3 or SEQ ID NO. 4.

In another composition, Composition 48, there is provided the composition of any one of Compositions 34 to 39 wherein the guide sequence is at least 90% identical to a nucleotide sequence set forth in any one of SEQ ID NOs 1 to 4.

In another composition, Composition 49, there is provided the composition of any one of Compositions 34 to 48 wherein the guide sequence is at least 90% identical to a nucleotide sequence set forth in SEQ ID NO. 3 or SEQ ID NO. 4.

In another composition, Composition 50, there is provided the composition of any one of Compositions 34 to 39 wherein the guide sequence is selected from a nucleotide sequence set forth in any one of SEQ ID NOs 1 to 4.

In another composition, Composition 51, there is provided the composition of any one of Compositions 34 to 50 wherein the guide sequence is selected from a nucleotide sequence set forth in SEQ ID NO. 3 and SEQ ID NO. 4.

In another composition, Composition 52, there is provided the composition of any one of Compositions 34 to 39 wherein the guide RNA is at least 90% identical to a nucleotide sequence set forth in any one of SEQ ID NOs 5 to 8.

In another composition, Composition 53, there is provided the composition of any one of Compositions 34 to 52 wherein the guide RNA is at least 90% identical to a nucleotide sequence set forth in SEQ ID NO. 7 or SEQ ID NO. 8.

In another composition, Composition 54, there is provided the composition of any one of Compositions 34 to 39 wherein the guide RNA comprises a nucleotide sequence set forth in any one of SEQ ID NOs 5 to 8.

In another composition, Composition 55, there is provided the composition of any one of Compositions 34 to 54 wherein the guide RNA comprises a nucleotide sequence set forth in SEQ ID NO. 7 or SEQ ID NO. 8.

In another composition, Composition 56, there is provided the composition of any one of Compositions 34 to 55 wherein the guide RNA is a single-molecule guide RNA (sgRNA).

In another composition, Composition 57, there is provided the composition of any one of Compositions 34 to 56 wherein the guide RNA is between about 100 nucleotides and 200 nucleotides in length.

In another composition, Composition 58, there is provided the composition of any one of Compositions 34 to 57 wherein the guide RNA is bound to the adapter protein.

In another composition, Composition 59, there is provided the composition of any one of Compositions 34 to 58 wherein the adapter protein comprises or is attached to a transcriptional activation domain.

In another composition, Composition 60, there is provided the composition of Composition 59 wherein the transcriptional activation domain is selected from the group consisting of VP16, or a plurality thereof, VP64, VP160, p65, MyoD1, HSF1, RTA, TET3CD, p300 and SET7/9.

In another composition, Composition 61, there is provided a ribonucleoprotein complex comprising: a guide RNA comprising a guide sequence that is substantially complementary to a target sequence within or near a human Klotho gene; and a CRISPR enzyme, wherein the CRISPR enzyme comprises or is attached to a transcriptional activation domain.

In another composition, Composition 62, there is provided the composition of Composition 61 wherein the target sequence is located within a region between the Klotho gene translation start site and 4000 nucleotides upstream of the Klotho gene translation start site.

In another composition, Composition 63, there is provided the composition of Composition 61 or Composition 62 wherein the guide sequence is substantially complementary to a nucleotide sequence set forth in SEQ ID NO. 9 or SEQ ID NO. 10.

In another composition, Composition 64, there is provided the composition of any one of Compositions 61 to 63 wherein the target sequence is located within a region between 200 nucleotides and 4000 nucleotides upstream of the Klotho gene translation start site.

In another composition, Composition 65, there is provided the composition of any one of Compositions 61 to 64 wherein the guide sequence is substantially complementary to a nucleotide sequence set forth in SEQ ID NO. 11 or SEQ ID NO. 12.

In another composition, Composition 66, there is provided the composition of any one of Compositions 61 to 65 wherein the target sequence is located within a region between 200 nucleotides and 300 nucleotides upstream of the Klotho gene translation start site.

In another composition, Composition 67, there is provided the composition of any one of Compositions 61 to 66 wherein the guide sequence is substantially complementary to a nucleotide sequence set forth in SEQ ID NO. 13 or SEQ ID NO. 14.

In another composition, Composition 68, there is provided the composition of any one of Compositions 61 to 67 wherein the guide sequence is between 14 nucleotides and 25 nucleotides in length.

In another composition, Composition 69, there is provided the composition of any one of Compositions 61 to 63 wherein the guide sequence comprises at least 14 contiguous nucleotides which are identical to a nucleotide sequence set forth in any one of SEQ ID NOs 1 to 4.

In another composition, Composition 70, there is provided the composition of any one of Compositions 61 to 69 wherein the guide sequence comprises at least 14 contiguous nucleotides which are identical to a nucleotide sequence set forth in SEQ ID NO. 3 or SEQ ID NO. 4.

In another composition, Composition 71, there is provided the composition of any one of Compositions 61 to 63 wherein the guide sequence is at least 90% identical to a nucleotide sequence set forth in any one of SEQ ID NOs 1 to 4.

In another composition, Composition 72, there is provided the composition of any one of Compositions 61 to 71 wherein the guide sequence is at least 90% identical to a nucleotide sequence set forth in SEQ ID NO. 3 or SEQ ID NO. 4.

In another composition, Composition 73, there is provided the composition of any one of Compositions 61 to 63 wherein the guide sequence is selected from a nucleotide sequence set forth in any one of SEQ ID NOs 1 to 4.

In another composition, Composition 74, there is provided the composition of any one of Compositions 61 to 73 wherein the guide sequence is selected from a nucleotide sequence set forth in SEQ ID NO. 3 and SEQ ID NO. 4.

In another composition, Composition 75, there is provided the composition of any one of Compositions 61 to 63 wherein the guide RNA is at least 90% identical to a nucleotide sequence set forth in any one of SEQ ID NOs 5 to 8.

In another composition, Composition 76, there is provided the composition of any one of Compositions 61 to 75 wherein the guide RNA is at least 90% identical to a nucleotide sequence set forth in SEQ ID NO. 7 or SEQ ID NO. 8.

In another composition, Composition 77, there is provided the composition of any one of Compositions 61 to 63 wherein the guide RNA comprises a nucleotide sequence set forth in any one of SEQ ID NOs 5 to 8.

In another composition, Composition 78, there is provided the composition of any one of Compositions 61 to 77 wherein the guide RNA comprises a nucleotide sequence set forth in SEQ ID NO. 7 or SEQ ID NO. 8.

In another composition, Composition 79, there is provided the composition of any one of Compositions 61 to 78 wherein the guide RNA is a single-molecule guide RNA (sgRNA).

In another composition, Composition 80, there is provided the composition of any one of Compositions 61 to 79 wherein the guide RNA is between about 100 nucleotides and about 200 nucleotides in length.

In another composition, Composition 81, there is provided the composition of any one of Compositions 61 to 80 wherein the transcriptional activation domain is selected from the group consisting of VP16, or a plurality thereof, VP64, VP160, p65, MyoD1, HSF1, RTA, TET3CD, p300 and SET7/9.

In another composition, Composition 82, there is provided the composition of any one of Compositions 34 to 81 wherein the CRISPR enzyme comprises a mutation which abolishes or reduces its nuclease activity.

In another composition, Composition 83, there is provided the composition of any one of Compositions 34 to 82 wherein the CRISPR enzyme is Cas9.

EXAMPLES

Guide RNAs

Guide RNA sequences relevant to the present examples are listed in Table 5.

FIG. 1 provides a representation of sgRNA3 (SEQ ID NO: 3) hybridised to a target sequence in the Klotho promoter. The secondary structure of the guide RNA is also indicated including the tetra-loop and the stem loop 2 which have been engineered to include a MS2 binding sequence.

Designing and Cloning of sgRNA Plasmid

Guide RNAs were designed to target loci within the first 300 bp upstream of the Klotho translation initiation site ("A" in ATG as number+1). Target sequences were selected according to predicted off-target scores using an online CRISPR design tool (http://crispr.mit.edu (Ran et al. 2013. *Nat. Protoc.* 8(11): 2291-2308) and subsequently filtered for a maximum GC content of 25%, and minimal overlap of the target sequence. After filtering, four guide RNAs on the sense strand with the best off-target scores were selected, and then cloned into sgRNA (MS2) backbone (Addgene #61424) at the BbsI site. Final plasmid constructs were confirmed by DNA sequencing. The following primers were used for cloning:

```
sgRNA1 sense:
                                       (SEQ ID NO. 30)
5'-CACCGGGCATAAAGGGGCGCGGCGC-3' sgRNA1 anti-sense:
                                       (SEQ ID NO. 31)
5'-AAACGCGCCGCGCCCCTTTATGCCC-3' sgRNA2 sense:
                                       (SEQ ID NO. 32)
5'-CACCGCGGCGGGGCGCGGGCATAAA-3'
```

TABLE 5

| SEQ ID NO. | Description | Sequence |
|---|---|---|
| 1 | sgRNA1 guide sequence | GGCAUAAAGGGGCGCGGCGC |
| 2 | sgRNA2 guide sequence | CGGCGGGGCGCGGGCAUAAA |
| 3 | sgRNA3 guide sequence | GUGCCUUUCUCCGACGUCCG |
| 4 | sgRNA4 guide sequence | GAAACGUCCUGCACGGCUCC |
| 5 | sgRNA1 guide sequence underlined MS2 stem loop in bold | <u>GGCAUAAAGGGGCGCGGCGC</u>GUUUUAGAGCUAGGCCAACAUGAGGAUC<br>ACCCAUGUCUGCAGGGCCUAGCAAGUUAAAAUAAGGCUAGUCCGUUAU<br>CAACUUGGCCAACAUGAGGAUCACCCAUGUCUGCAGGGCCAAGUGGCA<br>CCGAGUCGGUGCUUUUU |
| 6 | sgRNA2 guide sequence underlined MS2 stem loop in bold | <u>GGCGGGGCGCGGGCAUAAA</u>GUUUUAGAGCUAGGCCAACAUGAGGAUCA<br>CCCAUGUCUGCAGGGCCUAGCAAGUUAAAAUAAGGCUAGUCCGUUAUC<br>AACUUGGCCAACAUGAGGAUCACCCAUGUCUGCAGGGCCAAGUGGCAC<br>CGAGUCGGUGCUUUUU |
| 7 | sgRNA3 guide sequence underlined MS2 stem loop in bold | <u>GUGCCUUUCUCCGACGUCCG</u>GUUUUAGAGCUAGGCCAACAUGAGGAUC<br>ACCCAUGUCUGCAGGGCCUAGCAAGUUAAAAUAAGGCUAGUCCGUUAU<br>CAACUUGGCCAACAUGAGGAUCACCCAUGUCUGCAGGGCCAAGUGGCA<br>CCGAGUCGGUGCUUUUU |
| 8 | sgRNA4 guide sequence underlined MS2 stem loop in bold | <u>GAAACGUCCUGCACGGCUCC</u>GUUUUAGAGCUAGGCCAACAUGAGGAUC<br>ACCCAUGUCUGCAGGGCCUAGCAAGUUAAAAUAAGGCUAGUCCGUUAU<br>CAACUUGGCCAACAUGAGGAUCACCCAUGUCUGCAGGGCCAAGUGGCA<br>CCGAGUCGGUGCUUUUU |

```
sgRNA2 anti-sense:
                                   (SEQ ID NO. 33)
5'-AAACTTTATGCCCGCGCCCCGCCGC-3' sgRNA3 sense:
                                   (SEQ ID NO. 34)
5'-CACCGGTGCCTTTCTCCGACGTCCG-3' sgRNA3 anti-sense:
                                   (SEQ ID NO. 35)
5'-AAACCGGACGTCGGAGAAAGGCACC-3' sgRNA4 sense:
                                   (SEQ ID NO. 36)
5'-CACCGGAAACGTCCTGCACGGCTCC-3' sgRNA4 anti-sense:
                                   (SEQ ID NO. 37)
5'-AAACGGAGCCGTGCAGGACGTTTCC-3'
```

Cell Culture

Cell lines were maintained under standard growth conditions and propagated in DMEM (Dulbecco's modified Eagle's medium) (4.5 g/ml glucose) containing 10% FBS (fetal bovine serum) (Atlanta Biologicals) and 1% penicillin/streptomycin (100 units/ml). For HK-2 kidney cells, DMEM:F12 (1:1) medium was used. Cell culture solutions were obtained from Cellgro unless otherwise noted in the examples.

Cloning of Klotho (KL) 4 kb Promoter into FLuc and NLuc Luciferase Coincidence Reporter and Stable Cell Generation To clone the SV40 enhancer into pNLCol1[luc2-P2A-NlucP/Hygro] Vector (Promega), the SV40 enhancer was amplified from pGL3 using the following primers and Clontech HiFi according to the manufacturer's protocol:

```
Forward primer:
                                   (SEQ ID NO. 38)
5'-AAATCGATAAGGATCCGATGGAGCGGAGAATGGGCGG-3'

Reverse primer:
                                   (SEQ ID NO. 39)
5'-ATACGCAAACGGATCCGCTGTGGAATGTGTGTCAG-3'
```

The PCR product was isolated and ligated to the pNL vector by digestion with BamHI to generate the pNLCol1-SV40 vector. Approximately 1.8 kb of the Klotho promoter was digested from pGL3-KL1800 (King et al. 2012. Biochem. J. 441(1): 453-461) with HindIII and XhoI, and subcloned into pNLCol1-SV40 vector using the same restriction sites to generate pNLCol1-SV40-KL1800.

To clone an approximately 4 kb region of the Klotho promoter, the additional approximately 2.2 Kb (about −1800 to −4000) and the vector were amplified from HEK293 genomic DNA and pNLCol1-SV40-KL1800, respectively, using the following primers and ClonAmp HiFi polymerase according to the manufacturer's protocol:

```
Forward primer for 2.2kb KL promoter insert:
                                   (SEQ ID NO. 40)
5'-CTCGCTAGCCTCGAGATCTATAGTGCCACATGGTGAC-3'

Reverse primer for 2.2kb KL promoter insert:
                                   (SEQ ID NO. 41)
5'-AGTATCACATTTCCCTTCTAGAAGTGAAGATTGGAGTG-3'

Forward primer for vector:
                                   (SEQ ID NO. 42)
5'-GGGAAATGTGATACTCCATGTAG-3'

Reverse primer for vector:
                                   (SEQ ID NO. 43)
5'-CTCGAGGCTAGCGAGCTCAGGTACC-3'
```

The insert and vector bands (100 ng each) were ligated together using In Fusion kit (Clontech) to generate pNL-Col1-SV40-KL4000. Stable HEK-293 cells expressing 4 kb of the KL promoter or the PGK promoter with the coincidence reporter were generated from single clones and selected using Hygromycin (Invivogen, USA) at a concentration of 75 µg/ml for two weeks following Hygromycin 25 µg/ml for maintenance.

Generation of a NLuc Knock-in HEK293 Cell Line by CRISPR Genomic Editing

A double nicking strategy with Cas9n was used to introduce double-stranded breaks (DSB) by a pair of appropriately spaced and oriented sgRNAs at the Klotho 3'-UTR. Guide RNAs were designed to target the Klotho 3'-UTR using the online CRISPR design tools as described above. The best off-target scoring (with a score of 100, and 0 off-target) gRNA pair was selected, and then cloned into pSpCase9n(BB)-2A-Puro (PX462) V2.0 plasmid (Addgene #62987) digested with BbsI, and confirmed by DNA sequencing. The following primers were used for cloning:

```
gRNA pair 1 sense:
                                   (SEQ ID NO. 44)
5'-CACCGGTCTCACTGGCATCTTGTTG-3' gRNA pair 1 anti-sense:
                                   (SEQ ID NO. 45)
5'-AAACCAACAAGATGCCAGTGAGACC-3' gRNA pair 2 sense:
                                   (SEQ ID NO. 46)
5'-CACCGCAGGGACACAGGGTTTAGAC-3' gRNA pair 2 anti-sense:
                                   (SEQ ID NO. 47)
5'-AAACGTCTAAACCCTGTGTCCCTGC-3'
```

The P2A-NLuc sequence was inserted at the DSB site of the Klotho 3'-UTR by co-transfection of a template DNA with 1 kb homology arms to each side of the DSB site of the Klotho genomic DNA sequence. The template DNA containing the homology arms flanking the P2A-NLuc sequence was amplified from HEK cell genomic DNA or pNLCol1 [luc2-P2A-NlucP/Hygro] and constructed into pcDNA3.1 plasmid without the CMV promoter region using ClonAmp HiFi and In Fusion cloning kit (Clontech). The following primers were used:

```
pcDNA3.1 forward:
                                   (SEQ ID NO. 48)
5'-CTCGAGTCTAGAGGGCCCGCGGTTC-3' pcDNA3.1 reverse:
                                   (SEQ ID NO. 49)
5'-AAGCTTCGTATATCTGGCCCGTACATCGCG-3'

KL 2710 forward:
                                   (SEQ ID NO. 50)
5'-AGATATACGAAGCTTCCCACATACTGGATGGTATCAATC-3'

KL 3700 reverse:
                                   (SEQ ID NO. 51)
5'-AGTAGCTCCGCTTCCGACAGGACCTCAAAAATCATATAA-3'

P2A NLuc forward:
                                   (SEQ ID NO. 52)
5'-GGAAGCGGAGCTACTAACTTCAGCC-3'

P2A NLuc reverse:
                                   (SEQ ID NO. 53)
5'-TTAGACGTTGATGCGAGCTGAAGC-3'
```

```
KL 3743 forward:
                                    (SEQ ID NO. 54)
5'-CGCATCAACGTCTAATTGAGGGCCTTGCACATAGGAAAC-3'

KL 4978 reverse:
                                    (SEQ ID NO. 55)
5'-CCCTCTAGACTCGAGATTATGAAAGAAGGCAAAAAGTTGC-3'
```

Isolation of clonal cell lines comprising P2A-NLuc insertion was achieved after co-transfection of the two pairs of gRNA and template plasmids into HEK293 cells by isolating single cells through serial dilutions in 96 well plates, followed by an expansion period to establish a new clonal cell line. NLuc positive lines were confirmed by PCR using Terra PCR direct kit (Clontech) and the following primers:

```
Klotho intron 4 forward:
                                    (SEQ ID NO. 56)
5'- GTGTTGTGTGCAAAATACGTAATAA-3'

NLuc reverse:
                                    (SEQ ID NO. 57)
5'- TGACATGGATGTCGATCTTCAG-3'
```

The forward primer is located in intron 4 of Klotho upstream to the left homology arm, and can therefore avoid false positive stable colonies with random insertion into genomic DNA. As a control for a specific activation of the Klotho promoter in a coincidence reporter vector, the pNL-Col4[luc2-P2A-NlucP/PGK/Hygro] Vector (cat. 1492, Promega, USA) was used. Ataluren (PTC124) (cat. S6003, SelleckChem, USA) for FLuc and Cilnidipine (cat. S1293, SelleckChem, USA) for NLuc luciferase were used as positive controls for validation of the dual luciferase system.

Transfection

Cells were grown on poly-D-lysine-coated plates in 96-, 12- or 6-well formats. Twenty-four hours after plating, cells reached 70-80% confluency and were transfected with a 1:1:1 ratio of Klotho-specific sgRNA plasmid or control sgRNA cloning backbone plasmid, MS2-P65-HSF1effector plasmid (Addgene, #61423) and dCas9-VP64 effector plasmid (Addgene, #61422). For positive controls, cells were transfected with a 1:2 ratio of Egr1 (a transcription factor which activates Klotho transcription) or pcDNA3.1 empty vector. Transfections were carried out using Mirus TransIT-X2 with 100 ng, 1 µg or 2 µg of total plasmid DNA per well in 96-, 12- or 6-well plates, respectively. Transfection medium was removed and replaced with fresh medium after 5 hours.

Luciferase Assays

For measurement of FLuc and NLuc expression, the coincidence reporter vector under Klotho promoter, Nano-Glo® Dual-Luciferase® Reporter Assay System (cat. N1620, Promega) was used according to the manufacturer's instructions. Briefly, 24 hours after transfection in white 96-well culture plates, the medium was replaced with 70 µL of the fresh medium and assay was performed after an additional 24 hours. The 96-well plates and the reagents were equilibrated to room temperature and 70 µL ONE-Glo™ EX was added to the culture medium. The samples were incubated for 10 minutes and firefly luminescence was measured with a plate reader (GloMax® Discover System, Promega). To measure NLuc luciferase activity, 70 µL of NanoDLR™ Stop& Glo® Reagent was added to each well and the luminescence was measured after 20 minutes.

Klotho promoter-induced NLuc expression was measured in a NLuc knock-in HEK293 cell line using the Nano-Glo Luciferase Assay System (cat. N1110, Promega) according to the manufacturer's instructions. Briefly, 24 hours after transfection in white 96-well culture plates, the medium was replaced with 70 µL of the fresh medium and assayed after an additional 24 hours. The 96-well plates and reagents were equilibrated to room temperature and 70 µL of Nano-Glo® Luciferase Assay Reagent was added to the culture medium. The samples were incubated for 10 minutes and the luminescence was measured using a plate reader (GloMax® Discover System, Promega).

qPCR Experiments and Analysis 48 hours after transfection, total RNA was isolated using the RNeasy mini plus Kit (QIAGEN) and 1 µg of total RNA was reverse transcribed using the SuperScript™ VILO™ cDNA Synthesis Kit according to the manufacturer's instructions (cat. 11754050, ThermoFisher scientific). Reverse transcriptase quantitative polymerase chain reaction (RT-qPCR) was carried out using human TaqMan Gene Expression Assays (Life Technologies): Klotho (Assay ID Hs00934627_m1 FAM); Peptidylprolyl isomerase A (PPIA) (Assay ID Hs04194521_s1; FAM) and beta actin (ActinB) (Assay ID Hs01060665_g1; VIC), on a BioRad 7900HT Real-Time PCR system using Fast Advanced Master Mix (Life Technologies), according to the manufacturer's protocol. The Klotho transcript was normalized to PPIA and ActinB which were used as endogenous controls. Samples were run in triplicates at 1 µg of cDNA per reaction. The presence or absence of transcripts was assessed by whether a critical threshold (CT) value was determined or undetermined, respectively, at the threshold chosen by BioRad software v2.4. To normalize sample input, $\Delta$CT values were calculated for each gene. Data were analyzed further by the $\Delta\Delta$Ct method and fold changes in Klotho gene expression were determined by Gene Expression Module of CSX Manager software (BioRad), and a p-value ≤0.05 was considered significant.

Western Blotting

Protein Western blotting was performed as described (Chen et al. 2007. Proc. Natl. Acad. Sci. USA. 104(50): 19796-19801). Protein expression based on Western blots was assessed and normalized by densitometry using ImageJ.

Anti-Klotho (K0603, clone number KM2076, 1:500, Transgenic) and anti-Actin (1:1000, Cell Signaling, Danvers, Mass.) antibodies were used.

Statistical Analysis

For Western blotting and luciferase assay, the significance was calculated using the traditional Student's t-test. Quantitative data are expressed as the means±SD.

Statistical comparisons between experimental groups were made using the two-tailed, unpaired Student's t-test. P-values of p<0.05 were considered significant.

Example 1: sgRNA Target Site Selection

Figure 2:
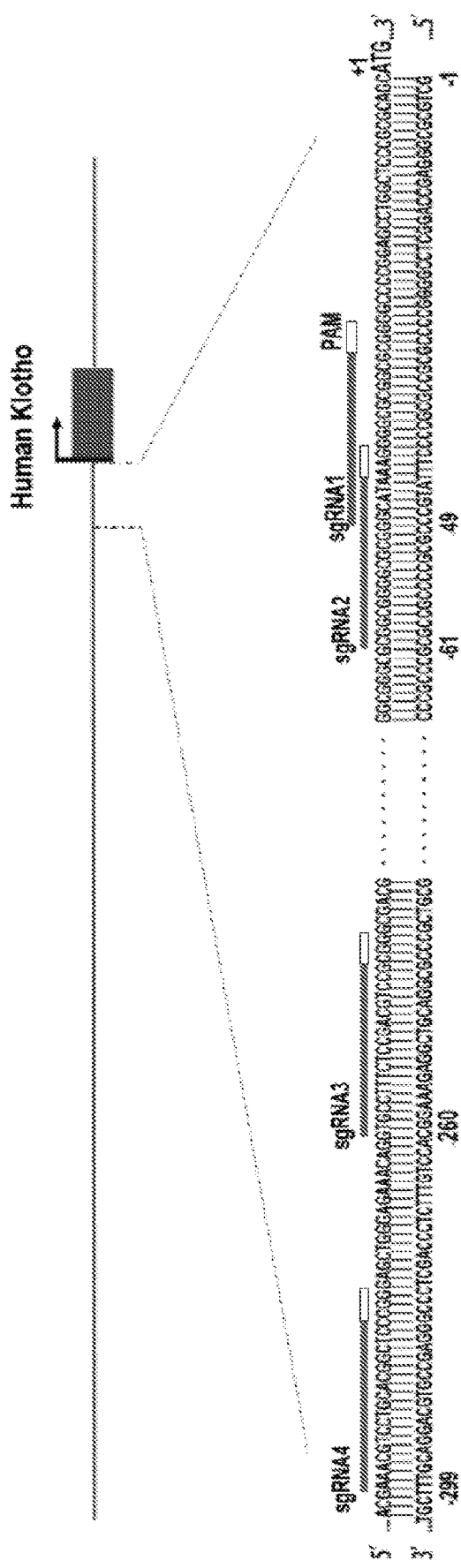
FIG. 2. Schematic view of the Klotho promoter region showing the location of the target sequences for sgRNA1-4. The 20 nt target sequence (solid box), and protospacer-adjacent motif (PAM) (empty box) are indicated. The number indicates the first nucleotide of the sgRNA relative to Klotho translation start site ("A" in ATG as number+1).

To increase endogenous Klotho gene transcription, a Synergistic Activation Mediator (SAM) system comprising NLS-dCas9-NLS-VP64, MS2-NLS-p65-HSF1 and a sgRNA, was employed. sgRNAs targeting the human Klotho promoter region were designed using the online CRISPR design tool http://crispr.mit.edu. Specifically, sgRNA targeting −300 to +1 of the Klotho promoter region were designed (FIG. 2). Four guide RNAs on the sense strand with the best off-target scores were selected for gene activation experiments.

Figure 3:
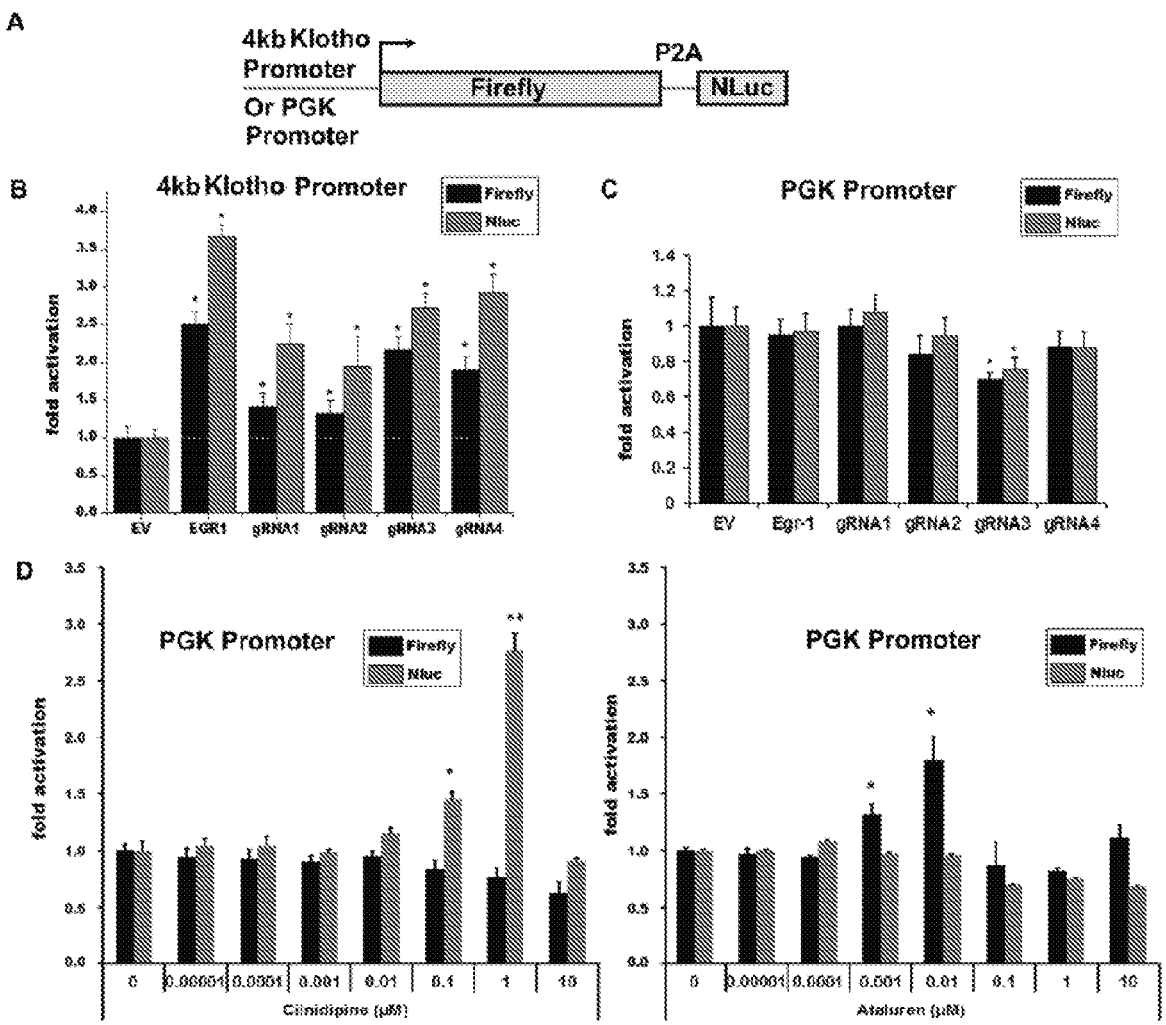
FIG. 3. Klotho gene activation using a dual luciferase coincidence reporter system. (A) Schematic view of the firefly, NLuc coincidence reporter system under the control of Klotho 4 kb promoter. The P2A ribosome skipping sequence is indicated. (B) Fold increase in Klotho gene expression by SAM in stable HEK293 cells. Cells were analyzed by dual luciferase assay two days after transfection with dCas9-VP64, MS2-P65-HSF1 and the indicated sgRNA. Negative control: sgRNA cloning backbone empty vector. Positive control: Egr-1 transfected cells. Data are expressed as fold over negative control. Error bars show standard deviation among six replicates. (C) Fold change of the PGK promoter activities by SAM in stable HEK293 cells as in (B). (D) Validation of the PGK promoter system in stable HEK293 cells using Cilnidipine and Ataluren that were added to the cells 24 hours after plating and results assayed 24 hours later. Asterisks (*) indicate statistical significance of $p<0.05$ by t-test.

Example 2: Evaluation of Klotho Gene Expression Using a Dual Luciferase Coincidence Reporter System 4,000 bp of the Klotho promoter drove the stoichiometric expression of two orthologous reporters, firefly luciferase (FLuc) and PEST-destabilized NLuc luciferase (NLuc). The reporters were expressed from the same Klotho promoter using ribosome skipping mediated by the P2A peptide (FIG. 3A). To examine the efficiency of the sgRNA on Klotho gene activation, the four guide RNA sequences were introduced into sgRNA expression plasmids and co-transfected with the dCas9-VP64 and MS2-P65-HSF1 expression plasmids into stable FLuc NLuc coincidence reporter HEK293 cells. The results showed that all sgRNAs increased Klotho transcription, with sgRNA3 and 4, surprisingly, having a more substantial effect on expression than sgRNA1 or 2 (FIG. 3B).

In the 4 kb Klotho promoter reporter system, the positive control transcription factor Egr-1 (Choi et al. 2010. *Gene.* 450(1-2): 121-127) resulted in a 3- to 4-fold increase in Klotho expression, comparable to sgRNA-mediated activation (FIG. 3B). The specificity of Klotho gene activation was tested in HEK293 cells stably transfected with a control promoter of the yeast gene encoding phosphoglycerate kinase (PGK) using the FLuc NLuc coincidence reporter vector. The results showed that none of the sgRNAs increased PGK promoter activity. sgRNA3 slightly reduced PGK-1 promoter activity (FIG. 3C). The PGK promoter system was validated using two known luciferase inhibitors: Cilnidipine, a Nluc luciferase inhibitor; and Ataluren (PTC124), a FLuc inhibitor. Cilnidipine treatment elicited a NLuc-specific increase that fit the 7-parameters bell-shape, while treatment with Ataluren led to stabilization of the FLuc reporter, manifested as an enhanced signal at intermediate concentrations followed by a signal decrease at high concentrations (FIG. 3D). The validation results using Cilnidipine and Ataluren are in line with the results obtained with the Klotho 4 kb promoter in the coincidence reporter vector (data not shown) and with the previously published protocol (Schuck et al. 2017. *Curr. Protoc. Neurosci.* 79:5 32 31-35 32 27). These results indicate that the sgRNAs specifically activated Klotho gene expression but not the PGK promoter.

Figure 4:
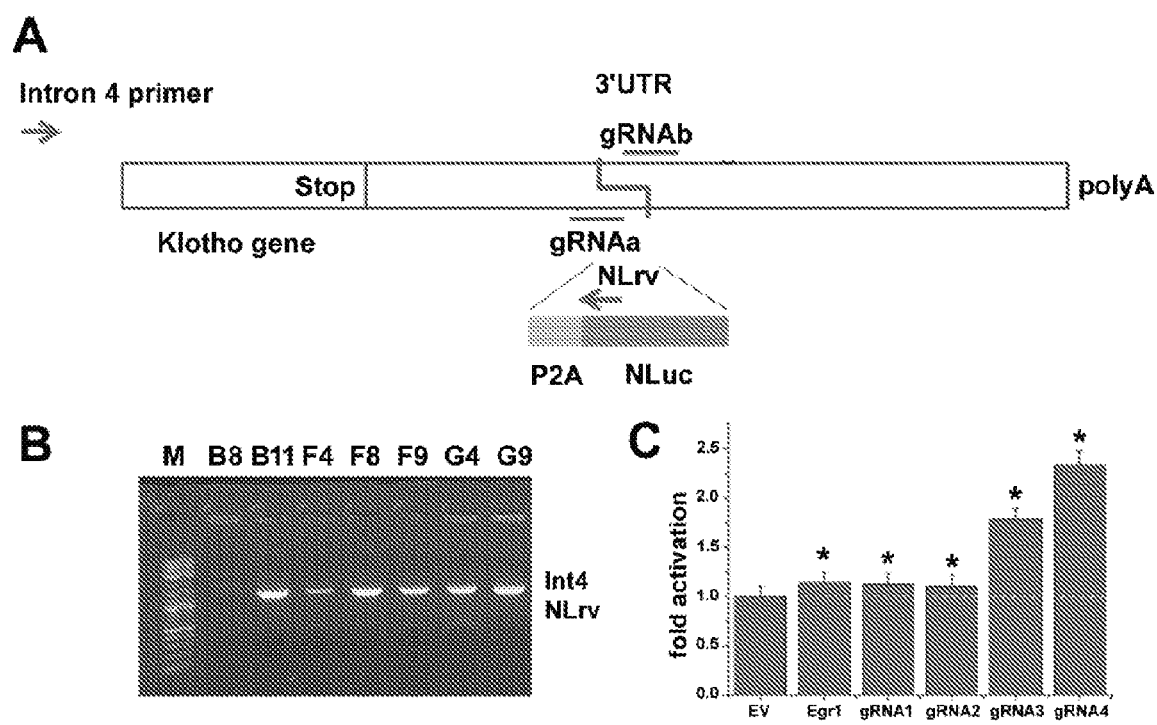
FIG. 4. Klotho gene activation using a CRISPR NLuc knock-in HEK293 cell line. (A) Schematic view of the 3' end of Klotho including the 3'-UTR region. The stop codon, the sgRNA targets and polyA tail are shown. The P2A-NLuc sequence was inserted at the DSB site in the Klotho 3'-UTR. (B) PCR confirmation of positive clones using a forward primer located in intron 4 of Klotho and a NLuc reverse primer (NLrv) indicated in (A). Cell line numbers are indicated. (C) Fold increase in Klotho gene expression by SAM evaluated with a CRISPR NLuc knock-in HEK293 line. Cells were analyzed by NLuc luciferase assay two days after transfection with dCas9-VP64, MS2-P65-HSF1 and the indicated sgRNA. Negative control: sgRNA cloning backbone empty vector. Positive control: Egr-1 transfected cells. Data are expressed as fold over negative control. Error bars show standard deviation among six replicates. Asterisks (*) indicate statistical significance of $p<0.05$ by t-test.

Example 3: Evaluation of Klotho Activation Using CRISPR NLuc Knock-in HEK293 Cell Line To monitor endogenous Klotho gene expression, a CRISPR system was used to generate a HEK knock-in line with NLuc inserted into 3'-UTR of the Klotho gene (FIG. 4A). In this system, Klotho and NLuc are expressed from the same Klotho promoter by the P2A sequence. Thus, Klotho transcription can be monitored based on NLuc activity. The positive lines were selected by NLuc assay. Further confirmation of successful CRISPR genomic editing was performed by direct PCR amplification from NLuc positive cells using two primer pairs, the forward primer located in intron 4 of Klotho, upstream of the left homology arm, and the NL reverse primer located in the NLuc sequence (FIG. 4B). To examine the efficiency of the sgRNA on endogenous Klotho expression, sgRNA/dCas9-VP64/MS2-P65-HSF1 plasmids were introduced into the NLuc knock-in HEK293 cell line. The results showed that all sgRNAs increased Klotho transcription, with sgRNA3 and 4 directing the highest level of Klotho expression (FIG. 4C). Egr-1 was used as positive control (FIG. 4C).

Example 4: Evaluation of Klotho Activation in HK-2 and SY5Y Cells

Figure 5:
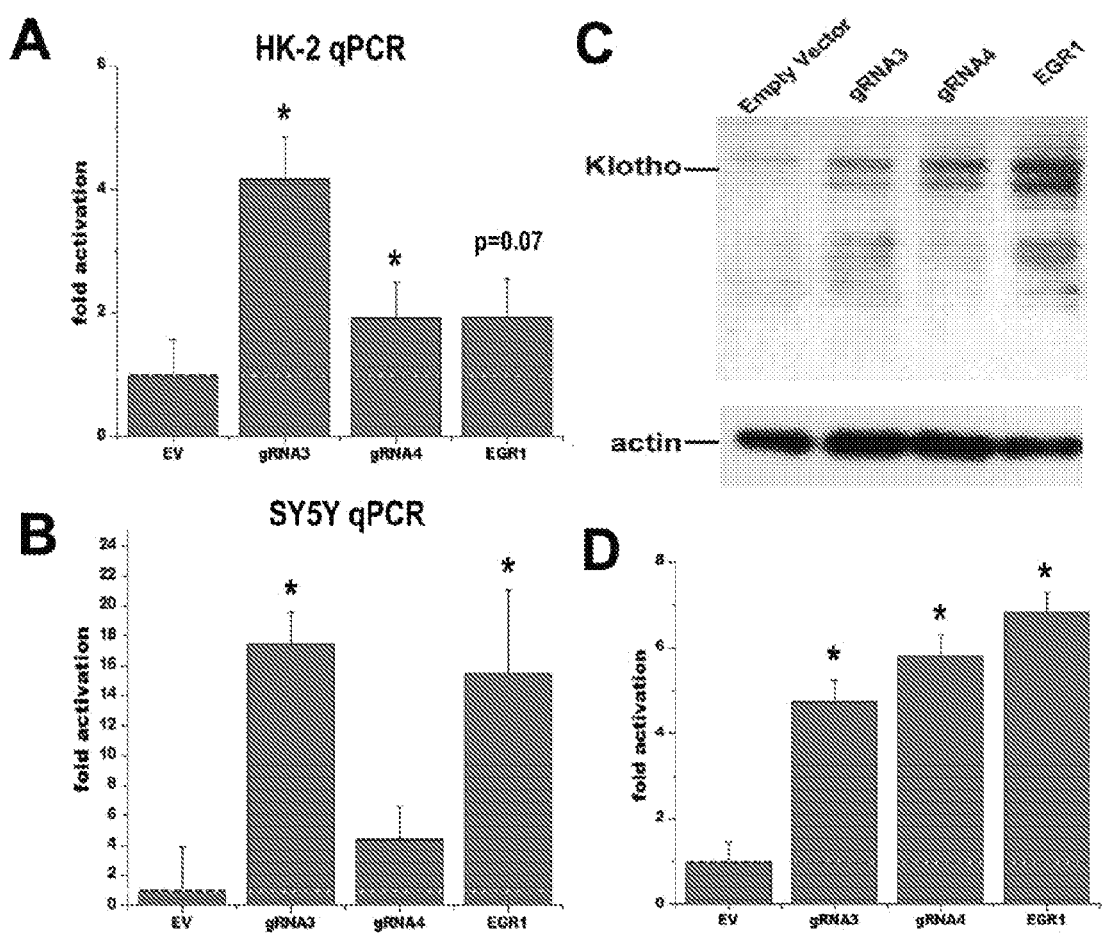
FIG. 5. Klotho expression in kidney HK-2 (A, C, D) and neuronal SY5Y cells (B). (A) Fold change in Klotho mRNA evaluated in the HK-2 line by qPCR two days after transfection with SAM complex. Data are expressed as fold over negative control. Error bars show standard deviation among six replicates. (B) Fold change in Klotho mRNA evaluated in neuronal SY5Y line by qPCR two days after transfection with SAM complex. Data are expressed as fold over negative control. Error bars show standard deviation among six replicates. (C) Western blot analysis of Klotho gene expression by SAM evaluated in HK-2 cells. Two days after transfection with the SAM complex, cell lysates were analyzed by Western blot using an anti-Klotho antibody and an Actin control. (D) Statistical analysis of the results from (B). The intensities of the 130 kDa Klotho bands were analyzed and normalized to the Actin bands using the average intensity of the controls as 1 from 3 independent experiments. Error bar indicates standard deviation. Significance of results using student's t-test: *, p<0.05.

Klotho is largely expressed in the brain and kidney (Masuda et al. 2005. *Mech. Ageing Dev.* 126(12): 1274-1283). Experiments were therefore conducted to investigate whether the sgRNA targeting the Klotho promoter region can enhance Klotho expression in cell lines from these organs. The SAM complex was transfected into HK-2 cells, and Klotho mRNA and protein levels were measured. qPCR showed that sgRNA3 and 4 enhanced Klotho mRNA levels by 2- to 4-fold (FIG. 5A). Klotho protein levels were evaluated by Western blot. The results showed that sgRNA increased Klotho protein levels by about 4- to 6-fold (FIGS. 5B and 5C). Egr-1 overexpression also enhanced Klotho gene expression (FIG. 5C).

Klotho expression was then tested in neuronal SY5Y cells. In this system, Klotho mRNA level is detectable by qPCR, however the protein level is undetectable by Western blot. The SAM complex was transfected into SY5Y cells, and Klotho mRNA levels were measured by qPCR. sgRNA3 and the positive control Egr-1 enhanced Klotho expression by 15- to 20-fold (FIG. 5B). sgRNA4 enhanced Klotho gene expression by about 4-fold (FIG. 5B). In both HK-2 and SY5Y cells, sgRNA3 increased mRNA expression more than sgRNA4. However, in terms of protein level enhancement, sgRNA4 had a stronger effect than sgRNA3 in HK-2 cells (FIGS. 5C and 5D).

Example 5: Increasing Klotho Expression Using a Variety of CRISPR Complexes

Figure 6:
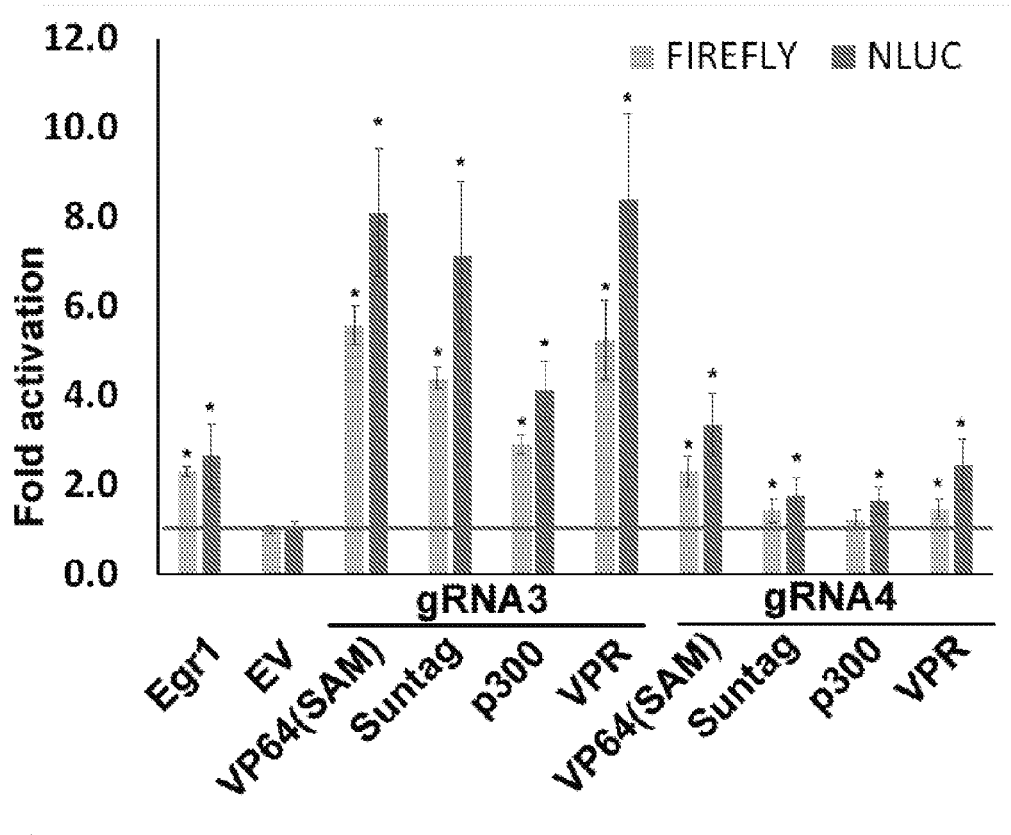
FIG. 6. Klotho gene activation using the dual luciferase coincidence reporter system. Graph illustrates fold increase in Klotho gene expression using different dCas9 systems in stable HEK293 cells. Cells were analyzed by dual luciferase assay two days after transfection with the indicated sgRNA, MS2-P65-HSF1 and various dCas9-activation systems (either SAM, Suntag, p300 or VPR). Negative control: sgRNA cloning backbone empty vector. Positive control: Egr-1 transfected cells. Data are expressed as fold over negative control. Error bars show standard deviation among six replicates. Asterisks (*) indicate statistical significance of p<0.05 by t-test compared to negative control.

Using the FLuc and NLuc reporters, the SAM system was compared to other CRISPR-mediated systems of increasing Klotho expression. In that regard, sgRNA3 or sgRNA4 were co-transfected with MS2-P65-HSF1, and either dCas9-VP64, dCas9-Suntag, dCas9-p300 or dCas9-VPR into stable FLuc NLuc coincidence reporter HEK293 cells. As shown in FIG. 6, all of the systems tested increased Klotho expression, with dCas9-VPR and dCas9-VP64 (SAM) providing the greatest increase.

The invention claimed is:

1. A method of increasing expression of a Klotho gene in a human neuronal or kidney cell, the method comprising introducing into the cell:
- a CRISPR-dCas9 enzyme; and
- a guide RNA comprising a guide sequence that is at least 95% identical to SEQ ID NO. 1 or SEQ ID NO. 3, wherein the guide sequence is substantially complementary to a target sequence located within a region between the Klotho gene translation start site and −1 to −300 nucleotides upstream of the Klotho gene translation start site, wherein the guide RNA associates with a transcriptional activation domain comprising VP64, p65 and HSF1, and wherein the guide RNA is associated with the adapter protein MS2, to thereby increase expression of the Klotho gene.

2. The method of claim 1 wherein the guide RNA is at least 90% identical to a nucleotide sequence set forth in SEQ ID NO. 5 or SEQ ID NO. 7.

3. The method of claim 1 wherein the guide RNA is a single-molecule guide RNA (sgRNA).

4. The method of claim 1 wherein the cell is inside a human body.

5. A method of increasing expression of a Klotho gene in a human neuronal or kidney cell, the method comprising introducing into the cell:
- a guide RNA comprising a guide sequence that is at least 95% identical to SEQ ID NO. 1 or SEQ ID NO. 3, wherein the guide sequence is substantially complementary to a target sequence located within a region between the Klotho gene translation start site and −1 to −300 nucleotides upstream of the Klotho gene translation start site; and
- a CRISPR-dCas9 enzyme, wherein the CRISPR enzyme comprises or is attached to a transcriptional activation domain comprising VP64, p65, and HSF1.

6. The method of claim 5 wherein the guide RNA is at least 90% identical to a nucleotide sequence set forth in SEQ ID NO. 5 or SEQ ID NO. 7.

7. The method of claim 5 wherein the guide RNA is a single-molecule guide RNA (sgRNA).

8. The method of claim 5 wherein the cell is inside a human body.

9. A method of treating a kidney disorder in a human subject, the method comprising administering to the subject:
- a CRISPR-dCas9 enzyme; and
- a guide RNA comprising a guide sequence that is at least 95% identical to SEQ ID NO. 1 or SEQ ID NO. 3, wherein the guide sequence is substantially complementary to a target sequence located within a region between a Klotho gene translation start site and −1 to −300 nucleotides upstream of the Klotho gene translation start site in the subject, wherein the guide RNA associates with a transcriptional activation domain comprising VP64, p65 and HSF1, and wherein the guide RNA is associated with the adapter protein MS2, to thereby increase expression of the Klotho gene.

10. The method of claim 9 wherein the kidney disorder is selected from the group consisting of renal dysfunction, acute kidney injury and kidney disease such as chronic kidney disease.

11. The method of claim 9 wherein the guide RNA is at least 90% identical to a nucleotide sequence set forth in SEQ ID NO. 5 or SEQ ID NO. 7.

* * * * *